US012618837B2

(12) United States Patent
Ginhoux et al.

(10) Patent No.: US 12,618,837 B2
(45) Date of Patent: May 5, 2026

(54) METHOD OF IDENTIFYING PRO-INFLAMMATORY DENDRITIC CELLS

(71) Applicant: Agency for Science, Technology and Research, Singapore (SG)

(72) Inventors: Florent Ginhoux, Singapore (SG); Charles Antoine Dutertre, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1109 days.

(21) Appl. No.: 17/596,950

(22) PCT Filed: Jun. 26, 2020

(86) PCT No.: PCT/SG2020/050369
§ 371 (c)(1),
(2) Date: Dec. 22, 2021

(87) PCT Pub. No.: WO2020/263192
PCT Pub. Date: Dec. 30, 2020

(65) Prior Publication Data
US 2023/0184762 A1      Jun. 15, 2023

(30) Foreign Application Priority Data
Jun. 26, 2019      (SG) ............................ 10201905956V

(51) Int. Cl.
*G01N 33/569*          (2006.01)

(52) U.S. Cl.
CPC .................. *G01N 33/56972* (2013.01); *G01N 2333/70596* (2013.01); *G01N 2800/7095* (2013.01)

(58) Field of Classification Search
CPC ............................................... G01N 33/56972
See application file for complete search history.

(56) References Cited

U.S. PATENT DOCUMENTS

2022/0397568 A1 * 12/2022 Villani ................... A61K 40/24

FOREIGN PATENT DOCUMENTS

WO          2018/035364 A1      2/2018

OTHER PUBLICATIONS

Yin et al. Human Blood CD1c+ Dendritic Cells Encompass CD5high and CD5low lo Subsets That Differ Significantly in Phenotype. J Immunol 198: 1553-1564 (Jan. 13, 2017).*
Collin et al. Human dendritic cell subsets: an update. Immunology 154: 3-20 (2018).*
Aliberti, J., et al., "Essential role for ICSBP in the in vivo development of murine CD8alpha + dendritic cells", Blood 101, 305-310 (2003).

Becher, B., et al., "High-dimensional analysis of the murine myeloid cell system", Nat Immunol 15, 1181-1189 (2014).
Becht, E., McInnes, L., Healy, J., Dutertre, C.-A., Kwok, I.W.H., Ng, L.G., Ginhoux, F., and Newell, E.W. (2018). Dimensionality reduction for visualizing single-cell data using UMAP. Nat. Biotechnol.
Becht, E., et al., "Reverse-engineering flow-cytometry gating strategies for phenotypic labelling and high-performance cell sorting",. Bioinforma. Oxf. Engl. 35, 301-308 (2018).
Brynjolfsson, S.F., et al., "An Antibody Against Triggering Receptor Expressed on Myeloid Cells 1 (TREM-1) Dampens Proinflammatory Cytokine Secretion by Lamina Propria Cells from Patients with IBD", 2016 Inflamm. Bowel Dis. 22, 1803-1811.
Calzetti, F., et al., "Human dendritic cell subset 4 (DC4) correlates to a subset of CD14dim/–CD16++ monocytes", 2018 J. Allergy Clin. Immunol. 141, 2276-2279.e3.
Chen, H., et al., "Cytofkit: A Bioconductor Package for an Integrated Mass Cytometry Data Analysis Pipeline", PLoS Comput. Biol. 12, e1005112 (Sep. 2016).
Davis, S., et al., "GEOquery: a bridge between the Gene Expression Omnibus (GEO) and BioConductor", Bioinforma. Oxf. Engl. 23, 1846-1847 (2007).
DiGiuseppe, J.A., et al., "PhenoGraph and viSNE facilitate the identification of abnormal T-cell populations in routine clinical flow cytometric data", Cytometry B Clin. Cytom. 94, 588-601 (2018.
Dress, R., et al., "Plasmacytoid dendritic cell differentiation is distinct from the myeloid lineage and occurs from Ly6D+ early lymphoid progenitors", 2019, Nat. Immunol, vol. 20, 852-864.
Dutertre, C.-A., et al., "Pivotal role of M-DC8+ monocytes from viremic HIV-infected patients in TNFα overproduction in response to microbial products", Blood 120, 2259-2268 (2012).
Dutertre, C.-A., et al., "Aligning bona fide dendritic cell populations across species", 2014, Cell. Immunol. 291, 3-10.
Finck, R., et al., "Normalization of mass cytometry data with bead standards", Cytom. Part J. Int. Soc. Anal. Cytol. 83, 483-494 (2013).
Ginhoux, F., et al., "Tissue-Resident Macrophage Ontogeny and Homeostasis", Immunity 44, 439-449 (2016).
Guilliams, M., et al., "Dendritic cells, monocytes and macrophages: a unified nomenclature based on ontogeny", Nat Rev Immunol 14, 571-578 (2014).
Guilliams, M., et al., "Unsupervised High-Dimensional Analysis Aligns Dendritic Cells across Tissues and Species", Immunity 45, 669-684 (2016).
Günther, P. et al., "A rule-based data-informed cellular consensus map of the human mononuclear phagocyte cell space" ioRxiv (2019).

(Continued)

*Primary Examiner* — Gailene Gabel
(74) *Attorney, Agent, or Firm* — Hamilton, Brook, Smith & Reynolds, P.C.

(57) ABSTRACT

There is provided a method of identifying pro-inflammatory dendritic cells, the method comprising: determining an expression of CD5, CD14 and/or CD163 in cells, wherein $CD5^-$, $CD14^+$ and/or $GD163^+$ cells are identified as pro-inflammatory dendritic cells. Also disclosed is a method of characterising inflammation and/or inflammatory disease in a subject, the method comprising: determining a proportion of $CD5^-$, $CD14^+$ and/or $GD163^+$ dendritic cells in the subject's sample, wherein the proportion positively correlates with the level of inflammation and/or the severity of inflammatory disease in the subject.

7 Claims, 33 Drawing Sheets

(56) References Cited

OTHER PUBLICATIONS

Hamers Anouk A.J., et al., "Human Monocyte Heterogeneity as Revealed by High-Dimensional Mass Cytometry", Arterioscler. Thromb. Vasc. Biol. 39, 25-36 (2019).

Haniffa, M., et al., "Human tissues contain CD141hi cross-presenting dendritic cells with functional homology to mouse CD103+ nonlymphoid dendritic cells", Immunity 37, 60-73 (2012).

Harrow, J., et al., "Gencode: the reference human genome annotation for The Encode", Project. Genome Res. 22, 1760-1774 (2012).

Hildner, K., et al., "Batf3 deficiency reveals a critical role for CD8alpha+ dendritic cells in cytotoxic T cell immunity", Science 322, 1097-1100 (2008).

Klarquist, J., et al., "Dendritic Cells in Systemic Lupus Erythematosus: From Pathogenic Players to Therapeutic Tools", Mediators Inflamm. 2016, 5045248 (2016).

Kuryliszyn-Moskal, A., et al., "Vascular endothelial growth factor in systemic lupus erythematosus: relationship to disease activity, systemic organ manifestation, and nailfold capillaroscopic abnormalities", Arch. Immunol. Ther. Exp. (Warsz.) 55, 179-185 (2007).

Lamb, J., et al., "The Connectivity Map: using gene-expression signatures to connect small molecules, genes, and disease", Science 313, 1929-1935 (2006).

Levine, J.H., et al., "Data-Driven Phenotypic Dissection of AML Reveals Progenitor-like Cells that Correlate with Prognosis", Cell 162, 184-197 (2015).

Li, H.-H., et al., "Interleukin-20 targets renal mesangial cells and is associated with lupus nephritis", 2008, Clin. Immunol. Orlando Fla 129, 277-285.

Liao, X., et al., "Chemokines and Chemokine Receptors in the Development of Lupus Nephritis", Mediators Inflamm. 2016, 6012715 (2016).

McInnes, L., et al., "UMAP: Uniform Manifold Approximation and Projection for Dimension Reduction", ArXiv180203426 Cs Stat (2018).

Menon, M., et al., "A Regulatory Feedback between Plasmacytoid Dendritic Cells and Regulatory B Cells Is Aberrant in Systemic Lupus Erythematosus", Immunity 44, 683-697 (2016).

Merad, M., et al., "The dendritic cell lineage: ontogeny and function of dendritic cells and their subsets in the steady state and the inflamed setting", Annu. Rev. Immunol. 31, 563-604 (2013).

Newell, E.W., et al., "Cytometry by time-of-flight shows combinatorial cytokine expression and virus-specific cell niches within a continuum of CD8+ T cell phenotypes", Immunity 36, 142-152 (2012).

Newman, A.M., "Robust enumeration of cell subsets from tissue expression profiles", Nat. Methods 12, 453-457 (2015).

Nguyen-Lefebvre, A.T., et al., "The innate immune receptor TREM-1 promotes liver injury and fibrosis", J. Clin. Invest. 128, 4870-4883 (2018).

Nielepkowicz-Goździńska, A., et al., "Exhaled IL-8 in systemic lupus erythematosus with and without pulmonary fibrosis", Arch. Immunol. Ther. Exp. (Warsz.) 62, 231-238 (2014).

Parks, C.G., et al., "Systemic lupus erythematosus and genetic variation in the interleukin 1 gene cluster: a population based study in the southeastern United States", Ann. Rheum. Dis. 63, 91-94 (2004).

Parks, D.R., et al., "A new "Logicle" display method avoids deceptive effects of logarithmic scaling for low signals and compensated data", Cytom. Part J. Int. Soc. Anal. Cytol. 69, 541-551 (2006).

Patro, R., et al., "Salmon provides fast and bias-aware quantification of transcript expression", Nat. Methods 14, 417-419 (2017).

Picelli, S., et al., "Full-length RNA-seq from single cells using Smart-seq2", Nat. Protoc. 9, 171-181 (2014).

Rodrigues, P.F., et al., "Distinct progenitor lineages contribute to the heterogeneity of plasmacytoid dendritic cells", 2018, Nat. Immunol. 19, 711-722.

Samy, E., et al., "Targeting BAFF and APRIL in systemic lupus erythematosus and other antibody-associated diseases", Int. Rev. Immunol. 36, 3-19 (2017).

Schlitzer, A., et al., "IRF4 transcription factor-dependent CD11b+ dendritic cells in human and mouse control mucosal IL-17 cytokine responses", Immunity 38, 970-983 (2013).

Schlitzer, A., et al., "Dendritic cells and monocyte-derived cells: Two complementary and integrated functional systems", Semin. Cell Dev. Biol. 41, 9-22 (2015).

Schlitzer, A., et al., "Identification of cDC1- and cDC2-committed DC progenitors reveals early lineage priming at the common DC progenitor stage in the bone marrow", Nat. Immunol. 16, 718-728 (2015).

Schölkopf, B., et al., "New support vector algorithms", Neural Comput. 12, 1207-1245 (2000).

See, P., Dutertre, et al., "Mapping the human DC lineage through the integration of high-dimensional techniques", Science 356 (2017).

Segura, E., et al., "Human inflammatory dendritic cells induce Th17 cell differentiation", Immunity 38, 336-348 (2013).

Setty, M., et al., "Wishbone identifies bifurcating developmental trajectories from single-cell data", Nat. Biotechnol. 34, 637-645 (2016).

Smyth, G.K. (2004). "Linear models and empirical bayes methods for assessing differential expression in microarray experiments". Stat. Appl. Genet. Mol. Biol. 3, Article3.

Smyth, G.K. "Limma: Linear Models for Microarray Data", In Bioinformatics and Computational Biology Solutions Using R and Bioconductor, R. Gentleman, V.J. Carey, W. Huber, R.A. Irizarry, and S. Dudoit, eds. (New York, NY: Springer New York), pp. 397-420 (2005).

Sun, F., et al., "Involvement of TWEAK and the NF-κB signaling pathway in lupus nephritis", Exp. Ther. Med. 15, 2611-2619 (2018).

Tan-Garcia, A., et al., "Intrahepatic CD206+ macrophages contribute to inflammation in advanced viral-related liver disease", 2017, J. Hepatol. 67, 490-500.

Tang-Huau, T.-L., et al., "Human in vivo-differentiated monocyte-derived dendritic cells", Semin. Cell Dev. Biol (2018).

Tenenbaum, J.B., et al., "A global geometric framework for nonlinear dimensionality reduction", 2000, Science 290, 2319-2323.

Tussiwand, R., et al., "Klf4 expression in conventional dendritic cells is required for T helper 2 cell responses", Immunity 42, 916-928 (2015).

Van der Maaten, L., et al., "Visualizing data using t-SNE", J. Mach. Learn. Res. 9, 2579-2605 (2008).

Villani, A.-C., et al., "Single-cell RNA-seq reveals new types of human blood dendritic cells, monocytes, and progenitors", Science 356 (2017).

Notification of Transmittal of the International Search Report and The Written Opinion of the International Searching Authority, or the Declaration for International Application No. PCT/SG2020/050369, "Method of Identifying Pro-Inflammatory Dendritic Cells" date of mailing: Sep. 16, 2020.

Yin, Y., et al., "Human Blood CD1c+ Dendritic Cells Encompass CD5high and CD5low Subsets That Differ Significantly in Phenotype, Gene Expression, and Functions" J Immunol 2017, 198; 1553-1564.

Dutertre C.-A. et al., "Single-Cell Analysis of Human Mononuclear Phagocytes Reveals Subset-Defining Markers and Identifies Circulating Inflammatory Dendritic Cells", Immunity, Aug. 29, 2019, vol. 51, No. 3, pp. 573-589.e8.

Collin, M., et al., Human dendritic cell subsets: an update, Cancer Research, May 1, 2018, 3-20, 154/1.

Heger, L., et al., "Subsets of CD1c+ DCs: Dendritic Cell Versus Monocyte Lineage", Frontiers in Immunology, Sep. 30, 2020, 1-11, 11.

Helft, J., et al., "Dendritic Cell Lineage Potential in Human Early Hematopoietic Progenitors" Cell Reports, Jul. 1, 2017, 529-537, 20/3.

Supplementary European Search Report for EP Application No. EP 20833631, "Method of Identifying Pro-Inflammatory Dendritic Cells" date of completion: Jun. 15, 2023.

* cited by examiner

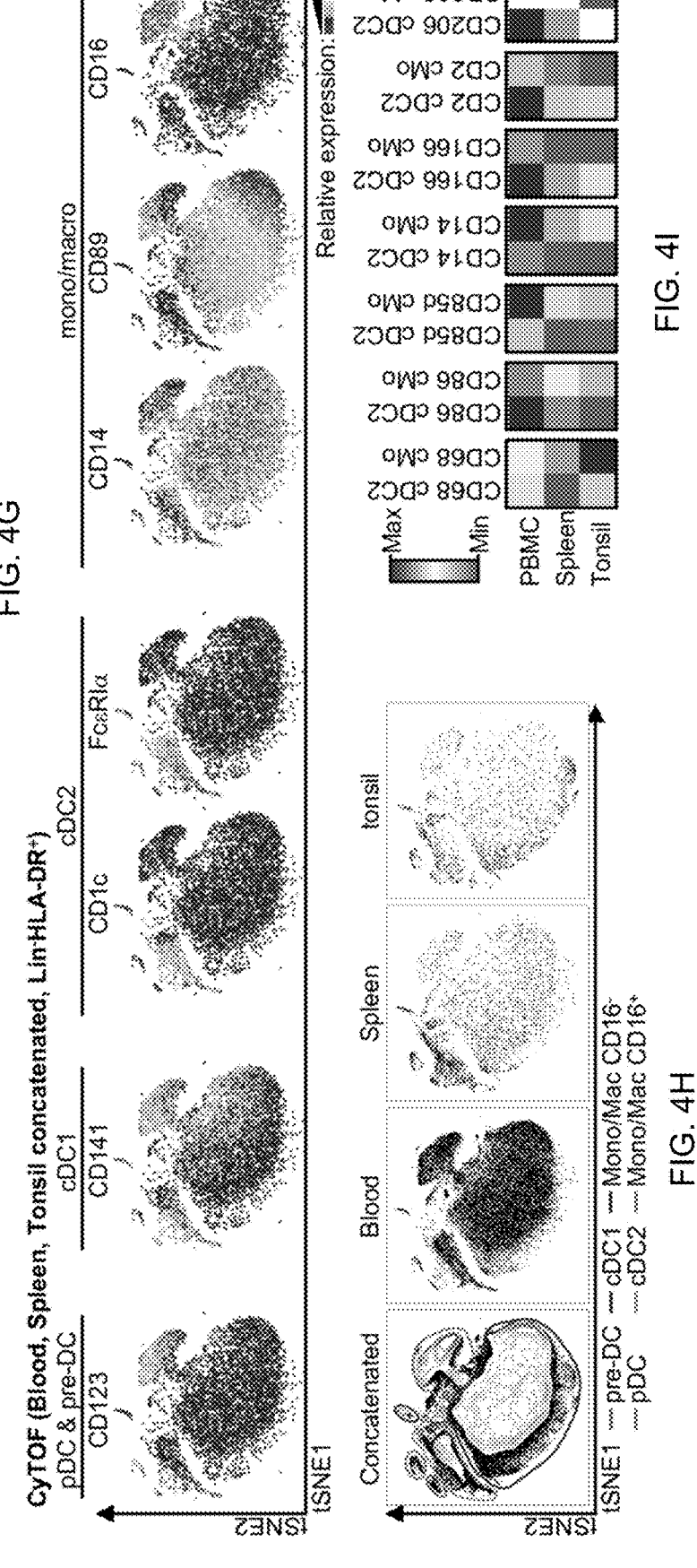

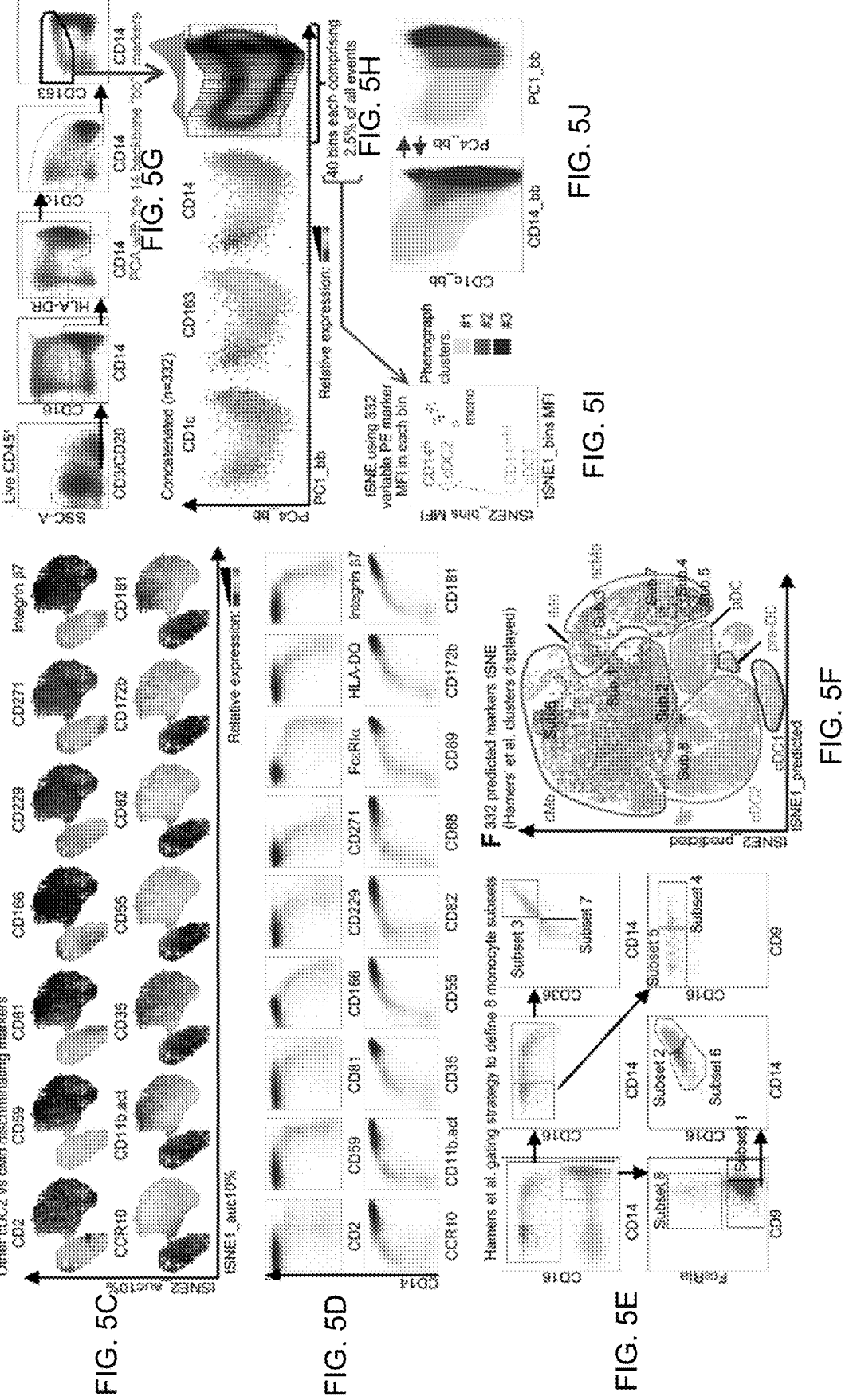

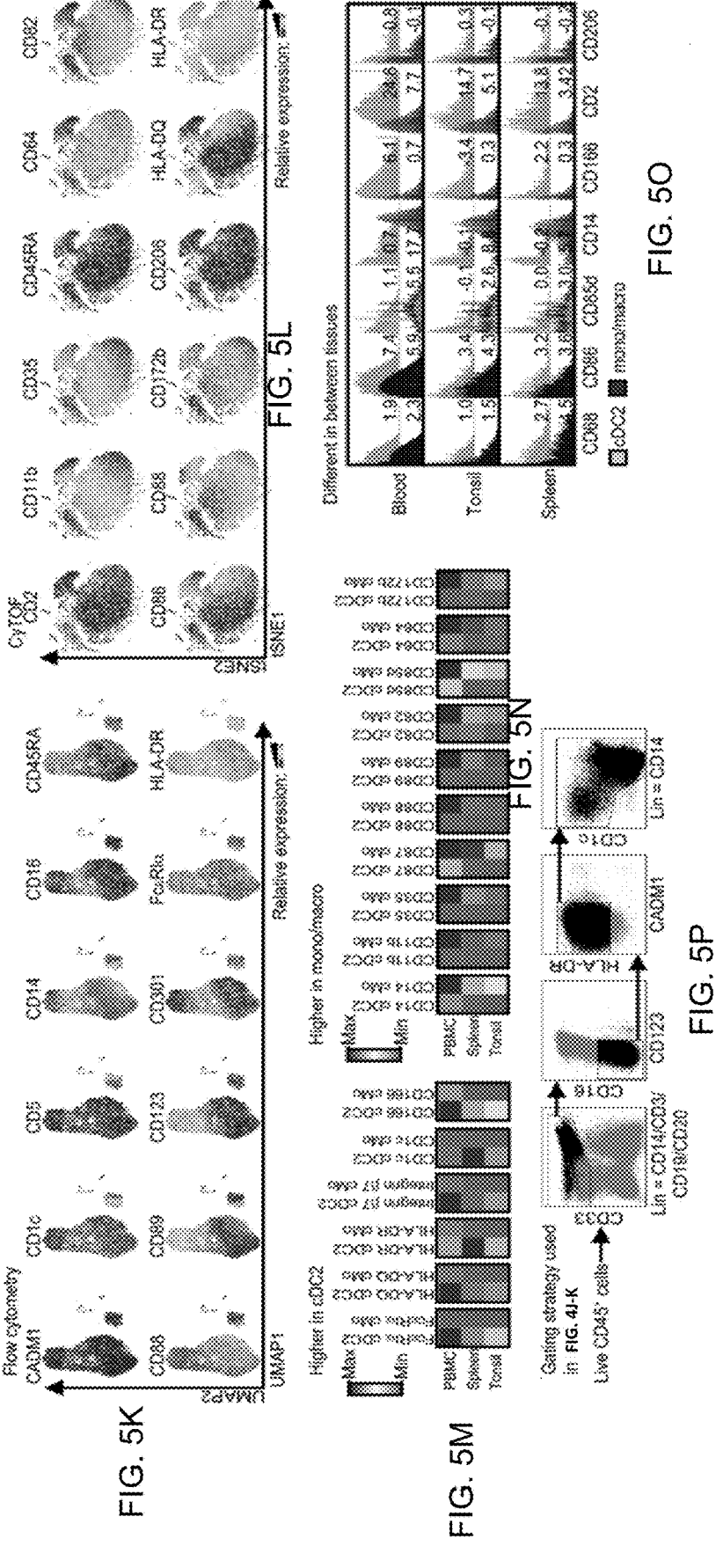

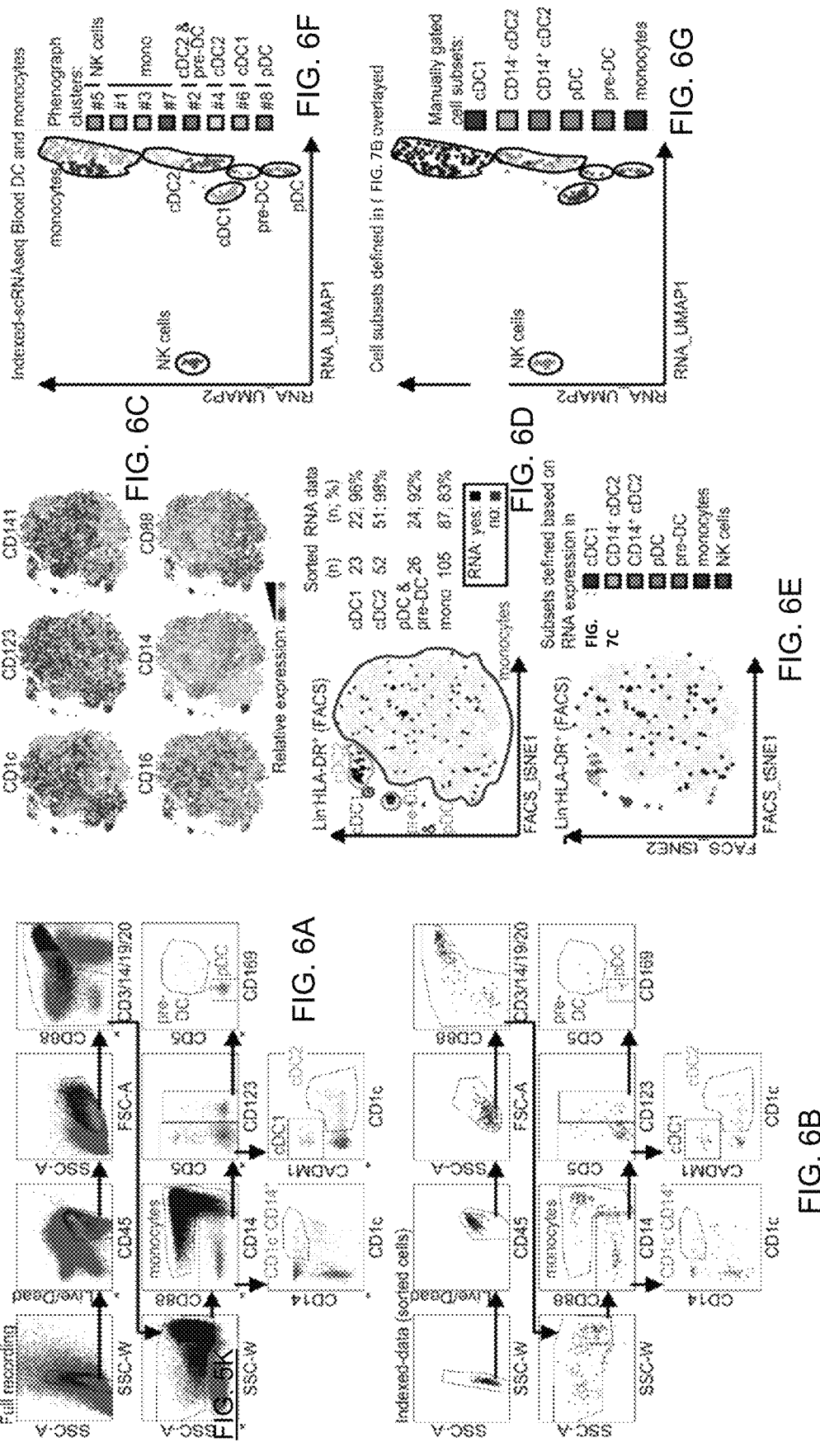

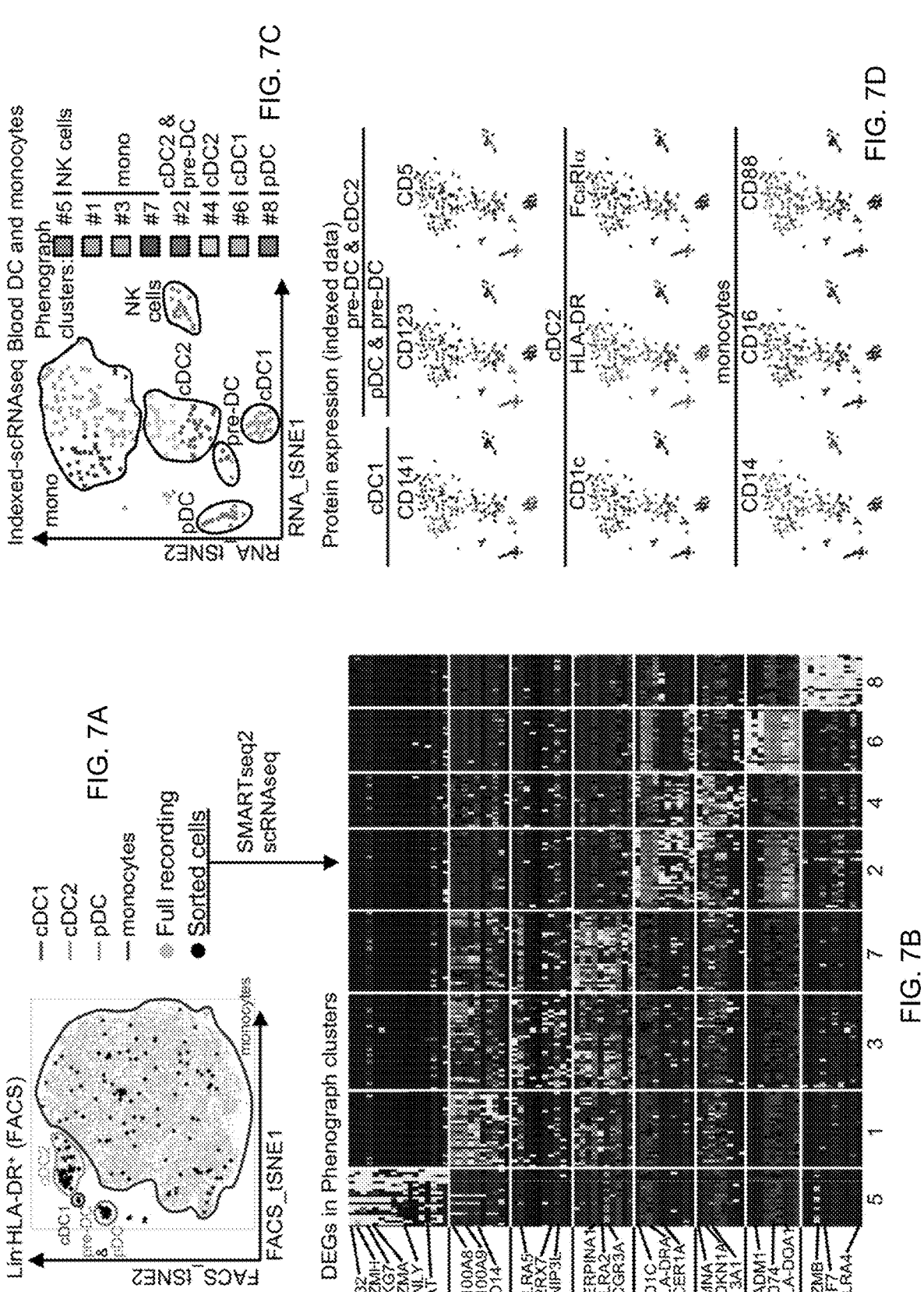

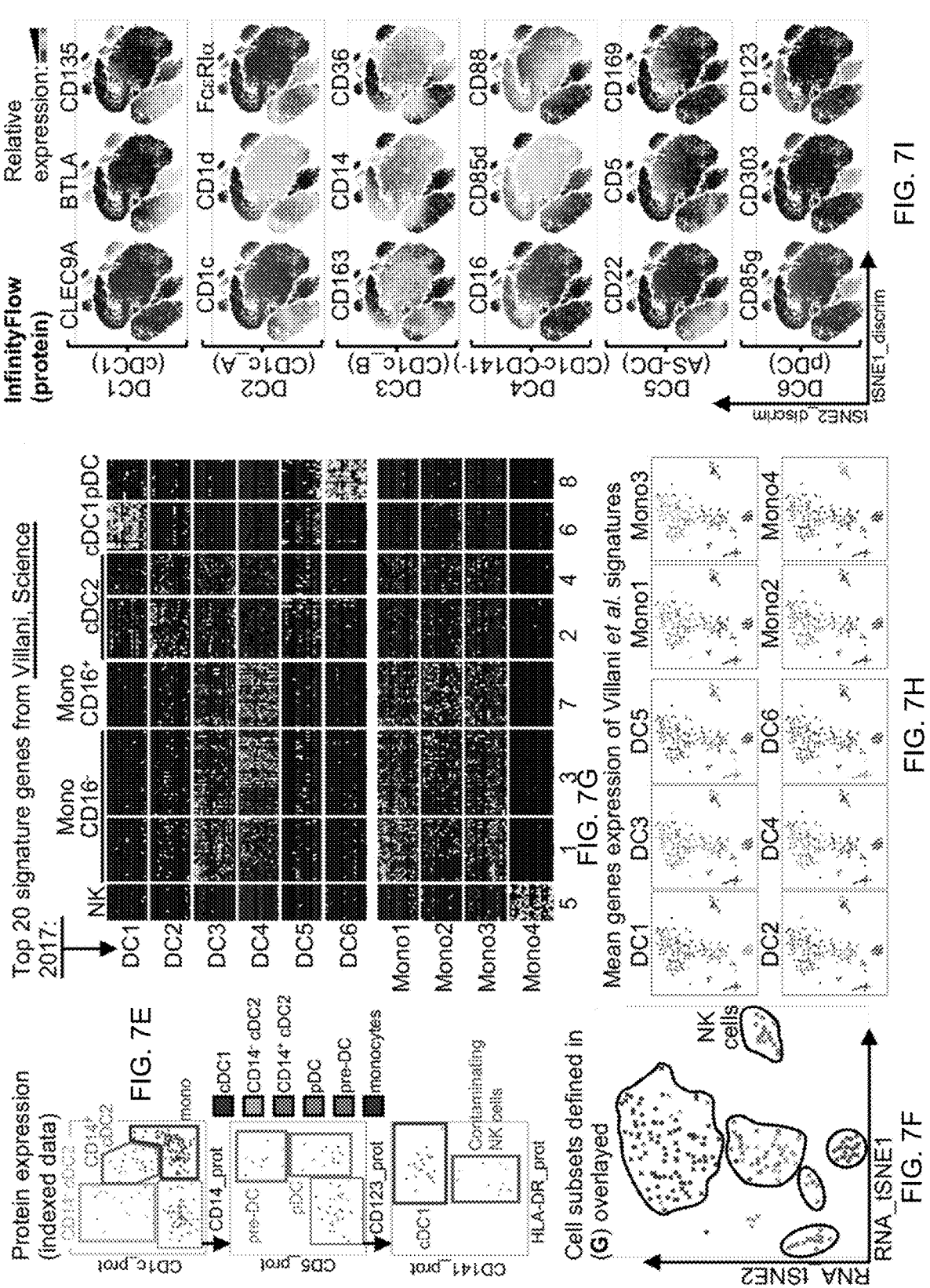

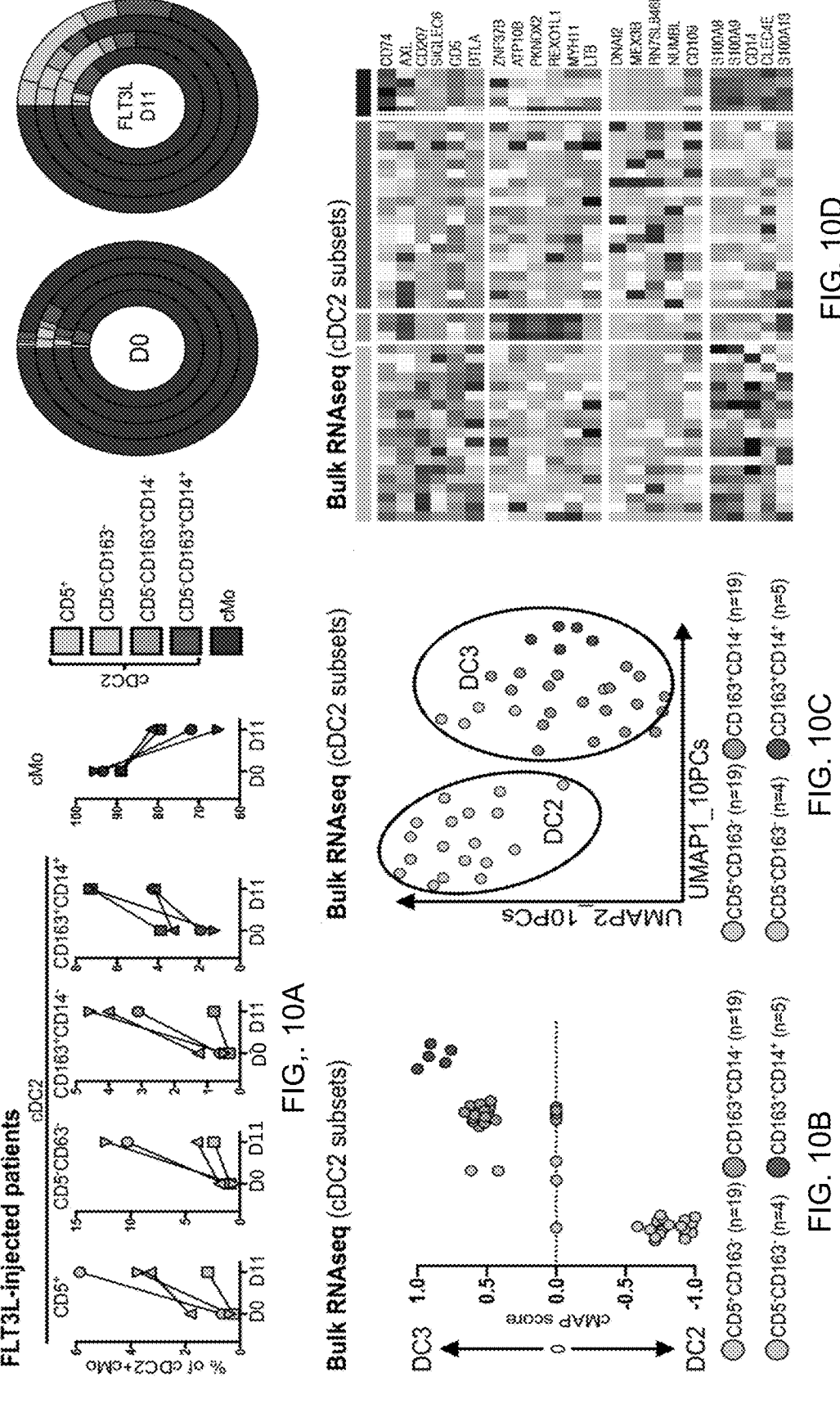

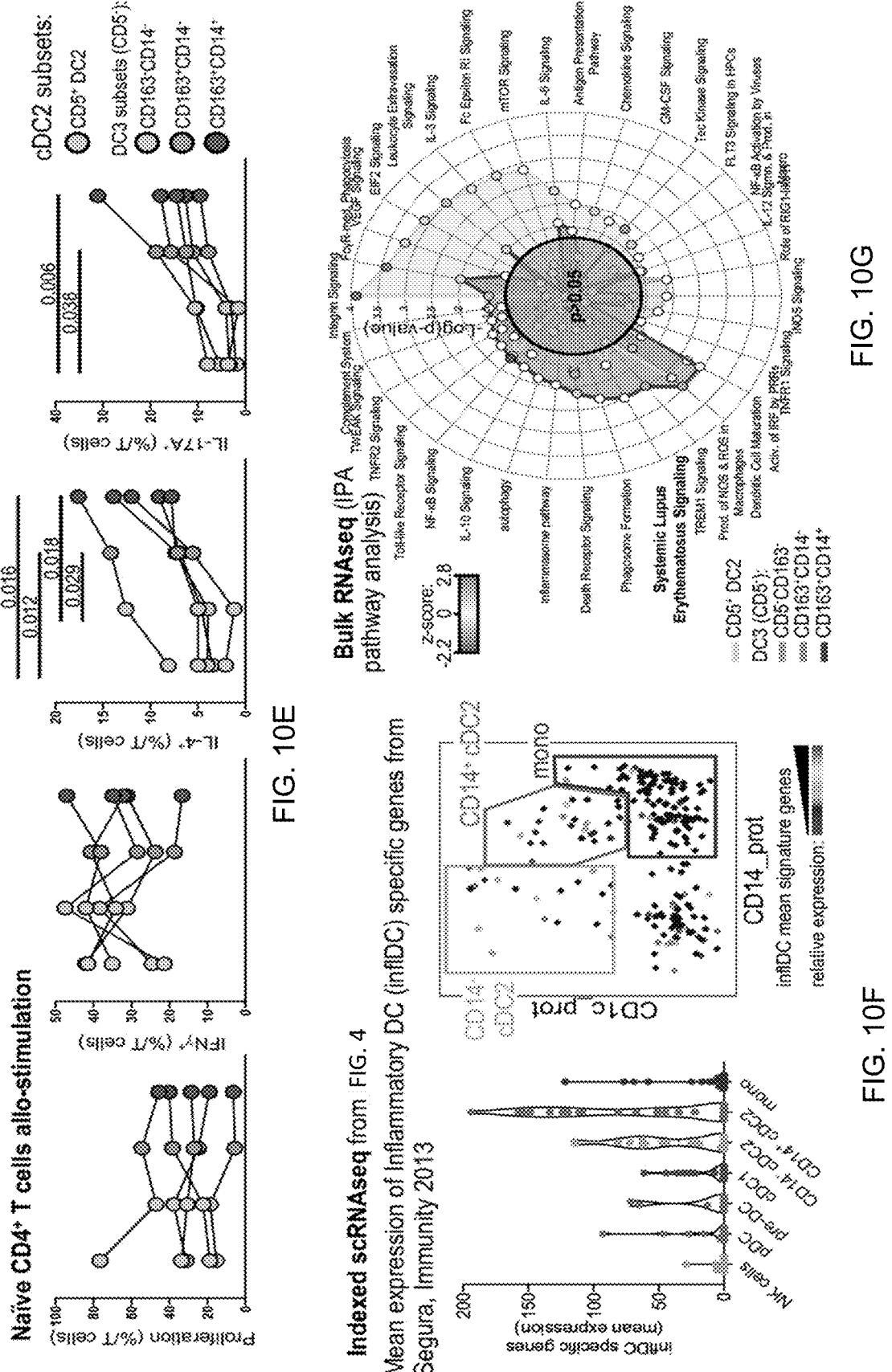

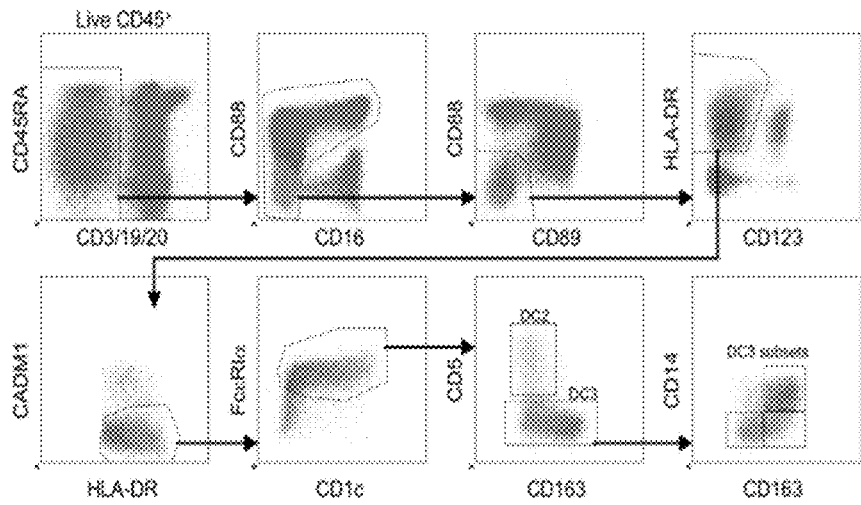
FIG. 13A
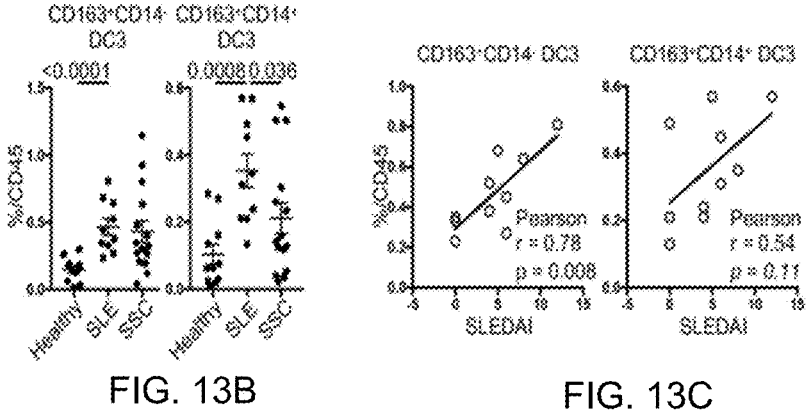
FIG. 13B                    FIG. 13C
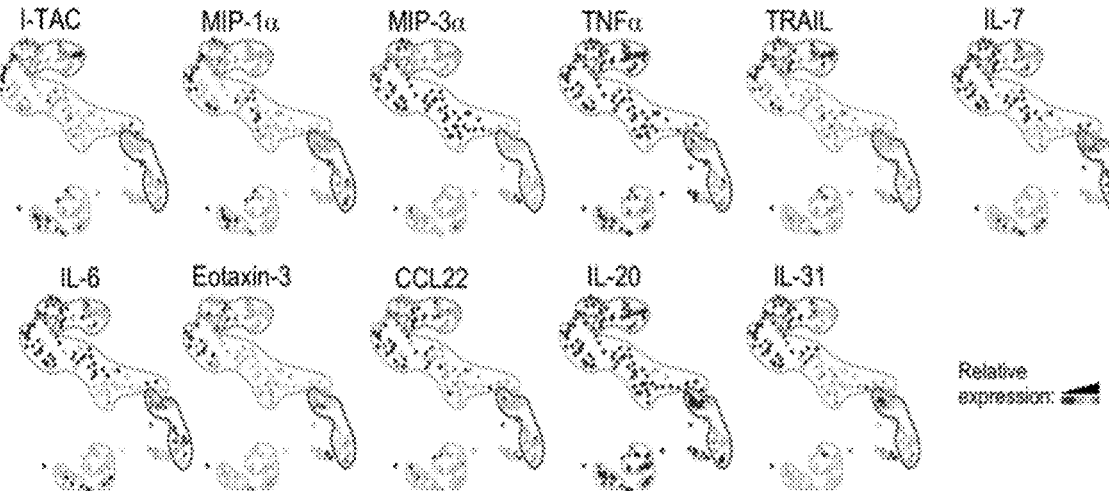
FIG. 13D

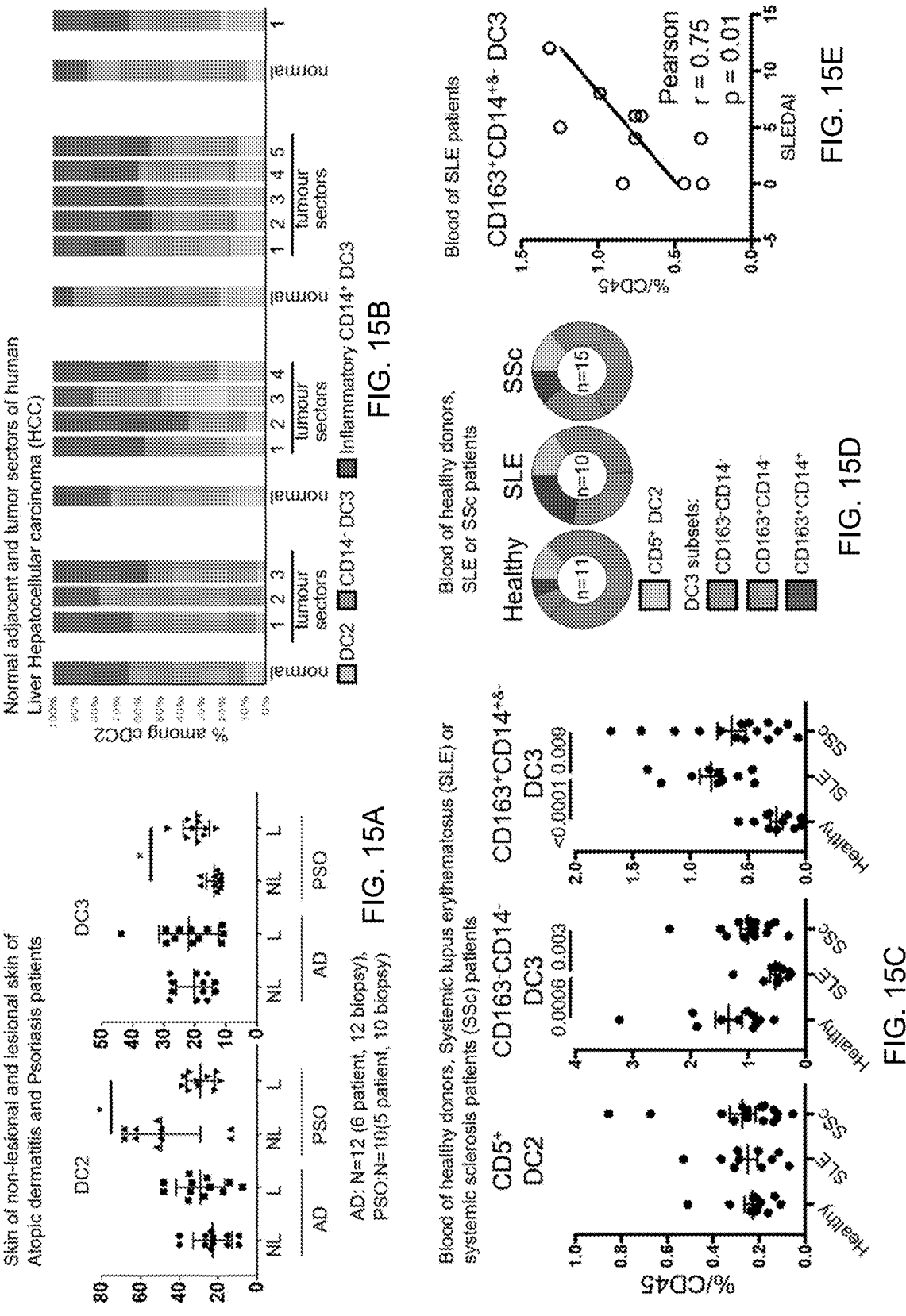

METHOD OF IDENTIFYING PRO-INFLAMMATORY DENDRITIC CELLS

RELATED APPLICATIONS

This application is the U.S. National Stage of International Application No. PCT/SG2020/050369, filed Jun. 26, 2020, which designates the U.S., published in English, and claims priority under 35 U.S.C. § 119 or 365(c) to Singapore Application No. 10201905956V, filed Jun. 26, 2019. The entire teachings of the above applications are incorporated herein by reference.

TECHNICAL FIELD

The present disclosure relates broadly to a method of characterising mononuclear phagocyte populations, such as dendritic cells, and related kits.

BACKGROUND

Mononuclear phagocytes (MNP) comprise a heterogeneous population of cells historically assigned to subsets based on their phenotype, ontogeny, transcriptomic profiles and their specialized functions. MNP comprise dendritic cell (DC) and monocyte subsets in the blood and tissues, as well as macrophages and monocyte-derived cells (MC) in tissues. It is important to clearly delineate these subsets to study their functions, as particular MNP subsets are increasingly recognized as having important roles in diseases. A clear method to identify these various subsets in the blood and tissues, as well as in health and disease, is challenging as their phenotypes are often overlapping.

DC and MC represent two complementary and integrated functional systems in time and space. DC specifically depend on FMS-like tyrosine kinase 3 (FLT3) for their differentiation and proliferation. They classically include plasmacytoid DC (pDC) that are highly specialized in type I interferon production, and conventional DC (cDC) that are major subsets involved in antigen presentation and modulation of immunity. Importantly, the DC nature of pDC is under debate, as they have been shown to differentiate from B-cell progenitors, and thus could be more related to the innate lymphoid cell family. cDC are further subdivided into two major lineages: cDC1, with superior antigen cross-presentation to $CD8^+$ T cells, and cDC2 that perform a wide spectrum of functions, including antigen presentation to $CD4^+$ T cells and priming to T helper 2 (Th2) and Th17-type responses. Importantly, DC subsets depend on critical transcription factors for their differentiation including IRF8 and BATF3 for cDC1 or IRF4 and KLF4 for cDC2. While cDC1 express several highly specific markers (CLEC9A, XCR1, CADM1) allowing their precise delineation, cDC2 express less specific defining markers that often overlap with monocytes.

Monocytes are highly heterogenous, plastic cells that patrol blood vessels and can migrate to tissues, where together with resident macrophages, they have central roles in tissue homeostasis maintenance and inflammation. Monocytes differentiate into MC with features characteristic of both macrophages and DC, the latter mostly during inflammation. MC can acquire a multitude of functional capabilities that are largely determined by the inflammatory milieu to which they are recruited. In human blood, monocyte subsets are defined based on their relative expression of CD14 and CD16—two membrane proteins with supposed restricted expression to monocytes among all circulating MNP. Such restricted expression is now under debate, as in the blood, classical monocytes (cMo; $CD14^{hi}CD16^-$) and $CD1c^+cDC2$ are phenotypically related and form a continuum, with cells falling in between that express markers of both cell types including the cDC2 marker CD1c, and the monocyte markers CD14 and CD11b. Similar intermediate pro-inflammatory cells also accumulate in inflamed tissues and while they seem to be derived from monocytes, they are functionally different due to their cDC2-specialized capacity to stimulate autologous $CD4^+$ T cells. Thus, understanding the currently debated nature of these cells could allow their manipulation in pathologic settings.

Thus, there is a need to provide an alternative method of characterising mononuclear phagocyte populations, such as dendritic cells, and related kits.

SUMMARY

In one aspect, there is provided a method of characterising dendritic cells, the method comprising: determining an expression of one or more of CD5, CD14 and CD163 in the dendritic cells.

In one embodiment, where the dendritic cells are determined to be $CD5^-$, $CD14^+$ and/or $CD163^+$, the method comprises identifying the dendritic cells as pro-inflammatory dendritic cells.

In one embodiment, wherein where the dendritic cells are determined to be $CD163^+CD14^+$, the method comprises identifying the dendritic cells as highly pro-inflammatory dendritic cells that are more pro-inflammatory than $CD163^-$ or $CD14^-$ dendritic cells.

In one embodiment, the method further comprises determining a proportion of $CD163^+CD14^+$ dendritic cells.

In one embodiment, the method further comprises determining an expression of one or more of CD11b, CD36, CD64, CD87, CD107a, CD206, CD274, CD354, FcεRIα, HLA-DQ, CD2, CD59, CD81, CD166, CD229, CD271 and Integrin β7 in the dendritic cells.

In one embodiment, the dendritic cells have one or more of the following properties:

(i) is a conventional dendritic cell 2 (cDC2);

(ii) is dependent on IRF4 for differentiation;

(iii) is dependent on KLF4 for differentiation;

(iv) is dependent on FLT3 ligand (FLT3L) for differentiation; and (v) is capable of activating and/or polarizing T cells.

In one aspect, there is provided a method of characterising inflammation and/or inflammatory disease in a subject, the method comprising: determining a proportion of $CD5^-$, $CD14^+$, $CD163^+$, and/or $CD14^+CD163^+$ dendritic cells in the subject's sample, wherein the proportion positively correlates with the level of inflammation and/or the severity of inflammatory disease in the subject.

In one embodiment, where the proportion of $CD5^-$, $CD14^+$, $CD163^+$, and/or $CD14^+CD163^+$ dendritic cells in the subject's sample is greater than a threshold proportion derived from a control sample, the method comprises identifying the presence of inflammation and/or inflammatory disease in the subject.

In one embodiment, where the proportion of $CD5^-$, $CD14^+$, $CD163^+$, and/or $CD14^+CD163^+$ dendritic cells in the sample is greater than the proportion in an earlier sample from the same subject, the method comprises identifying a worsening of inflammation and/or inflammatory disease in the subject, and wherein where the proportion of $CD5^-$, $CD14^+$, $CD163^+$, and/or $CD14^+CD163^+$ dendritic cells in the sample is lower than the proportion in the earlier sample, the method comprises identifying an improvement of inflammation and/or inflammatory disease in the subject.

In one embodiment, the inflammatory disease is selected from the group consisting of systemic inflammatory disease, metabolic disorder, autoimmune disease and cancer.

In one embodiment, the inflammatory disease is selected from the group consisting of inflammatory skin disease, inflammatory bowel diseases, asthma, acute respiratory distress syndrome, chronic obstructive pulmonary disease, acute lung injury, bronchopulmonary dysplasia, cystic fibrosis, bronchitis, bronchiolitis, arthritis, osteoarthritis, ankylosing spondylitis and rheumatism.

In one embodiment, the metabolic disorder is selected from the group consisting of obesity, diabetes satiety and endocrine deficiencies related to aging.

In one embodiment, the autoimmune disease is selected from the group consisting of Systemic Lupus Erythematosus (SLE), diabetes, rheumatoid arthritis (RA), multiple sclerosis (MS), myasthenia gravis (MG), scleroderma, Crohn's disease, ulcerative colitis, Hashimoto's disease, Graves' disease, Sjögren's syndrome, polyendocrine failure, vitiligo, peripheral neuropathy, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barré syndrome, hemochromatosis, Henoch-Schönlein purpura, idiopathic IgA nephropathy, insulin-dependent diabetes mellitus (IDDM), juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, atopic dermatitis, rapidly-progressive glomerulonephritis (RPGN), Reiter's syndrome, stiff-man syndrome and thyroiditis.

In one embodiment, the autoimmune disease is selected from the group consisting of psoriasis, atopic dermatitis, Systemic Lupus Erythematosus (SLE) and systemic sclerosis (SSc).

In one embodiment, the cancer comprises a non-solid tumour, optionally wherein the non-solid tumor is selected from the group consisting of leukaemia, multiple myelomas and lymphomas.

In one embodiment, the cancer comprises a solid tumor, optionally wherein the solid tumour comprises sarcoma and/or carcinoma, further optionally wherein the sarcoma and/or carcinoma is selected from the group consisting of hepatocellular carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In one embodiment, the cancer is selected from the group consisting of hepatocellular carcinoma, follicular lymphoma, small lymphocytic lymphoma, pancreatic tumour and breast cancer.

In one embodiment, wherein where the presence and/or the worsening of inflammation and/or an inflammatory disease in the subject is identified, the method further comprises allocating the subject to an inflammatory disease treatment regimen.

In one embodiment, the inflammatory disease treatment regimen comprises administering to the subject one or more agent selected from the group consisting of: an anti-inflammatory agent, an immunosuppressant agent, an anti-cancer agent, an inhibitor of FLT3L, an agent capable of binding to $CD5^-$, $CD14^+$, $CD163^+$, and/or $CD14^+CD163^+$ dendritic cells, an agent capable of neutralising $CD5^-$, $CD14^+$, $CD163^+$, and/or $CD14^+CD163^+$ dendritic cells, an antibody against $CD5^-$, $CD14^+$, $CD163^+$, and/or $CD14^+CD163^+$ dendritic cells, an agent capable of reducing the proportion of $CD5^-$, $CD14^+$, $CD163^+$, and/or $CD14^+CD163^+$ dendritic cells, an agent capable of reducing an activity of $CD5^-$, $CD14^+$, $CD163^+$, and/or $CD14^+CD163^+$ dendritic cells, an agent capable of reducing a number of a precursor of $CD5^-$, $CD14^+$, $CD163^+$, and/or $CD14^+CD163^+$ dendritic cells and an agent capable of inhibiting a differentiation of the precursor to $CD5^-$, $CD14^+$, $CD163^+$, and/or $CD14^+CD163^+$ dendritic cells.

In one aspect, there is provided a kit for characterising dendritic cells, inflammation and/or inflammatory disease, the kit comprising one or more reagent for detecting CD5, CD14 and/or CD163.

Definitions

The term "characterising" as used herein refers broadly to the identification of a nature and/or properties associated with a cell (e.g. a dendritic cell), a cell population, a tissue, a body response (e.g. an inflammation) or a disease (e.g. an inflammatory disease). The determination may be qualitative, quantitative or semi-quantitative The term "treatment", "treat" and "therapy", and synonyms thereof as used herein refer to both therapeutic treatment, prophylactic/preventative and/or palliative measures, wherein the object is to prevent or slow down (lessen) a medical condition, which includes but is not limited to diseases (such as inflammatory diseases), symptoms and disorders. A medical condition also includes a body's response to a disease or disorder, e.g. inflammation. Those in need of such treatment include those already with a medical condition as well as those prone to getting the medical condition or those in whom a medical condition is to be prevented.

The term "subject" as used herein includes patients and non-patients. The term "patient" refers to individuals suffering or are likely to suffer from a medical condition such as inflammation or inflammatory disease, while "non-patients" refer to individuals not suffering and are likely to not suffer from the medical condition. "Non-patients" include healthy individuals, non-diseased individuals and/or an individual free from the medical condition. The term "subject" includes humans and animals. Animals include murine and the like. "Murine" refers to any mammal from the family Muridae, such as mouse, rat, and the like.

The term "micro" as used herein is to be interpreted broadly to include dimensions from about 1 micron to about 1000 microns.

The term "nano" as used herein is to be interpreted broadly to include dimensions less than about 1000 nm.

The term "particle" as used herein broadly refers to a discrete entity or a discrete body. The particle described herein can include an organic, an inorganic or a biological particle. The particle used described herein may also be a macro-particle that is formed by an aggregate of a plurality of sub-particles or a fragment of a small object. The particle of the present disclosure may be spherical, substantially spherical, or non-spherical, such as irregularly shaped particles or ellipsoidally shaped particles. The term "size" when used to refer to the particle broadly refers to the largest dimension of the particle. For example, when the particle is substantially spherical, the term "size" can refer to the diameter of the particle; or when the particle is substantially non-spherical, the term "size" can refer to the largest length of the particle.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a method of characterising mononuclear phagocyte populations, such as dendritic cells, and related kits are disclosed hereinafter.

In various embodiments, there is provided a method of characterising mononuclear phagocyte (MNP) populations. Examples of mononuclear phagocyte populations include dendritic cells (DC), monocytes, macrophages and monocyte-derived cells (MC). Characterising MNP population(s) may comprise identifying a nature and/or a property associated with the MNP population(s). In various embodiments, characterising the MNP populations comprises subsetting the populations based on one or more of their phenotypes, ontogenies, transcriptomic profiles and specialized functions. In various embodiments, characterising the MNP populations comprises determining a type (including a subtype), an expression profile, and/or a property (e.g. an ability/capability and/or propensity to induce/promote inflammation) associated with the MNP populations. In some embodiments, characterising MNP population(s) comprises determining a type or a subtype of the MNP population(s). For example, characterising MNP populations may comprise distinguishing dendritic cells from monocytes. For example, characterising a dendritic cell, optionally a cDC2 dendritic cell, may comprise identifying a subtype of the dendritic cell, optionally the cDC2 dendritic cell. In some embodiments, an MNP population is characterised by its ability and/or propensity to induce inflammation. In some embodiments, an MNP population is characterised by its expression of one or more biomarkers.

In various embodiments, the method comprises determining and/or detecting and/or quantifying an expression and/or a level of at least about one, at least about two, at least about three, at least about four, at least about five, at least about six, at least about seven, at least about eight, at least about nine or at least about ten nucleic acids/genes/proteins/ markers in the MNP population(s). In various embodiments, the method comprises determining an expression of no more than about ten, no more than about nine, no more than about eight, no more than about seven, no more than about six, no more than about five, no more than about four, no more than about three, no more than about two or no more than about one nucleic acid/gene/protein/marker in the MNP population(s).

In various embodiments, the nucleic acid/gene/protein/ marker is selected from the group consisting of AXL, BLTA, BTLA, CD101, CD107a, CD109, CD112, CD115, CD11b, CD124, CD14, CD155, CD163, CD166, CD172a, CD180, CD183, CD195, CD1c, CD1d, CD2, CD200, CD200R, CD206, CD218a, CD22, CD229, CD26, CD271, CD274, CD282, CD303, CD324, CD34, CD354, CD36, CD45RA, CD5, CD56, CD59, CD63, CD64, CD71, CD74, CD81, CD84, CD87, CD87, CD88, CD89, CD95, CLEC12A, CLEC4E, DNAI2, FcεRIα, HLA-DQ, Igk, Integrin β7, LTB (Lymphotoxin-b), MEX3B, NOTCH2, NUMBL, RN7SL846P, S100A13, S100A8, S100A9, S100A9, SIGLEC6 (CD327) and combinations thereof.

In various embodiments, the nucleic acid/gene/protein/ marker comprises a surface nucleic acid/gene/protein/ marker. In various embodiments, the nucleic acid/gene/ protein/marker comprises a membrane nucleic acid/gene/ protein/marker.

In one embodiment, the MNP population comprises dendritic cells. The dendritic cells may be a population that circulate in the blood tissue.

In various embodiments therefore, there is provided a method of characterising dendritic cells. A method of characterising dendritic cells may include a method of identifying/determining a presence or absence of dendritic cells, a method of identifying/determining a subtype of dendritic cells, a method of classifying dendritic cells, a method of identifying/determining a property of dendritic cells, a method of identifying/determining a function of dendritic cells, a method of identifying/determining an expression profile, an expression signature and/or a transcriptomic profile of dendritic cells, a method of identifying/determining a phenotype of dendritic cells, a method of identifying/ determining an ontogeny of dendritic cells and the like. In some embodiments, a method of identifying/determining a property of dendritic cells includes identifying/determining an ability of the dendritic cells to induce inflammation or a pro-inflammatory effect of the dendritic cells. In various embodiments, the identification/determination can be qualitative, quantitative or semi-quantitative.

In various embodiments, the method comprises determining and/or detecting and/or quantifying an expression and/or a level of one or more of CD5, CD14 and CD163 in the dendritic cells.

In various embodiments therefore, there is provided a method of characterising dendritic cells, the method comprising determining an expression of one or more of CD5, CD14 and CD163 in the dendritic cells. In some embodiments, the method comprises determining an expression of two or more of CD5, CD14 and CD163 in the dendritic cells. In some embodiments, the method comprises determining an expression of CD5, CD14 and CD163 in the dendritic cells.

In some embodiments, the method comprises determining an expression of CD5 and one or more of CD14 and CD163. In some embodiments, the method comprises determining an expression of CD14 and one or more of CD5 and CD163.

In some embodiments, the method comprises determining an expression of CD163 and one or more of CD5 and CD14.

In various examples, $CD5^{-/lo}$ dendritic cells are more pro-inflammatory than $CD5^{+/hi}$ dendritic cells. In various examples, $CD14^{+/hi}$ dendritic cells are more pro-inflammatory than $CD14^{-/lo}$ dendritic cells. In various examples, $CD163^{+/hi}$ dendritic cells are more pro-inflammatory than $CD163^{-/lo}$ dendritic cells. In various examples, $CD163^{+/hi}$ $CD14^{+/hi}$ dendritic cells are more pro-inflammatory than $CD163^{-/lo}$, $CD14^{-/lo}$, $CD163^{+/hi}CD14^{-/lo}$ and/or $CD163^{-/lo}$ $CD14^{-/lo}$ dendritic cells. In various examples, $CD5^{-/lo}$ $CD163^{+/hi}CD14^{+/hi}$ dendritic cells more pro-inflammatory than $CD5^{+/hi}$, $CD5^{+/hi}CD163^{-/lo}$ $CD14^{-/lo}$, $CD163^{-/lo}$, $CD14^{-/lo}$, $CD163^{+/hi}CD14^{-/lo}$, $CD163^{-/lo}$ $CD14^{-/lo}$, $CD5^{-/lo}$ $CD163^{-/lo}$, $CD5^{-/lo}$ $CD14^{-/lo}$, $CD5^{-/lo}$ $CD163^{+/hi}CD14^{-/lo}$ and $CD5^{-/lo}$ $CD163^{-/lo}$ $CD14^{-/lo}$ dendritic cells. In various examples, $CD5^{-/lo}$ $CD163^{+/hi}CD14^{-/lo}$ dendritic cells are more pro-inflammatory than $CD5^{-/lo}$ $CD163^{-/lo}$ and $CD5^{-/lo}$ $CD163^{-/lo}$ $CD14^{-/lo}$ dendritic cells. Advantageously, the method may allow for the identification of dendritic cells having different capabilities or tendencies or propensities to induce/promote inflammation.

In various embodiments, an absence of CD5 expression or a substantially low CD5 expression, a presence of CD14 expression or a substantially high CD14 expression and/or a presence of CD163 expression or a substantially high CD163 expression in the dendritic cells is indicative that the dendritic cells are capable of inducing inflammation or that the dendritic cells are pro-inflammatory. In various embodiments therefore, wherein where the dendritic cells are determined to be $CD5^-$, $CD14^+$ and/or $CD163^+$, the method further comprises identifying the dendritic cells as pro-inflammatory dendritic cells. In various embodiments, wherein where the dendritic cells are determined to be $CD163^+CD14^+$, the method comprises identifying the dendritic cells as highly pro-inflammatory dendritic cells. In various embodiments, highly pro-inflammatory dendritic cells are more pro-inflammatory than $CD163^-$ or $CD14^-$ dendritic cells. In various embodiments, wherein where the dendritic cells are determined to be $CD5^-CD163^+CD14^+$, the method comprises identifying the dendritic cells as highly pro-inflammatory dendritic cells.

In various embodiments, the method further comprises determining a level and/or a proportion of dendritic cells expressing $CD5^{-/lo}$ $CD163^{+/hi}CD14^{+/hi}$, $CD5^{+/hi}$, $CD5^{+/hi}$ $CD163^{-/lo}$ $CD14^{-/lo}$, $CD163^{-/lo}$, $CD14^{-/lo}$, $CD163^{-/lo}$ $CD14^{+/hi}$, $CD163^{+/hi}CD14^{-/lo}$, $CD163^{-/lo}$ $CD14^{-/lo}$, $CD5^{-/lo}$ $CD163^{-/lo}$, $CD5^{-/lo}$ $CD14^{-/lo}$, $CD5^{-/lo}CD163^{-/lo}CD14^{+/hi}$, $CD5^{-/lo}CD163^{+/hi}CD14^{-/lo}$ and/or $CD5^{-/lo}CD163^{-/lo}$ $CD14^{-/lo}$. In some embodiments, the method comprises determining a level and/or a proportion of $CD5^+$, $CD5^-$ $CD163^-$, $CD5^-CD163^+CD14^-$ and/or $CD5^-CD163^+CD14^+$ dendritic cells. In one embodiment, the method comprises determining a proportion of $CD163^+CD14^+$ dendritic cells. In one embodiment, the method comprises determining a proportion of $CD5^-CD163^+CD14^+$ dendritic cells. As used herein, the term "proportion" refers to the ratio of the specified dendritic cells to the total number of dendritic cells in a population or subpopulation. In some embodiments, a proportion of $CD5^-CD163^+CD14^+$ dendritic cells refers to the ratio of the $CD5^-CD163^+CD14^+$ dendritic cells to the total number of conventional dendritic cell 2 (cDC2). In some embodiments, a proportion of $CD5^-CD163^+CD14^+$ dendritic cells refers to the ratio of the $CD5^-CD163^+CD14^+$ dendritic cells to the total number of a subpopulation of dendritic cells having one or more of the following properties: (i) is a conventional dendritic cell 2 (cDC2); (ii) is dependent on IRF4 for differentiation; (iii) is dependent on KLF4 for differentiation; (iv) is dependent on FLT3 ligand (FLT3L) for differentiation; and (v) is capable of activating and/or polarizing T cells e.g. naïve T cells or allogeneic naïve CD4$^+$ T cells.

In some examples, the dendritic cells, e.g. dendritic cells expressing CD163, express one or more nucleic acids/genes/proteins/markers selected from the group consisting of CD5, CD14, CD11b, CD36, CD64, CD87, CD107a, CD206, CD274, CD354, FcεRIα, HLA-DQ, CD2, CD59, CD81, CD166, CD229, CD271, and Integrin β7. In some examples, the dendritic cells, e.g. dendritic cells expressing CD163, express one or more nucleic acids/genes/proteins/markers selected from the group consisting of FcεRIα, HLA-DQ, CD2, CD59, CD81, CD166, CD229, CD271, and Integrin β7. In some examples, the dendritic cells, e.g. dendritic cells expressing CD163, express one or more nucleic acids/genes/proteins/markers selected from the group consisting of CD56, CD5, CD303, CD271, CD22, CD124, CD324, integrin β7, BTLA, CD26, CD183, CD71, CD59, CD218a, CD200, CD195, CD1c, CD282, CD107a, CD11b, CD274, CD14, CD166, CD81, CLEC12A, CD63, CD84, CD115, CD95, CD163, CD112, CD155, CD206, CD172a, CD354, CD36, CD64, and CD87. In some examples, the dendritic cells, e.g. dendritic cells expressing CD163, may highly express DNAI2, MEX3B, RN7SL846P, NUMBL, CD109, S100A8, S100A9, CD14, CLEC4E, and/or S100A13.

In some examples, the dendritic cells, e.g. CD5$^+$CD163$^+$CD14$^+$ dendritic cells, has the following phenotype (one or more nucleic acids/genes/proteins/markers selected) from the group consisting of CD56$^-$, CD5$^-$, CD303$^-$, CD271$^-$, CD22$^-$, CD124$^-$, CD324$^-$, integrin β7$^-$, BTLA$^-$, CD26$^-$, CD183$^-$, CD71$^-$, CD59$^-$, CD218a$^-$, CD200$^-$, CD195$^-$, CD1c$^-$, CD282$^{int}$, CD107a$^{int}$ CD11b$^{int}$, CD274$^+$, CD14$^+$, CD166$^-$, CD81$^-$, CLEC12A$^+$, CD63$^+$, CD84$^+$, CD115$^+$, CD95$^+$, CD163$^+$, CD34$^-$, CD112$^+$, CD155$^+$, CD206$^+$, CD172a$^+$, CD354$^+$, CD36$^+$, Igk$^+$, CD64$^+$, and CD87$^+$. In some examples, the dendritic cells, e.g. CD163$^+$CD14$^+$ dendritic cells, expresses one or more nucleic acids/genes/proteins/markers selected from the group consisting of CD56$^-$, CD5$^-$, CD303$^-$, CD271$^-$, CD22$^-$, CD124$^-$, CD324$^-$, integrin β7$^-$, BTLA$^-$, CD26$^-$, CD183$^-$, CD71$^-$, CD59$^-$, CD218a$^-$, CD200$^-$, CD195$^-$, CD1c$^-$, CD282$^{int}$, CD107$^{int}$, CD11b$^{int}$, CD274$^+$, CD14$^+$, CD166$^-$, CD81$^-$, CLEC12A$^+$, CD63$^+$, CD84$^+$, CD115$^+$, CD95$^+$, CD163$^+$, CD34$^-$, CD112$^+$, CD155$^+$, CD206$^+$, CD172a$^+$, CD354$^+$, CD36$^+$, Igk$^+$, CD64$^+$, and CD87$^+$.

In some examples, the dendritic cells, e.g CD163$^+$CD14$^-$ dendritic cells, has the following phenotype (one or more nucleic acids/genes/proteins/markers selected) from the group consisting of CD56$^-$, CD5$^-$, CD303$^-$, CD271$^-$, CD22$^-$, CD124$^-$, CD324$^-$, integrin β7$^-$, BTLA$^-$, CD26$^-$, CD183$^-$, CD71$^{int}$, CD59$^+$, CD218a$^-$, CD200$^-$, CD195$^-$, CD1c$^-$, CD282$^-$, CD107a$^-$, CD11b$^-$, CD274$^-$, CD14$^-$, CD166$^+$, CD81$^+$, CLEC12A$^+$, CD63$^+$, CD84$^+$, CD115$^+$, CD95$^+$, CD163$^+$, CD112$^+$, CD155$^+$, CD206$^+$, CD172a$^+$, CD354$^+$, CD36$^{int}$, CD64$^-$, and CD87$^-$. In some examples, the dendritic cells, e.g CD163$^+$CD14$^-$ dendritic cells, express one or more nucleic acids/genes/proteins/markers selected from the group consisting of CD56$^-$, CD5$^-$, CD303$^-$, CD271$^-$, CD22$^-$, CD124$^-$, CD324$^-$, integrin β7$^-$, BTLA$^-$, CD26$^-$, CD183$^-$, CD71$^{int}$, CD59$^+$, CD218a$^-$, CD200$^-$, CD195$^-$, CD1c$^-$, CD282$^-$, CD107a$^-$, CD11b$^-$, CD274$^-$, CD14$^-$, CD166$^+$, CD81$^+$, CLEC12A$^+$, CD63$^+$, CD84$^+$, CD115$^+$, CD95$^+$, CD163$^+$, CD112$^+$, CD155$^+$, CD206$^+$, CD172a$^+$, CD354$^+$, CD36$^{int}$, CD64$^-$, and CD87$^-$.

In some examples, the dendritic cells, e.g the CD5$^-$CD163$^+$CD14$^+$ dendritic cells, express one or more nucleic acids/genes/proteins/markers selected from the group consisting of nucleic acids/genes/proteins/markers involved in dendritic cell maturation, production of nitric and reactive oxygen species (NOS and ROS) in macrophages, phagosome formation, death receptor signalling, inflammasome pathway, autophagy pathways, as well as systemic lupus erythematosus (SLE) signalling. In some examples, the dendritic cell as described herein expresses the nucleic acids/genes/proteins as illustrated in FIG. 10 (such as FIG. 10D, 10G).

In various embodiments therefore, the method further comprises determining an expression of one or more of the above listed nucleic acids/genes/proteins/markers in the dendritic cells. In some embodiments, the method comprises determining an expression of one or more of AXL, BLTA, CD1c, CD1d, CD5, CD11b, CD64, CD74, CD88, CD89, CD101, CD109, CD180, CD200R, CD45RA, FcεRIα FcεRIα, HLA-DQ, Integrin β7, LTB (Lymphotoxin-f3), NOTCH2, S100A8, S100A9 and SIGLEC6 (CD327) in the dendritic cells. In some embodiments, the method further comprises determining an expression of one or more of CD11b, CD36, CD64, CD87, CD107a, CD206, CD274, CD354, FcεRIα, HLA-DQ, CD2, CD59, CD81, CD166, CD229, CD271 and Integrin β7 in the dendritic cells.

In some examples, the CD5$^-$CD163$^+$CD14$^+$ cell is one of the largest cells, is rough and has more granular membrane as compared to CD5$^+$, CD163$^-$ and/or CD14$^-$ dendritic cells, and other MNP populations such as monocytes (as can be observed in the forward scatter (FSC-A) and side scatter (SSC-A) view in a flow cytometry analysis). In various embodiments therefore, the method further comprises determining an appearance or morphology of the dendritic cells including but not limited to the size, roughness and granularity.

In various embodiments, the dendritic cells comprise cDC2 cells. In various embodiments, the dendritic cells have one or more of the following properties: (i) is a conventional dendritic cell 2 (cDC2); (ii) is dependent on IRF4 for differentiation; (iii) is dependent on KLF4 for differentiation; (iv) is dependent on FLT3 ligand (FLT3L) for differentiation; and (v) is capable of activating and/or polarizing T cells e.g. naïve T cells or allogeneic naïve CD4$^+$ T cells.

In various embodiments, the determining and/or detecting and/or quantifying is via a marker cell sorting such as magnetic beads cell sorting, fluorescence-activated cell sorting, flow cytometry, ELISA, Western Blotting, immunohistochemistry, and the like. In some examples, the determining and/or detecting and/or quantifying is via flow cytometry. In various embodiments, the determining and/or detecting and/or quantifying is performed to detect protein expression and/or intracellular gene transcription expression. In various embodiments, the determining and/or detecting and/or quantifying is via methods for detecting amplification products, such as, but is not limited to, PCR, RT-PCR, q-PCR, and the like. It will be appreciated that other suitable methods of detecting a nucleic acid/gene/protein/marker that are known in the art may also be used.

In various embodiments, there is provided a method of distinguishing pro-inflammatory dendritic cells from the less or non-pro-inflammatory dendritic cells, the method comprising determining an expression of one or more CD5, CD14 and/or CD163 in the dendritic cells. In various embodiments, an absence of CD5 expression or a substantially low CD5 expression, a presence of CD14 expression or a substantially high CD14 expression and/or a presence of CD163 expression or a substantially high CD163 expression in the dendritic cells is indicative that the dendritic cells are pro-inflammatory. In various embodiments, there is provided a method of distinguishing a pro-inflammatory subpopulation of dendritic cells (e.g. CD163$^+$ DC3) from the less or non-pro-inflammatory subpopulation of dendritic cells (e.g. CD5$^+$ DC2), the method comprising determining an expression of one or more of CD14, CD11b, CD36, CD64, CD87, CD107a, CD206, CD274 and CD354 in the dendritic cells, wherein an expression and/or substantially high expression of one or more of the markers is indicative that the cells are pro-inflammatory dendritic cells, optionally CD163$^+$ dendritic cells, optionally CD163$^+$ DC3 cells.

In various embodiments, there is provided a method of distinguishing dendritic cells from other MNP populations such as monocytes, macrophages and monocyte-derived cells. In one embodiment, the method comprises determining an expression of one or more CD5, CD14 and/or CD163 in the cells. In one embodiment, the method comprises distinguishing dendritic cells from monocytes, the method comprising determining an expression of one or more of HLA-DQ, FcεRIα, CD88 and CD89 in the cells. In various embodiments, an absence of CD88 expression or a substantially low CD88 expression, an absence of CD89 expression or a substantially low CD89 expression, a presence of HLA-DQ expression or a substantially high HLA-DQ expression and/or a presence of FcεRIα expression or a substantially high FcεRIα expression is indicative that the cells are dendritic cells. In various embodiments, an absence of HLA-DQ expression or a substantially low HLA-DQ expression, an absence of FcεRIα expression or a substantially low FcεRIα expression, a presence of CD88 expression or a substantially high CD88 expression and/or a presence of CD89 expression or a substantially high CD89 expression is indicative that the cells are monocytes. In various embodiments, the method comprises determining an expression of one or more of FcεRIα, HLA-DQ, CD2, CD59, CD81, CD166, CD229, CD271 and Integrin β7 in the cells, wherein an expression and/or substantially high expression of one or more of the markers is indicative that the cells are dendritic cells, optionally inflammatory dendritic cells, optionally DC3 cells. In various embodiments, the method comprises determining an expression of one or more markers selected from the group consisting of FcεRIα, HLA-DQ, CD2, CD59, CD81, CD166, CD229, CD271 and Integrin β7, and one or more markers selected from the group consisting of CD14, CD11b, CD36, CD64, CD87, CD107a, CD206, CD274 and CD354.

In various embodiments, there is provided a method of separating/isolating/extracting pro-inflammatory dendritic cells e.g. from less or non-pro-inflammatory dendritic cells, the method comprising contacting the dendritic cells with an agent, e.g. a capture agent, capable of recognising and/or binding to one or more of CD5, CD14 and/or CD163. In some embodiments, the method further comprises contacting the dendritic cells with an agent, e.g. a capture agent, capable of recognising and/or binding to one or more nucleic acid/gene/protein/marker selected from the group consisting of AXL, BLTA, BTLA, CD101, CD107a, CD109, CD112, CD115, CD11b, CD124, CD14, CD155, CD163, CD166, CD172a, CD180, CD183, CD195, CD1c, CD1d, CD2, CD200, CD200R, CD206, CD218a, CD22, CD229, CD26, CD271, CD274, CD282, CD303, CD324, CD34, CD354, CD36, CD45RA, CD5, CD56, CD59, CD63, CD64, CD71, CD74, CD81, CD84, CD87, CD87, CD88, CD89, CD95, CLEC12A, CLEC4E, DNAI2, FcεRIα, HLA-DQ, Igk, Integrin β7, LTB (Lymphotoxin-b), MEX3B, NOTCH2, NUMBL, RN7SL846P, S100A13, S100A8, S100A9, S100A9, SIGLEC6 (CD327) and combinations thereof.

In various embodiments, the method of characterising dendritic cells may also be useful for characterising a body response such as inflammation and/or a disease such as an inflammatory disease in a subject since certain dendritic cells may be associated with the body response and/or the disease. Thus, when characterising a body response such as inflammation and/or or a disease such as an inflammatory disease in a subject, the subject's sample may be collected, and the dendritic cells contained in the sample may be characterised to identify (e.g. qualitatively, quantitatively or semi-quantitatively) any dendritic cells that may be pro-inflammatory or associated with the body response and/or the disease. In various embodiments, characterising the dendritic cells in a subject's sample, e.g. identifying/measuring a presence/amount/level/proportion of pro-inflammatory dendritic cells in the sample, may give an indication of the presence or absence of a body response such as inflammation and/or or a disease such as an inflammatory disease in the subject. In various embodiments, characterising the dendritic cells in a subject's sample, e.g. identifying/measuring a presence/amount/level/proportion in a subject's sample may give an indication of a level/severity/extent/burden/aggressiveness/disease stage/disease state a body response such as inflammation and/or or a disease such as an inflammatory disease in the subject.

In various embodiments, characterising a body response in the form of an inflammation and/or a disease such as an inflammatory disease in a subject may include determining a presence or an absence of the body response and/or the disease in the subject, determining the subject's susceptibility to the body response and/or the disease, determining a level/severity/extent/burden/aggressiveness/disease stage/disease state of the body response and/or the disease in the subject, diagnosing the body response and/or the disease in the subject, determining a prognosis of the body response and/or the disease in the subject, and determining an improvement and/or a worsening of the body response and/or the disease in the subject.

Thus, in various embodiments, there is provided a method of characterising inflammation and/or inflammatory disease in a subject, the method comprising determining an expression of one or more of CD5, CD14 and CD163. In various embodiments, there is provided a method of characterising inflammation and/or inflammatory disease in a subject, the method comprising determining a level or a proportion of dendritic cells expressing CD5$^{-/lo}$CD163$^{+/hi}$CD14$^{+/hi}$, CD5$^{+/hi}$, CD5$^{+/hi}$CD163$^{-/lo}$ CD14$^{-/lo}$, CD163$^{-/lo}$, CD14$^{-/lo}$, CD163$^{-/lo}$CD14$^{+/hi}$ CD163$^{+/hi}$CD14$^{-/lo}$, CD163$^{-/lo}$ CD14$^{-/lo}$, CD5$^{-/lo}$CD163$^{-/lo}$, CD5$^{-/lo}$ CD14$^{-/lo}$, CD5$^{-/lo}$ CD163$^{-/lo}$ CD14$^{+/hi}$ CD5$^{-/lo}$CD163$^{+/hi}$CD14$^{-/lo}$ and/or CD5$^{-/lo}$ CD163$^{-/lo}$ CD14$^{-/lo}$. In some embodiments, the method comprises determining a level or a proportion of CD5$^-$, CD14$^+$, CD163$^+$, and/or CD14$^+$CD163$^+$ dendritic cells. In some embodiments, the method comprises determining a level or a proportion of CD5$^-$, CD14$^+$, CD163$^+$, CD14$^+$CD163$^+$, CD5$^-$CD163$^-$, CD5$^-$CD163$^+$CD14$^-$ and/or CD5$^-$CD163$^+$CD14$^+$ dendritic cells. In one embodiment, the method comprises determining a proportion of CD163$^+$ CD14$^+$ dendritic cells. In one embodiment, the method comprises determining a proportion of CD5$^-$CD163$^+$CD14$^+$ dendritic cells. In some examples, the level or proportion of the dendritic cells correlates, e.g. positively correlates, with the level of inflammation and/or the severity of inflammatory disease in the subject.

In various embodiments, there is provided a method of characterising inflammation and/or inflammatory disease in a subject, the method comprising: determining a proportion of $CD5^-$, $CD14^+$, $CD163^+$, $CD14^+CD163^+$ and/or $CD5^-CD14^+CD163^+$ dendritic cells in the subject's sample, wherein the proportion positively correlates with the level of inflammation and/or the severity of inflammatory disease in the subject.

In various embodiments, wherein where the proportion of $CD5^-$, $CD14^+$, $CD163^+$, $CD14^+CD163^+$ and/or $CD5^-CD14^+CD163^+$ dendritic cells in the subject's sample is greater than a threshold proportion derived from a control sample, the method comprises identifying the presence of inflammation and/or inflammatory disease in the subject. In various embodiments, wherein where the proportion of $CD5^-$, $CD14^+$, $CD163^+$, $CD14^+CD163^+$ and/or $CD5^-CD14^+CD163^+$ dendritic cells in the sample is greater than the proportion in an earlier sample from the same subject, the method comprises identifying a worsening of inflammation and/or inflammatory disease in the subject. In various embodiments, wherein where the proportion of $CD5^-$, $CD14^+$, $CD163^+$, and/or $CD14^+CD163^+$ dendritic cells in the sample is lower than the proportion in the earlier sample, the method comprises identifying an improvement of inflammation and/or inflammatory disease in the subject.

In some embodiments, there is provided a method for diagnosing an inflammatory disease in a subject in need thereof, the method comprising: determining and/or detecting and/or quantifying a level or a proportion of a dendritic cell expressing CD5, CD14 and/or CD163 in a sample obtained from the subject; wherein an increased level or proportion of the dendritic cell expressing CD163 and/or CD14, and/or a decreased/reduced level or proportion of the dendritic cell expressing CD5 as compared to a control subject is indicative of the subject having the inflammatory disease. In some embodiments, an increased level or an increased proportion of $CD5^-$, $CD14^+$, $CD163^+$, $CD14^+CD163^+$ and/or $CD5^-CD14^+CD163^+$ dendritic cells as compared to a control subject is indicative of the subject having the inflammatory disease. As used herein, the terms "diagnosing", "diagnosed", and "diagnose" refer to determining the presence and/or absence of a disease or condition based upon an evaluation of physical signs, symptoms, history, laboratory test results, and/or procedures. It would be understood that the final "diagnosing" would ultimately be performed by a qualified medical profession and that the method as disclosed herein merely provides an assistance to the qualified medical profession in providing the diagnosis. Thus, the methods as disclosed herein cannot be construed to be replacing the function of a qualified medical profession. As used herein, the term "an increased level" refers to the number of cells and/or the level of a protein expression and/or gene transcription and/or other related biomarkers in a sample (biological sample) obtained from the subject which is greater than the number of cells and/or level of protein expression and/or gene transcription and/or other related biomarkers in a control. As used herein, the term "a decreased level" or "a reduced level" refers to the number of cells and/or the level of a protein expression and/or gene transcription and/or other related biomarkers in a sample (biological sample) obtained from the subject which is greater than the number of cells and/or level of protein expression and/or gene transcription and/or other related biomarkers in a control. As used herein, the term "detecting" or "detection" means any of a variety of methods known in the art for determining the presence of a nucleic acid or a protein or a cell. In some examples, to detect a cell of interest, an antibody that is either directly or indirectly labelled can be used to bind the cell of interest and/or a protein expressed on the cell of interest. In some examples, to detect a nucleic acid sequence of interest, a portion of the nucleic acid of interest can be detected by hybridizing a labelled probe to the portion of the nucleic acid. In some examples, to detect a protein of interest, an antibody that is either directly or indirectly labelled can be used to bind to the protein of interest. Methods for labelling nucleic acid and/or antibodies (or other proteins capable of binding to a target of interest) are well known in the art. Labels can be either detectable or functional labels, and include radio-isotope label (such as $^{131}I$, $^{125}I$, $^{35}S$, and $^{99}Tc$), enzymatic labels (such as horseradish peroxidase, alkaline phosphatase, and the like), chemiluminescent labels, and other chemical moieties (such as biotin). It is also envisaged that the term "detecting" as used herein includes either qualitative or quantitative detection. Advantageously, embodiments of the method may be implemented as a diagnostic tool.

In various embodiments, the control subject is a person and/or a population of general public who is/are not suffering from the disease/disorder/condition. In various embodiments, the control sample is a sample obtained from a person and/or a population of general public who is/are not suffering from the disease/disorder/condition. A control sample may also be a healthy or undiseased sample, e.g. a healthy or undiseased paired sample, obtained from the subject.

In various embodiments, the inflammatory disease is selected from the group consisting of systemic inflammatory disease, metabolic disorder, autoimmune disease and cancer.

In various embodiments, the inflammatory disease is selected from the group consisting of inflammatory skin disease, inflammatory bowel diseases, asthma, acute respiratory distress syndrome, chronic obstructive pulmonary disease, acute lung injury, bronchopulmonary dysplasia, cystic fibrosis, bronchitis, bronchiolitis, arthritis, osteoarthritis, ankylosing spondylitis and rheumatism.

In various embodiments, the metabolic disorder is selected from the group consisting of obesity, diabetes (for example diabetes type II, gestational diabetes, MODY) satiety and endocrine deficiencies related to aging.

As used herein, the term "metabolic disorder" refers to any pathological condition resulting from an alteration in a subject's metabolism. For example, a metabolic disorder may result from an alteration in glucose homeostasis resulting in hyperglycaemia.

In various embodiments, the autoimmune disease comprises a systemic autoimmune disease.

In various embodiments, the autoimmune disease is selected from the group consisting of Systemic Lupus Erythematosus (SLE), diabetes, rheumatoid arthritis (RA), multiple sclerosis (MS), myasthenia gravis (MG), scleroderma, Crohn's disease, ulcerative colitis, Hashimoto's disease, Graves' disease, Sjögren's syndrome, polyendocrine failure, vitiligo, peripheral neuropathy, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barré syndrome, hemochromatosis, Henoch-Schönlein purpura, idiopathic IgA nephropathy, insulin-dependent diabetes mellitus (IDDM), juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, atopic dermatitis, rapidly-progressive glomerulonephritis (RPGN), Reiter's syndrome, stiff-man syndrome and thyroiditis.

In some embodiments, the autoimmune disease is selected from the group consisting of psoriasis, atopic dermatitis, Systemic Lupus Erythematosus (SLE) and systemic sclerosis (SSc).

As used herein, "autoimmune disease" refers to those disease states and conditions wherein the immune response of the subject is directed against the subject's own constituents, resulting in an undesirable and often debilitating condition. "Autoimmune disease" is intended to further include autoimmune conditions, syndromes, and the like.

In various embodiments, the cancer comprises a non-solid tumour, optionally wherein the non-solid tumor is selected from the group consisting of leukaemia, multiple myelomas and lymphomas.

In various embodiments, the cancer comprises a solid tumor, optionally wherein the solid tumour comprises sarcoma and/or carcinoma, further optionally wherein the sarcoma and/or carcinoma is selected from the group consisting of hepatocellular carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In some embodiments, the cancer is selected from the group consisting of hepatocellular carcinoma, follicular lymphoma, small lymphocytic lymphoma, pancreatic tumour and breast cancer.

In various embodiments, the method further includes a step of treating the subject with a modulatory agent and/or an inhibitory agent and/or a depleting agent to reduce the level or proportion of the dendritic cells expressing CD163 and/or CD14, and/or the level or proportion of the CD5$^-$, CD14$^+$, CD163$^+$, CD14$^+$CD163$^+$ and/or CD5$^-$CD14$^+$ CD163$^+$ dendritic cells. As used herein, the term "modulatory agent" refers to any compound, molecule or substance capable of "modulating" dendritic cell gene expression at the transcriptional, translational, or post-translational levels or modulating the biological activity of a dendritic cell population of interest or removing (or reducing the total number) the dendritic cell population of interest. The term "modulate" and its cognates refer to the capability of a compound/molecule/substance acting as either an agonist or an antagonist of a certain reaction or activity. The term "modulate", therefore, encompasses the terms "activate" and "inhibit." The term "activate" or "increase" for example, refers to an increase in the expression of the dendritic cell (such as DC3) gene or activity of a dendritic cell (such as DC3) secretions (such as chemokines, cytokines, and the like) or increase in the number of dendritic cell in the presence of a modulatory compound, relative to the activity of the gene or the polypeptide in the absence of the same compound. The increase in the expression level or the activity or total number of dendritic cells may be at least about 10%, 20%, 30%, 40%, 50%, 60%, 70%, 80%, 90%, or higher. Analogously, the term "inhibit" or "reduce" refers to a decrease in the expression of the dendritic cell (such as DC3) gene or activity of the dendritic cell (such as DC3) polypeptide or decreased in total number of dendritic cells in the presence of a modulatory compound, relative to the activity of the gene or the polypeptide or total number of cells in the absence of the same agent/compound/molecule. The decrease in the expression level or the activity or total cell number may be at least about 10%, 20%, 30%, 40%, 50%, 60%, 70%, 80%, 90%, or higher. The expression level of the dendritic cell (such as DC3) gene or activity or total number of the dendritic cell (such as DC3) can be measured as described herein or by techniques generally known in the art.

In various embodiments, wherein where the presence and/or the worsening of inflammation and/or an inflammatory disease in the subject is identified, the method further comprises allocating the subject to an inflammation and/or an inflammatory disease treatment regimen.

In various embodiments, the inflammation and/or inflammatory disease treatment regimen comprises administering to the subject a modulatory agent and/or an inhibitory agent and/or a depleting agent to reduce the level or proportion of the dendritic cells expressing CD163 and/or CD14, and/or the level or proportion of the CD5$^-$, CD14$^+$, CD163$^+$, CD14$^+$CD163$^+$, CD5$^-$CD163$^-$, CD5$^-$CD163$^+$CD14$^-$ and/or CD5$^-$CD163$^+$CD14$^+$ dendritic cells. In various embodiments, the inflammation and/or inflammatory disease treatment regimen comprises administering to the subject one or more agent selected from the group consisting of: an anti-inflammatory agent, an immunosuppressant agent, an anti-cancer agent, an inhibitor of FLT3L, an agent capable of binding to CD5$^-$, CD14$^+$, CD163$^+$, CD14$^+$CD163$^+$, CD5$^-$ CD163$^-$, CD5$^-$CD163$^+$CD14$^-$ and/or CD5$^-$CD163$^+$CD14$^+$ dendritic cells, an agent capable of neutralising CD5$^-$, CD14$^+$, CD163$^+$, CD14$^+$CD163$^+$, CD5$^-$CD163$^-$, CD5$^-$ CD163$^+$CD14$^-$ and/or CD5$^-$CD163$^+$CD14$^+$ dendritic cells, an antibody against CD5$^-$, CD14$^+$, CD163$^+$, CD14$^+$ CD163$^+$, CD5$^-$CD163$^-$, CD5$^-$CD163$^+$CD14$^-$ and/or CD5$^-$ CD163$^+$CD14$^+$ dendritic cells, an agent capable of reducing the proportion of CD5$^-$, CD14$^+$, CD163$^+$, CD14$^+$CD163$^+$, CD5$^-$CD163$^-$, CD5$^-$CD163$^+$CD14$^-$ and/or CD5$^-$CD163$^+$ CD14$^+$ dendritic cells, an agent capable of reducing an activity of CD5$^-$, CD14$^+$, CD163$^+$, CD14$^+$CD163$^+$, CD5$^-$ CD163$^-$, CD5$^-$CD163$^+$CD14$^-$ and/or CD5$^-$CD163$^+$CD14$^+$ dendritic cells, an agent capable of reducing a number of a precursor of CD5$^-$, CD14$^+$, CD163$^+$, CD14$^+$CD163$^+$, CD5$^-$ CD163$^-$, CD5$^-$CD163$^+$CD14$^-$ and/or CD5$^-$CD163$^+$CD14$^+$ dendritic cells and an agent capable of inhibiting a differentiation of the precursor of CD5$^-$, CD14$^+$, CD163$^+$, CD14$^+$ CD163$^+$, CD5$^-$CD163$^-$, CD5$^-$CD163$^+$CD14$^-$ and/or CD5$^-$ CD163$^+$CD14$^+$ dendritic cells.

In one embodiment, the treatment regimen comprises administering to the subject an inhibitor of FLT3L.

In one embodiment, the treatment regimen comprises contacting the sample to an agent capable of binding and/or neutralising the dendritic cells expressing CD163 and/or CD14 and/or binding and/or neutralising CD5$^-$, CD14+, CD163$^+$, CD14$^+$CD163$^+$, CD5$^-$CD163$^-$, CD5$^-$CD163$^+$ CD14$^-$ and/or CD5$^-$CD163$^+$CD14$^+$ dendritic cells. In some examples, the agent capable of binding and/or neutralising the dendritic cells is an antibody. In some embodiments, therefore, the treatment regimen comprises administering to the subject an antibody capable of specifically binding to the dendritic cells expressing CD163 and/or CD14, and/or CD5⁻, CD14⁺, CD163⁺, CD14⁺CD163⁺, CD5⁻CD163⁻, CD5⁻CD163⁺CD14⁻ and/or CD5⁻CD163⁺CD14⁺ dendritic cells. As used herein, the term "antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific (such as bi-specific), humanized, human, single-chain, chimeric, synthetic, recombinant, hybrid, mutated, grafted, and in vitro generated antibodies. The term "antibody" may include antibody fragments such as Fab, F(ab')₂, Fv, scFv, Fd, dAb, and other antibody fragments that retain antigen-binding function. An antibody is not necessarily from any particular source, nor is it produced by any particular method.

In one embodiment, the treatment regimen comprises administering an agent capable of removing and/or depleting a precursor of dendritic cells expressing CD163 and/or CD14, and/or a precursor of CD5⁻, CD14⁺, CD163⁺, CD14⁺ CD163⁺, CD5⁻CD163⁻, CD5⁻CD163⁺CD14⁻ and/or CD5⁻ CD163⁺CD14⁺ dendritic cells. In various embodiments, the precursor comprises a dendritic precursor cell expressing CD5. In various embodiments, the precursor has one or more of the following expression or phenotype: CD56⁺, CD303⁺, CD271⁺, CD22⁺, CD124⁺, CD324⁺, integrin β7⁺, BTLA⁺, CD26⁺, CD183⁺, CD71⁻, CD59⁻, CD218a⁺, CD200⁺, CD195⁺, CD1c⁺, CD282⁻, CD107a⁻, CD11b⁻, CD274⁺, CD14⁺, CD166⁺, CD81⁻, CLEC12A⁻, CD63⁻, CD84⁻, CD115⁻, CD95⁻, CD163⁻, CD34ⁱⁿᵗ, CD112⁻, CD155⁻, CD206⁻, CD172a⁻, CD354⁻, CD36⁻, Igk⁻, CD64⁻, and CD87⁻. In various embodiments, the precursor further expresses one or more nucleic acids/genes/proteins/ markers selected from the group consisting of nucleic acids/ genes/proteins/markers related to integrin signalling, FcγR-mediated phagocytosis, VEGF signalling, EIF2 signalling, leukocyte extravasation signalling, IL-3 signalling, Fc Epsilon RI signalling, mTOR signalling, IL-6 signalling, antigen presentation pathway, chemokine signalling, GM-CSF signalling, Tec Kinase signalling, FLT3 signalling in HPCs, NF-κB activation by viruses, IL-12 signalling and production in macrophages, and the like. In some examples, the genes expressed by the precursor of the dendritic cell expressing CD163 is listed in FIG. 10D and FIG. 10G. In various embodiments, the precursor expresses one or more nucleic acids/genes/proteins/markers selected from the group consisting of CD74, AXL, CD207, SIGLEC6, CD5, and BTLA.

In various embodiments, dendritic cells expressing CD5 (e.g. CD5⁺ DC2) are precursors to dendritic cells that do not express or minimally express CD5 (e.g. CD5⁻ DC3). Thus, blockage of CD5⁺ precursors to CD5⁻ dendritic cells differentiation and/or activation can be a therapeutic strategy for inflammatory diseases.

In various embodiments, the method further comprises determining a prognosis of the inflammation and/or inflammatory disease in the subject by measuring the level and/or the proportion of the dendritic cells expressing CD163 and/or CD14, and/or the level and/or the proportion of CD5⁻, CD14⁺, CD163+, CD14⁺CD163⁺, CD5⁻CD163⁻, CD5⁻CD163⁺CD14⁻ and/or CD5⁻CD163⁺CD14⁺ dendritic cells in a sample obtained from the subject after the subject has received the treatment regimen. As used herein, the term "prognosis" refers to the prediction of the likelihood of disease-attributable progression, including increased in severity or death, metastatic spread (of cancer), drug resistance (of cancer), or reversal, including reduction in severity or complete remission (from cancer).

Advantageously, embodiments of the method may be used for the identification, quantification and subsequent targeting of a body response such as inflammation and/or a disease such as an inflammatory disease.

In various embodiments, the method of characterising dendritic cells may also be relevant to a method of treating a body response such as inflammation and/or a disease such as an inflammatory disease in a subject, a method of assessing the extent/severity of a body response such as inflammation and/or a disease such as an inflammatory disease in a subject, a method of assessing the prognosis of a body response such as inflammation and/or a disease such as an inflammatory disease in a subject and the like.

In various embodiments, there is provided a method of treating inflammation and/or inflammatory disease in a subject, the method comprising administering to the subject an agent and/or a treatment regimen as described herein. In some embodiments, the method comprises administering to the subject an agent capable of modulating the level and/or the proportion of the dendritic cells expressing CD163 and/or CD14, and/or the level and/or the proportion of CD5⁻, CD14⁺, CD163⁺, CD14⁺CD163⁺, CD5⁻CD163⁻, CD5⁻CD163⁺CD14⁻ and/or CD5⁻CD163⁺CD14⁺ dendritic cells. In various embodiments, the method further comprises determining a level and/or a proportion of the dendritic cells expressing CD163 and/or CD14, and/or a level and/or a proportion of CD5⁻, CD14⁺, CD163⁺, CD14⁺CD163⁺, CD5⁻CD163⁻, CD5⁻CD163⁺CD14⁻ and/or CD5⁻CD163⁺ CD14⁺ dendritic cells in a sample obtained from the subject. In various embodiments, the subject has or is determined to have an increased level and/or proportion of the dendritic cells expressing CD163 and/or CD14, and/or an increased level and/or proportion of CD5⁻, CD14⁺, CD163⁺, CD14⁺ CD163⁺, CD5⁻CD163⁻, CD5⁻CD163⁺CD14⁻ and/or CD5⁻ CD163⁺CD14⁺ dendritic cells in his/her sample as compared to a control sample or a sample obtained from a control subject.

In various embodiments, there is provided a method of assessing the severity of an inflammatory disease in a subject, the method comprising determining a level and/or a proportion of the dendritic cells expressing CD163 and/or CD14, and/or a level and/or a proportion of CD5⁻, CD14⁺, CD163⁺, CD14⁺CD163⁺, CD5⁻CD163⁻, CD5⁻CD163⁺ CD14⁻ and/or CD5⁻CD163⁺CD14⁺ dendritic cells in a sample obtained from the subject. In various embodiments, an increased level and/or a proportion of the dendritic cells expressing CD163 and/or CD14, and/or an increased level and/or a proportion of CD5⁻, CD14⁺, CD163⁺, CD14⁺ CD163⁺, CD5⁻CD163⁻, CD5⁻CD163⁺CD14⁻ and/or CD5⁻ CD163⁺CD14⁺ dendritic cells in the sample is correlated (e.g. positively correlated)/indicative of the severity of the inflammatory disease in the subject. In one embodiment, the method comprises a method of assessing the severity of a Systemic Lupus Erythematosus (SLE).

In various embodiments therefore, there is provided a method of assessing the severity of Systemic Lupus Erythematosus (SLE) in a subject, the method comprising determining a level and/or a proportion of the dendritic cells expressing CD163 and/or CD14, and/or a level and/or a proportion of CD5⁻, CD14⁺, CD163⁺, CD14⁺CD163⁺, CD5⁻CD163⁻, CD5⁻CD163⁺CD14⁻ and/or CD5⁻CD163⁺ CD14⁺ dendritic cells in a sample obtained from the subject. In various embodiments, an increased level and/or a proportion of the dendritic cells expressing CD163 and/or CD14, and/or an increased level and/or a proportion of CD5⁻, CD14⁺, CD163⁺, CD14⁺CD163⁺, CD5⁻CD163⁻, CD5⁻CD163⁺CD14⁻ and/or CD5⁻CD163⁺CD14⁺ dendritic cells in the sample is correlated (e.g. positively correlated)/ indicative of the severity of the SLE in the subject. For example, a subject with an increased level and/or a proportion of the dendritic cells expressing CD163 and/or CD14, and/or an increased level and/or a proportion of CD5⁻, CD14⁺, CD163⁺, CD14⁺CD163⁺, CD5⁻CD163⁻, CD5⁻ CD163⁺CD14⁻ and/or CD5⁻CD163⁺CD14⁺ dendritic cells in his/her sample may have a higher SLE Disease Activity Index (SLEDAI) score (i.e. having a more significant degree of disease activity). In some examples, dendritic cells (e.g. DC3) expressing CD163 molecule are found to be increased in SLE patients in correlation with the gravity of the disease as determined by the SLEDAI score. Advantageously, the level or the proportion of dendritic cells, e.g. pro-inflammatory dendritic cells, may be quantified by flow cytometry and be used to predict the disease score in patients with SLE. In various embodiments, the method further comprises administering to the subject a SLE treatment regimen. In various embodiments, the SLE treatment regimen comprises administering to the subject an agent that is capable of decreasing the activity of the dendritic cell expressing CD163 by decreasing/inhibiting the secretion of pro-inflammatory mediators involved in SLE physiopathology such as, but is not limited to, BAFF, IL-1α, GRO-α (CXCL1), MCP-3 (CCL7), MIG (CXCL9), SDF-1 (CDCL12), IL-8, VEGF-A, and WEAK.

In various embodiments, there is provided a method of assessing the prognosis of an inflammatory disease in a subject, the method comprising determining a level and/or a proportion of the dendritic cells expressing CD163 and/or CD14, and/or a level and/or a proportion of CD5⁻, CD14⁺, CD163⁺, CD14⁺CD163⁺, CD5⁻CD163⁻, CD5⁻CD163⁺ CD14⁻ and/or CD5⁻CD163⁺CD14⁺ dendritic cells in a sample obtained from the subject. In various embodiments, a decreased level and/or a proportion of the dendritic cells expressing CD163 and/or CD14, and/or an decreased level and/or a proportion of CD5⁻, CD14⁺, CD163⁺, CD14⁺ CD163⁺, CD5⁻CD163⁻, CD5⁻CD163⁺CD14⁻ and/or CD5⁻ CD163⁺CD14⁺ dendritic cells in the sample is correlated (e.g. positively correlated)/indicative of prognosis/improvement of the inflammatory disease in the subject.

In various embodiments, the sample (or biological sample) is a fluid or specimen from a person/patient/subject such as whole blood, serum, plasma, tears, saliva, nasal fluid, sputum, ear fluid, genital fluid, breast fluid, milk, colostrum, placental fluid, amniotic fluid, stool, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, e.g. from all suitable organs, e.g. the lung, the muscle, brain, liver, skin, pancreas, stomach, etc., a nucleated cell sample, a fluid associated with a mucosal surface, hair, or skin. In some examples, the sample may be blood (whole blood), serum, plasma, biological fluid, tissue biopsies, sputum, interstitial fluid, and the like.

In various embodiments, the sample comprises human biological material. In various embodiments, the sample comprises MNP. In various embodiments, the sample comprises a MNP subpopulation. In various embodiments, the sample comprises one or more of dendritic cells, monocytes, macrophages and monocyte-derived cells (MC). In one embodiment, the sample comprises dendritic cells. In one embodiment, the sample comprises cDC2. In one embodiment, the sample comprises dendritic cells having one or more of the following properties: (i) is a conventional dendritic cell 2 (cDC2); (ii) is dependent on IRF4 for differentiation; (iii) is dependent on KLF4 for differentiation; (iv) is dependent on FLT3 ligand (FLT3L) for differentiation; and (v) is capable of activating and/or polarizing T cells e.g. naïve T cells or allogeneic naïve CD4⁺ T cells.

In various embodiments, there is provided a kit for use in the methods described herein. In various embodiments, the kit comprises one or more reagents for detecting/determining/quantifying a dendritic cell expressing CD163 and/or CD14, and/or a level and/or a proportion of CD5⁻, CD14⁺, CD163⁺, CD14⁺CD163⁺, CD5⁻CD163⁻, CD5⁻CD163⁺ CD14⁻ and/or CD5⁻CD163⁺CD14⁺ dendritic cells. In various embodiments, there is provided a kit for characterising dendritic cells, inflammation and/or inflammatory disease, the kit comprising one or more reagent for detecting/determining/quantifying CD5, CD14 and/or CD163. In various embodiments. In some embodiments, the kit comprises one or more of an anti-CD5 antibody, an anti-CD14 antibody and/or an anti-CD163 antibody.

In various embodiments, the kit further comprises one or more reagent for detecting/determining/quantifying AXL, BLTA, BTLA, CD101, CD107a, CD109, CD112, CD115, CD11b, CD124, CD14, CD155, CD163, CD166, CD172a, CD180, CD183, CD195, CD1c, CD1d, CD2, CD200, CD200R, CD206, CD218a, CD22, CD229, CD26, CD271, CD274, CD282, CD303, CD324, CD34, CD354, CD36, CD45RA, CD5, CD56, CD59, CD63, CD64, CD71, CD74, CD81, CD84, CD87, CD87, CD88, CD89, CD95, CLEC12A, CLEC4E, DNAI2, FcεRIα, HLA-DQ, Igk, Integrin β7, LTB (Lymphotoxin-b), MEX3B, NOTCH2, NUMBL, RN7SL846P, S100A13, S100A8, S100A9, S100A9, SIGLEC6 (CD327). In some embodiments, the kit comprises one or more reagent for detecting/determining/quantifying AXL, BLTA, CD1c, CD1d, CD5, CD11b, CD64, CD74, CD88, CD89, CD101, CD109, CD180, CD200R, CD45RA, FcεRIα HLA-DQ, Integrin β7, LTB (Lymphotoxin-β), NOTCH2, S100A8, S100A9 and SIGLEC6 (CD327). In some embodiments, the kit comprises one or more reagent for detecting/determining/quantifying CD5, CD163, CD14, CD11b, CD36, CD64, CD87, CD107a, CD206, CD274, CD354, FcεRIα, HLA-DQ, CD2, CD59, CD81, CD166, CD229, CD271 and Integrin β7.

In various embodiments, there is provided a population, e.g. an isolated population, of dendritic cells selected from the group consisting of: CD5⁻ dendritic cells, CD14⁺ dendritic cells, CD163⁺ dendritic cells, CD14⁺CD163⁺ dendritic cells, CD5⁻CD163⁻ dendritic cells, CD5⁻CD163⁺ CD14⁻ dendritic cells and/or CD5⁻CD163⁺CD14⁺ dendritic cells. The term "isolated" as used herein in relation to a population of cells refers to a population of cells that is removed from its natural environment (e.g. tissue, body fluid, etc.), or otherwise increased in purity to any degree. A population may be "isolated" by separating it from some or all of the substances with which it is associated in nature. In various embodiments, the isolated population is substantially pure and/or homogenous (e.g. substantially free/devoid of dendritic cells having other expression profiles and/or phenotypes, and/or substantially free/devoid of other impurities and/or contaminants).

In various embodiments, there is provided a method, a kit, a reagent, a compound, or an agent as described herein.

BRIEF DESCRIPTION OF FIGURES

(FIG. 1A) Peripheral blood mononuclear cells from a single donor were stained with 14 back-bone markers, divided, stained with 332 PE-conjugated variable antibodies (LegendScreen kit) and then analyzed by flow cytometry. The 332 generated fcs files were analyzed with the InfinityFlow pipeline to generate fcs files containing 347 dimensions, consisting of 14 back-bone dimensions, 1 variable-PE real marker and 332 predicted markers. (FIG. 1B) tSNE dimensionality reduction and Phenograph clustering of $CD45^+CD3^-CD20^-$ $HLA-DR^+$ peripheral blood (PB) mononuclear phagocytes (MNP) based on the 332 predicted dimensions. Cell subsets were delineated using the 23 Phenograph clusters (pDC, n=2 clusters; pre-DC, n=1 cluster; cDC1, n=1 cluster; cDC2, n=4 clusters; cMo, n=8 clusters; iMo, n=2 clusters; ncMo, n=3 clusters; contaminating B cells and $CD34^+$ cells, n=1 cluster each; one minor undetermined cluster representing 1.1% of cells) that were regrouped into major previously defined cell subsets based on the expression of cell-subset specific phenotypic markers. (FIG. 1C) Expression heatmap of makers highly expressed by the different monocyte and DC subsets. Newly defined cell subset discriminating markers are indicated in grey. (FIG. 1D) tSNE dimensionality reduction and Phenograph clustering of $CD45^+CD3^-CD20^-HLA-$ $DR^+$ PB MNPs based on the 92 discriminating markers defined in FIG. 1C.

(FIG. 2A) Gating strategy of flow cytometry data starting from singlet, live, $CD45^+$ cells, for the export of $Lin^-HLA-DR^+$ cells analyzed with the InfinityFlow pipeline. (FIG. 2B) Meaning plots of the relative expression of backbone markers and their respective predicted dimensions in the 332 dimensions tSNE from FIG. 1B. (FIG. 2C) Heat map of the 332 predicted dimensions clustered by Euclidean distance for cell subsets defined in FIG. 1B-C. Markers that were highly expressed only by one of the 7 major cell types analysed (within the black rectangles) were defined as "discriminating markers" and displayed in FIG. 1C. (FIG. 2D) Meaning plots of the relative expression of backbone makers and their respective predicted dimensions in the discriminating markers tSNE from FIG. 1D. (FIG. 2B, FIG. 2D) Predicted "variable PE" dimensions were obtained by a regression-based approach integrating the expression of backbone markers (measured in each of the 332 FACS stainings).

(FIG. 3A) Histograms showing the expression of highly expressed markers by all cell subsets defined in FIG. 1B-C. (FIG. 3B) Histograms showing the expression of markers over-expressed by pre-cDC2 to cDC2 and early pre-DC, as defined by See et al. (See et al., 2017). Expression is also compared to cDC1 and pDC.

FIGS. 4A-L. $CD1c^+CD14^+$ circulating cells are phenotypically and functionally related to cDC2 and not monocytes. (FIG. 4A) cDC2 and cMo Phenograph clusters represented in the tSNE generated using the 92 markers described in FIG. 1D, and in a CD14/CD1c dot plot. (FIG. 4B) cMo versus cDC2 Phenograph clusters were compared by AUC analysis to determine their discriminating markers. (FIG. 4C) Relative expression of the classical and top four discriminating markers of cDC2 and cMo (real dimensions displayed). (FIG. 4D) Optimal gating strategy starting from $Lin^-HLA-DR^+$ defining all blood MNP subsets. (FIG. 4E) UMAP analysis of data from panel (FIG. 4D). (FIG. 4F) Phenotype of cells within cDC2 (grey) and monocyte (black) defined in the UMAP space. (FIGS. 4G-I) Human blood, spleen and tonsil were analyzed by CyTOF using the new cMo/cDC2 discriminating markers. Among $Lin^-HLA-DR^+$ cells (concatenated data), (FIG. 4G) the relative expression of MNP subsets-defining markers and (FIG. 4H) distribution of cells from the three tissues are shown. (I) Differentially expressed markers between tissues. (FIGS. 4J-4K) The relative proportions of cMo, $CD1c^+CD14^-$ and $CD1c^+CD14^+cDC2$ were measured in the blood of seven patients before and 11 days after FLT3L treatment. (FIG. 4K) Proportions of subsets and (FIG. 4L) Relative expression of IRF4, KLF4 and NOTCH2 for the cell subsets defined in (FIG. 4J).

FIGS. 5A-P. (FIG. 5A) Markers with an AUC <0.1 and >0.9. (FIG. 5B) Meaning plots of the relative expression of CD1c, CD14, FcεRIα, HLA-DQ, CD88 and CD89 markers showing real dimensions and their respective predicted dimensions on the tSNE using the discriminating markers defined in FIG. 1C. (FIG. 5C) Meaning plots of the relative expression of other cDC2 and cMo discriminating markers. (FIG. 5D) Flow cytometry dot plot of CD14 versus discriminating markers between cDC2 and cMo. (FIG. 5E) Manual gating strategy from Hamers et al. to define 8 monocyte subsets (Hamers Anouk A. J. et al., 2019). The cell subsets were back-gated in the mother gates of the gating strategy. (FIG. 5F) Projection of the 8 monocyte subsets defined in (FIG. 5A) into the tSNE obtained using the 332-predicted dimensions of the InfinityFlow data (see FIG. 1B of our manuscript). (FIG. 5G) Gating strategy of flow cytometry data starting from singlet, live, $CD45^+$ cells, for the export of $CD163^+$ cells falling between cDC2 and cMo. (FIG. 5H) PCA using the 14 backbone markers of cells exported in (FIG. 5G). Meaning plots showing the relative expression of CD1c, CD163 and CD14 real dimensions and the 40 binning gates. (FIG. 5I) tSNE/Phenograph analysis using the 332 predicted dimensions (PE markers) for the 40 bins defined in (FIG. 5H). (FIG. 5J) Dot plots showing the expression of CD14, CD1c (real dimensions), PC1 and PC4 of cells falling in the Phenograph clusters defined in (FIG. 5I). (FIG. 5K) Meaning plots of the relative expression of all makers used in the flow cytometry analysis of FIG. 4E-F. (FIG. 5L) Meaning plots of the relative expression of selected makers used in the CyTOF analysis of FIG. 4G-H. (FIGS. 5M-N) Expression heatmap of markers with a higher expression in (FIG. 5M) (cDC2) and (FIG. 5N) (monocyte/ macrophages). (FIG. 5O) Histograms showing the expression of markers selected as being differentially expressed between tissues (the median expression intensity values are shown). (FIG. 5P) Gating strategy starting from singlet, live, $CD45^+$ cells from FLT3L-injected patients analyzed in FIG. 4J-K.

FIGS. 6A-M. (FIGS. 6A-B) Gating strategy of the flow cytometry data from (FIG. 6A) the full recording and (FIG. 6B) indexed-sorted cells analyzed by SMARTseq2 scR-NAseq of FIGS. 7A-I. (FIG. 6C) Meaning plots of the relative expression of selected flow cytometry markers from the tSNE analysis of FIG. 7A. (FIGS. 6D-E) In the tSNE analysis of FIG. 7A, (FIG. 6D) cells that did or did not pass quality control for SMARTseq2 analysis are displayed in black or dark grey, respectively (numbers of total indexed-sorted cell, of cells that passed QC and their frequencies indicated), and (FIG. 6E) cell subsets defined in FIG. 7E-F are displayed. (FIG. 6F and FIG. 6G) From the scRNAseq data of FIG. 7B-C, visualizations are presented of UMAP and (FIG. 6F) Phenograph clusters or (FIG. 6G) cell subsets defined based on the indexed-protein expression in FIG. 7E-F. (FIG. 6H) Meaning plots of the relative expression of top signature genes in the DC subsets described by Villani et al. (Villani et al., 2017). (FIG. 6I) Meaning plots of the relative expression of specific, highly expressed genes (signature genes) by cDC2 clusters #2 and #4 defined by comparing them to all other cells. (FIG. 6J) Conventional flow cytometry gating strategy to define AS-DC (DC5, upper panel; light grey) and early pre-DC (lower panel; dark grey) from Villani et al. and See et al., respectively (See et al., 2017; Villani et al., 2017). (FIG. 6K) Density plots showing the expression of CD11c, CD1c, CD169, CD45RA and CD123 by AS-DC (light grey) and early pre-DC (dark grey). (FIG. 6L) Volcano plots comparing the expression of genes between cDC2 clusters #2 and #4 (defined in FIG. 7B-C) represented as the mean Log 2(Fold Change) vs –Log 10 (adjusted p value). (FIG. 6M) Ingenuity pathway analysis (IPA) of cDC2 clusters #2 versus #4 DEG. The histogram height represents the –log(p value), and the proportion of DEG from each pathway up-regulated in cDC2 clusters #2 (dark grey) and #4 (light grey) is shown. Significant pathways obtained when including only the upregulated genes in cDC2 clusters #2 or #4 (IPA) are marked by a dark grey or a light grey star, respectively.

FIGS. 7A-I. Indexed single-cell RNAseq analysis confirms that CD1c$^+$CD14$^+$ circulating cells are inflammatory cDC2 and not monocytes. (FIG. 7A) tSNE of indexed-sorted DC subsets and monocytes (black dots) overlayed on Lin$^-$ HLA-DR+ PBMCs (full recording). (FIGS. 7B-H) Indexed-sorted cells were analyzed by scRNAseq using the Seurat pipeline and phenograph clustering. (FIGS. 7B-C) For the eight phenograph clusters, (FIG. 7B) the heatmap of the top 20 DEG and (FIG. 7C) their projection on a tSNE obtained using 10 Seurat significant principal components (PCs; Principal Component Analysis, PCA) identified monocytes, DC subsets and CD16$^{+/-}$HLA-DR$^{lo}$ contaminating NK cells. (FIG. 7D) Protein expression of MNP subsets-defining markers obtained from the FACS-indexed data. (FIG. 7E) Monocyte and DC subsets were defined based on indexed-protein expression and (FIG. 7F) overlaid on the RNA_tSNE defined in (FIG. 7C). (FIGS. 7G-H) DC and monocyte subset signatures from Villani et al. (Villani et al., 2017) are shown as (FIG. 7E) a heat map of the top 20 signature genes expressed in the eight phenograph clusters [defined in (FIG. 7B)], and (FIG. 7H) as the mean expression of all signature genes. (FIG. 7I) Visualization of the relative expression of top discriminating membrane protein markers of DC and monocyte subsets described by Villani et al. (Villani et al., 2017) on the InfinityFlow tSNE generated using the discriminating markers shown in FIG. 1C.

(FIG. 8A) PCA/Phenograph analysis of cDC2 extracted from the discriminating markers' InfinityFlow tSNE (FIG. 1D) using the 332 predicted protein dimensions. (FIG. 8B) PC1/PC2 dimensions (%=PC loading) and Phenograph cluster visualization of cDC2. (FIG. 8C) Absolute loading of the top six PC1-2 markers. (FIG. 8D) 3D visualization of CD5/CD14/CD163 expression by cDC2. (FIG. 8E) Expression of heterogeneously expressed markers for the different cDC2 states [CD5$^+$CD163$^-$ (light grey circle) and among CD5$^-$ cells, CD163$^-$ (dark grey circle), CD163$^+$CD14$^-$ (light grey box) and CD163$^+$CD14$^+$ (dark grey box)]. (FIG. 8F) Heatmap of discriminating markers between the four cDC2 states. (FIG. 8G) Scanning electron microscopy of FACS-sorted cDC2 subsets and CD88$^+$CD89$^+$CD14$^{hi}$CD16$^-$ classical monocytes. Scale bar, 2 μm. (FIG. 8H) Forward scatter (FSC-A) and side scatter (SSC-A) median fluorescence intensity (MFI) of cells defined as CD5$^+$, CD5$^-$CD163$^-$, CD163$^+$CD14$^-$, CD163$^+$CD14$^+$cDC2 and as CD88$^+$CD89$^+$CD14$^+$CD16$^-$ cMo.

(FIG. 9A) Bimodal plots of PC1 to PC4 dimensions and Phenograph clusters from the analysis of FIG. 8B (%=PC loading). (FIG. 9B) Bimodal plots of PC1 and PC2 top six loading markers and Phenograph clusters from the analysis of FIG. 8B-C. (FIG. 9C) Meaning plot of the values of PC1 to PC4 overlaid on a dot pot of CD163 and CD5 real dimensions as in FIG. 8D. (FIG. 9D) Meaning plots of the relative expression of real dimensions and their respective predicted dimensions for heterogeneously expressed markers in-between the four cDC2 subsets defined in FIG. 8E. (FIG. 9E) Manual gating strategy to define DC and cDC2 subsets, starting from singlet, live CD45$^+$Lin HLA-DR$^+$ cells and after excluding monocytes (based on CD14/CD88 and CD16 expression). (FIG. 9F) Expression of markers (real dimensions) showing progression from early pre-DC to pre-cDC2 (as defined in See et al.) (See et al., 2017), to CD5$^+$cDC2 and then to the other cDC2 subsets ordered based on the Wishbone pseudotime analyses shown in (FIG. 9H). All of these cell subsets are defined in (FIG. 9I). (FIG. 9G) Expression of transcription factors by cell subsets defined in (FIG. 9I). (FIG. 9H) Meaning plots of the relative expression of real dimensions of CD5, CD163 and CD14 overlaid on the UMAP and isoMAP spaces obtained using the top 20 loading markers from the PCA of FIG. 8B. (FIG. 9I) Heatmap of the most variable markers along the NBOR pseudotime trajectory, starting from CD5$^+$ cDC2. (FIG. 9J) Graphical representation of the progression of CD5, CD163 and CD14 expression by individual cells along the NBOR pseudotime trajectory. (FIG. 9K) Wishbone analysis starting from CD5$^+$cDC2. The wishbone pseudotime dimension is displayed as early (black) to late (white) on a CD163/CD5 dot plot for total cDC2 and on a CD163/CD14 dot pot for CD5$^-$cDC2. (FIG. 9L) DEG between cDC2 and early pre-DC, taken from See et al. (See et al., 2017) microarray data. Genes encoding highly expressed proteins by CD5$^+$cDC2 are highlighted in grey and bold. (FIG. 9M) Scanning electron microscopy of cDC2 subsets and CD88$^+$CD89$^+$CD14$^{hi}$CD16$^-$ classical monocytes. Scale bar, 2 μm.

FIGS. 10A-G. Functional and molecular characterization of inflammatory CD14$^+$cDC2. (FIG. 10A) The relative proportions of the four cDC2 subsets and CD88$^+$CD89$^+$CD14$^+$ CD16$^-$ cMo, were measured in the blood of four patients before and 11 days after FLT3L treatment. The proportion among cDC2+cMo are displayed. (FIGS. 10B-D) Bulk RNAseq data obtained from FACS-sorted cDC2 subsets. (FIG. 10B) Connectivity map (cMAP) analysis showing the degree of enrichment for Villani's DC2 or DC3 signature genes in the four cDC2 subsets. (FIG. 10C) UMAP using the first 10 PC (PCA); Circles delineate DC2 (CD5$^+$cDC2) and DC3 (the three subsets of CD5$^-$cDC2). (FIG. 10D) Heatmap of six selected specifically expressed DEG for each subset. (FIG. 10E) Naïve allogenic CD4$^+$ T cells were cultured with the four different cDC2 subsets: frequencies of proliferating, IFNγ (Th1), IL-4 (Th2) or IL-17 (Th17)-producing CD4$^+$ T cells are represented [linked scatter plots (n=4)]. (FIG. 10F) In the indexed-scRNAseq data from FIGS. 7A-I, mean expression of specifically expressed genes by inflammatory DC (inflDC) defined by Segura et al. (Segura et al., 2013) (Table S2) represented as a violin plot and as a meaning plot on the CD1c/CD14 protein expression dot plot defined in FIG. 7E. (FIG. 10G) Ingenuity Pathway Analysis of cDC2 subsets bulk RNAseq displayed as a Radar plot showing −Log(p-value) and z-Score for each pathway using upregu-lated and downregulated DEG of each subset.

(FIG. 11A) UMAP analysis of FLT3L-injecred patients (data from FIG. 10A) the day of the injection (DO) and 11 days post-injection (D11). (FIG. 11B) Heatmap of all DEG obtained by comparing bulk RNAseq of the four cDC2 subsets analyzed in FIGS. 10B-C. (FIG. 11C) Flow cytometry histograms and dot plots showing the CellTrace Violet dye dilution to follow cell proliferation (x-axis) versus intracellular quantification of IFNγ, IL-4 and IL-17 (y-axis) in CD4$^+$ T cells after 6 days of mixed lymphocyte reaction (MLR) with allogenic cDC2 subsets. (FIG. 11D) Meaning plots of the relative expression of inflDC markers [defined by Segura et al. (Segura et al., 2013)] by cDC2 subsets defined in FIGS. 8D-E. (FIG. 11E) Venn diagram of the intersection of inflDC versus BDCA-1 [blood cDC2 BDCA-1 cells from Segura et al. (Segura et al., 2013)] DEG (Table S2) compared to the four cDC2 subset DEG obtained from bulk the RNAseq shown in FIGS. 10B-C.

(FIGS. 12A-D) PBMCs were isolated from healthy subjects (n=10), and patients with SLE (n=10) or systemic sclerosis (SSC; n=15), and cDC2 subsets were defined by FACS. (FIGS. 12B-C) The frequency of cDC2 subsets in the three patient groups is shown among (FIG. 12B) CD45$^+$ PBMCs and (FIG. 12C) total cDC2. (FIG. 12D) Pearson correlation of the frequency of CD163$^+$ (CD14$^-$ and CD14$^+$) DC3 versus the SLE disease activity score (SLEDAI) in SLE patients. (FIG. 12E) CD163 and CD169 membrane protein expression by cDC2 subsets in healthy subjects and SLE patients. (FIGS. 12F-H) Bulk RNAseq analysis of FACS-sorted cDC2 subsets from healthy subjects and patients with SLE. (FIGS. 12F-G) For CD5$^+$ DC2 (healthy, n=5; SLE, n=6) and CD163$^+$ DC3 (healthy, n=5; SLE, n=9), (FIG. 12F) an expression heatmap of the top 100 DEG and (FIG. 12G) volcano plots showing Log 2(Fold Change) vs −Log 10(p-value) of all gene expression data comparing healthy and SLE patients are shown. (FIG. 12H) Ingenuity Pathway Analysis of CD5$^+$ DC2 and CD163$^+$ DC3 bulk RNAseq data displayed as a Radar plot showing the −Log(p-value) and the z-Score for each pathway using upregulated and downregulated DEG of each subset.

FIGS. 13A-D. (FIG. 13A) Manual gating strategy to define (as shown in FIG. 14A) and sort cDC2 subsets used for bulk RNAseq analyses of FIGS. 12F-H, starting from singlet, live CD45$^+$ cells. (FIG. 13B) The frequency among CD45$^+$ mononuclear cells of CD163$^+$CD14$^-$ and CD163$^+$CD14$^+$ DC3 subsets in the three patient groups defined in FIGS. 12A-C is shown among CD45$^+$ PBMC. (FIG. 13C) Pearson correlation of the frequency of CD163$^+$CD14$^-$ and CD163$^+$CD14$^+$ DC3 versus the SLEDAI disease score in SLE patients. (FIG. 13D) Meaning plots of the relative expression of other soluble mediators as in FIG. 12D.

(FIG. 14A) cDC2 subsets from healthy blood donors (n=3) were FACS-sorted and cultured overnight with serum from healthy donors (n=12), or patients with inactive (n=12) or active (n=12) SLE and 55 soluble mediators were quantified in the culture supernatants. The cDC2 subset secretomes (concentration of each soluble factor) in the culture supernatants were analyzed with UMAP. (FIGS. 14B-D) In the Secretome-UMAP, each dot corresponds to one culture supernatant. Supernatants from (FIG. 14B) the four cDC2 subsets or from (FIG. 14C) the different patient groups are shown on the Secretome-UMAP projection. (FIG. 14D) Relative expression of pro-inflammatory soluble mediators involved in SLE immunopathology. (FIG. 14E) Heat map showing the difference in soluble mediators' concentration between supernatants of cultures with SLE patient serum compared to healthy serum. P values were determined by comparing absolute concentrations in supernatants of cultures with SLE patient serum compared to healthy serum using Kruskal Wallis (non-parametric one-way ANOVA) followed by Dunn's multiple comparisons test.

FIGS. 15A-E. Frequency and proportion of DC2 and DC3 in healthy and disease. (FIG. 15A) Frequency among myeloid cells of DC2 and DC3 in the non-lesional and lesional skin of Atopic dermatitis or Psoriasis patients. (FIG. 15B) Frequency among total cDC2 (DC2+DC3) of DC2 and DC3 in the normal adjacent liver of within different tumour sectors from four Liver Hepatocellular carcinoma (HCC) patients. (FIGS. 15C-E) PBMCs were isolated from healthy subjects (n=10), and patients with SLE (n=10) or systemic sclerosis (SSC; n=15), and cDC2 subsets were defined by FACS. (FIGS. 15C-D) The frequency of cDC2 subsets in the three patient groups is shown among (FIG. 15C) CD45$^+$ PBMCs and (FIG. 15D) total cDC2s. P values were calculated using the Mann-Whitney test. (FIG. 15E) Pearson correlation of the frequency of CD163$^+$ (CD14$^-$ and CD14$^+$) DC3s versus the SLE disease activity score (SLEDAI) in SLE patients.

EXAMPLES

Example embodiments of the disclosure will be better understood and readily apparent to one of ordinary skill in the art from the following discussions and if applicable, in conjunction with the figures. It should be appreciated that other modifications related to structural, electrical and optical changes may be made without deviating from the scope of the invention. Example embodiments are not necessarily mutually exclusive as some may be combined with one or more embodiments to form new exemplary embodiments.

Results

Unbiased Identification of New Monocyte and DC Specific Markers Using the InfinityFlow Pipeline To identify new monocyte-specific and DC-specific markers, 332 flow cytometry (FACS) stainings from a single human blood donor was carried out; all stainings included a set of 14 'backbone" markers (to define all known monocyte and DC subsets) and one "variable" PE-conjugated antibody (see Star Methods). It was reasoned that this experimental setting was amenable to machine learning approaches, to predict the signal from PE-conjugated antibodies (each measured on 1 staining out of 332) for all cells by a regression-based approach integrating the expression of backbone markers (measured in the 332 FACS stainings). To achieve this, Support Vector Machines (SVM) were used—a multi-purpose machine learning framework that is accurate, robust to noise and can be used for regression purposes and single-cell classification problems.

Figures 1A, 1B:
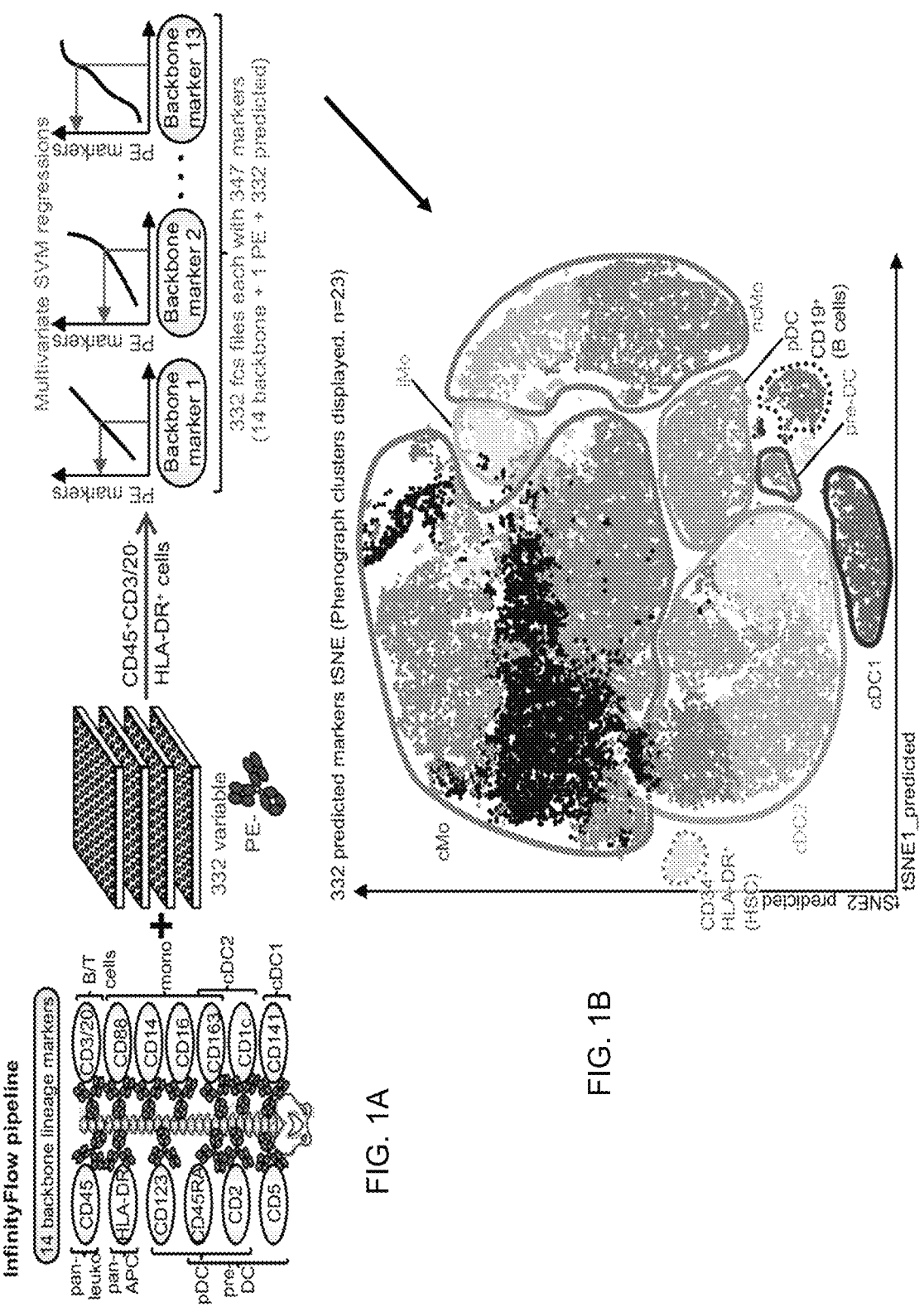
FIGS. 1A-D. InfinityFlow, a high-dimensional single-cell protein expression pipeline, unravels human circulating myeloid cell phenotypes and heterogeneity.
Figures 1C, 1D:
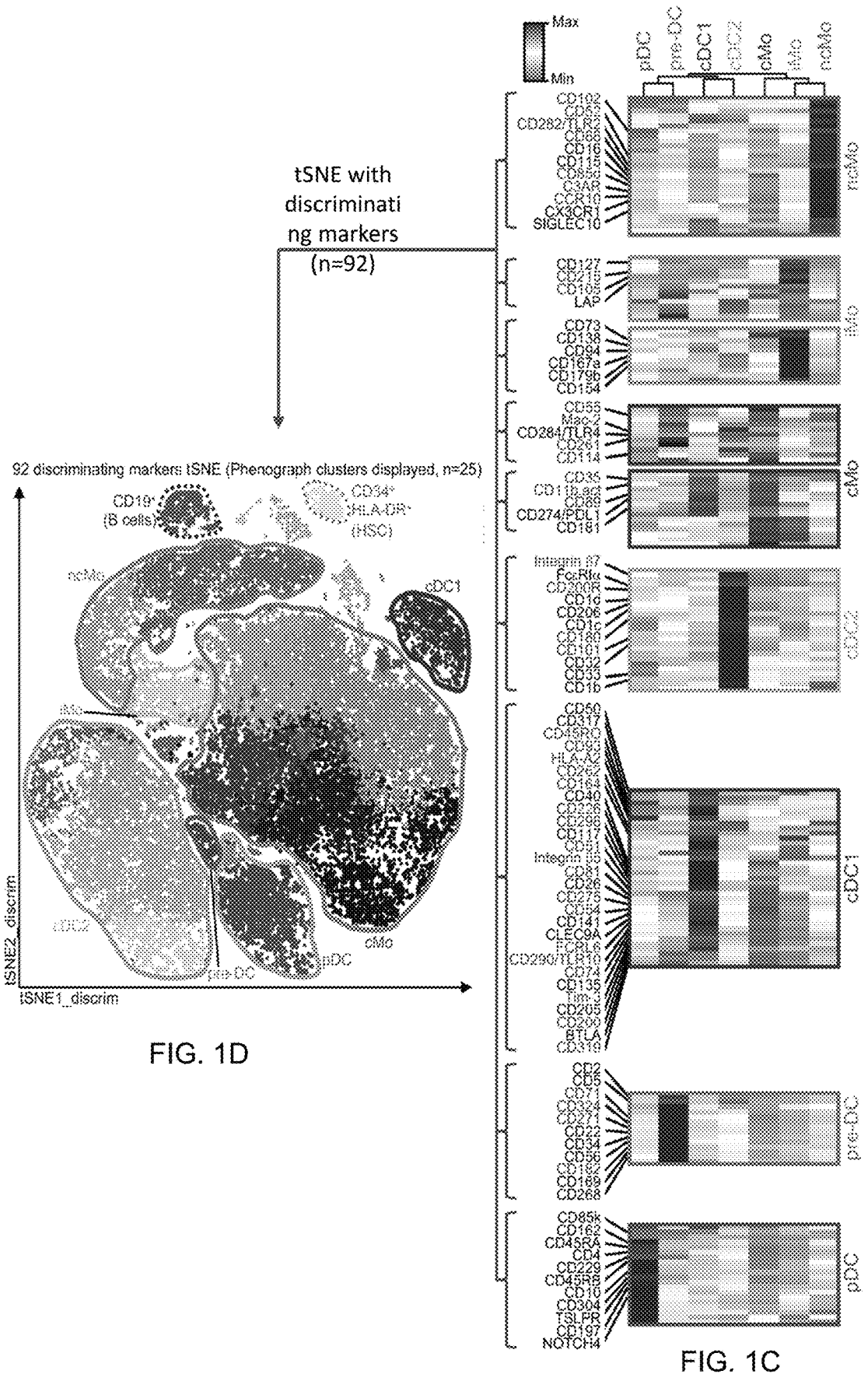
Figures 2A, 2B, 2C, 2D:
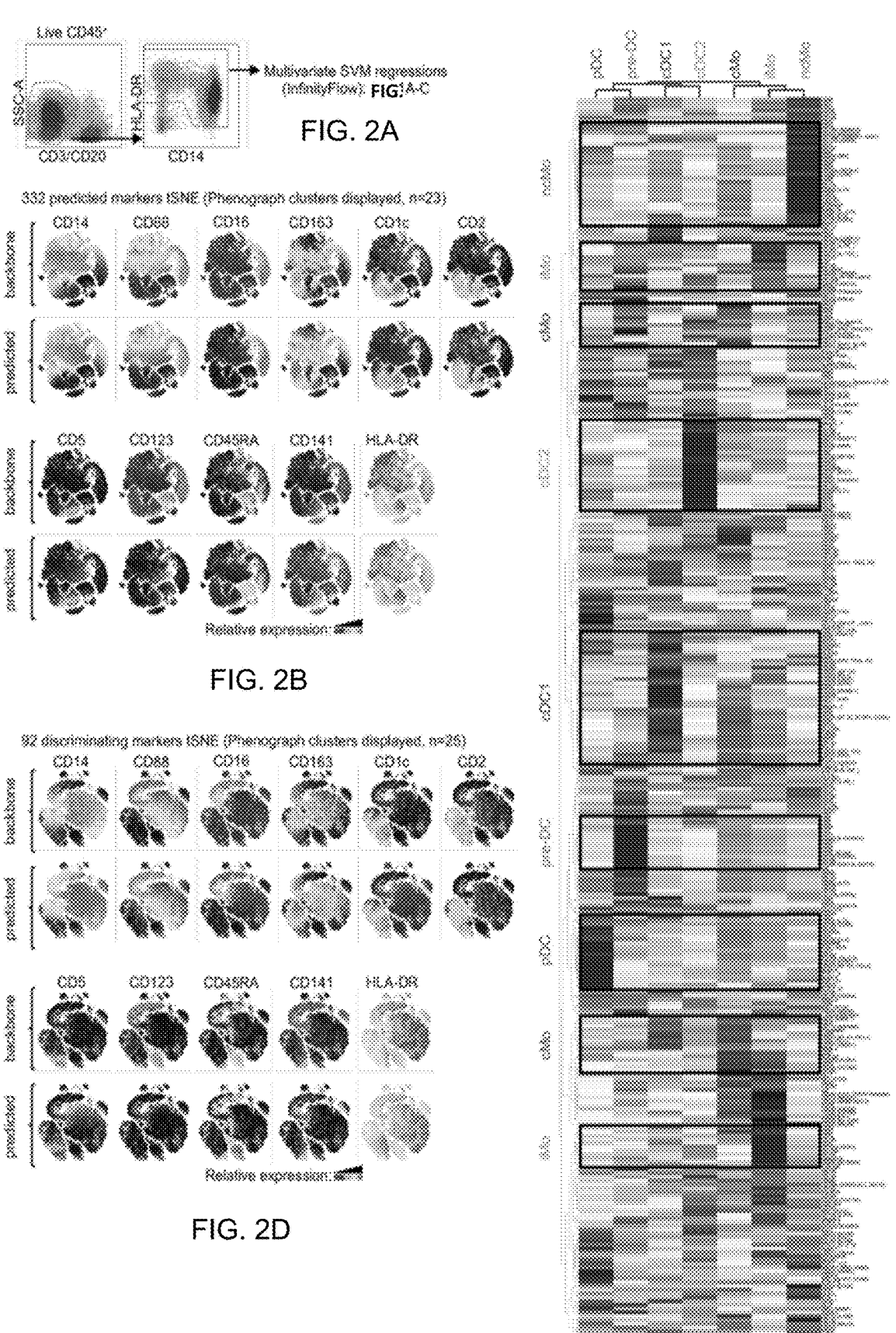
FIGS. 2A-D.
Figure 3A:
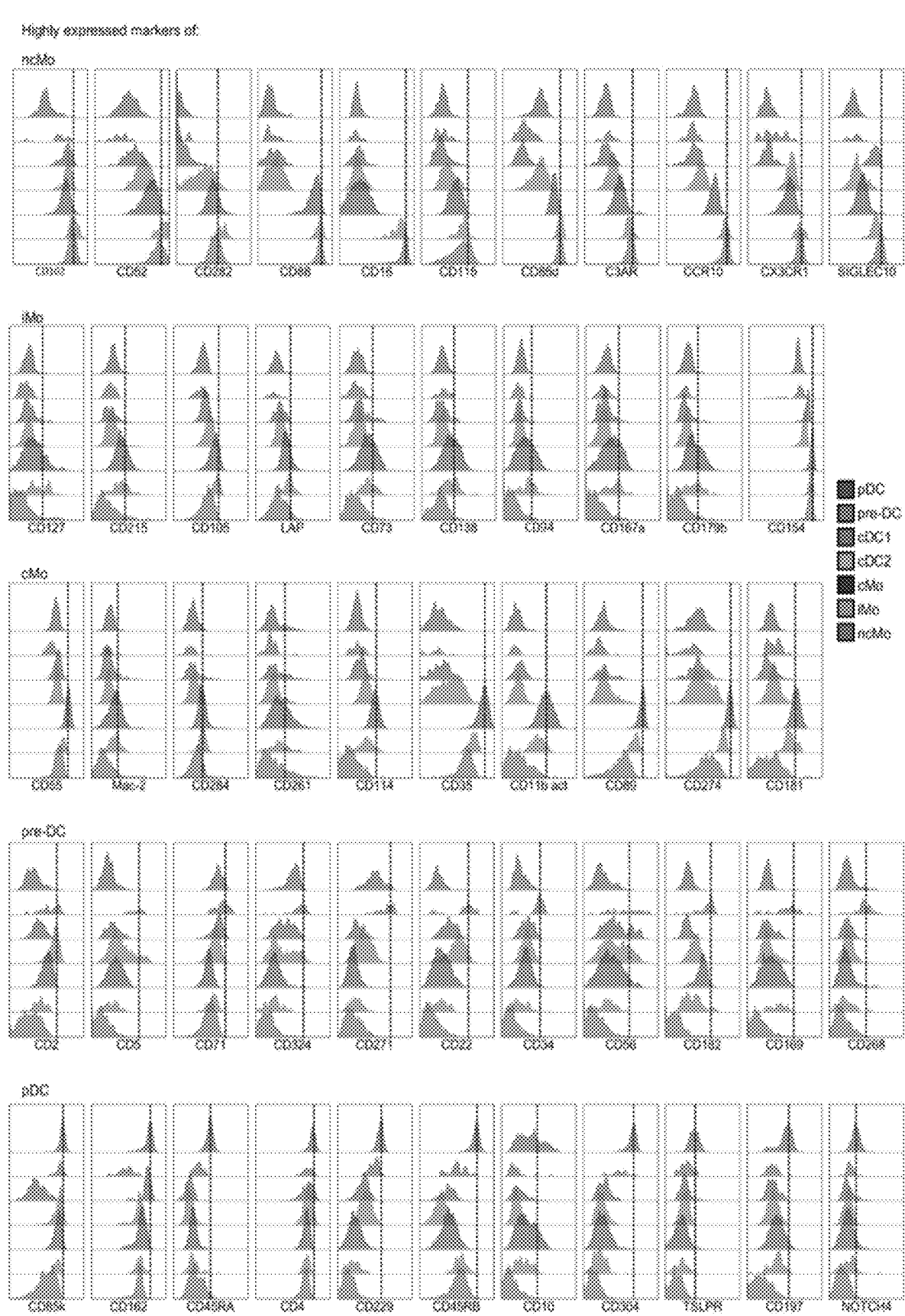
FIGS. 3A-B.

Using SVM regression and starting from live CD45$^+$ CD3$^-$CD20$^-$HLA-DR$^+$ cells, 332 new flow cytometry files (fcs) that included the 14 backbone markers, the PE variable marker and 332 predicted variable markers were generated (FIG. 1A, Table S1). These generated files were processed using non-linear dimensionality reduction via t-stochastic neighbour embedding (tSNE) (Van der Maaten and Hinton, 2008) and Phenograph clustering (DiGiuseppe et al., 2018; Levine et al., 2015) algorithms using the 332 predicted dimensions (FIG. 1B and FIGS. 2A-B). All previously described monocyte and DC subsets were delineated based on Phenograph clusters (n=24) and on known markers contained in the backbone staining but were shown to express new markers, including: CD45RO, CD93, HLA-A2, CD262 (TRAIL-R2/DR5), CD164, CD226 (DNAM-1), CD298, CD51 (Integrin $\alpha$V), Integrin $\beta$5, CD81, CD275 (ICOS-L), CD54 (ICAM-1), FCRL6, CD290 (TLR10), Tim-3 (CD366), CD200 and CD319 (CRACC) for cDC1; Integrin $\beta$7, CD200R, CD180 and CD101 for cDC2; CD71, CD324 (Cadherin-1), CD271 (NGFR) and CD182 (CXCR2) for pre-DC; CD55, Mac-2, CD261 (TRAIL-R1), CD114 (CSF3R), CD35 (CR1), CD11b-activated and CD89 (Fc$\alpha$R) for classical monocytes (cMo); CD215 (IL-15RA) and CD105 for intermediate monocytes (iMo); and CD102 (ICAM-2), CD52, CD282 (TLR2), CD88 (C5AR), CD85d, C3AR and CCR10 for non-classical monocytes (ncMo) (FIG. 1C, FIG. 2C and FIG. 3A).

Figures 3A, 3B:
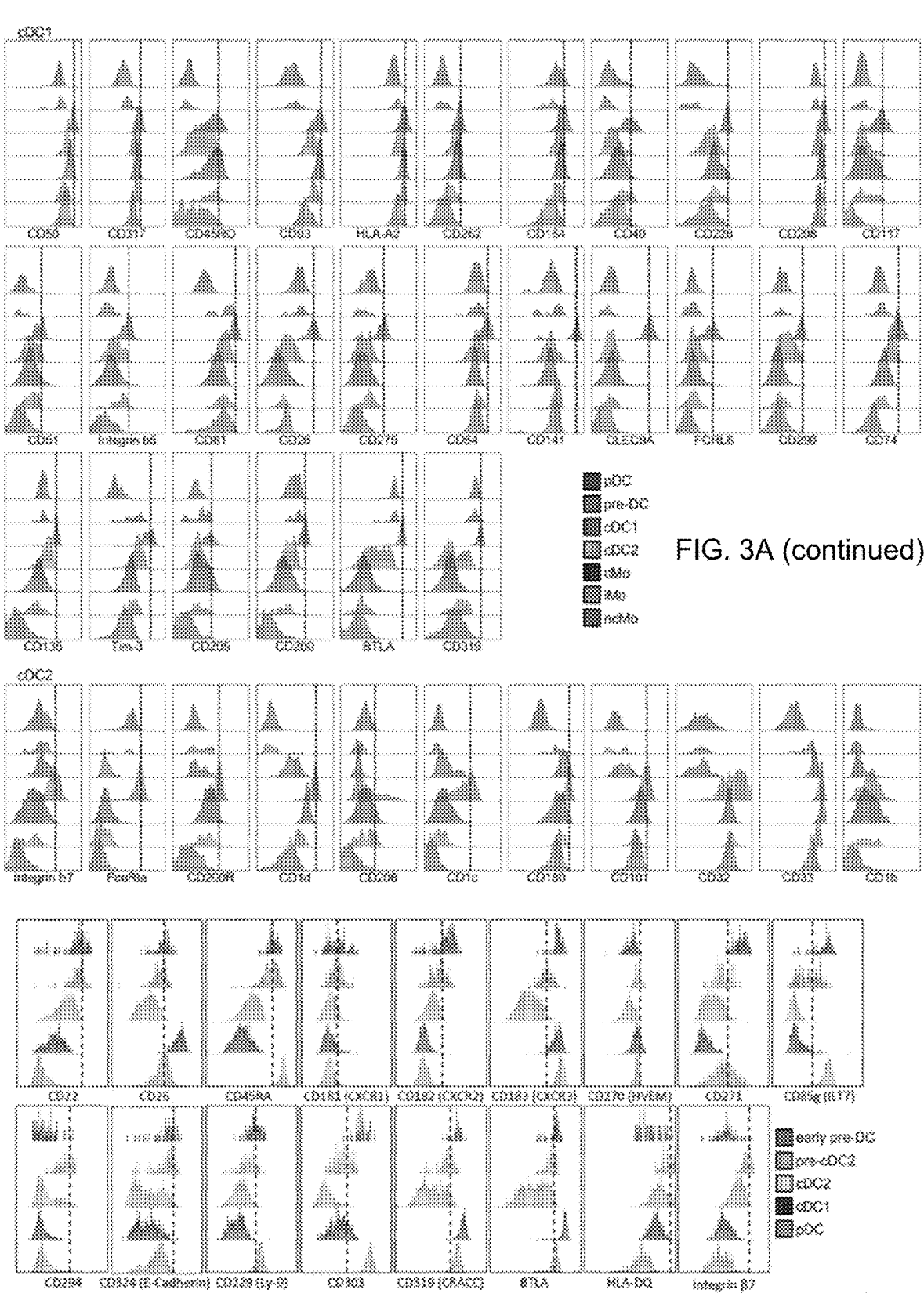

The presence of pre-DC and their corresponding committed pre-cDC1 and pre-cDC2 fractions was recently described. While pre-cDC1 were too rare to be analyzed here, pre-cDC2, which are an intermediate between early pre-DC and cDC2, expressed CD22, CD26, CD181 (CXCR1), CD182 (CXCR2), CD183 (CXCR3), CD270 (HVEM), CD271, CD85g, CD294, CD324 (E-Cadherin), CD229, CD303, BTLA and CD319. Interestingly, pre-cDC2 had the highest HLA-DQ and Integrin $\beta$7 expression compared to all DC (FIG. 3B).

cDC2 Include CD1c$^{lo}$CD14$^+$ Cells and are Phenotypically Different from Monocytes The analysis identified a need to clarify the relationship between cDC2 subsets and monocytes, as illustrated by the phenotypic overlap between cDC2 and cMo observed in the tSNE generated using the 332 predicted dimensions (FIG. 1B). When including the 332 predicted-dimensions, cDC2 and cMo were connected at their junction by cells that expressed low CD1c but intermediate-to-high CD14 expression (FIG. 1B and FIG. 2B). It was next addressed whether including only MNP discriminating markers defined in FIG. 1C could help resolve these subsets (FIG. 1D and FIG. 2D). Indeed, when reducing the analysis to only 92 MNP discriminating markers in a new tSNE space, the CD1c$^{lo}$CD14$^{hi}$ cells were distant from monocytes and formed, together with cDC2, an independent population (FIG. 1D and FIG. 4A).

Figures 4A, 4B, 4C, 4D, 4E, 4F:
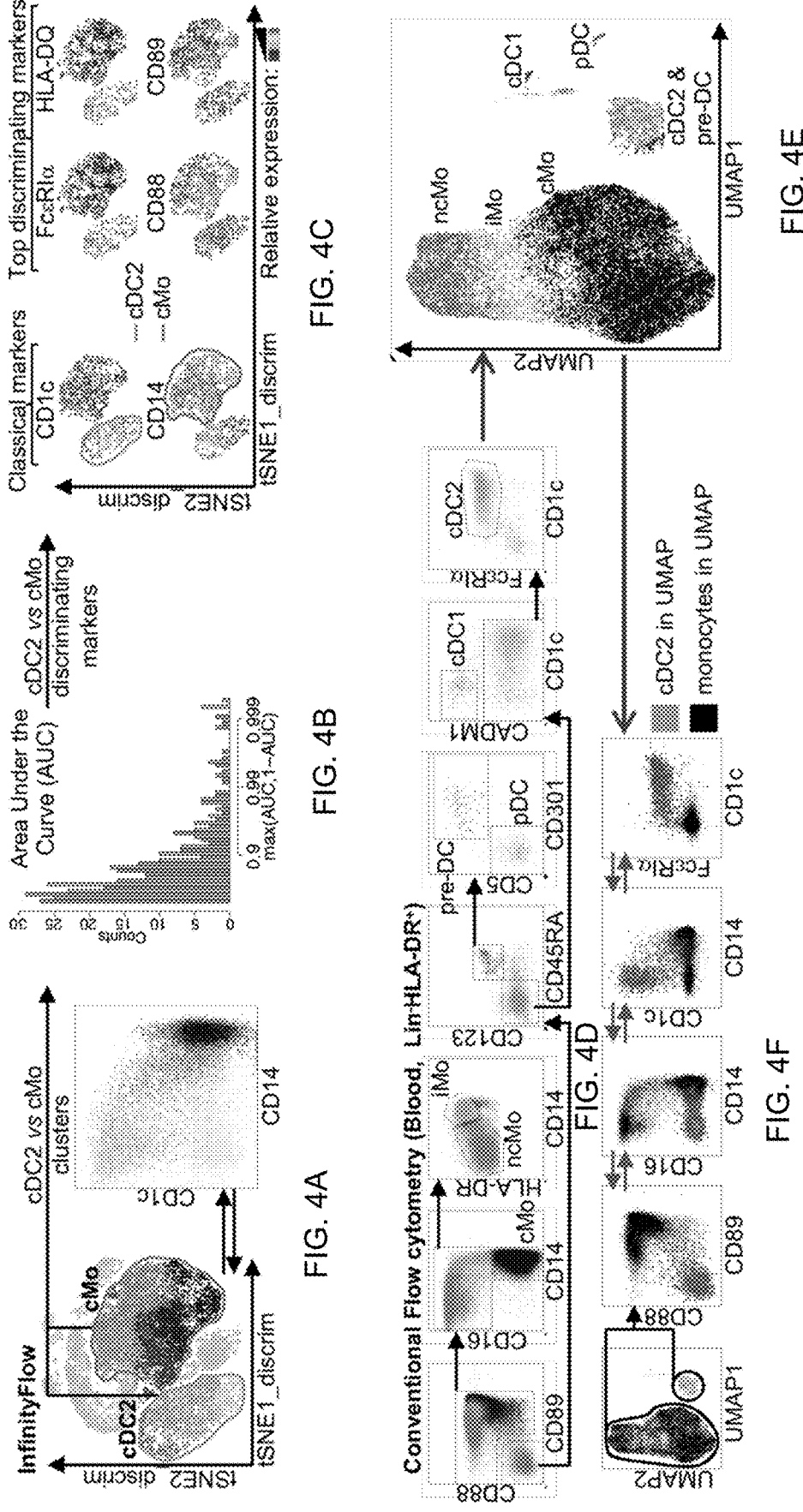
Figures 5A, 5B:
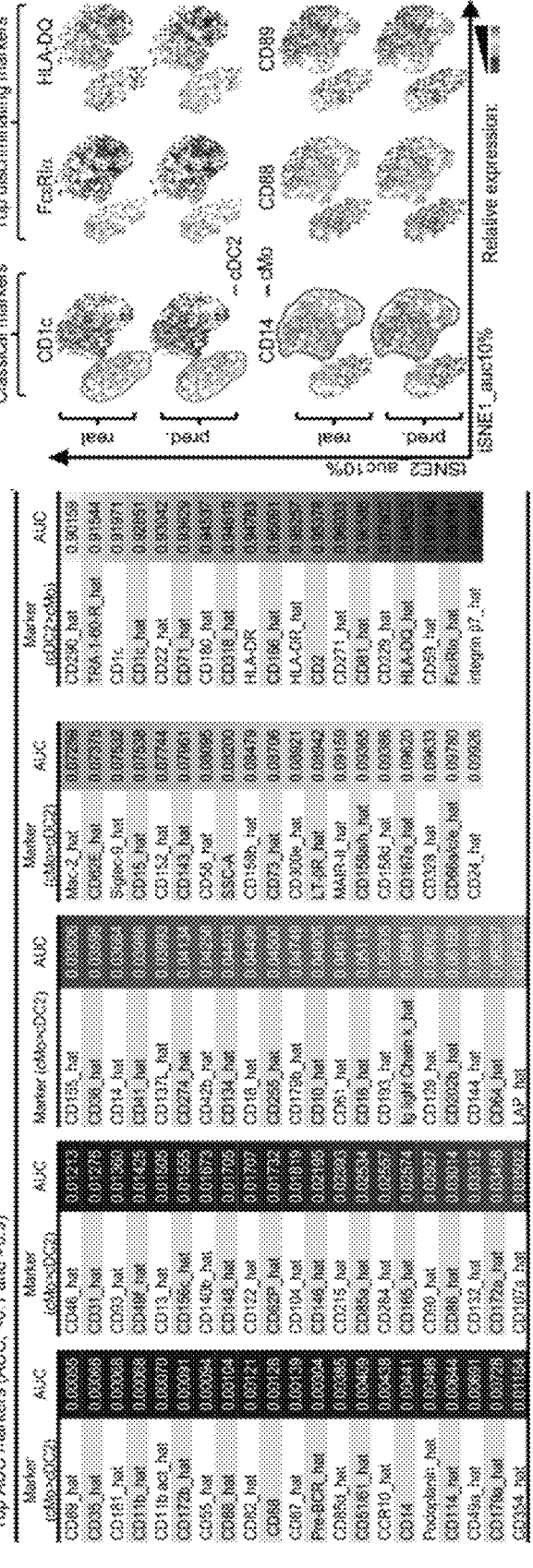

To identify the best markers to discriminate between cDC2 and cMo, Area Under the ROC Curve (AUC) statistics, which measures the overall specificity and sensitivity of a continuous variable to predict a binary one, was computed (FIGS. 4A-B and FIG. 5A). While the commonly used cDC2 and cMo markers (CD1c and CD14 respectively) showed variable expression among cDC2, AUC analysis revealed several more resolutive markers, including Fc$\epsilon$RI$\alpha$ and HLA-DQ as the best markers expressed by all cDC2, and CD88 and CD89 restricted to cMo (FIG. 4C and FIGS. 5B-D).

A recent study addressed the heterogeneity of human blood monocytes and subsetised them into 8 clusters among which, cluster #8 comprised CD14$^+$CD163$^+$CD1c$^+$ cells that bound IgE, most probably through the IgE-Fc receptor (Fc$\epsilon$RI$\alpha$). Interestingly, when applying a similar gating strategy (the "slan" marker being absent from the analysis, the inventors gated on CD16$^+$CD14$^{lo}$ monocytes to approximate Slan$^+$ monocytes, FIG. 5E), the InfinityFlow pipeline revealed that the cluster #8 cells in the study corresponded to CD14$^+$cDC2 (FIG. 5F).

To confirm that CD1c$^{lo}$CD14$^{hi}$ cells were phenotypically related to cDC2 and not to cMo using real and not predicted protein expression, a Principal Component analysis (PCA) of the cells that fell in between cDC2 and cMo using the 14 backbone markers was carried out (FIGS. 5G-J). The PC1 dimension, which explained the progression from cDC2 to cMo, was divided into 40 bins each containing 2.5% of the cells. These 40 bins were then processed by tSNE/Phenograph using their mean fluorescence intensity of the 332 predicted dimensions. The data confirmed that bins containing CD1c$^{lo}$CD14$^{hi}$ cells (Phenograph cluster #2) were connected to cDC2 bins (Phenograph #1) and distant from cMo bins (Phenograph #3) (FIGS. 5I-J). Combining these discriminating markers by conventional FACS allowed clear delineation of Fc$\epsilon$RI$\alpha$$^+$CD1c$^{+/lo}$ cDC2 from CD88$^+$CD89$^+$CD14$^+$ cMo, by both manual gating and the UMAP (Uniform Manifold Approximation and Projection for Dimension Reduction) dimensionality reduction algorithm (Becht et al., 2018; McInnes et al., 2018) (FIGS. 4D-F and FIG. 5K). Note that by manual gating, some cells falling in the cDC2 population (UMAP space) were defined as cMo (black), confirming that unsupervised analysis outperforms classical manual gating (FIGS. 4E-F).

To validate the findings in tissues other than blood, the inventors analyzed human blood, spleen and tonsil by Cytometry by Time-of-Flight (CyTOF). Using the discriminating markers mentioned above, it was found that cDC2 formed a clearly delineated population independent of monocytes/macrophages in these three tissues (FIGS. 4G-H and FIG. 5L). Although all cells from each MNP subset (e.g. cDC2) from all tissues were regrouped in independent clusters in the tSNE space, they showed some phenotypic variation in-between tissues but the discriminating marker expression patterns were conserved across tissues (FIG. 4I and FIGS. 5M-O). The top cDC2 and cMo discriminating markers, Fc$\epsilon$RI$\alpha$/HLA-DQ and CD88/CD89 respectively, were expressed and remained discriminating in both the spleen and tonsil.

Figures 4J, 4K, 4L:
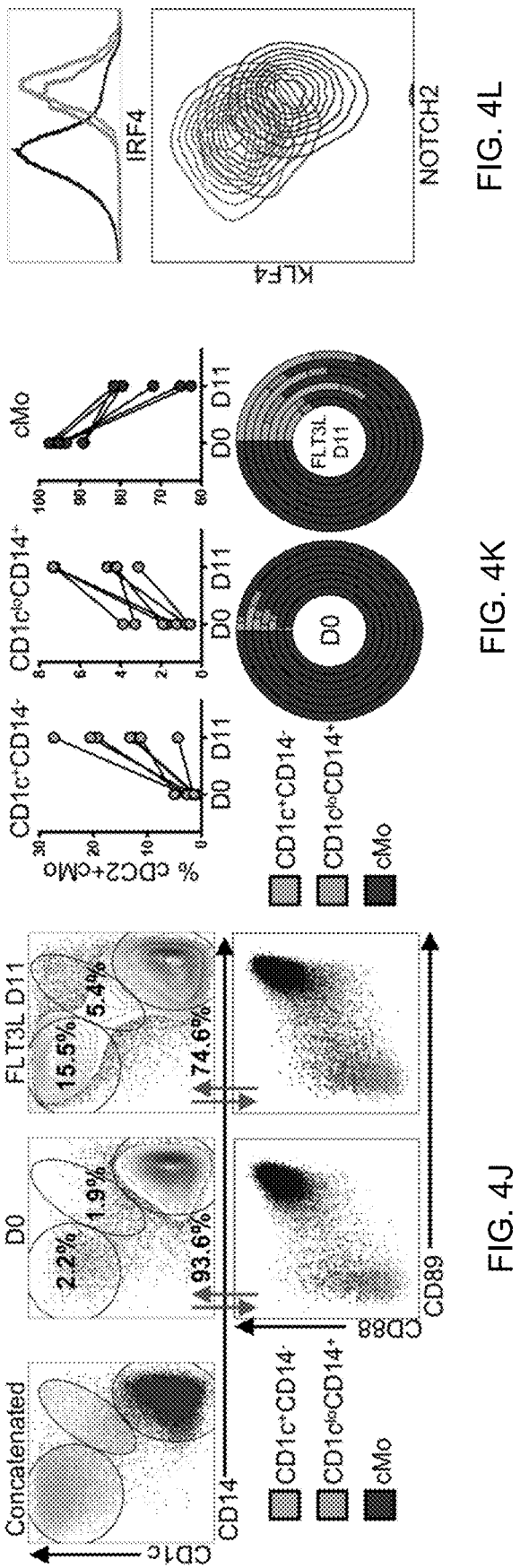

CD1c$^{lo}$CD14$^+$cDC2 are FLT3L-Dependent and Clearly Delineated from Monocytes A hallmark of cDC2 compared to monocytes is their dependency on FLT3 ligand (FLT3L) and transcription factors including IRF4 and KLF4 for differentiation and proliferation. Analysis of seven patients that received FLT3L treatment (see Star Methods for patient information), showed that the proportions of both CD1c$^+$CD14$^-$ and CD1c$^{lo}$CD14$^+$cDC2 (both being CD88$^{lo/-}$CD89$^{lo/-}$) were dramatically increased while the proportion of CD14$^{hi}$CD1c$^-$ cMo was reduced (FIG. 4J-K and FIG. 5P) compared to before having received FLT3L (DO). In addition, cMo exhibited low expression of the cDC2-specific IRF4 transcription factor that was highly expressed by CD1c$^+$CD14$^-$ and CD1c$^{lo}$CD14$^+$cDC2 and the latter cells also expressed lower KLF4 and higher NOTCH2 than CD1c$^+$CD14$^-$ cells (FIG. 4L). These findings are consistent with the functionally distinct murine cDC2 subsets defined in another study.

To further clarify the relationship between CD1c$^+$CD14$^+$ cells, cDC2 and cMo at the gene expression level, the inventors index-sorted all blood cDC and monocytes from the Lin$^-$HLA-DR$^+$ gate and analyzed the cells by single-cell RNA sequencing (scRNAseq) (FIGS. 6A-B). The indexed (FACS) data from sorted cells was processed together with the FACS data of the full sample using tSNE showing the distribution of sorted cells among DC subsets and monocytes (FIG. 7A and FIG. 6C). Here, 89% of sorted cells qualified for scRNAseq (SMARTseq2) and data analysis with the Seurat pipeline, and the Phenograph clustering algorithm identified eight cell clusters (FIGS. 7B-C and FIG.

6D). Based on clusters' differentially expressed gene (DEG) and protein (indexed) expression, all previously defined DC and monocyte subsets were identified, including cDC2 (clusters #2 and #4), monocytes (clusters #1 and #3, CD14$^{hi}$CD16$^-$; and cluster #7, CD16$^+$ monocytes), and a population of contaminating cells expressing natural killer (NK) cell signature genes (GZMH, NKG7 and GNLY) and at the protein level had a typical CD16$^{+/-}$HLA-DR$^{lo}$ NK cell phenotype (cluster #5; FIGS. 7C-D and FIG. 6F).

Next, it was addressed whether CD1c$^{lo}$CD14$^+$ cells were related to cDC2 rather than to monocytes at the transcriptome level, as observed by the high dimensional protein expression analysis (FIGS. 4A-I). Here, manual gating of DC subsets and monocytes was carried out using the indexed protein expression data. The inventors first confirmed the identity of the cell clusters obtained by the Seurat/Phenograph scRNAseq data analysis, and secondly demonstrated that CD1c$^{lo}$CD14$^+$ cells were detected among cDC2 cluster #4 and were distinct from monocytes, thus confirming the protein-level findings at the RNA level (FIGS. 7E-F, FIG. 6E and FIG. 6G).

Figures 6H, 6I, 6J, 6K, 6L, 6M:
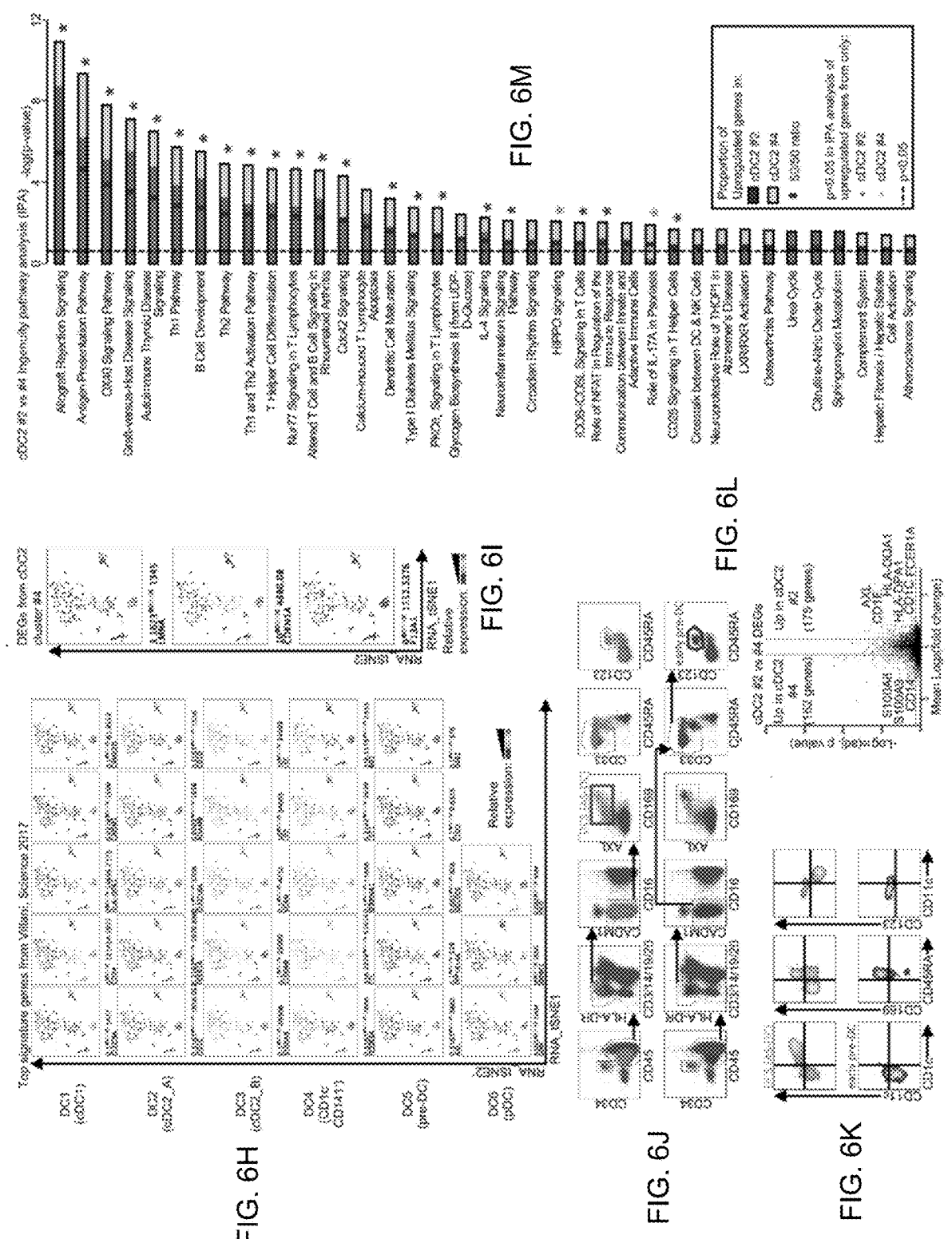

Villani et al. recently proposed a new classification of human blood MNP, identifying six DC (DC1 to DC6), among which DC2 and DC3 were defined as two cDC2 subsets, and four monocyte (Mono1 to Mono4) subtypes by scRNAseq (Villani et al., 2017). It was found that the signature genes for DC1, DC2, DC5 (AXL$^+$SIGLEC6$^+$AS-DC) and DC6 identified by Villani et al. were enriched in cells defined here as cDC1, cDC2 (more in cluster #2 then #4), pre-DC and pDC, respectively. The highest expression of signature genes of DC3 (subset of cDC2) was detected in cMo cluster #1 and at also at a lower level in cDC2 #4. DC4 signature was the highest in CD16$^+$ monocytes but not detected in any DC (FIGS. 7G-H and FIG. 6H). The fact that Villani et al. defined the DC signature by comparing them to the other DC and not to monocytes could explain the high expression of monocyte-related genes by DC3, but the results indicate that DC4 could correspond to CD16$^+$ monocytes. The inventors also compared how early pre-DC and DC5 (AS-DC) were defined by See et al. and Villani et al., respectively (See et al., 2017; Villani et al., 2017) by conventional flow cytometry. AS-DC indeed comprised most pre-DC but also included CD45RA$^+$CD123$^{lo}$CD1c$^+$ pre-cDC2 and AXL$^+$CD45RA$^-$CD1c$^+$cDC2 (FIGS. 6J-K). The inventors next looked at the expression of signature membrane protein markers of DC1 to DC6, as defined at the RNA level by Villani et al (FIG. 7I). While DC1 (cDC1), DC2 (subset of cDC2), DC5 (AS-DC) and DC6 (pDC) markers were highly expressed by cDC1 (CLEC9A, BTLA, CD135), cDC2 (CD1c, CD1d, FcεRIα), pre-DC (CD22, CD5, CD169) and pDC (CD85g, CD303, CD123), respectively, signature markers of DC3 (subset of cDC2; CD163, CD14, CD36) were expressed at a higher level by cMo and a subset of cDC2. The expression of DC4's (CD1c$^-$CD141$^-$DC; CD16, CD85d, CD88) signature markers was restricted to monocytes and was the highest in CD16$^+$CD14$^{lo}$ ncMo, confirming the indexed-scRNAseq-based findings. Taken together, the RNA and protein data suggest that DC4 are CD16$^+$ monocytes while DC3 may be related to cMo.

However, Villani et al., defined DC3 signature genes by comparing DC subsets with each other but not to monocytes, which could explain why their signature comprises mostly monocyte-related genes, such as S100A8, S100A9 and CD14. Because cDC2 clusters #2 and #4 were more enriched in DC2 and DC3 signature genes in the analysis, respectively (FIGS. 7G-H and FIG. 6H), the inventors first performed a DEG analysis comparing clusters #2 and #4 and then a DEG analysis between cluster #4 and all other cells. In this way, new, specific cluster #4 (related to DC3) signature genes, including LMNA, CDKN1A and F13A1 (FIG. 6I) were revealed. As compared to cDC2 cluster #2, cDC2 from cluster #4, that correlate with Villani et al.'s DC3, expressed more monocyte-related genes, including CD14, S100A8 and S100A9 and were enriched for genes involved in the "role for IL-17A in Psoriasis" pathway. cDC2 from cluster #2, that correlate with Villani et al.'s DC2, expressed more genes of professional antigen presenting cells, including MHC-II molecules, and were enriched for genes involved in many DC-related pathways including the "antigen presentation" and the "Th1" and "Th2" pathways (FIGS. 6L-M). It was also confirmed that the Mono1 and Mono3 signature genes identified by Villani et al. corresponded to cMo and that Mono2 corresponded to CD16$^+$ monocytes. Mono4 signature genes were detected only in cluster #5, which comprised contaminating NK cells (FIGS. 7G-H).

cDC2 are Phenotypically, Functionally and Molecularly Heterogeneous

Figures 8A, 8B, 8C, 8D, 8E, 8F:
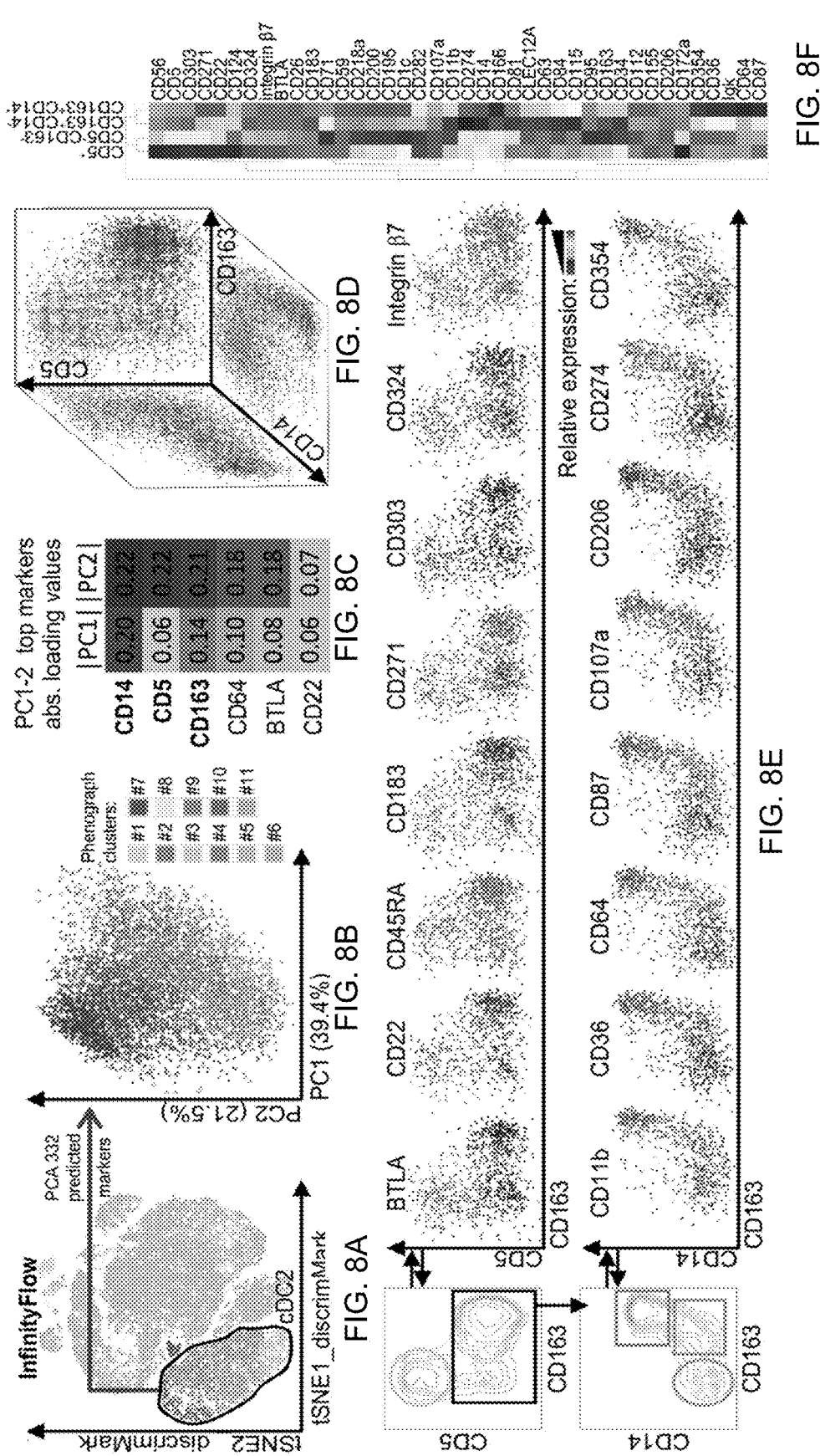
FIGS. 8A-H. High-dimensional analyses unravel heterogeneity of circulating cDC2.
Figures 8G, 8H:
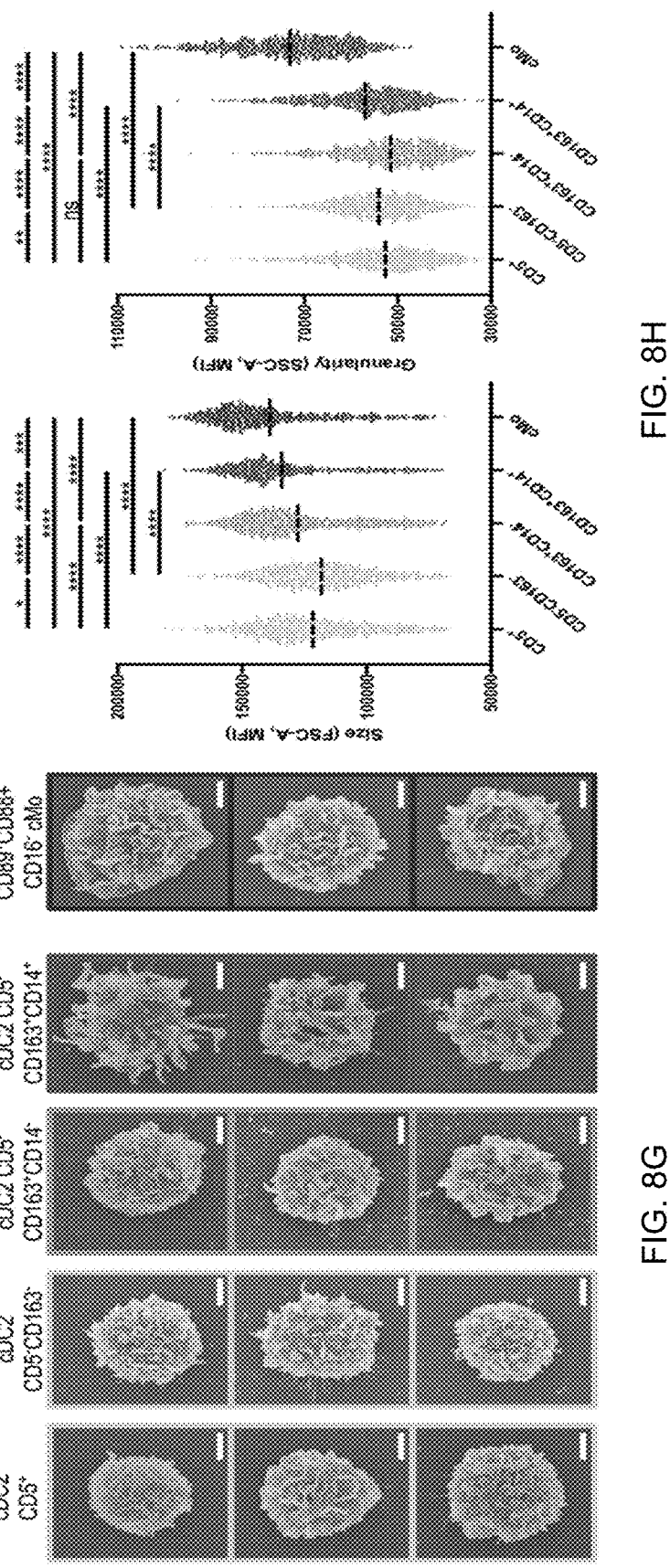
Figures 9A, 9B, 9C, 9D, 9E:
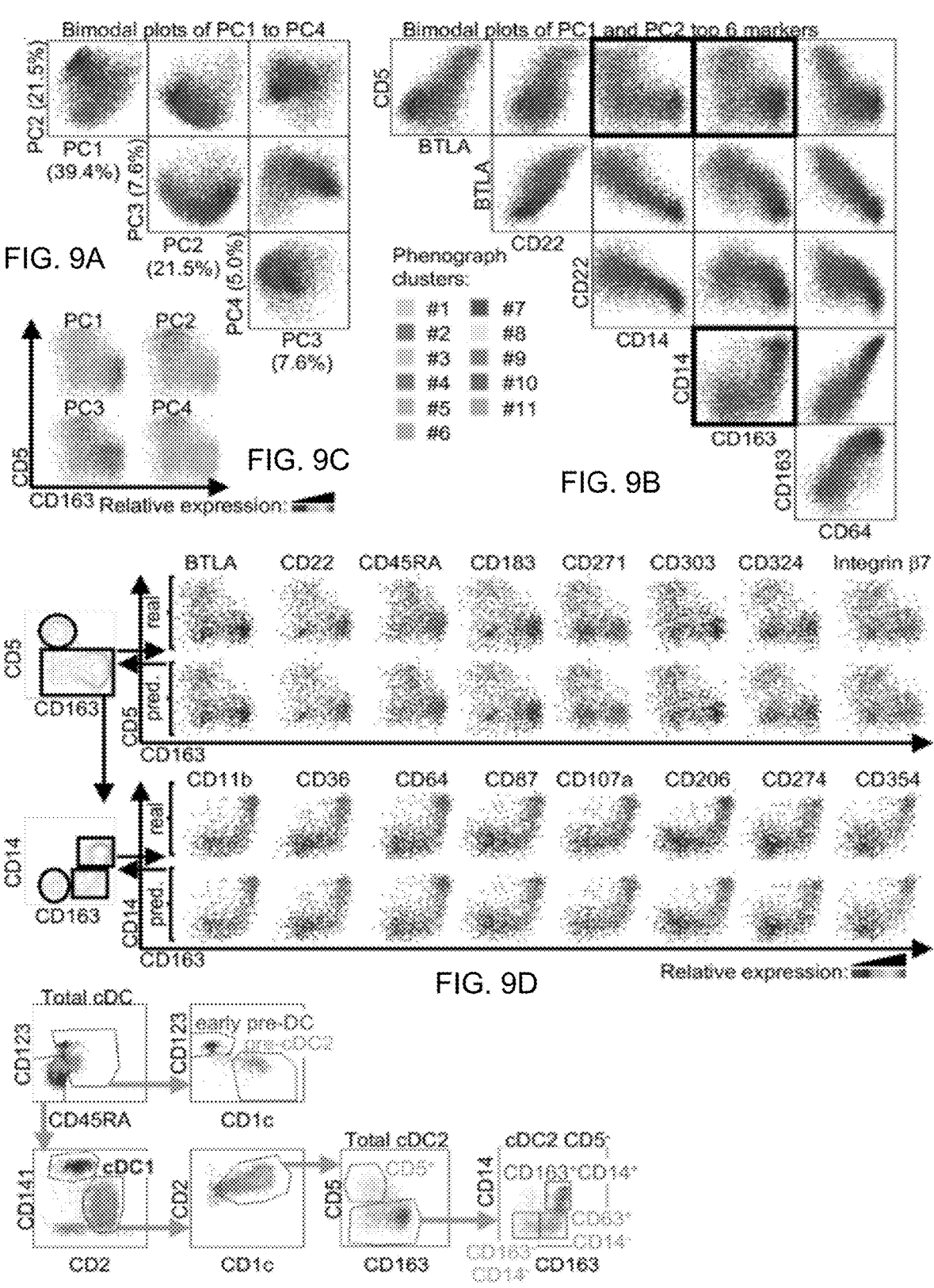
FIGS. 9A-M.

The study by Villani et al. unraveled cDC2 heterogeneity, and although they excluded CD14$^+$ cells in their gating strategy, it showed that this group of cells could be subdivided into two populations, DC2 and DC3. Since the inventors showed in the high dimensional protein (Infinity-Flow) and scRNAseq analyses that CD1c$^{lo}$CD14$^+$ cells are phenotypically related to cDC2 and not to monocytes, and comprised in the DC3-related subset of cDC2 (scRNAseq, cluster #4), the inventors aimed to address cDC2 heterogeneity in an unsupervised and unbiased manner. In the tSNE space obtained using the MNP discriminating markers from FIG. 1D, cDC2 was extracted and a PCA/Phenograph analysis using the 332 predicted markers (FIGS. 8A-B and FIG. 9A) was performed. This analysis revealed that CD14, CD5 and CD163 were the top three loading markers that explained the greatest variance of the first two principal components (PC; FIG. 8C and FIGS. 9B-C). CD5$^+$ cells were all CD163$^-$CD14$^-$ and showed the greatest expression of several markers also expressed by pre-DC and pre-cDC2 (FIGS. 8D-E, FIG. 9D). Three populations among CD5$^-$ cells were further identified: CD5$^-$CD163$^-$ cells, CD163$^+$CD14$^-$ cells and CD1c$^{lo}$CD163$^+$CD14$^+$ cells, which had the greatest CD163 expression, as well as several monocyte-related markers, including CD11b and CD64. Non-linear dimensionality reduction (UMAP, isoMAP) and pseudo-time (NBOR, Wishbone) analyses confirmed the phenotypic progression from CD5$^+$ cells, that expressed pre-DC-related markers, towards CD5$^-$CD163$^-$ cells, then towards CD163$^+$CD14$^-$ cells and finally CD163$^+$CD14$^+$ cells (FIGS. 9E-G and 9H-K). Some of these pre-DC-related markers were also defined in a previous study at the RNA level (FIG. 9L). Note that Wishbone, a branching pseudo-time analysis method, revealed only one branch starting from CD5$^+$ cells and finishing with CD163$^+$CD14$^+$ cells, suggesting that the cells represent a differentiation and/or activation continuum. The four defined cDC2 subsets each had a set of markers that they specifically highly expressed (FIG. 8F). Interestingly, scanning electron microscopy analysis showed that CD5$^-$CD163$^+$CD14$^+$ cells were the largest cells among cDC2 subsets and had a rougher and more granular membrane as compared to the others subsets and to CD88$^+$CD89$^+$CD14$^{hi}$CD16$^-$ classical monocytes, both characteristics being often associated to a greater activation/maturation (FIG. 8G, FIG. 9M. These observations were confirmed by their greater size and granularity as determined by respective forward (FSC-A, size) and side (SSC-A, granularity) scatter measured by flow cytometry (FIG. 8 H).

Figure 11A:
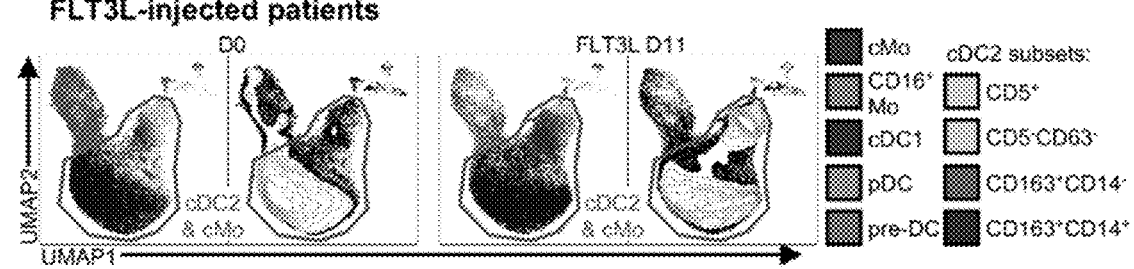
FIGS. 11A-E.

The FLT3L-dependency of these four cDC2 populations was also evaluated in vivo by profiling them in the blood of four FLT3L-injected patients (FIG. 10A and FIG. 11A). As compared to baseline (DO), cDC2 populations were all increased upon FLT3L injection (D14) as compared to CD14$^{hi}$CD1c$^-$ cMo, whose proportion was reduced.

Bulk RNAseq of the four cDC2 subsets was next carried out to evaluate their respective relationship with DC2 and DC3 (cDC2 subsets) described by Villani et al. (Villani et al., 2017). The phenotypic progression between cDC2 subsets (see FIGS. 9H-K) was also observed at the RNA level: Connectivity map (cMAP) analysis of bulk RNAseq on the cDC2 subsets showed a strong enrichment of Villani's DC2 gene signature in CD5$^+$cDC2 while the three other CD5$^-$ cDC2 subsets had a DC3 gene signature whose cMAP score progressed from CD5$^-$CD163$^-$ to CD163$^+$CD14$^-$ and was maximized in CD163$^+$CD14$^+$ cells (FIG. 10B). PCA followed by UMAP using the 10 first PCs analysis of these bulk RNAseq data showed that CD5$^+$ cells were regrouped while CD5$^-$ subsets were also regrouped but progressed from CD5$^-$CD163$^-$ to CD163$^+$CD14$^-$ cells and finally to CD163$^+$ CD14$^+$ cells, confirming the DC2 versus DC3 signatures of CD5$^+$cDC2 versus the three CD5$^-$cDC2 subsets, respectively (FIG. 10C). Furthermore, in the scRNAseq analysis (FIGS. 7B-H), all CD5$^+$cDC2 were detected only in cDC2 cluster #2 that is related to Villani's DC2. The cMAP analysis and the observation of two clear clusters of cDC2 in the UMAP space confirmed the DC2/DC3 subsetization of cDC2: One cluster comprised only CD5$^+$ cells thus corresponding to DC2, while the three CD5$^-$ subsets formed a cluster corresponding to DC3. From now on, CD5$^+$ cells will be qualified as DC2, while CD163$^-$CD5$^-$, CD5$^-$ CD163$^+$CD14$^-$ and CD5$^-$CD163$^+$CD14$^+$ cells will be qualified as DC3.

Figure 11B:
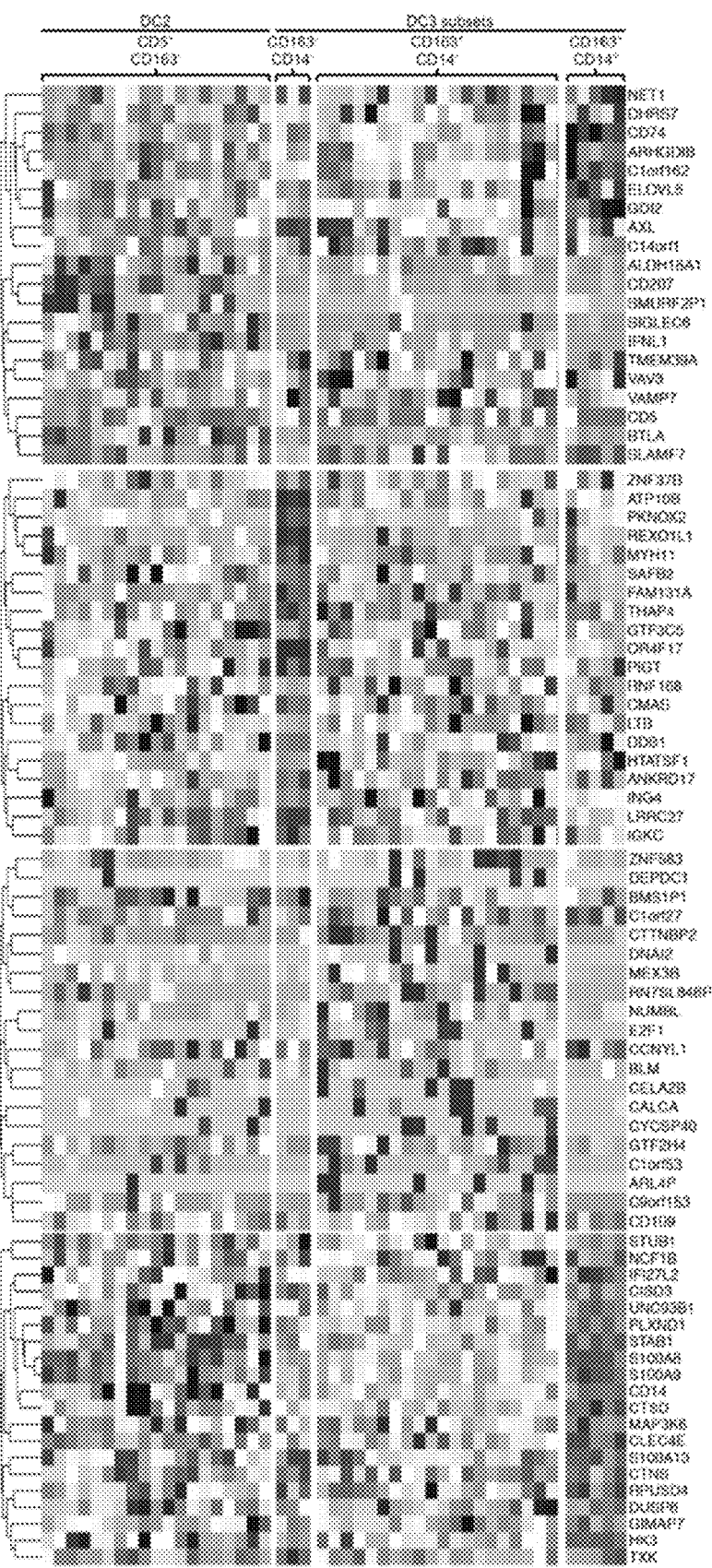

Note that these four subsets each had specific, highly expressed genes such as CD74 (MHC-II invariant gamma chain) and the pre-DC-related genes AXL, SIGLEC6 (CD327), CD5 and BLTA (as reported in (Villani et al., 2017)) for CD5$^+$ DC2, LTB (Lymphotoxin-β) for CD5$^-$ CD163$^-$ DC3, CD109 for CD163$^+$CD14$^-$ DC3 and the monocyte-related genes S100A8, S100A9 and CD14 for CD163$^+$CD14$^+$ DC3 (FIG. 10D, FIG. 11B and Tables S3).

Figure 11C:
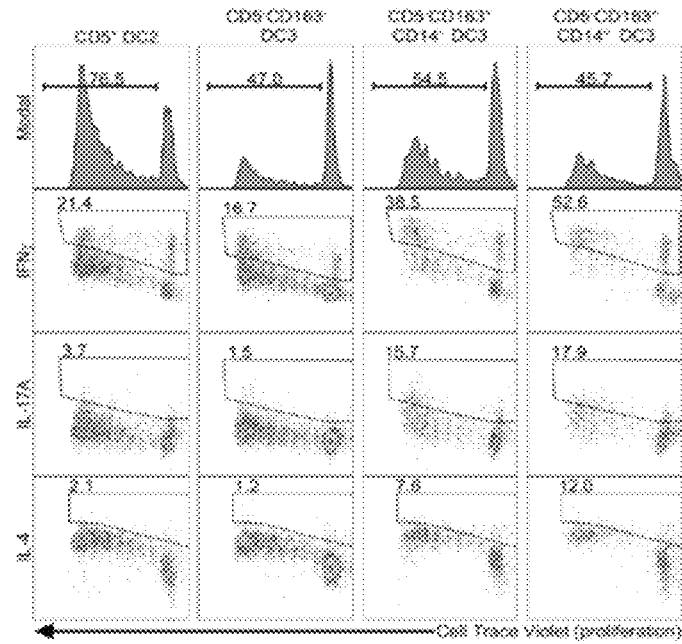
Figure 11D:
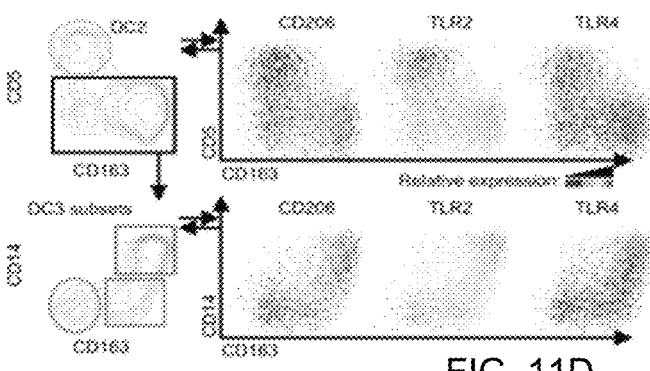

DC are the only cells able to activate and polarize naïve T cells. The inventors thus co-cultured allogeneic naïve CD4$^+$ T cells with DC2 and DC3 subsets to evaluate their potential functional specialization (FIG. 10E and FIG. 11C). While all subsets induced similar degrees of proliferation and Th1 polarization (IFNγ+) of CD4$^+$ T cells, their capacity to induce IL-4$^+$ (Th2) and IL-17$^+$ (Th17) CD4$^+$ T cells progressively increased from CD163$^-$ (both CD5$^+$ DC2 and CD5$^-$CD163$^-$CD14$^-$ DC3) to CD163$^+$CD14$^-$ DC3 and finally CD163$^+$CD14$^+$ DC3. This higher Th17 polarizing capacity of CD163$^+$ DC3 (which was the highest for CD163$^+$CD14$^+$ DC3) confirmed the pro-Th17 signature observed in cDC2 cluster #4 (DC3) that was enriched in the CD14$^+$ DC3 subset of cDC2 (FIG. 6M). Interestingly, a study previously identified pro-Th17 inflammatory DC (inflDC) in ascites from patients with breast cancer, which were described as being monocyte-derived based on their gene signature that strongly correlated with that of in vitro monocyte-derived DC. Given the strong Th17 polarizing capacity of CD163$^+$CD14$^+$ DC3, it was hypothesized that they could correspond to circulating inflDC genes but would be related to cDC2 rather than monocytes. Strikingly, the only cells that strongly expressed inflDC-specific genes were CD14$^+$cDC2 (subset of DC3) (FIG. 10F and Table S2). Putative "inflammatory" blood CD14$^+$cDC2 also had the highest expression of CD206, TLR2 and TLR4, which were described as being highly expressed in inflDC. (FIG. 11D).

Figure 11E:
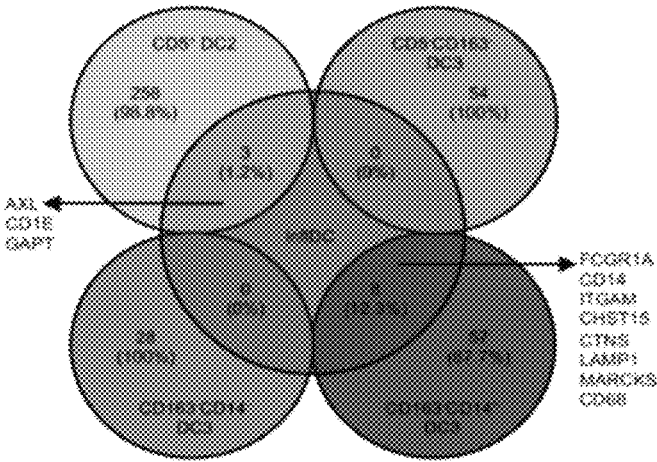

The inventors next carried out a pathway analysis of the cDC2 subset bulk RNAseq data of FIG. 10B-D. cDC2 subsets were enriched for genes involved in different pathways, with CD5$^+$ DC2 pathways partially overlapping with cDC2 cluster #2 (related to DC2) from FIGS. 7B-C. CD163$^+$ CD14$^+$ inflammatory DC3 shared 12.3% of their specific DEG with those of the described inflDC, while the three other subsets had no or only minimal overlap with inflDC (FIG. 11E). CD163$^+$CD14$^+$ inflammatory DC3 were also enriched in genes involved in "dendritic cell maturation", "production of nitric and reactive oxygen species (NOS and ROS) in macrophages", "phagosome formation", "death receptor signaling", "inflammasome pathway", "autophagy" pathways, as well as "Systemic Lupus Erythematosus (SLE) Signaling", indicating their putative role in this disease (FIG. 10G).

Altogether, the high dimensional, single cell protein and RNA data analyses revealed a previously underestimated heterogeneity of blood cDC2. The inventors delineated, in an unbiased manner, blood inflammatory CD1c$^{lo}$CD14$^+$ cells (circulating inflDC) that were not included in the DC3 subset described by Villani et al., because CD14$^+$ cells were excluded from their analysis.

Highly Activated CD163$^+$ DC3 Accumulate in the Blood of Lupus Patients

Figures 12A, 12B, 12C, 12D:
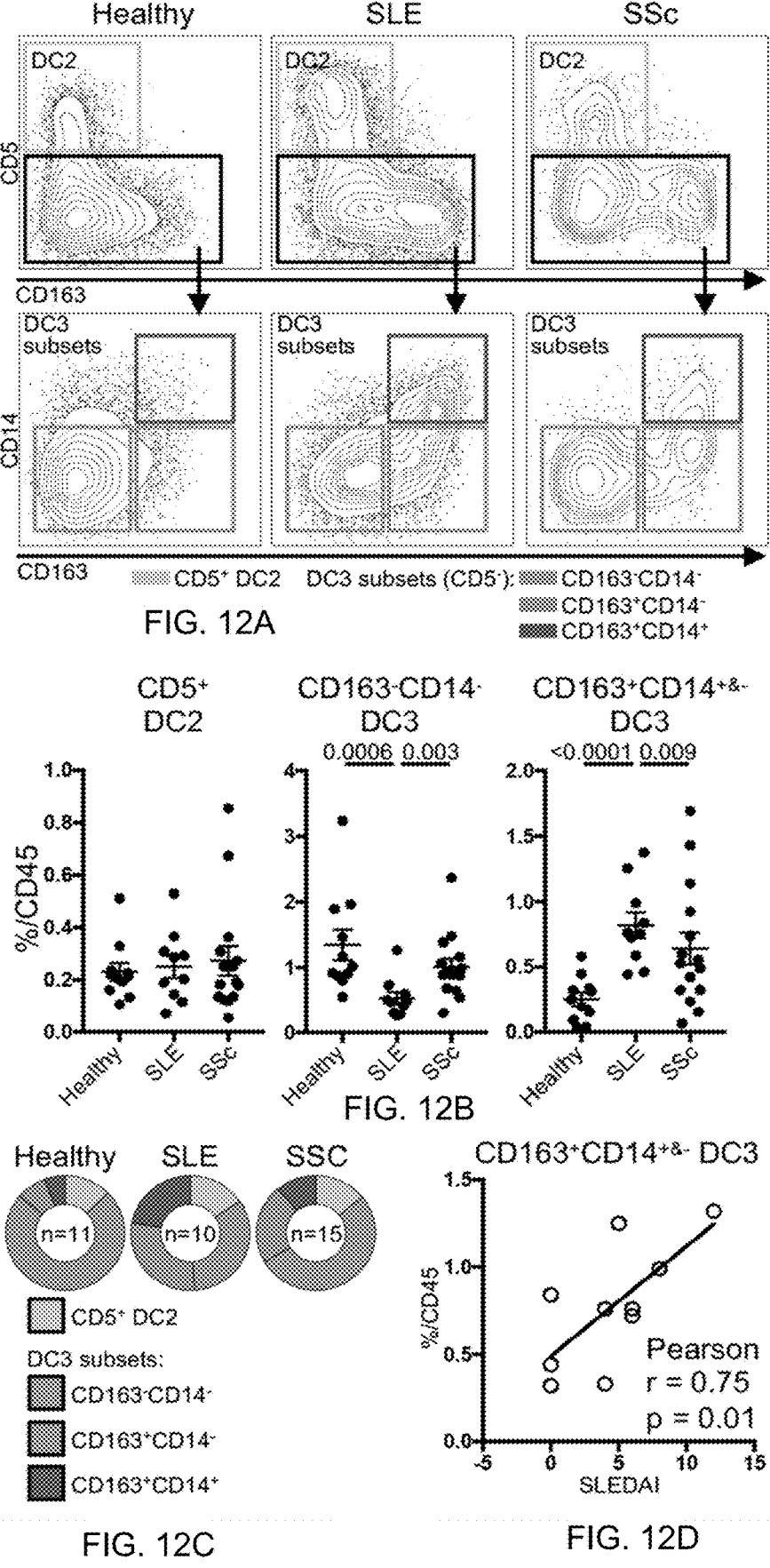
FIGS. 12A-H. CD5$^-$CD163$^+$ DC3 accumulate in patients with Systemic Lupus Erythematosus (SLE).

DC can either induce adaptive immune responses or maintain tolerance, and autoimmunity occurs when this balance is lost. Interestingly, one of the top pathways identified from the bulk RNAseq of the cDC2 subsets was the "SLE Signaling" pathway in inflammatory CD14$^+$ DC3. The inventors thus evaluated the involvement of the newly defined cDC2 subsets in the blood of patients with SLE as compared to healthy subjects and patients with Systemic Sclerosis (SSc), another systemic autoimmune disease (see Materials and Methods for patient information). While the proportion of CD5$^+$ DC2 was comparable across all subjects, among CD5$^-$ DC3, a significant increase in total CD163$^+$ DC3 (both the CD14$^-$ and CD14$^+$ subsets) was observed, mirrored by a decrease in CD163$^-$ DC3 only in SLE patients (FIGS. 12A-C and FIGS. 13A-B). Importantly, the proportion of circulating CD163$^+$ DC3 significantly correlated with the SLE Disease Activity Index (SLEDAI, disease score) in SLE patients (FIG. 12D and FIG. 13C). SLE patient CD163$^+$ DC3 also showed increased expression of CD163 (a scavenger receptor) and CD169 (a type I interferon (IFN-I)-inducible marker), which were the highest on CD163$^+$CD14$^+$ DC3 (FIG. 12E).

Figures 12E, 12F:
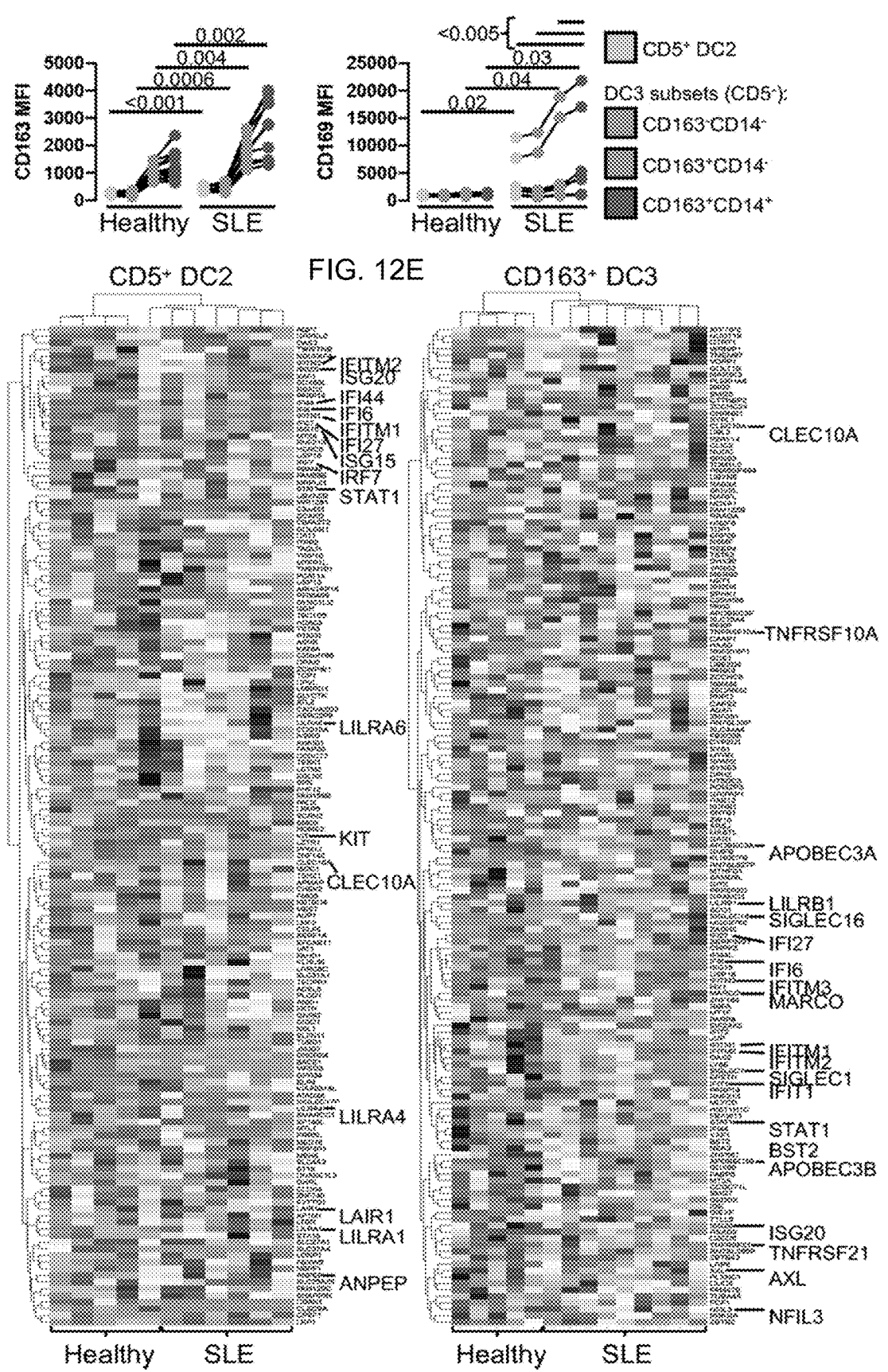
Figures 12G, 12H:
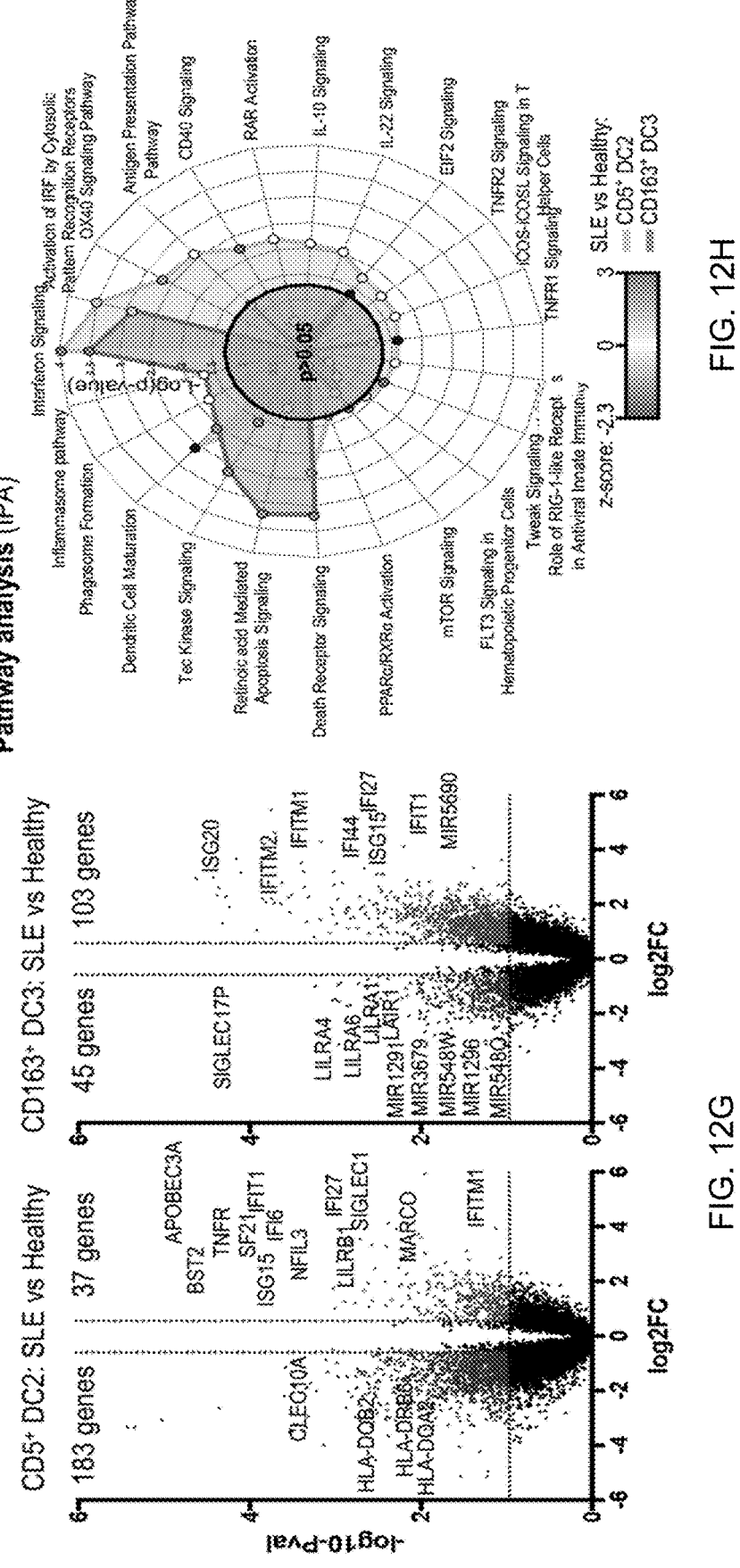

The inventors carried out bulk RNAseq only on circulating CD5$^+$ DC2 and CD163$^+$ DC3, which could be sorted from healthy subjects and SLE patients in sufficient numbers for analysis (FIG. 12F-H). When comparing healthy subjects and SLE patients, most of the genes upregulated in SLE CD5$^+$ DC2 were IFN-I stimulated genes (ISG), but the vast majority of DEG were reduced in SLE patients (FIGS. 12F-G and Table S3). This finding was in stark contrast to CD163$^+$ DC3 that showed a vast majority of upregulated genes in SLE patients, including ISG, but also several pro-inflammatory molecules, including TNFRSF10A (CD261/TRAIL-R1), LILRB1 (CD85j/ILT2) and TNFRSF21 (CD358/Death Receptor 6).

The higher maturation and activation state of CD163$^+$ DC3 in SLE patients were confirmed by pathway analysis, which showed a strong activation (positive z-score) of the "Death Receptor Signaling" and "Dendritic Cell Maturation" pathways (FIG. 12H). This latter pathway was also significant but strongly inhibited (negative z-score) in CD5$^+$ DC2. Pathway analysis also confirmed that most significant pathways of SLE CD5$^+$ DC3 were inhibited (negative z-score), and that strong positive activation of "Interferon (IFN-I) signaling" occurred in both CD5$^+$ DC2 and CD163$^+$ DC3. The overall inhibition of CD5$^+$ DC2 paralleled by the strong activation of CD163$^+$ DC3 in SLE patients underscores that cDC2 cannot be analyzed as a whole but must be considered individually as subsets to understand their role in the physiopathology of any disease.

CD14$^+$ DC3 Become Highly Pro-Inflammatory in a SLE Environment

Figures 14A, 14B, 14C:
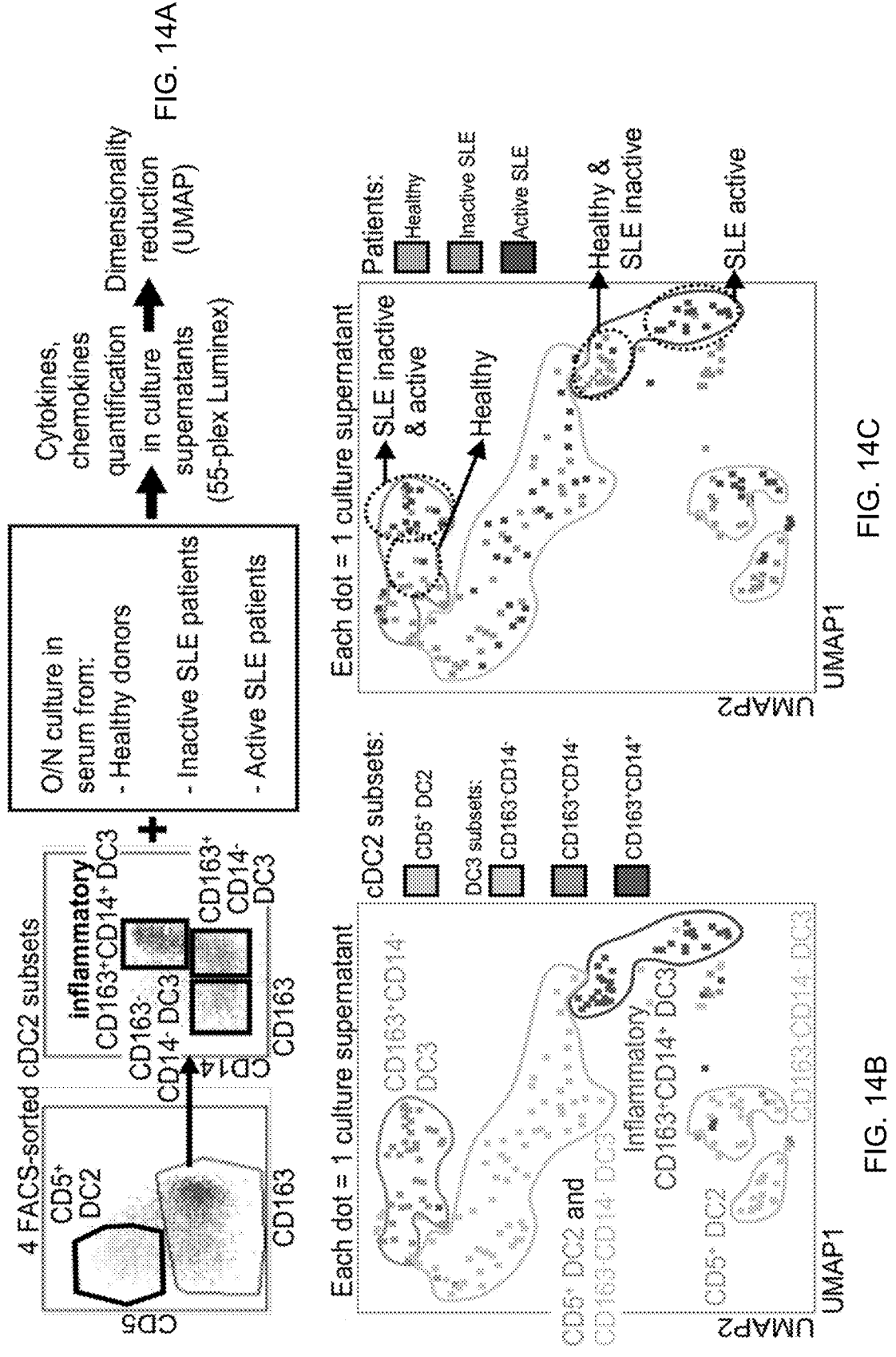
FIGS. 14A-E. Serum from patients with active SLE preferentially activates inflammatory CD163$^+$CD14$^+$ DC3.
Figures 14D, 14E:
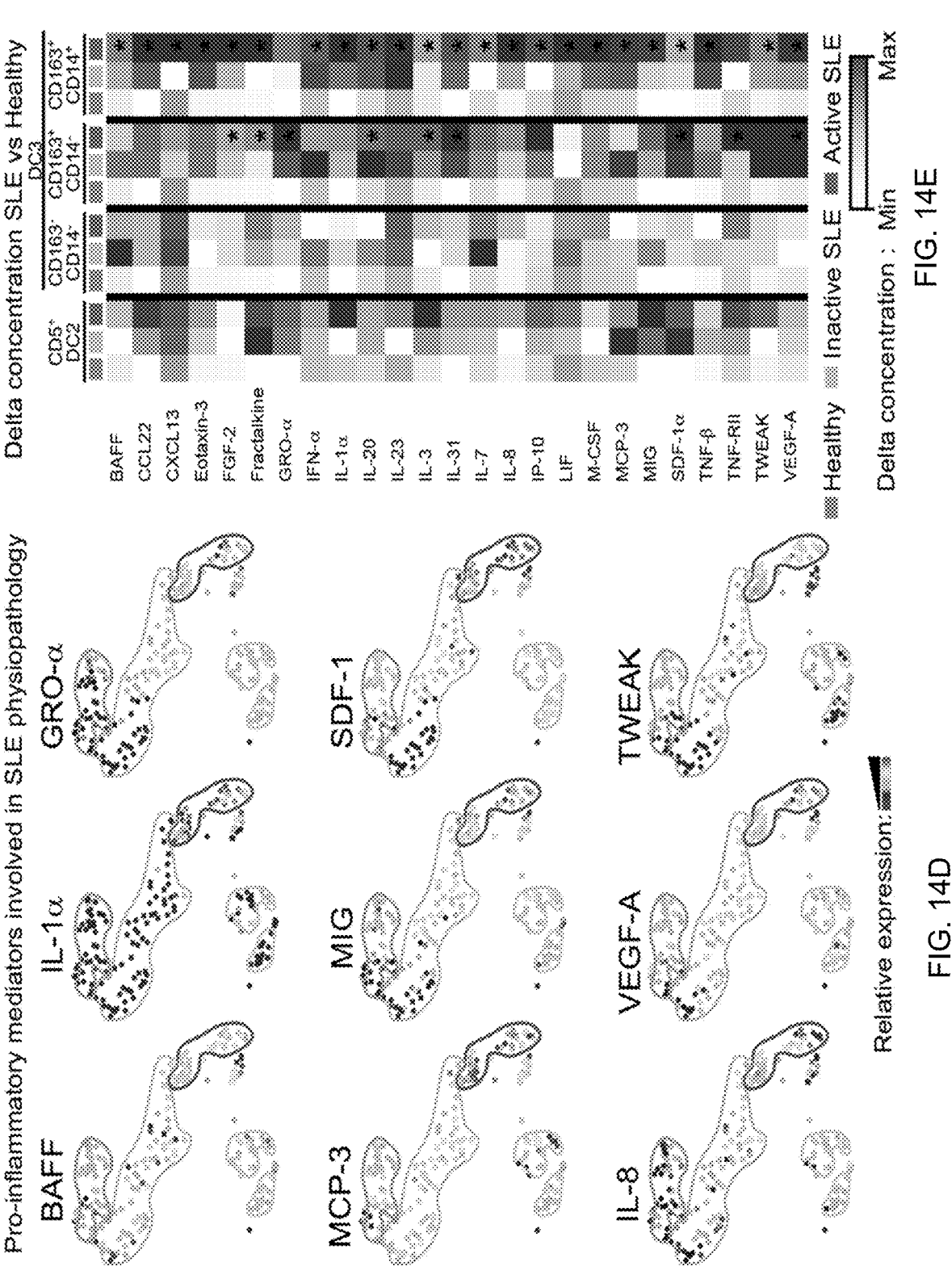

It was next addressed whether the SLE phenotype of healthy cDC2 subsets could be recapitulated in an SLE environment. The inventors first evaluated whether cDC2 subsets from healthy blood donors could be specifically activated when cultured in the presence of serum from inactive or active SLE patients or serum from healthy subjects (FIG. 14A). Unsupervised analysis using UMAP revealed that the secretomes of CD163$^+$CD14$^-$ DC3 and inflammatory CD163$^+$CD14$^+$ DC3 formed two independent clusters while those of CD5$^+$ DC2 and CD163$^-$CD14$^-$ DC3 were mostly regrouped (FIG. 14B), confirming the functional specialization of these cDC2 subsets. For both CD163$^+$ DC3 subsets, the secretomes further regrouped based on disease status, with sub-clusters comprising only secretomes obtained by culturing with active and inactive SLE (CD163$^+$CD14$^-$ DC3) and only active SLE (inflammatory CD163$^+$CD14$^+$ DC3) serum (FIG. 14C). Compared to cultures with serum from healthy subjects, only the two CD163$^+$ DC3 subsets significantly increased their secretory capacity when cultured with active SLE serum, especially inflammatory CD163$^+$CD14+DC3, which secreted more pro-inflammatory mediators known to participate in SLE physiopathology, such as BAFF, IL-1α, GRO-α (CXCL1), MCP-3 (CCL7), MIG (CXCL9), SDF-1 (CXCL12), IL-8, VEGF-A and TWEAK (FIGS. 14D-E and FIG. 13D). These data reaffirm that cDC2 should not be studied as a whole, because when exposed to a pathologic environment (e.g. serum from SLE patients), cDC2 subsets show striking functional differences in their responses: both CD163$^+$ DC3 subsets, and particularly inflammatory CD163$^+$CD14$^+$ DC3, each show a specific and strong pro-inflammatory response.

Increased DC3 Detected in Diseased Samples

In the context of inflammatory skin disease, matched non-lesional and lesional (diseased) skin from Atopic dermatitis (AD) and Psoriasis (PSO) patients were analysed by flow cytometry revealing a significant increase of DC3 specifically in the lesional skin of PSO patients (FIG. 15A). Next, flow cytometry analysis of matched normal adjacent liver tissue and different tumour sectors from four Liver Hepatocellular carcinoma (HCC) cancer patients showed an increased proportion of CD14$^+$ inflammatory DC3 in the tumour of the four patients as compared to their matched normal adjacent liver (FIG. 15B). An increase of the frequency of DC3 in the blood in Systemic lupus erythematosus (SLE) patients was also observed as compared to healthy blood donors (FIG. 15C), an increase that did not occur in systemic sclerosis patients (SSc) patients, another systemic autoimmune disease.

DISCUSSION

Using high dimensional, single-cell protein and RNA expression analyses of human blood MNPs, the inventors have precisely delineated all MNP subsets and identified new markers to unambiguously define cDC2 and monocyte populations. The inventors have also unraveled cDC2 heterogeneity, revealing an FLT3L-responsive IRF4$^+$CD14$^+$ cDC2 subset that accumulates in the blood of patients with SLE and exhibits pro-inflammatory functions.

Villani et al. previously identified four monocyte (Mono1 to Mono4) and six DC (DC1 to DC6) populations in human blood (Villani et al., 2017). Mono1 and Mono3 corresponded to classical CD14$^+$CD16$^-$ monocytes (cMo), Mono2 to CD16$^+$ monocytes and Mono4 was proposed to constitute a previously undefined population. Back mapping this population onto the indexed-scRNAseq analysis revealed that Mono4 signature genes were exclusively expressed by a cluster of cells expressing GZMH, NKG7 and GNLY NK cell signature transcripts and thus the inventors identified them as CD16$^{+/-}$HLA-DR$^{lo}$ NK cells. In agreement with the conclusion, Gunther et al., who have established an updated consensus map of the human blood MNP system using indexed-scRNAseq (Günther, 2019), also concluded that the Mono4 population corresponded to HLA-DR$^-$CD16$^+$CD56$^-$ NK-cells, which likely contaminated the monocyte populations identified by Villani et al.

Concerning DC subsets, DC1 and DC6 identified by Villani et al. corresponded to the previously described cDC1 and pDC subsets, respectively, while DC2 and DC3 corresponded to two cDC2 subsets; the later cells expressed CD163 and were qualified as inflammatory DC. However, Villani et al. also identified two other previously un-described DC subsets: DC4 (CD141$^-$CD1c$^-$) and a rare DC5 (AXL$^+$SIGLEC6$^+$/AS-DC) subset. The present data confirmed the identity of DC1 as cDC1, DC2 and DC3 as cDC2 and DC6 as pDC. Gunther et al. also showed that pre-DC and DC5 overlapped in their map, but that DC5 represented a larger population that also overlapped with the DC2 subset of cDC2, as defined both by the gating strategies used by Villani et al. and See et al. It was also confirmed that DC5 signature genes were most highly expressed by pre-DC, but that DC5 also included pre-cDC2 and some AXL$^+$CD45RA$^-$ DC2 (FIGS. 6J-K), these later being also CD5$^+$ (data not shown). Concerning CD141$^-$CD1c$^-$ DC4, Villani et al. showed that these cells expressed CD14, C5AR (CD88, one of the top two monocyte markers) and FCGR3A (CD16). Gunther et al. reclassified these cells as CD16$^+$ non-classical monocytes (ncMo), which is in line with the indexed-scRNAseq data showing enrichment of DC4 signature genes in CD16$^+$ monocytes. This finding is also in agreement with a recent report that proposed that DC4 rather correlated with a subset of CD14$^{dim/-}$CD16$^-$ monocytes. Altogether, the findings regarding DC4 and Mono4 are in line with those of Gunther et al., who have demonstrated that these two cell types are CD16$^+$slan$^{+/-}$CD14$^{lo}$ ncMo and CD56$^-$ NK cells, respectively (Gunther, 2019).

In the indexed-scRNAseq data, Villani et al.'s top DC2 and DC3 signature genes mapped with cDC2 cluster #2 and cluster #4, respectively, that respectively contained all CD5$^+$ cDC2 and most CD14$^+$cDC2. Further, both the InfinityFlow protein expression and the bulk RNAseq analyses revealed that CD5$^+$cDC2 and the three subsets of CD5$^-$cDC2 showed the greatest expression of DC2 and DC3 protein and signature genes, respectively. Altogether, CD5$^+$cDC2 correspond to DC2 and CD5$^-$cDC2 (three subsets) correspond to subsets of DC3. Because Villani et al. stringently excluded CD14$^+$ cells to sort DC, they may have only captured a minor fraction of the inflammatory CD14$^+$ subset of DC3 defined here. Rather, the CD163$^+$ DC3 that Villani et al. qualified as "inflammatory" based on CD14 and S100A9 expression likely correspond to the minor CD163$^+$CD14$^-$ DC3 subset that the inventors defined. Here, in addition to extend the phenotypic characterization of this DC3 subset, the inventors functionally demonstrated the inflammatory nature of CD14$^+$ DC3, which are not only increased in number, but are also reprogrammed to enhance their pro-inflammatory function in the blood of patients with SLE. The inventors further demonstrated their pro-inflammatory potential because CD14$^+$ DC3 from healthy donors had a highly pro-inflammatory secretome triggered by the serum of patients with active SLE. Although CD163$^+$CD14$^-$ DC3 were also increased in the patient's blood, they secreted intermediate quantities of pro-inflammatory mediators, at a higher level than CD5$^+$ DC2 and CD163$^-$CD14$^-$ DC3 but at a lower level than inflammatory CD14$^+$ DC3. While CD5$^+$ cells were separated from the three other subsets in the UMAP analysis of the bulk RNAseq data, the three other CD5$^-$cDC2 subsets (DC3) were connected both at the protein and RNA levels and progressed from CD5$^-$CD163$^-$ to CD163$^+$CD14$^-$ and finally towards CD163$^+$CD14$^+$ cells, as confirmed by NBOR and Wishbone pseudo-time analyses. This progressive conversion was also suggested by the observation of an inversely correlated proportion of CD5$^-$CD163$^-$ and CD163$^+$CD14$^{+/-}$ DC3 in the blood of patients with SLE. These results confirmed that CD5$^+$ DC2 may represent an independent population corresponding to Villani et al.'s DC2 that differs from the CD5$^-$cDC2 (DC3) fraction (which rather contain populations at different stages of maturation and/or activation states). Future studies should aim to understand the relationship between these two populations in terms of their ontogeny and define whether CD5$^+$ cDC2 (DC2), which are molecularly and phenotypically related to pre-DC, can differentiate into CD5$^-$CD163$^{+/-}$ DC3 and finally into inflammatory CD163$^+$CD14$^+$ DC3.

A study previously described a population of inflammatory DC (inflDC), described as monocyte-derived, in ascites from patients with breast tumors that strongly promoted Th17 CD4$^+$ T-cell polarization. Interestingly, inflDC-specific genes mapped to CD14$^+$cDC2, with the latter being also the greatest Th17 inducers. Furthermore, cDC2 cluster #4 (indexed-scRNAseq data), which contained most CD14$^+$ DC3, were enriched in genes involved in the "Role of IL-17A in Psoriasis" pathway, confirming that in vivo, CD14$^+$ DC3 are programmed to favor Th17 polarization. It was also observed that CD14$^+$ DC3 have higher NOTCH2 and lower KLF4 expression compared to all the other cDC2. Another study also observed some heterogeneity among murine cDC2, with subsets expressing the KFL4 or NOTCH2 transcription factors that favor Th2 or Th17 polarization, respectively. Finally, all cDC2 subsets were shown to be responsive to FLT3L treatment; therefore, it was proposed that human inflammatory CD14$^+$ DC3 are not monocyte-derived, but rather belong to the DC lineage and could correspond to mouse NOTCH2$^+$cDC2. In contrast to the murine data, however, these cells also primed naïve CD4$^+$ T cells towards Th2; this CD4$^+$ T-cell polarization is a hallmark of SLE, which is a B-cell-driven disease. The pro-inflammatory nature of CD14$^+$ DC3 was also confirmed by their high expression of CD354 (TREM1) protein and enrichment in genes involved in the "TREM1 signaling pathway". Further studies should address the role of TREM1 in inflammatory CD14$^+$ DC3, as it amplifies inflammatory responses triggered by bacterial and fungal infections by stimulating the release of pro-inflammatory chemokines and cytokines, as well as increased surface expression of activation markers. Finally, inflammatory CD14$^+$ DC3 were also enriched in genes from the "TWEAK signaling pathway" and TWEAK is one of the multiple pro-inflammatory mediators involved in SLE immunopathology, which these cells secreted when cultured in the presence of active SLE patients' serum.

STAR Methods

| REAGENT or RESOURCE | SOURCE | IDENTIFIER |
|---|---|---|
| Key Resources Table | | |
| Antibodies | | |
| CADM1 (clone 3E1) Purified | MBL | Cat# CM004-3 |
| CD11b (clone M1/70) Biotin | BD Biosciences | Cat# 553309 |
| CD11c (clone B-Ly6) BV650 | BD Biosciences | Cat# 563404 |
| CD123 (clone 7G3) BUV395 | BD Biosciences | Cat# 564195 |
| CD135 (clone 4G8) BV711 | BD Biosciences | Cat# 563908 |
| CD14 (clone M5E2) BUV737 | BD Biosciences | Cat# 564444 |
| CD14 (clone M5E2) BV650 | BD Biosciences | Cat# 563419 |
| CD14 (clone BM-16) AF700 | Biolegend | Cat# 350124 |
| CD141 (clone AD5-14H12) APC | Miltenyi | Cat# 130-090-907 |
| CD16 (clone 3G8) APC/Cy7 | BD Biosciences | Cat# 302018 |
| CD16 (clone 3G8) BV650 | Biolegend | Cat# 563692 |
| CD163 (clone GHI/61) BV605 | Biolegend | Cat# 333616 |
| CD169 (clone 7-239) PE | BD Biosciences | Cat# 565248 |
| CD19 (clone SJ25C1) BV650 | BD Biosciences | Cat# 563226 |
| CD1c (clone L161) PercP/Cy5.5 | Biolegend | Cat# 331514 |
| CD1c (clone L161) BV421 | Biolegend | Cat# 331526 |
| CD1c (clone L161) PE/Cy7 | Biolegend | Cat# 331516 |
| CD2 (clone RPA-2.10) BV421 | BD Biosciences | Cat# 562639 |
| CD20 (clone 2H7) BV650 | BD Biosciences | Cat# 563780 |
| CD206 (clone 19.2) PE/CF594 | BD Biosciences | Cat# 564063 |
| CD268 (clone 11C1) PE/Dazzle594 | Biolegend | Cat# 316922 |
| CD3 (clone SP34-2) BV650 | BD Biosciences | Cat# 563916 |
| CD301 (clone H037G3) PE | Biolegend | Cat# 354704 |
| CD303 (clone AC144) Biotin | Miltenyi | Cat# 130-090-691 |
| CD33 (clone WM53) PE/CF594 | BD Biosciences | Cat# 562492 |
| CD34 (clone 581) AF700 | BD Biosciences | |
| CD45 (clone HI30) V500 | BD Biosciences | Cat# 560777 |
| CD45RA (clone 5H9) FITC | BD Biosciences | Cat# 556626 |

-continued

| Key Resources Table | | |
| --- | --- | --- |
| REAGENT or RESOURCE | SOURCE | IDENTIFIER |
| CD45RA (clone L48) PE/Cy7 | BD Biosciences | Cat# 337167 |
| CD5 (clone UCHT2) BV711 | BD Biosciences | Cat# 563170 |
| CD88 (clone S5/1) PE/Cy7 | Biolegend | Cat# 344308 |
| CD89 (clone A59) BV510 | BD Biosciences | Cat# 744375 |
| CD89 (clone A59) APC | Biolegend | Cat# 354106 |
| FcεR1α (clone AER-37 (CRA-1)) PerCP | Biolegend | Cat# 334616 |
| FcεR1α (clone AER-37 (CRA-1)) APC/Cy7 | Biolegend | Cat# 334632 |
| HLA-DR (clone L243) BV785 | Biolegend | Cat# 307642 |
| IKAROS (clone R32-1149) BV421 | BD Biosciences | Cat# 564865 |
| IRF4 (clone 3E4) PE | eBioscience | Cat# 12-9858-82 |
| IRF8 (clone V3GYWCH) PercP/eFluor710 | eBioscience | Cat# 46-9852 |
| KLF4 (clone NA) APC | R&D Systems | Cat# IC3640A |
| LAMP5 (clone 124-40B) PE | Biolegend | Cat# 355804 |
| NOTCH2 (clone 16F11) PE | eBioscience | Cat# 12-5786-80 |
| PU.1 (clone 7C6B05) Alexa Fluor 647 | Biolegend | Cat# 658003 |
| RelB (clone EP613Y) Alexa Fluor 488 | Abcam | Cat# ab199089 |
| 112Cd_CD14 (clone TUK4) | Invitrogen | Cat# MHCD1400 |
| 141Pr_Clec12A (clone 687317) | R&D Systems | Cat# MAB2946 |
| 142Nd_CD5 (clone UCHT2) | Biolegend | Cat# 300602 |
| 143Nd_CD2 (clone RPA-2.10) | Biolegend | Cat# 300202 |
| 145Nd_CD68 (clone KP1) | eBioscience | Cat# 14-0688-80 |
| 146Nd_CD19 (clone HIB19) | eBioscience | Cat# 14-0199-82 |
| 146Nd_CD20 (clone 2H7) | eBioscience | Cat# 14-0209-82 |
| 146Nd_CD3 (clone OKT3) | Biolegend | Cat# 317302 |
| 147Sm_CD86 (clone IT2.2) | BD Biosciences | Cat# 555663 |
| 148Nd_CD45RA (clone HI100) | Biolegend | Cat# 304102 |
| 149Sm_HLA-DR (clone L243) | Biolegend | Cat# 307602 |
| 150Nd_CD80 (clone L307.4) | BD Biosciences | Cat# 557223 |
| 151Eu_CD141 (clone 1A4) | BD Biosciences | Cat# 559780 |
| 152Sm_CD1c (clone L161) | Biolegend | Cat# 331502 |
| 153Eu_FcεR1α (clone AER-37) | eBioscience | Cat# 14-5899-82 |
| 154Sm_CD87 (clone VIM5) | Biolegend | Cat# 336902 |
| 155Gd_CD33 (clone WM53) | BD Biosciences | Cat# 555449 |
| 156Gd_CD22 (clone HIB22) | Biolegend | Cat# 302502 |
| 157Gd_CXCR3 (clone 1C6) | BD Biosciences | Cat# 557183 |
| 158Gd_CD82 (clone ASL-24) | Biolegend | Cat# 342102 |
| 159Tb_CD301 (clone H037G3) | Biolegend | Cat# 354702 |
| 160Gd_CD206 (clone 19.2) | BD Biosciences | Cat# 555953 |
| 161Dy_CD123 (clone 7G3) | BD Biosciences | Cat# 554527 |
| 162Dy_CD88 (clone S5/1) | Biolegend | Cat# 344302 |
| 163Dy_BTLA (clone MIH26) | Fluidigm | Cat# 3163009B |
| 164Dy_CD89 (clone A59) | Biolegend | Cat# 354102 |
| 165Ho_CD71 (clone CY1G4) | Biolegend | Cat# 334102 |
| 166Er_CD85d (clone 42D1) | Biolegend | Cat# 338704 |
| 167Er_Integrin-B7 (clone FIB504) | Biolegend | Cat# 321202 |
| 168Er_CD26 (clone BA5b) | Biolegend | Cat# 302702 |
| 169Tm_CD163 (clone GHI) | Biolegend | Cat# 333602 |
| 170Er_CD35 (clone 594708) | R&D Systems | Cat# MAB5748 |
| 171Yb_CD166 (clone 3A6) | Biolegend | Cat# 343902 |
| 172Yb_HLA-DQ (clone Tü169) | Biolegend | Cat# 361502 |
| 173Yb_CD294 (clone BM16) | Biolegend | Cat# 350102 |
| 174Yb_CD354 (clone TREM-26) | Biolegend | Cat# 314902 |
| 175Lu_CD172b (clone B4B6) | Biolegend | Cat# 323902 |
| 176Yb_CD11b (clone ICRF44) | Biolegend | Cat# 301302 |
| 209Bi_CD16 (clone 3G8) | Biolegend | Cat# 302002 |
| 89Y_CD45 (clone HI30) | Fluidigm | Cat# 3089003B |
| Biological Samples | | |
| Buffy coat for the LegendScreen/InfinityFlow analysis | SingHealth, Singapore | N/A |
| Buffy coat for functional experiments | SingHealth, Singapore | N/A |
| PBMC from whole blood for scRNAseq analysis | SingHealth, Singapore | N/A |

-continued

| Key Resources Table | | |
|---|---|---|
| REAGENT or RESOURCE | SOURCE | IDENTIFIER |
| FLT3L-treated patients' whole blood PBMC | Icahn School of Medicine at Mount Sinai, Hess Center for Science and Medicine, New York, USA | N/A |
| SLE patients' whole blood PBMC | Department of Rheumatology and Clinical Immunology, University Medical Center Utrecht, Utrecht, The Netherlands | N/A |
| Serum from SLE patients | Department of Rheumatology and Clinical Immunology, University Medical Center Utrecht, Utrecht, The Netherlands | N/A |
| Critical Commercial Assays | | |
| LEGENDScreen ™ Human PE Kit | Biolegend | Cat# 700007 |
| Deposited Data | | |
| SMARTseq2 single cell transcriptome data of human peripheral blood DC and monocytes | This paper | GEO: GSE132566 |
| Microarray data of Segura et al. | Segura et al., 2013, J Exp Med. https//doi:10.1084/jem.20121103 | GEO: GSE40484 |
| Software and Algorithms | | |
| DIVA | BD Biosciences | https://www.bdbiosciences.com/en-us |
| FlowJo v.10.5.3 | Tree Star Inc. | https://www.flowjo.com |
| SeqGeq | FlowJo, LLC | https://www.flowjo.com/solutions/seqgeq |
| GraphPad Prism 6 | Graphpad | https://www.graphpad.com/scientific-software/prism/ |
| R 4.4 | The R Foundation | https://www.r-project.org |
| tSNE | Van Der Maaten et al., 2008, Journal of Machine Learning Research. https://doi.org/10.1007/s10479-011-0841-3 | https://github.com/jkrijthe/Rtsne |
| UMAP | McInnes et al., 2018, arXiv: 1802.03426 | https://github.com/lmcinnes/umap |
| SVM regression used in InfinityFlow | The R Foundation | https://cran.r-project.org/web/packages/e1071 |
| Seurat V2 | Butler et al., 2018, Nature Biotech. | https://doi.org/10.1038/nbt.4096 https://satijalab.org/seurat/ |
| Phenograph | Levine et al., 2015, Cell. doi:10.1016/j.cell.2015.05.047 | https://github.com/JinmiaoChenLab/Rphenograph |
| NBOR | J. Chen et al., 2016, Nat. Commun. 7, 11988 (2016). https://doi:10.1038/ncomms11988 | https://github.com/JinmiaoChenLab/Mpath |
| Wishbone | M. Setty et al., 2016, Nat Biotechnol. https://doi:10.1038/nbt.3569 | https://github.com/ManuSetty/wishbone |
| cMAP | Haniffa et al., 2012. Immunity. https://doi:10.1016/j.immuni.2012.04.012 | Customizedcode |
| Salmon | Patro et al., 2017, Nat Methods, doi:10.1038/nmeth.4197 | https://github.com/COMBINE-lab/salmon |
| txImport | Soneson et al., 2015, F1000Research. https://doi:10.12688/f1000research.7563.2 | https://bioconductor.org/packages/release/bioc/html/tximport.html |
| DESeq2 | Love, et al., 2014, Genome Biology. https:doi:10.1186/s13059-014-0550-8 | https://bioconductor.org/packages/release/bioc/html/DESeq2.html |
| Ingenuity Pathway Analysis | Qiagen | https://www.qiagenbioinformatics.com/products/ingenuity-pathway-analysis/ |

Blood and Serum Samples

Human samples were obtained in accordance with a favorable ethical opinion from Singapore SingHealth and National Health Care Group Research Ethics Committees and from. Collection of the samples from Utrecht was approved by the Medical Ethical Committee from the University Medical Centre Utrecht. FLT3L-treated patient samples were obtained in accordance with a clinical protocol which was approved by the Mount Sinai Institutional Review Board and in accordance with U.S. Law. Written informed consent was obtained from all donors according to the procedures approved by the National University of Singapore Institutional Review Board and SingHealth Centralised Institutional Review Board. Peripheral blood mono-nuclear cells (PBMC) used for the LegendScreen experiment (FIG. 1A) were obtained from apheresis residue and PBMC used for the single cell RNAseq (scRNAseq) experiment (FIG. 7C) were obtained from whole blood (two different donors). For functional experiments, PBMC were isolated by Ficoll-Paque (GE Healthcare) density gradient centrifugation of apheresis residue samples obtained from volunteer donors through the Health Sciences Authorities (HSA, Singapore). PBMC were obtained from 15 patients with systemic sclerosis (SSc), from 10 patients with systemic lupus erythematosus (SLE) that fulfilled the 1997 ACR classification criteria for SLE and from 10 healthy subjects. Healthy SSc, SLE patients' and healthy subjects' PBMC were all from the university medical centre (Utrecht, Netherlands) (Table S4). PBMC from 7 patients with folli-cular lymphoma or small lymphocytic lymphoma before and 11 days after having received FLT3L treatment were obtained from Mount Sinai Medical School (New York, U.S.A.) (Table S5). Serum samples were obtained from 24 patients with inactive (n=12) and active (n=12) SLE patients, and from 12 healthy subjects (Table S6). Spleen tissue was obtained from patients with tumors in the pan-creas who underwent distal pancreatomy (Singapore Gen-eral Hospital, Singapore). Tonsil tissue was obtained from patients with adeno-tonsillar obstruction and who underwent adeno-tonsillectomy (KK Hospital, Singapore). Spleen and tonsil tissues were processed as previously described (Hani-ffa et al., 2012).

LegendScreen and the InfinityFlow Pipeline

PBMCs (700 million) were isolated by Ficoll-Paque (GE Healthcare) density gradient centrifugation of apheresis resi-due samples obtained from one volunteer donor identified through the Health Sciences Authorities (HSA, Singapore). Cells were incubated with Live/Dead blue dye (Invitrogen) for 30 min at 4° C. in phosphate buffered saline (PBS) and then incubated in 5% heat-inactivated fetal calf serum (FCS) for 15 min at 4° C. (Sigma Aldrich). The following 14 anti-backbone markers antibodies were added to the cells and incubated for 30 min at 4° C., and then washed: CD123-BUV395 (clone 7G3), HLA-DR-BV786 (clone L243), CD5-BV711 (clone UCHT2), CD3-BV650 (clone SP34-2), CD20-BV650 (clone 2H7), CD45-V500 (clone HI30), CD2-BV421 (clone RPA-2.10), CD45RA-FITC (clone 5H9), CD14-AlexaFluor700 (clone M5E2), all from BD Biosciences; CD163-BV605 (clone GHI/61), CD1c-PercP/Cy5.5 (clone L161), CD88-PE/Cy7 (clone S5/1), CD16-APC/Cy7 (clone 3G8), all from Biolegend; CD141-APC (clone AD5-14H12, Miltenyi biotec). The cells were then stained with 332 different PE-conjugated antibodies (Table S1) using the LegendScreen® Human PE kit (Biole-gend) following the manufacturer's instructions.

The InfinityFlow pipeline involves regression analysis of the intensities of the PE-bound markers using the intensities of the backbone markers. In detail, the compensated cytom-etry data were transformed using a logicle transformation with parameters w=0.1, t=500000, m=4.5 and a=0, as defined in the flowCore R package. For each fcs file of the Legend Screen (Biolegend) experiment, half of the events were randomly selected to train an epsilon-regression Sup-port Vector Machine (SVM) model using the e1071 R package with default parameters, resulting in 332 SVM regression models. For each model, the PE-bound marker intensity was used as the response variable and the intensi-ties of the backbone markers were used as independent variables. For each event, each SVM regression model was applied on its associated vector of backbone marker inten-sities to predict the intensities of 332 PE-bound markers. For each of the 332 initial Legend Screen fcs files, these 332 regressed values were transformed back to a linear intensity scale, concatenated with the backbone and the PE-marker expression values and exported back as 332 new single .fcs files.

These predictions were used as the input for t-distributed Stochastic Neighbor Embedding (t-SNE) dimensionality reduction (using the Barnes-Hut implementation of t-SNE from the Rtsne R package) and Phenograph clustering from the Rphenograph R package. For the analysis of cDC2 and monocyte discriminating markers (FIGS. 4A-B), monocytes or cDC2 were identified in the tSNE space generated using all MNP discriminating markers. For each PE-conjugated predicted intensity vector, the unsigned Area Under the ROC Curve (AUC) was computed to summarize its ability to delineate cDC2 and monocytes.

PCA and Binning Analysis of CD163+cDC2 and cMo

From the 332 fcs files generated using the PBMCs stained with 14 anti-backbone marker antibodies and the Legend-Screen® Human PE kit, cells gated using the strategy shown in FIG. 5G were exported and a PCA was performed using the mean fluorescence intensity (MFI) of the 14 backbone markers. In the resulting PCA space, cells were separated into 40 bins (each comprising 2.5% of the total cells) defined along the PC1 axis. The 40 bins were analyzed by tSNE/Phenograph using the MFI of the 332 variable PE markers.

Algorithms for Dimensionality Reduction and Pseudo-Time Analyses

For CyTOF (FIGS. 4G-I), scRNAseq (FIG. 7C) and Luminex data (FIGS. 14B-D) marker, PC expression values and soluble mediators concentrations (respectively) were transformed using the logicle transformation function (Parks et al., 2006). For flow cytometry data, marker expression values were transformed using the auto-logicle transforma-tion function from the flowCore R package.

tSNE and Uniform Manifold Approximation and Projec-tion (UMAP) were carried out using all markers or signifi-cant PCs (based on Seurat analysis). For tSNE, the Rtsne function in the Rtsne R package with default parameters was used for flow cytometry and CyTOF data, and using a perplexity equal to 10 for the scRNAseq analysis. UMAP version 2.4.0 was implemented in Python, but executed through the reticulate R package to interface R objects with Python. UMAP was run using 15 nearest neighbors (nn), a min_dist of 0.2 and euclidean distance (Becht et al., 2018; McInnes et al., 2018). Phenograph clustering (Levine et al., 2015) was performed using all markers or significant PCs (based on Seurat analysis) before dimension reduction, and with the number of nearest neighbours equal to 30 for flow cytometry and CyTOF analyses and equal to 15 for scR-NAseq analysis.

Isometric feature mapping (isoMAP) (Tenenbaum et al., 2000) dimension reduction was performed using vegdist, spantree and isomap functions in the vegan R package (Chen et al., 2016). The vegdist function was run with method="euclidean". The spantree function was run with default parameters. The isoMAP function was run with the ndim equal to the number of original dimensions of the input data, and k=5.

Wishbone analysis (Setty et al., 2016) was conducted using the top 40 loading markers from the PCA in FIGS. 8B-C. Candidate cells (n=106) that had high CD5 expres-sion were selected as the start of the pseudo-time analysis. Then, the median pseudo-time trajectory was calculated and used for further NBOR analysis (Schlitzer et al., 2015b). The trajectory was separated into four bins as the NBOR input. NBOR then refined the order of cells and clustered the genes into four clusters. The smoothed marker expression values in each gene cluster were generated to illustrate the trend of expression in the clusters.

The results obtained from the tSNE, UMAP, isoMAP, Wishbone pseudo-time dimension and Phenograph analyses were incorporated as additional parameters and converted to .fcs files, which were then loaded into FlowJo to generate heatmaps of marker expression on the reduced dimensions.

Human Cell Flow Cytometry: Labeling, Staining, Analysis and Cell Sorting

All antibodies used for fluorescence-activated cell sorting (FACS) and flow cytometry were mouse anti-human mono-clonal antibodies (mAbs), except for the chicken anti-human CADM1 IgY primary mAb. The mAbs used for flow cytometry are listed in Table S7 and all flow cytometry panels are listed in Table S8. Briefly, $5\times10^6$ cells/tube were washed and incubated with Live/Dead blue dye (Invitrogen) for 30 min at 4° C. in PBS and then incubated in 5% heat-inactivated FCS for 15 min at 4° C. (Sigma Aldrich). The appropriate antibodies diluted in PBS with 2% FCS and 2 mM EDTA were added to the cells and incubated for 30 min at 4° C., and then washed and detected with the secondary reagents. For intra-cytoplasmic or intra-nuclear labeling or staining, cells were fixed and permeabilized with BD Cytofix/Cytoperm (BD Biosciences) or with eBioscience FoxP3/Transcription Factor Staining Buffer Set (eBioscience/Affimetrix), respectively according to the manufacturer's instructions. Flow cytometry was performed on a BD FACS-Fortessa (BD Biosciences) and the data were analyzed using BD FACSDiva 6.0 (BD Biosciences) or FlowJo v.10.5.3 (Tree Star Inc.).

Mass Cytometry Staining, Barcoding, Acquisition and Data Analysis

For mass cytometry, pre-conjugated or purified antibodies were obtained from Invitrogen, Fluidigm (pre-conjugated antibodies), Biolegend, eBioscience, Becton Dickinson or R&D Systems as listed in Table S9. For some markers, fluorophore-conjugated or biotin-conjugated antibodies were used as primary antibodies, followed by secondary labeling with anti-fluorophore metal-conjugated antibodies (such as the anti-FITC clone FIT-22) or metal-conjugated streptavidin, produced as previously described (Becher et al., 2014). Briefly, $3\times10^6$ cells/well in a U-bottom 96 well plate (BD Falcon, Cat #3077) were washed once with 200 µL FACS buffer (4% FBS, 2 mM EDTA, 0.05% Azide in 1×PBS), then stained with 100 µL 200 µM cisplatin (Sigma-Aldrich, Cat #479306-1G) for 5 min on ice to exclude dead cells. Cells were then washed with FACS buffer and once with PBS before fixing with 200 µL 2% paraformaldehyde (PFA; Electron Microscopy Sciences, Cat #15710) in PBS overnight or longer. Following fixation, the cells were pelleted and resuspended in 200 µL 1× permeabilization buffer (Biolegend, Cat #421002) for 5 min at room temperature to enable intracellular labeling. Bromoacetamido-benzyl-EDTA (BABE)-linked metal barcodes were prepared by dissolving BABE (Dojindo, Cat #B437) in 100 mM HEPES buffer (Gibco, Cat #15630) to a final concentration of 2 mM. Isotopically-purified $PdCl_2$ (Trace Sciences Inc.) was then added to the 2 mM BABE solution to a final concentration of 0.5 mM. Similarly, DOTA-maleimide (DM)-linked metal barcodes were prepared by dissolving DM (Macrocyclics, Cat #B-272) in L buffer (MAXPAR, Cat #PN00008) to a final concentration of 1 mM. $RhCl_3$ (Sigma) and isotopically-purified $LnCl_3$ was then added to the DM solution at a final concentration of 0.5 mM. Six metal barcodes were used: BABE-Pd-102, BABE-Pd-104, BABE-Pd-106, BABE-Pd-108, BABE-Pd-110 and DM-Ln-113.

All BABE and DM-metal solution mixtures were immediately snap-frozen in liquid nitrogen and stored at –80° C. A unique dual combination of barcodes was chosen to stain each tissue sample. Barcode Pd-102 was used at a 1:4000 dilution, Pd-104 at a 1:2000, Pd-106 and Pd-108 at a 1:1000, and Pd-110 and Ln-113 at a 1:500. Cells were incubated with 100 µL barcode in PBS for 30 min on ice, washed in permeabilization buffer and then incubated in FACS buffer for 10 min on ice. Cells were then pelleted and resuspended in 100 µL nucleic acid Ir-Intercalator (MAXPAR, Cat #201192B) in 2% PFA/PBS (1:2000), at room temperature. After 20 min, cells were washed twice with FACS buffer and twice with water before being resuspended in water. In each set, the cells were pooled from all tissue types, counted, and diluted to $0.5\times10^6$ cells/mL. EQ Four Element Calibration Beads (DVS Science, Fluidigm) were added at a 1% concentration prior to acquisition. Cell data were acquired and analyzed using a CyTOF Mass cytometer (Fluidigm).

The CyTOF data were exported in a conventional flow-cytometry file (.fcs) format and normalized using previously-described software (Finck et al., 2013). Events with zero values were randomly assigned a value between 0 and –1 using a custom R script employed in a previous version of the mass cytometry software (Newell et al., 2012). Cells for each barcode were deconvolved using the Boolean gating algorithm within FlowJo. The $CD45^+Lin$ (CD3/CD19/CD20)$^-HLA-DR^+$ population of PBMC were gated using FlowJo and exported as an .fcs file.

Generation of Indexed-Sorting and SMARTseq2 Single Cell Transcriptome Data

PBMCs from a blood donor were indexed-sorted using the Indexed-sorting panel (Table S8) on a BD FACSARIAIII (BD Biosciences) into 96 well plates containing 3 µL Lysis buffer (see below) using a 70 µm nozzle. Single-cell cDNA libraries were prepared using the SMARTSeq v2 protocol (Picelli et al., 2014) with the following modifications: (i) 1 mg/ml BSA Lysis buffer (Ambion® Thermo Fisher Scientific, Waltham, MA, USA); and (ii) 200 pg cDNA with ⅕ reaction of Illumina Nextera XT kit (Illumina, San Diego, CA, USA). The length distribution of the cDNA libraries was monitored using a DNA High Sensitivity Reagent Kit on the Perkin Elmer Labchip (Perkin Elmer, Waltham, MA, USA). All samples were subjected to an indexed paired-end sequencing run of 2×151 cycles on an Illumina HiSeq 4000 system (Illumina, San Diego, CA, USA), with 300 samples/lane. Data are available through GEO (GEO: GSE132566).

Pre-Processing, Quality Assessment and Control and Analysis of SMARTseq2 Single Cell Transcriptome Data Paired-end raw reads were aligned to the human reference genome (GRCh38 version 25 release; Gencode) using RSEM version 1.3.0. Transcript Per Million read (TPM) values were calculated using RSEM and used for downstream analysis. Quality control, selection of highly variable genes, PCA, and differential gene analysis was performed using the Seurat R package. tSNE and UMAP were used for dimensionality reduction and cell clusters were identified using the phenograph algorithm, as detailed above. The expression levels of key signature genes by known cell types was used to annotate the cell clusters accordingly. Lastly, signature genes of six DC subsets and four monocyte subsets were extracted from a previous study by Villani et al., (Villani et al., 2017) and the expression of the top 20 signature genes was overlaid on the data in a heatmap format (FIG. 7G) or as the mean expression of all signature genes as meaning plots (FIG. 7H). From the microarray data of Segura et al., (GEO, accession number GSE40484; see below for more details on the analysis) (Segura et al., 2013), a list of inflammatory DC (inflDC)-specific genes [defined as the intersection of differentially expressed genes (DEG) between inflDC and the four other cell types] was generated and their mean expression was overlaid as meaning plots or as a violin plot compiled in Prism 8 (GraphPad) (FIG. 10F). All scRNAseq dot plots and meaning plots displaying the gene expression levels or mean signature genes were generated using SecGec software (Flow Jo LLC).

Analysis of Microarray Data from Segura et al.

To reanalyze microarray data from Segura et al. (Segura et al., 2013), comparisons were made on the original submitter-supplied processed data tables using the GEOquery and limma R packages from theBioconductor project (Davis and Meltzer, 2007; Smyth, 2004, 2005). The GEOquery R package parses GEO data into R data structures that can be used by other R packages.

Generation and Analysis of Bulk RNAseq Data cDNA libraries were prepared from 100 cells using the SMARTSeq v2 protocol (Picelli et al., 2014) with the following modifications: (i) 1 mg/ml BSA Lysis buffer (Ambion® Thermo Fisher Scientific, Waltham, MA, USA); (ii) addition of 20 μM TSO; and (iii) 200 pg cDNA with ⅕ reaction of Illumina Nextera XT kit (Illumina, San Diego, CA, USA). The length distribution of the cDNA libraries was monitored using a DNA High Sensitivity Reagent Kit on the Perkin Elmer Labchip (Perkin Elmer, Waltham, MA, USA). All samples were subjected to an indexed paired-end sequencing run of 2×151 cycles on an Illumina HiSeq 4000 system (Illumina, San Diego, CA, USA), with 23-24 samples/lane. Paired-end reads obtained from RNA sequencing were mapped to human transcript sequences obtained from Gencode version 28 (Harrow et al., 2012) using Salmon (version 0.9.1) (Patro et al., 2017). Transcript abundances quantified by Salmon were summarized to gene-level counts and normalized gene-level abundances in transcript per million (TPM) units using the tximport R/Bioconductor package (version 1.2.0). Cell subset-specific DEG were identified as those that were significantly upregulated or downregulated compared to all other cell subsets. To identify these genes, DEG analysis was performed using DESeq2 between each cell subset of interest and each of the other cell subsets. The maximum p-value (nominal) of the t-test in all comparisons ($p_{max}$) was used to control the type-I error rate with a threshold of $p_{max}<0.05$. After filtering for genes that were significant by p-value, the upregulated (or downregulated) genes were selected as those for which the fold change in all comparisons was consistently greater (or less) than zero. DEG heatmaps were generated using $Log_2$ TPM values. Genes modulated in a cell subset due to SLE were identified by performing DEG analysis that compared samples derived from SLE patients and healthy controls, where p-values adjusted for multiple testing correction by the Benjamini Hochberg method were used to control for the type-I error rate. For pathway analyses, lists of genes identified as cell subset-specific or SLE modulated by the abovementioned methods, together with the respective fold change and p-values, were supplied to Ingenuity Pathway Analysis™ (IPA) software. IPA analysis reported the p-value of enrichment of pathways in the supplied gene lists based on the proportions of genes in a pathway that were differentially expressed. Based on the direction of the fold change, IPA predicted the up-regulation or down-regulation of pathways as a Z-score, where positive and negative scores implied predicted up-regulation and down-regulation, respectively. Within the significant pathways reported by IPA, 48 pathways relevant to the immunological response were shortlisted and radar plots were used to summarize the p-values and Z-scores of these pathways in a gene list. cMAP analysis (Lamb et al., 2006) was performed using lists of DEGs between DC2 and DC3 (up and low genes) published by Villani et al. For each bulk RNAseq sample, cMAP generated enrichment scores that quantified the degree of enrichment (or "closeness") to the given gene signatures. The enrichment scores were scaled and assigned positive or negative values to indicate enrichment for DC3 or DC2 signature genes, respectively.

Scanning Electron Microscopy

Scanning electron microscopy was performed as previously described (See et al., 2017).

Luminex® Drop Array™ Assay on Sorted cDC2 Populations Cultured in SLE Patients' and Healthy Donors' Serum $CD5^+CD163^-$, $CD5^-CD163^-$, $CD5^-CD163^+CD14^-$ and $CD5^-CD163^+CD14^+cDC2$ were sorted using a BD FACS ARIAIII (BD Biosciences) using the sort panel for stimulations and Luminex (Table S8). The cells ($2\times10^3$) were cultured for 18 h in V-bottomed 96-well culture-treated plates (total volume, 50 μL) in Roswell Park Memorial Institute 1640 Glutmax media (Life Technologies) supplemented with 10% FBS, 1% penicillin/streptomycin (complete media) and in the presence of 2% serum from healthy subjects or SLE patients with an inactive or an active disease. After the 18 h stimulation, supernatants were collected for Luminex® analysis using the ProcartaPlex, Human Customized 55-plex Panel (Thermo Fisher Scientific, #PPX-55) to measure the following targets: APRIL, BAFF, BLC, ENA-78, Eotaxin, Eotaxin-2, Eotaxin-3, FGF-2, Fractalkine, G-CSF, GM-CSF, Gro-α, HGF, IFN-α, IFN-γ, IL-10, IL-12p70, IL-13, IL-15, IL-18, IL-1α, IL-1β, IL-2, IL-20, IL-23, IL-27, IL-2R, IL-3, IL-31, IL-6, IL-7, IL-8, IL-9, IP-10, I-TAC, LIF, MCP-1, MCP-2, MCP-3, MDC, MIF, MIG, MIP-la, MIP-1β, MIP-3α, MMP-1, SCF, SDF-1α, TNF-α, TNF-β, TNF-RII, TRAIL, TSLP, TWEAK, VEGF-A. Harvested supernatants were analysed using DA-Cell™ (Curiox Biosystems) Luminex® bead-based multiplex assays, which simultaneously measure multiple specific protein targets in a single sample. Using DA-Cell™ samples or standards were incubated with fluorescent-coded magnetic beads, which had been pre-coated with respective capture antibodies. After an overnight incubation at 4° C., the plates were washed twice. Biotinylated detection antibodies were incubated with the complex for 30 min and then Streptavidin-PE was added and incubated for a further 30 min. The plates were washed twice, then the beads were re-suspended with sheath fluid before acquiring on a FLEX-MAP® 3D platform (Luminex) using xPONENT® 4.0 (Luminex) acquisition software. Data analysis was performed using Bio-Plex Manager™ 6.1.1 (Bio-Rad). Standard curves were generated with a 5-parameter logistic (5-PL) algorithm, reporting values for both MFI and concentration data. Normalized concentrations of analytes were transformed using the logicle transformation function (Parks et al., 2006) and analyzed using UMAP, as described above.

Allogenic Mixed Lymphocyte Reaction

Naïve $CD4^+$ T cells were isolated from PBMCs using a Naïve $CD4^+$ T-Cell Isolation Kit II (Miltenyi Biotec), according to the manufacturer's instructions, and labeled with 5 μM CellTrace™ Violet dye (ThermoFischer) for 20 min at 20° C. A total of 5,000 cells from sorted cDC2 subsets were co-cultured with 50,000 CFSE-labeled allogenic naïve T cells for 6 days in Iscove's Modified Dulbecco's Medium (Life Technologies) supplemented with 10% KnockOut™ Serum Replacement (Life Technologies). On day 6, the T cells were stimulated with 10 μg/ml phorbol myristate acetate (InvivoGen) and 500 μg/ml ionomycin (Sigma Aldrich) for 1 h at 37° C. Then, 10 μg/ml Brefeldin A solution was added for 4 h, after which the cells were labeled with membrane markers (described above) and for intracellular cytokines (described below). Cells were fixed and permeabilized with BD Cytofix/Cytoperm (BD Biosciences), according to the manufacturer's instructions and stained with cytokine-specific antibodies. Flow cytometry was performed using a BD LSRII or a BD FACSFortessa (BD Biosciences) and the data were analyzed using BD FACSDiva 6.0 (BD Biosciences) or FlowJo v.10 (Tree Star Inc.).

Statistical Analyses

Significance for pathways analyses (see FIG. 10G, FIG. 12H and FIG. 6M) was defined by the IPA software (Qiagen). Differences in MFI for cDC2 subsets and cMo in FIG. 8H were defined by parametric one-way ANOVA followed by Tukey's multiple comparisons test. Friedman test (Nonparametric repeated measures ANOVA) followed by Dunn's multiple comparisons test was used to compare the capacity of the four cDC2 subsets to induce proliferation and cytokine production by CD4[+] T cells in the MLR experiments of FIG. 10E. Kruskal Wallis (non-parametric one-way ANOVA) followed by Dunn's multiple comparisons test was used to compare the median of each analyte produced by each cDC2 subset in the SLE groups against the healthy control group (see FIG. 14E). The Mann-Whitney test was used to compare data derived from patients with SLE versus healthy subjects or patients with SSc. Correlation coefficients and p values were calculated as the Pearson's correlation coefficient (see. FIG. 12D and FIG. 13C).

SUPPLEMENTARY TABLES

TABLE S1

| PLATE | Tube No | Specificity |
|---|---|---|
| | LegendScreen markers | |
| 1 | 1 | Blank |
| 1 | 2 | CD1a |
| 1 | 3 | CD1b |
| 1 | 4 | CD1c |
| 1 | 5 | CD1d |
| 1 | 6 | CD2 |
| 1 | 7 | CD3 |
| 1 | 8 | CD4 |
| 1 | 9 | CD5 |
| 1 | 10 | CD6 |
| 1 | 11 | CD7 |
| 1 | 12 | CD8a |
| 1 | 13 | CD9 |
| 1 | 14 | CD10 |
| 1 | 15 | CD11a |
| 1 | 16 | CD11b |
| 1 | 17 | CD11bactiv |
| 1 | 18 | CD11c |
| 1 | 19 | CD13 |
| 1 | 20 | CD14 |
| 1 | 21 | CD15 |
| 1 | 22 | CD16 |
| 1 | 23 | CD18 |
| 1 | 24 | CD19 |
| 1 | 25 | CD20 |
| 1 | 26 | CD21 |
| 1 | 27 | CD22 |
| 1 | 28 | CD23 |
| 1 | 29 | CD24 |
| 1 | 30 | CD25 |
| 1 | 31 | CD26 |
| 1 | 32 | CD27 |
| 1 | 33 | CD28 |
| 1 | 34 | CD29 |
| 1 | 35 | CD30 |
| 1 | 36 | CD31 |
| 1 | 37 | CD32 |
| 1 | 38 | CD33 |
| 1 | 39 | CD34 |
| 1 | 40 | CD35 |
| 1 | 41 | CD36 |
| 1 | 42 | CD38 |
| 1 | 43 | CD39 |
| 1 | 44 | CD40 |
| 1 | 45 | CD41 |
| 1 | 46 | CD42b |
| 1 | 47 | CD43 |

TABLE S1-continued

| PLATE | Tube No | Specificity |
|---|---|---|
| | LegendScreen markers | |
| 1 | 48 | CD44 |
| 1 | 49 | CD45 |
| 1 | 50 | CD45RA |
| 1 | 51 | CD45RB |
| 1 | 52 | CD45RO |
| 1 | 53 | CD46 |
| 1 | 54 | CD47 |
| 1 | 55 | CD48 |
| 1 | 56 | CD49a |
| 1 | 57 | CD49c |
| 1 | 58 | CD49d |
| 1 | 59 | CD49e |
| 1 | 60 | CD49f |
| 1 | 61 | CD50 |
| 1 | 62 | CD51 |
| 1 | 63 | CD51/61 |
| 1 | 64 | CD52 |
| 1 | 65 | CD53 |
| 1 | 66 | CD54 |
| 1 | 67 | CD55 |
| 1 | 68 | CD56 (NCAM) |
| 1 | 69 | CD57 |
| 1 | 70 | CD58 |
| 1 | 71 | CD59 |
| 1 | 72 | CD61 |
| 1 | 73 | CD62E |
| 1 | 74 | CD62L |
| 1 | 75 | CD62P |
| 1 | 76 | CD63 |
| 1 | 77 | CD64 |
| 1 | 78 | CD66a/c/e |
| 1 | 79 | CD66b |
| 1 | 80 | CD69 |
| 1 | 81 | CD70 |
| 1 | 82 | CD71 |
| 1 | 83 | CD73 |
| 1 | 84 | CD74 |
| 1 | 85 | CD79b |
| 1 | 86 | CD80 |
| 1 | 87 | CD81 |
| 1 | 88 | CD82 |
| 1 | 89 | CD83 |
| 1 | 90 | CD84 |
| 1 | 91 | CD85a (ILT5) |
| 1 | 92 | CD85d (ILT4) |
| 1 | 93 | CD85g (ILT7) |
| 1 | 94 | CD85h (ILT1) |
| 1 | 95 | CD85j (ILT2) |
| 1 | 96 | CD85k (ILT3) |
| 2 | 1 | Blank |
| 2 | 2 | CD86 |
| 2 | 3 | CD87 |
| 2 | 4 | CD88 |
| 2 | 5 | CD89 |
| 2 | 6 | CD90 (Thy1) |
| 2 | 7 | CD93 |
| 2 | 8 | CD94 |
| 2 | 9 | CD95 |
| 2 | 10 | CD96 |
| 2 | 11 | CD97 |
| 2 | 12 | CD99 |
| 2 | 13 | CD100 |
| 2 | 14 | CD101 (BB27) |
| 2 | 15 | CD102 |
| 2 | 16 | CD103 |
| 2 | 17 | CD104 |
| 2 | 18 | CD105 |
| 2 | 19 | CD106 |
| 2 | 20 | CD107a (LAMP-1) |
| 2 | 21 | CD108 |
| 2 | 22 | CD109 |
| 2 | 23 | CD111 |
| 2 | 24 | CD112 |
| 2 | 25 | CD114 |
| 2 | 26 | CD115 |
| 2 | 27 | CD116 |

TABLE S1-continued

TABLE S1-continued

| LegendScreen markers | | |
|---|---|---|
| PLATE | Tube No | Specificity |
| 2 | 28 | CD117 (c-kit) |
| 2 | 29 | CD119 |
| 2 | 30 | CD122 |
| 2 | 31 | CD123 |
| 2 | 32 | CD124 |
| 2 | 33 | CD126 (IL-6Rα) |
| 2 | 34 | CD127 (IL-7Rα) |
| 2 | 35 | CD129 (IL-9 R) |
| 2 | 36 | CD131 |
| 2 | 37 | CD132 |
| 2 | 38 | CD134 |
| 2 | 39 | CD135 |
| 2 | 40 | CD137 (4-1BB) |
| 2 | 41 | CD137L |
| 2 | 42 | CD138 |
| 2 | 43 | CD140a |
| 2 | 44 | CD140b |
| 2 | 45 | CD141 |
| 2 | 46 | CD143 |
| 2 | 47 | CD144 |
| 2 | 48 | CD146 |
| 2 | 49 | CD148 |
| 2 | 50 | CD150 (SLAM) |
| 2 | 51 | CD152 |
| 2 | 52 | CD154 |
| 2 | 53 | CD155 (PVR) |
| 2 | 54 | CD156c (ADAM10) |
| 2 | 55 | CD158a/h |
| 2 | 56 | CD158b |
| 2 | 57 | CD158d |
| 2 | 58 | CD158e1 |
| 2 | 59 | CD158f |
| 2 | 60 | CD161 |
| 2 | 61 | CD162 |
| 2 | 62 | CD163 |
| 2 | 63 | CD164 |
| 2 | 64 | CD165 |
| 2 | 65 | CD166 |
| 2 | 66 | CD167a (DDR1) |
| 2 | 67 | CD169 |
| 2 | 68 | CD170 (Siglec-5) |
| 2 | 69 | CD172a (SIRPa) |
| 2 | 70 | CD172b (SIRPb) |
| 2 | 71 | CD172g (SIRPg) |
| 2 | 72 | CD178 (Fas-L) |
| 2 | 73 | CD179a |
| 2 | 74 | CD179b |
| 2 | 75 | CD180 (RP105) |
| 2 | 76 | CD181 (CXCR1) |
| 2 | 77 | CD182 (CXCR2) |
| 2 | 78 | CD183 |
| 2 | 79 | CD184 (CXCR4) |
| 2 | 80 | CD193 (CCR3) |
| 2 | 81 | CD195 (CCR5) |
| 2 | 82 | CD196 |
| 2 | 83 | CD197 (CCR7) |
| 2 | 84 | CD200 (OX2) |
| 2 | 85 | CD200 R |
| 2 | 86 | CD201 (EPCR) |
| 2 | 87 | CD202b (Tie2/Tek) |
| 2 | 88 | CD203c (E-NPP3) |
| 2 | 89 | CD205 (DEC-205) |
| 2 | 90 | CD206 (MMR) |
| 2 | 91 | CD207 (Langerin) |
| 2 | 92 | CD209 (DC-SIGN) |
| 2 | 93 | CD210 (IL- 10 R) |
| 2 | 94 | CD213a2 |
| 2 | 95 | CD215 (IL- 15Rα) |
| 2 | 96 | CD218a (IL-18Rα) |
| 3 | 1 | Blank |
| 3 | 2 | CD220 |
| 3 | 3 | CD221 (IGF-1R) |
| 3 | 4 | CD226 (DNAM-1) |
| 3 | 5 | CD229 (Ly-9) |
| 3 | 6 | CD231 (TALLA) |
| 3 | 7 | CD235ab |

| LegendScreen markers | | |
|---|---|---|
| PLATE | Tube No | Specificity |
| 3 | 8 | CD243 |
| 3 | 9 | CD244 (2B4) |
| 3 | 10 | CD245 (p220/240) |
| 3 | 11 | CD252 (OX40L) |
| 3 | 12 | CD253 (Trail) |
| 3 | 13 | CD254 |
| 3 | 14 | CD255 (TWEAK) |
| 3 | 15 | CD257 (BAFF) |
| 3 | 16 | CD258 (LIGHT) |
| 3 | 17 | CD261 (TRAIL-R1) |
| 3 | 18 | CD262 (TRAIL-R2) |
| 3 | 19 | CD263 (TRAIL-R3) |
| 3 | 20 | CD266 |
| 3 | 21 | CD267 (TACI) |
| 3 | 22 | CD268 (BAFF-R) |
| 3 | 23 | CD270 (HVEM) |
| 3 | 24 | CD271 |
| 3 | 25 | CD273 (PD-L2) |
| 3 | 26 | CD274 (PD-L1) |
| 3 | 27 | CD275 |
| 3 | 28 | CD276 |
| 3 | 29 | CD277 |
| 3 | 30 | CD278 (ICOS) |
| 3 | 31 | CD279 (PD-1) |
| 3 | 32 | CD282 (TLR2) |
| 3 | 33 | CD284 (TLR4) |
| 3 | 34 | CD286 (TLR6) |
| 3 | 35 | CD290 |
| 3 | 36 | CD294 |
| 3 | 37 | CD298 |
| 3 | 38 | CD300e (IREM-2) |
| 3 | 39 | CD300F |
| 3 | 40 | CD301 |
| 3 | 41 | CD303 |
| 3 | 42 | CD304 |
| 3 | 43 | CD307 |
| 3 | 44 | CD307d (FcRL4) |
| 3 | 45 | CD314 (NKG2D) |
| 3 | 46 | CD317 |
| 3 | 47 | CD318 (CDCP1) |
| 3 | 48 | CD319 (CRACC) |
| 3 | 49 | CD324 (E-Cadherin) |
| 3 | 50 | CD325 |
| 3 | 51 | CD326 (Ep-CAM) |
| 3 | 52 | CD328 (Siglec-7) |
| 3 | 53 | CD334 (FGFR4) |
| 3 | 54 | CD335 (NKp46) |
| 3 | 55 | CD336 (NKp44) |
| 3 | 56 | CD337 (NKp30) |
| 3 | 57 | CD338 (ABCG2) |
| 3 | 58 | CD340 (HER-2) |
| 3 | 59 | CD344 (Frizzled-4) |
| 3 | 60 | CD351 |
| 3 | 61 | CD352 (NTB-A) |
| 3 | 62 | CD354 (TREM-1) |
| 3 | 63 | CD355 (CRTAM) |
| 3 | 64 | CD357 (GITR) |
| 3 | 65 | CD360 (IL-21R) |
| 3 | 66 | β2- microglobulin |
| 3 | 67 | BTLA |
| 3 | 68 | C3AR |
| 3 | 69 | C5L2 |
| 3 | 70 | CCR10 |
| 3 | 71 | CLEC12A |
| 3 | 72 | CLEC9A |
| 3 | 73 | CX3CR1 |
| 3 | 74 | CXCR7 |
| 3 | 75 | δ-Opioid Receptor |
| 3 | 76 | DLL1 |
| 3 | 77 | DLL4 |
| 3 | 78 | DR3 (TRAMP) |
| 3 | 79 | EGFR |
| 3 | 80 | erbB3/HER-3 |
| 3 | 81 | FcεRIα |
| 3 | 82 | FcRL6 |
| 3 | 83 | Galectin-9 |

TABLE S1-continued

LegendScreen markers

| PLATE | Tube No | Specificity |
|---|---|---|
| 3 | 84 | GARP (LRRC32) |
| 3 | 85 | HLA-A, B, C |
| 3 | 86 | HLA-A2 |
| 3 | 87 | HLA-DQ |
| 3 | 88 | HLA-DR |
| 3 | 89 | HLA-E |
| 3 | 90 | HLA-G |
| 3 | 91 | IFN-g R b chain |
| 3 | 92 | Ig light chain k |
| 3 | 93 | Ig light chain λ |
| 3 | 94 | IgD |
| 3 | 95 | IgM |
| 3 | 96 | IL-28RA |
| 4 | 1 | Blank |
| 4 | 2 | Integrin α9β1 |
| 4 | 3 | integrin β5 |
| 4 | 4 | integrin β7 |
| 4 | 5 | Jagged 2 |
| 4 | 6 | LAP |
| 4 | 7 | LT-bR |
| 4 | 8 | Mac-2 |
| 4 | 9 | MAIR-II |
| 4 | 10 | MICA/MICB |
| 4 | 11 | MSC (W3D5) |
| 4 | 12 | MSC (W5C5) |
| 4 | 13 | MSC (W7C6) |
| 4 | 14 | MSC and NPC |
| 4 | 15 | MSCA-1 |
| 4 | 16 | NKp80 |
| 4 | 17 | Notch 1 |
| 4 | 18 | Notch 2 |

TABLE S1-continued

LegendScreen markers

| PLATE | Tube No | Specificity |
|---|---|---|
| 4 | 19 | Notch 3 |
| 4 | 20 | Notch 4 |
| 4 | 21 | NPC (57D2) |
| 4 | 22 | Podoplanin |
| 4 | 23 | Pre-BCR |
| 4 | 24 | PSMA |
| 4 | 25 | Siglec-10 |
| 4 | 26 | Siglec-8 |
| 4 | 27 | Siglec-9 |
| 4 | 28 | SSEA-1 |
| 4 | 29 | SSEA-3 |
| 4 | 30 | SSEA-4 |
| 4 | 31 | SSEA-5 |
| 4 | 32 | TCR g/d |
| 4 | 33 | TCR Vβ13.2 |
| 4 | 34 | TCR Vβ23 |
| 4 | 35 | TCR Vβ8 |
| 4 | 36 | TCR Vβ9 |
| 4 | 37 | TCR Vδ2 |
| 4 | 38 | TCR Vg9 |
| 4 | 39 | TCR Vα24- Jα18 |
| 4 | 40 | TCR Vα7.2 |
| 4 | 41 | TCR α/β |
| 4 | 42 | Tim-1 |
| 4 | 43 | Tim-3 |
| 4 | 44 | Tim-4 |
| 4 | 45 | TLT-2 |
| 4 | 46 | TRA-1-60-R |
| 4 | 47 | TRA-1-81 |
| 4 | 48 | TSLPR (TSLP-R) |

TABLE S2

InflDC differentially expressed genes (DEGs)

| Intersection of inflDC DEGs vs BDCA1 or CD14 or CD16 or inflMacro | | | | inflDC vs BDCA1 blood cDC2 upregulated DEGs | | | | |
|---|---|---|---|---|---|---|---|---|
| HPGDS | SPP1 | IL10 | P2RY12 | RASGEF1B | GBGT1 | OAS2 | MRAS | C16orf45 |
| CFI | FN1 | FPR3 | CD9 | CAMSAP2 | FMNL3 | PTPRO | FMN1 | NAV1 |
| HPGD | CCL2 | SPRED1 | GALM | ITGB5 | HMOX1 | MYO1C | SMCO4 | MX2 |
| ADAM19 | LYVE1 | EGR3 | TMEM51 | TIMD4 | CD84 | CD1E | FABP3 | IKZF2 |
| TRPC6 | CLEC5A | TREM2 | ITGAM | CR1 | EHD1 | FBP1 | SLC31A2 | MIR222 |
| MRC1 | MMP12 | FCGR3A | IL7R | HSPB1 | IFITM3 | AK4 | SH3RF3 | SAMD9 |
| CD72 | FCGR1A | IFIT3 | IFI44L | NRP2 | KIFC3 | DSE | SERPINA1 | MMP14 |
| CCR4 | GPNMB | CXCL10 | EGR1 | PLA2G15 | YWHAH | DDX60L | ABCC5 | ECM1 |
| AXL | FCGR1CP | ABCA6 | DOCK4 | TCN2 | STARD4 | MARCH2 | LAMP1 | C11orf24 |
| PARM1 | C3AR1 | OLFML2B | PIM1 | CD72 | UPP1 | ADAP2 | FLOT1 | PROCR |
| CD226 | CTSL | RGL1 | C15orf48 | BCL2A1 | SIPA1L2 | AMPD3 | DHCR7 | MRC2 |
| GAS6 | FAM20A | C1QA | RAPH1 | HSPA1A | CECR6 | VNN1 | HSD3B7 | LAP3 |
| CD1E | ENPP2 | RSAD2 | HPGD | NECTIN2 | TNFSF10 | HLX | CD2 | GPC4 |
| FCGR2B | CCL4 | IER3 | PPARG | HSPA1A | CD226 | RNF122 | DPYSL3 | GBA |
| CD2 | A2M | LAMP3 | CFB | HSPA1A | MARCO | DHRS3 | SH3PXD2B | MANF |
| GPX7 | C3 | TLR7 | MITF | IFITM1 | MX1 | GAPT | SQLE | XAF1 |
| BCL2 | RNASE1 | SLC39A8 | LRP12 | ENDOD1 | MLXIPL | NEK6 | ITGAE | HCST |
|  | ANKRD22 | MS4A4A | ADAM19 | ADM | LDLRAD3 | PPIL1 | GPX7 | GK3P |
|  | PLTP | NRP1 | IFI6 | CD81 | RIN2 | CCR5 | CYYR1 | TMEM52B |
|  | C1QB | RHOBTB3 | DHCR24 | SDC4 | SLC37A2 | TNS1 | LILRB1 | CSF1R |
|  | HPGDS | SLC7A8 | MSLN | FPR1 | GPR84 | ARNTL2 | ST14 | DOCK1 |
|  | C1QC | CCL22 | ALOX5AP | IL4I1 | FPR2 | PDIA4 | CTSB | PDLIM7 |
|  | MERTK | PTGER2 | TRPC6 | NCEH1 | GAS6 | SGMS2 | ANKH | SBNO2 |
|  | CD14 | CX3CR1 | FMNL2 | TGM2 | BCAR3 | TLR1 | SAMD9L | EPAS1 |
|  | TNFRSF11A | FLT1 | SLAMF8 | CXCL11 | EHD4 | MYOF | TBL2 | LINC01001 |
|  | CCL4L2 | SIGLEC1 | CHST15 | CTNS | OAS3 | FILIP1L | MARCKS | CHSY1 |
|  | CCR1 | CCND1 | DRAM1 | CCR4 | HIVEP3 | ADORA2B | PSD3 | JAK3 |
|  | SLCO2B1 | USP18 | SERPING1 | AXL | SRD5A3 | TNFAIP8L3 | FCGR2A | MAN1A1 |
|  | EGR2 | PALLD | PTPN13 | ARHGAP18 | SCD | PLA2G4C | TTC7B | SDF2L1 |
|  | OLR1 | MGAT4A | GPR82 | SLC46A1 | IRAK2 | SLC43A3 | FAM114A1 | HSPA5 |
|  | LHFPL2 | SIGLEC16 | IDH1 | TLR2 | GBP2 | FCGR2B | PTAFR | PROS1 |
|  | CFI | CD80 | MRC1 | VMO1 | APOC1 | ZFP36L1 | GK | GK |
|  | DSC2 | ITGA9 | IFIT2 | MMP2 | CD180 | PARP9 | CD68 | PLOD2 |

TABLE S2-continued

| InflDC differentially expressed genes (DEGs) | | | | | | | |
|---|---|---|---|---|---|---|---|

Intersection of
inflDC DEGs vs
BDCA1 or CD14 or

| CD16 or inflMacro | | | inflDC vs BDCA1 blood cDC2 upregulated DEGs | | | | |
|---|---|---|---|---|---|---|---|
| ETV5 | SLC1A3 | SUCNR1 | PARM1 | OAS1 | RAB39A | NABP1 | BCL2 |
| IFIT1 | CYP27A1 | SOCS3 | TNFAIP3 | PLXNA1 | STXBP1 | TMEM37 | PLEKHH1 |
| VSIG4 | PLEK2 | ITGB8 | CDCP1 | ADAMTSL4 | CMPK2 | DOK5 | SCO2 |
| GPR34 | SLC16A10 | FLVCR2 | FAM20C | IL21R | LY6E | RRAS | RBM47 |
| BHLHE41 | ENG | EMP1 | ATF5 | TREML1 | SNX7 | FICD | DNAJC12 |
| MSR1 | EPS8 | PLAU | DDX58 | BMP2K | LPAR5 | RND3 | CCDC167 |
| USP41 | MIR221 | LAIR1 | PAPSS2 | GNG12 | CDYL2 | PVR | TBC1D14 |

TABLE S3

| Differentially expressed genes (DEGs) FIGS. 12F-G | |
|---|---|
| Column header | Description |
| tpm.X | Expression level in transcripts per million units in the X subset, geometric mean over replicates |
| lfc.Y | Log2 fold change of population X/population Y comparison |
| p.Y | p-value of population X/population Y comparison |
| lfc.MostConservative | Minimum fold change among the three comparisons (or maximum in case of negative values) |
| p.Most Conservative | Maximum p-value among the three comparisons |

| | | | | | | | CD5+ DC2 DEGs | | |
|---|---|---|---|---|---|---|---|---|---|
| geneSymbol | tpm.CD5+ | lfc.CD163− | p.CD163− | lfc.CD14− | p.CD14− | lfc.CD14+ | p.CD14+ | lfc.MostCon-servative | p.MostCon-servative |
| SLAMF7 | 42.88 | 3.17 | 2.02E−07 | 3.36 | 6.42E−09 | 4.80 | 1.56E−09 | 3.17 | 2.02E−07 |
| VCAN | 25.51 | −2.62 | 2.75E−10 | −2.12 | 1.18E−06 | −3.32 | 1.41E−08 | −2.12 | 1.18E−06 |
| S100A8 | 38.76 | −4.27 | 1.91E−06 | −3.21 | 2.64E−09 | −5.92 | 1.01E−05 | −3.21 | 1.01E−05 |
| ELOVL5 | 88.83 | 1.45 | 1.60E−04 | 1.15 | 5.03E−05 | 2.00 | 9.11E−05 | 1.15 | 1.60E−04 |
| CD74 | 19617.75 | 1.33 | 1.71E−04 | 1.17 | 7.45E−05 | 2.26 | 2.30E−06 | 1.17 | 1.71E−04 |
| C1orf162 | 1141.42 | 0.77 | 4.41E−04 | 1.39 | 1.98E−04 | 2.05 | 2.05E−06 | 0.77 | 4.41E−04 |
| S100A9 | 339.67 | −2.99 | 4.61E−04 | −2.52 | 1.26E−10 | −4.54 | 7.82E−06 | −2.52 | 4.61E−04 |
| ARHGDIB | 1611.88 | 0.81 | 5.93E−04 | 0.91 | 4.58E−04 | 1.43 | 2.19E−04 | 0.81 | 5.93E−04 |
| AXL | 41.59 | 5.62 | 7.98E−12 | 2.81 | 3.44E−06 | 3.99 | 6.64E−04 | 2.81 | 6.64E−04 |
| CES1 | 7.68 | −4.08 | 1.84E−04 | −3.21 | 2.64E−07 | −3.20 | 7.02E−04 | −3.20 | 7.02E−04 |
| RAC1 | 110.46 | −1.19 | 4.71E−04 | −0.88 | 8.84E−04 | −1.14 | 3.54E−05 | −0.88 | 8.84E−04 |
| ARHGEF1 | 35.78 | −1.91 | 8.09E−08 | −1.09 | 9.28E−04 | −1.67 | 3.52E−06 | −1.09 | 9.28E−04 |
| HK3 | 2.71 | −3.84 | 5.56E−05 | −2.28 | 1.04E−03 | −4.57 | 1.24E−10 | −2.28 | 1.04E−03 |
| MIR1248 | 1.75 | −5.53 | 1.45E−04 | −4.21 | 1.09E−03 | −6.59 | 2.11E−04 | −4.21 | 1.09E−03 |
| MYL12A | 1665.81 | 0.95 | 3.19E−05 | 0.88 | 1.56E−03 | 1.37 | 3.09E−05 | 0.88 | 1.56E−03 |
| ACTG1 | 1722.97 | 0.76 | 1.32E−03 | 0.91 | 1.60E−03 | 1.54 | 2.37E−06 | 0.76 | 1.60E−03 |
| ARPC2 | 1138.44 | 0.93 | 5.23E−04 | 0.85 | 1.71E−03 | 1.34 | 2.12E−04 | 0.85 | 1.71E−03 |
| ADRBK1 | 21.32 | −1.28 | 1.82E−04 | −1.24 | 1.93E−04 | −1.95 | 1.81E−03 | −1.24 | 1.81E−03 |
| B2M | 25625.60 | 0.70 | 2.77E−05 | 0.87 | 2.35E−03 | 0.84 | 2.05E−03 | 0.70 | 2.35E−03 |
| PRCP | 183.58 | 1.13 | 3.91E−05 | 0.91 | 2.09E−03 | 2.05 | 3.08E−03 | 0.91 | 3.08E−03 |
| YWHAZ | 313.40 | 0.64 | 4.76E−04 | 0.59 | 3.16E−03 | 1.21 | 1.01E−06 | 0.59 | 3.16E−03 |
| BTLA | 3.60 | 5.70 | 3.20E−03 | 5.28 | 1.20E−06 | 5.92 | 4.04E−04 | 5.28 | 3.20E−03 |
| C14orf1 | 9.42 | 2.77 | 2.38E−03 | 2.40 | 8.60E−04 | 2.59 | 3.28E−03 | 2.40 | 3.28E−03 |
| VAV3 | 32.27 | 1.89 | 3.32E−03 | 1.14 | 1.49E−03 | 2.16 | 2.19E−03 | 1.14 | 3.32E−03 |
| SPNS1 | 24.32 | −1.69 | 4.75E−06 | −1.38 | 2.56E−04 | −1.82 | 3.48E−03 | −1.38 | 3.48E−03 |
| H3F3B | 1872.25 | 0.77 | 3.51E−03 | 0.97 | 1.13E−03 | 1.69 | 1.17E−03 | 0.77 | 3.51E−03 |
| FCN1 | 102.82 | −1.38 | 3.65E−03 | −1.66 | 9.61E−06 | −2.07 | 7.94E−04 | −1.38 | 3.65E−03 |
| RETN | 3.10 | −3.09 | 6.29E−04 | −2.78 | 3.70E−03 | −4.67 | 1.67E−05 | −2.78 | 3.70E−03 |
| SARAF | 320.01 | 1.11 | 2.79E−04 | 1.06 | 3.71E−03 | 1.17 | 6.96E−05 | 1.06 | 3.71E−03 |
| TMEM39A | 21.79 | 3.82 | 3.74E−03 | 1.83 | 1.49E−03 | 2.93 | 1.64E−06 | 1.83 | 3.74E−03 |
| CAT | 151.59 | 0.88 | 3.96E−03 | 1.59 | 1.64E−04 | 1.70 | 1.09E−03 | 0.88 | 3.96E−03 |
| SIGLEC6 | 2.25 | 7.19 | 4.59E−03 | 7.61 | 2.87E−05 | 8.37 | 6.29E−05 | 7.19 | 4.59E−03 |
| GDI2 | 286.29 | 0.74 | 4.91E−03 | 0.83 | 1.19E−04 | 1.58 | 1.03E−04 | 0.74 | 4.91E−03 |
| NET1 | 11.17 | 3.44 | 4.90E−03 | 1.65 | 5.26E−03 | 4.18 | 2.29E−03 | 1.65 | 5.26E−03 |
| VAMP7 | 21.00 | 3.14 | 5.38E−03 | 2.34 | 1.00E−03 | 1.51 | 4.29E−03 | 1.51 | 5.38E−03 |
| ADAM28 | 154.49 | 2.65 | 5.60E−03 | 1.10 | 3.58E−06 | 3.83 | 8.43E−04 | 1.10 | 5.60E−03 |
| LAMP1 | 0.43 | −2.91 | 5.73E−03 | −2.60 | 1.94E−05 | −4.51 | 1.05E−05 | −2.60 | 5.73E−03 |
| PLXND1 | 1.18 | −4.29 | 5.74E−03 | −4.01 | 3.42E−07 | −5.33 | 2.44E−09 | −4.01 | 5.74E−03 |
| CD207 | 1.05 | 6.30 | 5.79E−03 | 6.28 | 1.43E−04 | 8.40 | 8.82E−05 | 6.28 | 5.79E−03 |
| COX7CP1 | 0.03 | 4.99 | 6.01E−03 | 4.99 | 6.01E−03 | 4.99 | 6.01E−03 | 4.99 | 6.01E−03 |
| NEUROD2 | 0.50 | −1.59 | 1.02E−04 | −0.97 | 3.50E−03 | −1.79 | 6.09E−03 | −0.97 | 6.09E−03 |
| MAPK1IP1L | 64.83 | 2.09 | 6.11E−03 | 1.04 | 1.03E−04 | 1.84 | 1.12E−03 | 1.04 | 6.11E−03 |
| S100A12 | 4.43 | −4.22 | 6.37E−03 | −2.83 | 1.63E−05 | −5.46 | 7.71E−04 | −2.83 | 6.37E−03 |

TABLE S3-continued

| | | | | Differentially expressed genes (DEGs) FIGS. 12F-G | | | | | |
|---|---|---|---|---|---|---|---|---|---|
| PAK1 | 182.23 | 1.51 | 6.57E−03 | 1.51 | 1.02E−03 | 1.89 | 1.88E−04 | 1.51 | 6.57E−03 |
| ITM2C | 10.64 | 1.60 | 5.23E−05 | 1.15 | 6.85E−03 | 4.05 | 9.71E−08 | 1.15 | 6.85E−03 |
| TXNL4B | 8.93 | 7.16 | 7.15E−04 | 2.35 | 7.03E−03 | 4.38 | 1.48E−06 | 2.35 | 7.03E−03 |
| ALDH18A1 | 0.92 | 3.06 | 8.93E−04 | 2.78 | 7.58E−03 | 4.83 | 1.46E−03 | 2.78 | 7.58E−03 |
| STAB1 | 0.70 | −5.61 | 8.06E−03 | −4.87 | 6.34E−08 | −7.37 | 2.12E−08 | −4.87 | 8.06E−03 |
| LPIN3 | 0.30 | −1.27 | 4.91E−04 | −1.00 | 8.21E−03 | −1.84 | 3.51E−04 | −1.00 | 8.21E−03 |
| KLF2 | 5.80 | −2.45 | 4.09E−03 | −1.70 | 2.56E−05 | −2.61 | 8.54E−03 | −1.70 | 8.54E−03 |
| POGLUT1 | 21.98 | 3.16 | 8.57E−03 | 1.10 | 9.51E−04 | 1.58 | 7.50E−03 | 1.10 | 8.57E−03 |
| AFF3 | 38.72 | 0.92 | 5.32E−04 | 0.88 | 8.64E−03 | 3.05 | 7.11E−08 | 0.88 | 8.64E−03 |
| SDC3 | 0.66 | −1.02 | 8.63E−03 | −1.03 | 4.88E−03 | −1.21 | 8.76E−03 | −1.02 | 8.76E−03 |
| DHRS7 | 107.09 | 1.00 | 1.27E−04 | 1.24 | 9.16E−04 | 1.58 | 9.06E−03 | 1.00 | 9.06E−03 |
| TUBA1B | 989.80 | 1.27 | 9.24E−03 | 1.31 | 7.53E−05 | 2.66 | 1.47E−03 | 1.27 | 9.24E−03 |
| MARCH7 | 32.28 | 2.14 | 9.68E−03 | 0.72 | 3.40E−03 | 1.74 | 8.26E−03 | 0.72 | 9.68E−03 |
| PYGB | 1.09 | −3.59 | 9.70E−03 | −1.97 | 6.76E−03 | −3.34 | 5.86E−05 | −1.97 | 9.70E−03 |
| DPP7 | 30.33 | −1.41 | 6.57E−03 | −1.00 | 1.04E−02 | −1.79 | 1.34E−06 | −1.00 | 1.04E−02 |
| CSDE1 | 141.60 | 1.67 | 4.46E−03 | 0.79 | 2.79E−03 | 1.44 | 1.07E−02 | 0.79 | 1.07E−02 |
| ARPC5 | 344.81 | 0.96 | 7.70E−03 | 0.77 | 1.88E−03 | 0.65 | 1.10E−02 | 0.65 | 1.10E−02 |
| C6orf62 | 113.44 | 1.16 | 2.19E−03 | 1.04 | 5.03E−03 | 1.43 | 1.15E−02 | 1.04 | 1.15E−02 |
| CAP1 | 277.95 | 1.61 | 1.15E−02 | 0.68 | 2.67E−04 | 1.39 | 5.65E−04 | 0.68 | 1.15E−02 |
| SLC35F2 | 4.84 | 3.14 | 5.28E−04 | 2.28 | 1.16E−02 | 6.56 | 1.41E−05 | 2.28 | 1.16E−02 |
| PLSCR1 | 311.43 | 1.17 | 1.17E−02 | 1.22 | 4.28E−03 | 1.91 | 1.00E−02 | 1.17 | 1.17E−02 |
| SCOC | 14.76 | 5.45 | 2.86E−07 | 2.93 | 7.95E−04 | 2.21 | 1.20E−02 | 2.21 | 1.20E−02 |
| CEBPB | 0.98 | −2.33 | 1.23E−02 | −2.72 | 6.60E−08 | −3.58 | 1.14E−03 | −2.33 | 1.23E−02 |
| HIST2H3D | 1.86 | 10.86 | 2.13E−06 | 5.40 | 1.24E−02 | 8.42 | 5.66E−03 | 5.40 | 1.24E−02 |
| RABL6 | 1.45 | −2.33 | 2.56E−03 | −2.01 | 3.26E−05 | −2.66 | 1.25E−02 | −2.01 | 1.25E−02 |
| TMEM156 | 13.85 | 3.43 | 1.25E−02 | 1.28 | 3.38E−03 | 3.58 | 2.22E−04 | 1.28 | 1.25E−02 |
| MYD88 | 137.83 | 2.35 | 1.26E−02 | 1.10 | 2.31E−03 | 2.04 | 1.32E−03 | 1.10 | 1.26E−02 |
| SMG9 | 6.33 | −1.87 | 1.28E−02 | −1.32 | 1.02E−02 | −2.01 | 4.10E−03 | −1.32 | 1.28E−02 |
| ACTB | 8688.24 | 0.74 | 1.28E−02 | 0.71 | 2.55E−03 | 0.98 | 3.21E−05 | 0.71 | 1.28E−02 |
| PSMB4 | 643.80 | 0.94 | 6.45E−03 | 0.92 | 4.35E−03 | 0.86 | 1.29E−02 | 0.86 | 1.29E−02 |
| NPM1 | 545.66 | 1.18 | 1.31E−02 | 0.88 | 2.28E−03 | 1.21 | 2.24E−03 | 0.88 | 1.31E−02 |
| UGCG | 27.64 | 2.54 | 1.31E−02 | 1.45 | 7.39E−05 | 3.06 | 6.15E−03 | 1.45 | 1.31E−02 |
| TNK2 | 4.49 | −2.04 | 1.32E−02 | −1.20 | 4.41E−03 | −1.75 | 9.67E−03 | −1.20 | 1.32E−02 |
| HMGN1 | 184.86 | 0.93 | 1.25E−02 | 0.70 | 1.32E−02 | 1.57 | 7.96E−03 | 0.70 | 1.32E−02 |
| C1orf228 | 0.37 | −3.99 | 1.33E−02 | −4.12 | 5.86E−04 | −6.42 | 1.53E−04 | −3.99 | 1.33E−02 |
| CD5 | 13.61 | 4.64 | 1.36E−02 | 6.08 | 1.91E−10 | 7.92 | 1.65E−03 | 4.64 | 1.36E−02 |
| MYO9B | 32.94 | −1.96 | 3.68E−03 | −1.02 | 1.28E−02 | −1.17 | 1.36E−02 | −1.02 | 1.36E−02 |
| CTPS1 | 35.38 | 3.29 | 1.37E−02 | 1.29 | 4.62E−04 | 2.77 | 3.46E−03 | 1.29 | 1.37E−02 |
| TMEM131 | 19.52 | 3.85 | 8.56E−05 | 0.79 | 1.37E−02 | 1.81 | 2.46E−03 | 0.79 | 1.37E−02 |
| PLEKHG3 | 0.04 | −7.07 | 1.39E−02 | −3.79 | 3.82E−03 | −5.27 | 4.82E−03 | −3.79 | 1.39E−02 |
| CYB5B | 30.97 | 2.84 | 8.42E−03 | 1.37 | 3.39E−03 | 2.26 | 1.40E−02 | 1.37 | 1.40E−02 |
| MSL3 | 42.51 | 1.79 | 3.32E−03 | 0.82 | 1.41E−02 | 1.74 | 3.92E−04 | 0.82 | 1.41E−02 |
| RPS28 | 406.47 | −1.05 | 1.34E−02 | −0.71 | 1.42E−02 | −1.74 | 1.25E−03 | −0.71 | 1.42E−02 |
| RPLP2 | 504.43 | −1.11 | 3.48E−04 | −0.57 | 1.44E−02 | −1.30 | 3.55E−03 | −0.57 | 1.44E−02 |
| ZFR | 45.72 | 0.87 | 2.42E−03 | 0.83 | 1.47E−02 | 1.61 | 4.83E−03 | 0.83 | 1.47E−02 |
| IFNL1 | 0.29 | 6.15 | 1.50E−02 | 4.62 | 1.82E−03 | 8.17 | 1.15E−06 | 4.62 | 1.50E−02 |
| CDK5RAP3 | 71.71 | −1.34 | 1.03E−02 | −0.76 | 1.51E−02 | −1.41 | 8.48E−05 | −0.76 | 1.51E−02 |
| FARS2 | 17.25 | 2.93 | 1.52E−02 | 2.29 | 1.14E−02 | 4.39 | 2.54E−03 | 2.29 | 1.52E−02 |
| DDX5 | 828.62 | 0.85 | 1.63E−02 | 0.97 | 3.39E−03 | 1.31 | 2.86E−05 | 0.85 | 1.63E−02 |
| RAC2 | 216.74 | 1.04 | 1.64E−02 | 0.95 | 4.08E−03 | 1.08 | 2.76E−03 | 0.95 | 1.64E−02 |
| OR9K1P | 0.03 | −3.09 | 1.66E−02 | −2.65 | 3.22E−03 | −3.58 | 6.89E−04 | −2.65 | 1.66E−02 |
| RBBP4 | 62.11 | 2.09 | 1.74E−02 | 1.15 | 2.27E−03 | 3.00 | 1.90E−04 | 1.15 | 1.74E−02 |
| HSPA8 | 438.79 | 0.86 | 1.78E−02 | 0.98 | 4.25E−03 | 1.01 | 8.32E−04 | 0.86 | 1.78E−02 |
| TINCR | 0.05 | −5.09 | 1.79E−02 | −2.96 | 9.20E−03 | −6.35 | 9.18E−03 | −2.96 | 1.79E−02 |
| BEND5 | 1.26 | 7.82 | 1.52E−02 | 4.71 | 9.88E−03 | 6.46 | 1.81E−02 | 4.71 | 1.81E−02 |
| EIF2S3 | 152.86 | 0.51 | 1.81E−02 | 0.54 | 4.35E−03 | 1.22 | 2.42E−04 | 0.51 | 1.81E−02 |
| GTF2IP18 | 0.06 | −3.86 | 7.26E−03 | −2.00 | 6.37E−03 | −3.88 | 1.83E−03 | −2.00 | 1.83E−02 |
| ARHGAP5 | 28.62 | 1.69 | 1.84E−02 | 1.20 | 4.67E−03 | 3.11 | 1.08E−03 | 1.20 | 1.84E−02 |
| EIF3E | 363.38 | 0.44 | 4.33E−03 | 0.38 | 1.85E−02 | 0.94 | 5.56E−03 | 0.38 | 1.85E−02 |
| CXCR4 | 547.33 | 1.23 | 1.46E−02 | 1.04 | 1.89E−02 | 2.04 | 3.14E−06 | 1.04 | 1.89E−02 |
| CD48 | 477.56 | 1.09 | 5.95E−03 | 1.12 | 1.19E−02 | 1.09 | 1.90E−02 | 1.09 | 1.90E−02 |
| RPL37A | 675.50 | −0.68 | 1.91E−02 | −0.49 | 1.34E−02 | −1.07 | 5.63E−03 | −0.49 | 1.91E−02 |
| TMEM14C | 152.18 | 1.24 | 8.82E−03 | 0.80 | 1.91E−02 | 1.68 | 5.76E−03 | 0.80 | 1.91E−02 |
| VCL | 33.65 | 0.90 | 1.91E−02 | 1.06 | 1.80E−03 | 1.58 | 7.99E−04 | 0.90 | 1.91E−02 |
| BRK1 | 295.26 | 1.23 | 1.91E−02 | 0.82 | 1.26E−02 | 1.49 | 7.27E−03 | 0.82 | 1.91E−02 |
| HCST | 68.16 | −1.82 | 1.92E−02 | −1.33 | 9.35E−06 | −2.58 | 1.42E−04 | −1.33 | 1.92E−02 |
| FEM1C | 4.92 | 2.75 | 5.08E−06 | 1.41 | 9.07E−03 | 0.99 | 1.94E−02 | 0.99 | 1.94E−02 |
| RHOC | 144.57 | 2.03 | 6.05E−03 | 0.95 | 1.40E−03 | 1.07 | 1.96E−02 | 0.95 | 1.96E−02 |
| MYL12B | 503.83 | 1.05 | 1.31E−05 | 0.86 | 1.97E−02 | 0.77 | 6.13E−03 | 0.77 | 1.97E−02 |
| ANKRD44 | 117.23 | 1.96 | 3.39E−04 | 0.81 | 1.31E−02 | 0.93 | 2.01E−02 | 0.81 | 2.01E−02 |
| PDIA3 | 154.05 | 1.14 | 2.02E−02 | 0.67 | 1.74E−02 | 1.19 | 4.25E−04 | 0.67 | 2.02E−02 |
| S100A6 | 636.40 | −0.79 | 3.02E−03 | −0.51 | 2.05E−02 | −1.44 | 3.04E−04 | −0.51 | 2.05E−02 |
| F13A1 | 1.03 | −5.43 | 2.05E−02 | −4.60 | 1.58E−05 | −4.60 | 2.88E−02 | −4.60 | 2.05E−02 |
| ZRSR1 | 0.03 | 4.75 | 2.11E−03 | 3.67 | 2.11E−02 | 4.75 | 2.11E−03 | 3.67 | 2.11E−02 |
| MOB1A | 87.13 | 0.79 | 2.12E−02 | 1.06 | 6.04E−04 | 1.29 | 2.49E−03 | 0.79 | 2.12E−02 |
| GLTSCR2 | 22.00 | −0.98 | 4.34E−03 | −0.70 | 2.12E−02 | −1.45 | 6.59E−03 | −0.70 | 2.12E−02 |
| BASP1 | 35.11 | 1.38 | 2.22E−02 | 0.89 | 5.06E−04 | 2.25 | 1.34E−03 | 0.89 | 2.22E−02 |
| MET | 0.01 | −2.77 | 1.40E−02 | −2.89 | 8.41E−03 | −3.42 | 2.24E−02 | −2.77 | 2.24E−02 |

TABLE S3-continued

| | | | | Differentially expressed genes (DEGs) FIGS. 12F-G | | | | |
|---|---|---|---|---|---|---|---|---|
| NIPA2 | 38.90 | 2.59 | 9.75E−04 | 1.18 | 9.22E−03 | 2.22 | 2.26E−02 | 1.18 | 2.26E−02 |
| RRM1 | 12.66 | 2.12 | 2.26E−02 | 1.56 | 1.43E−02 | 2.26 | 2.53E−03 | 1.56 | 2.26E−02 |
| MAPK1 | 18.55 | 2.85 | 1.76E−02 | 1.17 | 6.06E−04 | 1.35 | 2.28E−02 | 1.17 | 2.28E−02 |
| TSPYL1 | 24.93 | 2.60 | 2.29E−02 | 1.04 | 8.67E−03 | 0.73 | 7.41E−03 | 0.73 | 2.29E−02 |
| FGF23 | 2.52 | −1.14 | 3.71E−03 | −0.71 | 1.33E−02 | −1.25 | 2.30E−02 | −0.71 | 2.30E−02 |
| VN1R81P | 0.01 | 3.33 | 2.31E−02 | 3.33 | 2.31E−02 | 3.33 | 2.31E−02 | 3.33 | 2.31E−02 |
| CD163 | 18.36 | −2.08 | 2.32E−02 | −2.25 | 1.95E−06 | −2.45 | 2.38E−03 | −2.08 | 2.32E−02 |
| H2AFZ | 411.34 | 0.44 | 2.30E−02 | 0.81 | 9.43E−04 | 1.37 | 2.32E−02 | 0.44 | 2.32E−02 |
| EGR1 | 7.98 | −1.95 | 2.33E−02 | −1.89 | 1.57E−04 | −2.21 | 6.47E−04 | −1.89 | 2.33E−02 |
| FAM129B | 0.13 | −7.13 | 2.33E−02 | −3.76 | 1.18E−04 | −5.64 | 1.91E−03 | −3.76 | 2.33E−02 |
| CD63 | 161.76 | −0.71 | 1.73E−02 | −0.48 | 2.34E−02 | −1.27 | 2.87E−08 | −0.48 | 2.34E−02 |
| RQCD1 | 48.77 | 2.70 | 2.36E−02 | 0.82 | 5.65E−03 | 1.13 | 6.27E−03 | 0.82 | 2.36E−02 |
| ANXA5 | 494.05 | 0.69 | 2.38E−02 | 0.79 | 1.26E−02 | 1.35 | 2.31E−04 | 0.69 | 2.38E−02 |
| LY75 | 13.86 | 1.57 | 8.20E−04 | 1.18 | 2.97E−03 | 2.26 | 2.39E−02 | 1.18 | 2.39E−02 |
| PPT1 | 260.19 | 1.34 | 2.43E−02 | 0.99 | 1.65E−02 | 1.23 | 7.15E−04 | 0.99 | 2.43E−02 |
| AP1S2 | 313.63 | 1.17 | 2.46E−02 | 1.13 | 8.13E−04 | 0.95 | 1.01E−04 | 0.95 | 2.46E−02 |
| MZT2B | 10.71 | −2.66 | 1.40E−04 | −0.76 | 2.47E−02 | −1.76 | 1.54E−03 | −0.76 | 2.47E−02 |
| HEPACAM | 0.20 | −1.47 | 7.59E−05 | −0.71 | 1.49E−02 | −1.48 | 2.47E−02 | −0.71 | 2.47E−02 |
| NMD3 | 25.52 | 1.90 | 7.80E−03 | 1.06 | 2.43E−02 | 2.21 | 2.48E−02 | 1.06 | 2.48E−02 |
| TPP1 | 117.50 | 0.75 | 2.52E−02 | 0.58 | 1.04E−02 | 1.18 | 2.19E−03 | 0.58 | 2.52E−02 |
| RAP2B | 25.51 | 1.30 | 2.39E−02 | 0.65 | 2.54E−02 | 1.05 | 1.00E−02 | 0.65 | 2.54E−02 |
| KBTBD4 | 0.11 | 6.83 | 1.51E−04 | 3.75 | 2.55E−02 | 4.32 | 1.15E−02 | 3.75 | 2.55E−02 |
| FAM50A | 7.40 | −1.71 | 1.74E−02 | −1.19 | 2.58E−02 | −2.35 | 1.12E−02 | −1.19 | 2.58E−02 |
| SHKBP1 | 65.03 | −1.92 | 1.53E−02 | −0.75 | 2.61E−02 | −1.26 | 9.61E−03 | −0.75 | 2.61E−02 |
| NOG | 0.53 | −1.00 | 4.33E−03 | −0.72 | 2.65E−02 | −1.57 | 1.11E−04 | −0.72 | 2.65E−02 |
| HNRNPA1L2 | 1.16 | 6.42 | 1.68E−02 | 2.36 | 2.66E−02 | 2.99 | 1.20E−03 | 2.36 | 2.66E−02 |
| FLT3 | 50.03 | 1.86 | 2.71E−02 | 0.97 | 1.59E−02 | 2.33 | 3.45E−04 | 0.97 | 2.71E−02 |
| CIDECP | 28.22 | 4.21 | 3.27E−03 | 1.12 | 2.72E−02 | 3.01 | 2.06E−02 | 1.12 | 2.72E−02 |
| PEF1 | 43.45 | 3.12 | 2.08E−03 | 1.68 | 2.72E−02 | 1.31 | 1.46E−02 | 1.31 | 2.72E−02 |
| GLRX3 | 90.02 | 1.18 | 6.58E−03 | 0.54 | 1.70E−02 | 0.86 | 2.73E−02 | 0.54 | 2.73E−02 |
| CLEC4A | 339.84 | 0.43 | 2.76E−02 | 0.91 | 1.61E−04 | 2.47 | 1.69E−03 | 0.43 | 2.76E−02 |
| CCDC66 | 16.12 | 2.83 | 4.58E−03 | 1.25 | 2.76E−02 | 1.24 | 6.25E−03 | 1.24 | 2.76E−02 |
| ZNF410 | 27.74 | 3.35 | 4.29E−03 | 0.86 | 2.76E−02 | 2.81 | 1.87E−02 | 0.86 | 2.76E−02 |
| SNORD100 | 48.98 | 15.58 | 1.77E−10 | 8.55 | 2.41E−05 | 12.12 | 2.77E−02 | 8.55 | 2.77E−02 |
| KCNJ3 | 0.23 | −1.34 | 4.64E−04 | −0.71 | 2.65E−02 | −1.33 | 2.79E−02 | −0.71 | 2.79E−02 |
| CD1E | 52.15 | 4.01 | 1.05E−02 | 1.61 | 2.84E−02 | 4.87 | 8.62E−04 | 1.61 | 2.84E−02 |
| PPA1 | 317.49 | 1.06 | 2.87E−02 | 0.87 | 3.08E−05 | 1.90 | 5.68E−06 | 0.87 | 2.87E−02 |
| SLC24A2 | 0.14 | −1.30 | 1.22E−02 | −0.90 | 2.88E−02 | −0.92 | 7.77E−03 | −0.90 | 2.88E−02 |
| MBD3 | 7.39 | −2.51 | 1.71E−02 | −1.15 | 8.57E−03 | −1.61 | 2.89E−02 | −1.15 | 2.89E−02 |
| PRELID1 | 431.81 | 0.80 | 3.01E−04 | 0.57 | 1.98E−02 | 1.13 | 2.91E−02 | 0.57 | 2.91E−02 |
| SRSF3 | 292.52 | 0.45 | 2.94E−02 | 0.55 | 1.27E−02 | 1.22 | 1.24E−03 | 0.45 | 2.94E−02 |
| ASAP1 | 101.11 | 2.09 | 2.95E−02 | 1.35 | 2.07E−04 | 2.04 | 2.05E−02 | 1.35 | 2.95E−02 |
| CAPZA1 | 262.11 | 1.00 | 2.98E−02 | 0.96 | 3.90E−03 | 0.86 | 2.09E−02 | 0.86 | 2.98E−02 |
| CDK5RAP1 | 10.46 | −2.23 | 2.68E−02 | −1.73 | 2.98E−02 | −2.40 | 8.04E−03 | −1.73 | 2.98E−02 |
| TRPM6 | 0.04 | −2.79 | 1.65E−03 | −1.96 | 3.08E−02 | −1.98 | 2.30E−02 | −1.96 | 3.08E−02 |
| RN7SL32P | 0.03 | −6.83 | 1.63E−04 | −3.32 | 3.14E−02 | −7.36 | 2.40E−03 | −3.32 | 3.14E−02 |
| DGKZ | 3.03 | −2.71 | 3.64E−05 | −1.92 | 3.73E−05 | −1.87 | 3.18E−02 | −1.87 | 3.18E−02 |
| ELMO1 | 181.98 | 1.80 | 1.62E−07 | 1.15 | 1.47E−04 | 1.81 | 3.18E−02 | 1.15 | 3.18E−02 |
| ZDHHC17 | 28.06 | 1.04 | 2.09E−02 | 1.10 | 3.20E−02 | 2.75 | 6.77E−08 | 1.04 | 3.20E−02 |
| STK4 | 148.91 | 2.09 | 3.21E−02 | 1.15 | 1.11E−04 | 2.24 | 4.46E−03 | 1.15 | 3.21E−02 |
| ATP6AP1 | 123.35 | 0.90 | 3.22E−02 | 0.75 | 1.76E−02 | 0.91 | 1.58E−02 | 0.75 | 3.22E−02 |
| PLEK | 178.61 | 1.64 | 3.22E−02 | 0.73 | 5.49E−04 | 1.55 | 5.80E−07 | 0.73 | 3.22E−02 |
| HAVCR2 | 79.19 | 1.38 | 3.23E−02 | 0.60 | 4.23E−03 | 1.86 | 2.26E−03 | 0.60 | 3.23E−02 |
| C11orf76 | 0.29 | −1.70 | 1.77E−02 | −1.31 | 3.25E−02 | −1.86 | 6.02E−04 | −1.31 | 3.25E−02 |
| STK17B | 313.04 | 1.16 | 3.27E−02 | 0.74 | 1.62E−02 | 0.94 | 2.27E−04 | 0.74 | 3.27E−02 |
| CNBP | 487.37 | 0.53 | 3.28E−02 | 1.17 | 5.95E−04 | 1.67 | 5.79E−04 | 0.53 | 3.28E−02 |
| WDR13 | 11.48 | −2.56 | 1.35E−02 | −1.47 | 5.03E−03 | −2.32 | 3.29E−02 | −1.47 | 3.29E−02 |
| RRAS | 0.19 | −6.03 | 3.21E−02 | −2.72 | 3.34E−02 | −6.17 | 1.07E−02 | −2.72 | 3.34E−02 |
| CHCHD10 | 1.07 | −4.16 | 3.41E−02 | −3.20 | 2.20E−05 | −5.17 | 3.59E−04 | −3.20 | 3.41E−02 |
| ESD | 133.67 | 1.94 | 3.55E−04 | 0.75 | 2.16E−02 | 1.06 | 3.42E−02 | 0.75 | 3.42E−02 |
| CCT5 | 112.57 | 0.72 | 3.25E−02 | 0.75 | 3.43E−02 | 1.90 | 8.64E−06 | 0.72 | 3.43E−02 |
| COMMD9 | 105.37 | 0.76 | 6.10E−03 | 0.76 | 3.46E−02 | 1.95 | 6.57E−04 | 0.76 | 3.46E−02 |
| RN7SL163P | 0.04 | −6.66 | 3.48E−02 | −5.32 | 3.81E−04 | −8.97 | 2.07E−05 | −5.32 | 3.48E−02 |
| CTSC | 128.88 | 2.07 | 3.50E−02 | 0.81 | 4.79E−03 | 1.50 | 5.53E−03 | 0.81 | 3.50E−02 |
| PDGFA | 4.88 | −0.97 | 5.78E−04 | −0.66 | 3.51E−02 | −1.15 | 1.63E−02 | −0.66 | 3.51E−02 |
| GAPT | 85.61 | 1.74 | 3.33E−02 | 1.13 | 2.82E−02 | 1.13 | 3.54E−02 | 1.13 | 3.54E−02 |
| PTPRC | 398.37 | 0.82 | 3.54E−02 | 0.80 | 2.06E−03 | 1.46 | 6.73E−05 | 0.80 | 3.54E−02 |
| TMEM154 | 15.29 | 2.45 | 3.55E−03 | 0.80 | 3.58E−02 | 1.45 | 2.80E−02 | 0.80 | 3.58E−02 |
| PCMT1 | 81.75 | 1.02 | 1.96E−02 | 1.01 | 7.18E−03 | 0.91 | 3.65E−02 | 0.91 | 3.65E−02 |
| SLC43A3 | 13.67 | −1.52 | 3.68E−02 | −1.05 | 7.37E−03 | −1.44 | 1.60E−03 | −1.05 | 3.68E−02 |
| SPIB | 11.46 | 1.42 | 3.72E−02 | 1.23 | 1.93E−02 | 3.16 | 5.55E−06 | 1.23 | 3.72E−02 |
| PSMA6 | 397.34 | 1.19 | 8.30E−03 | 0.60 | 2.25E−02 | 0.87 | 3.73E−02 | 0.60 | 3.73E−02 |
| NT5DC1 | 15.33 | 3.33 | 7.35E−04 | 1.54 | 3.68E−02 | 2.33 | 3.74E−02 | 1.54 | 3.74E−02 |
| ATP5I | 114.89 | −1.15 | 1.55E−02 | −0.60 | 3.76E−02 | −1.26 | 3.38E−03 | −0.60 | 3.76E−02 |
| BAZ2A | 8.41 | −1.58 | 3.77E−02 | −1.48 | 1.56E−03 | −1.53 | 2.73E−03 | −1.48 | 3.77E−02 |
| H2AFJ | 52.38 | −1.05 | 1.27E−02 | −0.49 | 3.81E−02 | −1.22 | 1.82E−02 | −0.49 | 3.81E−02 |
| HSF2 | 3.11 | 3.68 | 1.42E−02 | 2.70 | 1.14E−02 | 5.90 | 3.81E−02 | 2.70 | 3.81E−02 |
| CD1C | 1088.39 | 0.97 | 3.84E−02 | 1.11 | 2.70E−03 | 3.43 | 1.96E−03 | 0.97 | 3.84E−02 |

TABLE S3-continued

| Differentially expressed genes (DEGs) FIGS. 12F-G | | | | | | | | | |
|---|---|---|---|---|---|---|---|---|---|
| CCDC6 | 27.94 | 3.00 | 3.85E−02 | 0.85 | 1.02E−02 | 1.11 | 5.04E−05 | 0.85 | 3.85E−02 |
| OAS3 | 21.89 | 3.86 | 4.10E−05 | 1.47 | 3.85E−02 | 1.25 | 1.31E−03 | 1.25 | 3.85E−02 |
| SLC38A1 | 44.97 | 1.00 | 3.86E−02 | 0.58 | 3.07E−02 | 2.04 | 6.66E−03 | 0.58 | 3.86E−02 |
| DBF4 | 15.30 | 2.74 | 1.12E−03 | 0.99 | 3.85E−02 | 2.27 | 3.87E−02 | 0.99 | 3.87E−02 |
| PRR27 | 0.01 | −4.56 | 1.69E−03 | −2.04 | 3.89E−02 | −3.51 | 2.22E−04 | −2.04 | 3.89E−02 |
| AP5Z1 | 2.51 | −3.18 | 3.89E−02 | −2.58 | 2.31E−03 | −3.57 | 2.09E−03 | −2.58 | 3.89E−02 |
| LURAP1 | 0.02 | −3.14 | 3.91E−02 | −3.38 | 1.06E−02 | −3.69 | 3.48E−04 | −3.14 | 3.91E−02 |
| ATP5F1 | 496.34 | 0.65 | 3.92E−02 | 0.88 | 1.24E−02 | 1.73 | 2.18E−03 | 0.65 | 3.92E−02 |
| LGALS9 | 162.70 | 1.31 | 1.33E−02 | 0.74 | 1.13E−02 | 1.13 | 3.93E−02 | 0.74 | 3.93E−02 |
| OR2V1 | 0.01 | −7.41 | 3.96E−02 | −3.30 | 9.31E−03 | −4.77 | 7.64E−03 | −3.30 | 3.96E−02 |
| EMP3 | 123.56 | −0.78 | 3.97E−02 | −0.75 | 2.87E−03 | −1.50 | 9.47E−08 | −0.75 | 3.97E−02 |
| TAB2 | 37.23 | 1.10 | 1.35E−02 | 0.52 | 4.03E−02 | 1.96 | 3.21E−03 | 0.52 | 4.03E−02 |
| IDO1 | 3.36 | 1.28 | 2.44E−02 | 2.33 | 4.04E−02 | 4.46 | 3.21E−03 | 1.28 | 4.04E−02 |
| CHD9 | 77.60 | 1.70 | 1.17E−02 | 0.88 | 1.83E−03 | 1.56 | 4.10E−02 | 0.88 | 4.10E−02 |
| PABPC1 | 2105.31 | 0.59 | 4.15E−02 | 0.68 | 7.89E−03 | 1.00 | 1.54E−05 | 0.59 | 4.15E−02 |
| FABP2 | 1.92 | −1.68 | 5.35E−03 | −1.02 | 2.41E−02 | −1.26 | 4.16E−02 | −1.02 | 4.16E−02 |
| SCP2 | 118.32 | 1.41 | 1.25E−04 | 0.63 | 4.16E−02 | 1.31 | 1.11E−02 | 0.63 | 4.16E−02 |
| FAM103A1 | 22.18 | 2.79 | 3.99E−04 | 0.98 | 3.82E−02 | 3.20 | 4.16E−02 | 0.98 | 4.16E−02 |
| RABAC1 | 80.09 | −1.10 | 8.60E−04 | −0.51 | 4.17E−02 | −1.22 | 5.49E−03 | −0.51 | 4.17E−02 |
| HDAC9 | 121.18 | 0.67 | 2.42E−03 | 0.85 | 1.01E−02 | 1.82 | 4.22E−02 | 0.67 | 4.22E−02 |
| GAK | 20.87 | −1.52 | 4.23E−02 | −1.63 | 1.12E−04 | −1.94 | 2.38E−02 | −1.52 | 4.23E−02 |
| CST3 | 6747.21 | 0.93 | 1.04E−02 | 0.69 | 4.24E−02 | 1.46 | 2.44E−05 | 0.69 | 4.24E−02 |
| TUBGCP2 | 32.63 | −1.55 | 4.24E−02 | −1.10 | 1.96E−03 | −1.52 | 6.74E−03 | −1.10 | 4.24E−02 |
| GPM6A | 0.78 | −1.67 | 5.94E−03 | −1.39 | 2.27E−03 | −2.93 | 4.25E−02 | −1.39 | 4.25E−02 |
| RN7SL670P | 0.15 | −5.02 | 3.30E−02 | −3.26 | 3.69E−02 | −4.17 | 4.25E−02 | −3.26 | 4.25E−02 |
| NLRP12 | 0.67 | −3.88 | 4.26E−02 | −2.54 | 2.16E−04 | −4.20 | 5.43E−07 | −2.54 | 4.26E−02 |
| MCOLN2 | 36.26 | 2.42 | 8.95E−03 | 1.90 | 1.13E−05 | 2.85 | 4.30E−02 | 1.90 | 4.30E−02 |
| KIT | 0.96 | 4.87 | 4.30E−02 | 3.73 | 4.03E−02 | 8.21 | 3.05E−06 | 3.73 | 4.30E−02 |
| MIB2 | 0.46 | −3.05 | 4.30E−02 | −2.13 | 2.47E−02 | −4.09 | 1.20E−02 | −2.13 | 4.30E−02 |
| TNFRSF1B | 16.59 | −1.32 | 4.32E−02 | −1.57 | 1.90E−06 | −2.27 | 1.55E−04 | −1.32 | 4.32E−02 |
| TMEM55A | 54.33 | 3.55 | 4.32E−02 | 2.47 | 2.52E−04 | 5.08 | 9.90E−03 | 2.47 | 4.32E−02 |
| SSBP4 | 7.78 | −2.24 | 4.33E−02 | −1.54 | 6.31E−04 | −2.09 | 1.67E−02 | −1.54 | 4.33E−02 |
| BLNK | 26.24 | 2.33 | 2.97E−02 | 2.19 | 2.36E−04 | 2.70 | 4.38E−02 | 2.19 | 4.38E−02 |
| RANP1 | 0.01 | 2.71 | 5.09E−03 | 2.03 | 4.41E−02 | 2.71 | 5.09E−03 | 2.03 | 4.41E−02 |
| MIR548AD | 0.03 | 4.87 | 8.58E−03 | 4.10 | 4.41E−02 | 4.87 | 8.58E−03 | 4.10 | 4.41E−02 |
| RN7SL25P | 0.11 | −6.32 | 2.74E−03 | −2.53 | 4.42E−02 | −4.30 | 1.14E−02 | −2.53 | 4.42E−02 |
| BTAF1 | 21.76 | 2.55 | 4.45E−02 | 1.02 | 4.61E−03 | 2.46 | 9.79E−04 | 1.02 | 4.45E−02 |
| SYNE4 | 0.01 | −4.51 | 4.45E−02 | −2.92 | 8.57E−03 | −3.12 | 1.51E−02 | −2.92 | 4.45E−02 |
| UFC1 | 195.10 | 1.17 | 4.48E−02 | 0.59 | 3.14E−03 | 2.13 | 1.86E−02 | 0.59 | 4.48E−02 |
| RNA5SP395 | 0.01 | 2.59 | 4.48E−02 | 2.59 | 4.48E−02 | 2.59 | 4.48E−02 | 2.59 | 4.48E−02 |
| TCEA3 | 5.48 | 5.83 | 4.50E−02 | 2.57 | 5.29E−03 | 4.48 | 1.69E−04 | 2.57 | 4.50E−02 |
| UQCR11 | 135.10 | −0.74 | 1.91E−06 | −0.33 | 4.51E−02 | −0.83 | 2.59E−03 | −0.33 | 4.51E−02 |
| ZNF483 | 0.45 | −1.85 | 4.52E−02 | −1.43 | 1.84E−02 | −2.14 | 2.92E−03 | −1.43 | 4.52E−02 |
| RIPPLY3 | 0.06 | −3.69 | 3.70E−04 | −2.00 | 4.53E−02 | −2.71 | 1.56E−02 | −2.00 | 4.53E−02 |
| SCUBE1 | 0.12 | −3.37 | 1.14E−02 | −1.99 | 2.54E−02 | −4.29 | 4.54E−02 | −1.99 | 4.54E−02 |
| LCP1 | 349.04 | 0.87 | 4.56E−02 | 1.11 | 3.21E−04 | 1.47 | 5.08E−04 | 0.87 | 4.56E−02 |
| ALG3 | 39.85 | 1.62 | 7.20E−03 | 1.11 | 4.19E−02 | 1.36 | 4.57E−02 | 1.11 | 4.57E−02 |
| ARPC3 | 1063.21 | 0.80 | 5.73E−04 | 0.40 | 4.59E−02 | 0.91 | 3.88E−03 | 0.40 | 4.59E−02 |
| RHBDL2 | 0.09 | −2.70 | 9.09E−04 | −1.63 | 3.75E−02 | −2.20 | 4.59E−02 | −1.63 | 4.59E−02 |
| SNX21 | 0.09 | −4.08 | 4.28E−02 | −2.86 | 4.55E−02 | −3.85 | 4.60E−02 | −2.86 | 4.60E−02 |
| EHF | 1.17 | 7.28 | 4.64E−02 | 7.06 | 6.96E−05 | 7.91 | 8.30E−03 | 7.06 | 4.64E−02 |
| RNPC3 | 17.11 | 2.61 | 2.18E−02 | 0.88 | 4.64E−02 | 1.60 | 1.15E−04 | 0.88 | 4.64E−02 |
| MBOAT4 | 0.20 | 5.57 | 4.68E−02 | 3.09 | 1.97E−02 | 7.67 | 2.98E−07 | 3.09 | 4.68E−02 |
| TGFBI | 233.08 | 0.42 | 4.17E−02 | 0.67 | 4.70E−02 | 0.75 | 3.61E−02 | 0.42 | 4.70E−02 |
| PRPF38A | 24.09 | 2.62 | 4.73E−02 | 1.36 | 5.06E−03 | 1.13 | 4.04E−02 | 1.13 | 4.73E−02 |
| FPGS | 6.74 | −2.22 | 7.69E−02 | −1.50 | 6.23E−03 | −1.33 | 4.77E−02 | −1.33 | 4.77E−02 |
| PPP1R14B | 1.01 | −3.40 | 4.77E−02 | −2.74 | 8.07E−04 | −3.04 | 5.79E−04 | −2.74 | 4.77E−02 |
| GYPC | 25.55 | 2.09 | 2.60E−03 | 0.75 | 4.78E−02 | 3.01 | 8.94E−03 | 0.75 | 4.78E−02 |
| ACER3 | 51.91 | 2.26 | 2.89E−02 | 0.89 | 4.79E−02 | 2.12 | 3.00E−06 | 0.89 | 4.79E−02 |
| UNC93B1 | 5.05 | −1.82 | 4.80E−02 | −1.39 | 5.10E−03 | −2.92 | 4.93E−07 | −1.39 | 4.80E−02 |
| GPR160 | 19.73 | 2.32 | 4.81E−02 | 1.81 | 9.73E−04 | 2.23 | 2.54E−02 | 1.81 | 4.81E−02 |
| CACNA2D3 | 60.08 | 2.41 | 4.23E−03 | 0.93 | 4.81E−02 | 2.47 | 4.35E−03 | 0.93 | 4.81E−02 |
| TSPO | 405.39 | −0.55 | 4.83E−02 | −0.56 | 1.59E−02 | −1.21 | 6.94E−03 | −0.55 | 4.83E−02 |
| SRSF6 | 63.05 | 1.00 | 3.41E−02 | 0.73 | 1.87E−02 | 0.86 | 4.85E−02 | 0.73 | 4.85E−02 |
| PLPP1 | 1.33 | 4.11 | 4.19E−02 | 2.86 | 8.39E−03 | 5.08 | 4.88E−02 | 2.86 | 4.88E−02 |
| FAM117B | 6.55 | 2.59 | 4.90E−02 | 0.89 | 3.08E−02 | 1.20 | 2.42E−02 | 0.89 | 4.90E−02 |
| UBP1 | 18.87 | 1.92 | 4.91E−02 | 0.65 | 3.54E−02 | 1.01 | 2.68E−02 | 0.65 | 4.91E−02 |
| MIR4502 | 0.01 | 2.68 | 4.95E−02 | 2.68 | 4.95E−02 | 2.68 | 4.95E−02 | 2.68 | 4.95E−02 |
| SCARNA20 | 0.01 | 3.56 | 2.82E−02 | 3.04 | 4.99E−02 | 3.56 | 2.82E−02 | 3.04 | 4.99E−02 |

| CD5−CD163− DC3 DEGs | | | | | | | | | |
|---|---|---|---|---|---|---|---|---|---|
| geneSymbol | tpm.CD163− | lfc.CD5+ | p.CD5+ | lfc.CD14− | p.CD14− | lfc.CD14+ | p.CD14+ | lfc.MostConservative | p.MostConservative |
| SH2D4B | 0.04 | 4.90 | 2.09E−06 | 4.13 | 1.02E−05 | 5.45 | 1.13E−04 | 4.13 | 1.13E−04 |
| LRRC27 | 50.44 | 4.11 | 5.75E−07 | 4.49 | 3.94E−07 | 3.73 | 1.16E−04 | 3.73 | 1.16E−04 |
| DIO3OS | 4.92 | 9.02 | 1.92E−05 | 10.54 | 2.28E−05 | 9.67 | 2.15E−04 | 9.02 | 2.15E−04 |

TABLE S3-continued

| | | | | Differentially expressed genes (DEGs) FIGS. 12F-G | | | | |
|---|---|---|---|---|---|---|---|---|
| ING4 | 82.42 | 2.72 | 2.43E−04 | 3.12 | 6.71E−06 | 1.72 | 9.29E−04 | 1.72 | 9.29E−04 |
| PYDC1 | 1.98 | 10.28 | 3.67E−05 | 9.41 | 5.41E−05 | 10.95 | 1.45E−03 | 9.41 | 1.45E−03 |
| DUSP22 | 15.76 | −2.04 | 3.04E−04 | −1.51 | 1.57E−03 | −2.04 | 1.14E−03 | −1.51 | 1.57E−03 |
| DDX60 | 0.08 | −6.36 | 3.44E−05 | −5.46 | 7.31E−05 | −6.79 | 1.61E−03 | −5.46 | 1.61E−03 |
| ATP10B | 3.41 | 2.91 | 1.74E−04 | 2.99 | 1.50E−04 | 2.23 | 1.65E−03 | 2.23 | 1.65E−03 |
| REXO1L1 | 12.25 | 5.71 | 2.73E−05 | 6.66 | 9.49E−06 | 4.88 | 1.99E−03 | 4.88 | 1.99E−03 |
| THAP4 | 58.25 | 2.81 | 2.77E−06 | 3.95 | 8.20E−07 | 4.05 | 2.29E−03 | 2.81 | 2.29E−03 |
| L3HYPDH | 0.76 | −3.87 | 7.66E−07 | −3.01 | 8.71E−05 | −4.33 | 2.51E−03 | −3.01 | 2.51E−03 |
| DDB1 | 94.63 | 1.29 | 8.61E−06 | 1.09 | 2.85E−07 | 1.86 | 2.66E−03 | 1.09 | 2.66E−03 |
| OR4F17 | 25.20 | 2.85 | 1.62E−03 | 3.05 | 4.48E−04 | 2.52 | 3.01E−03 | 2.52 | 3.01E−03 |
| TRIM34 | 0.53 | −3.52 | 3.64E−03 | −4.40 | 1.62E−03 | −5.07 | 1.66E−03 | −3.52 | 3.64E−03 |
| WBSCR16 | 0.37 | −2.94 | 3.76E−03 | −3.27 | 2.10E−03 | −4.61 | 9.71E−04 | −2.94 | 3.76E−03 |
| CLDN18 | 0.12 | 3.14 | 6.53E−04 | 3.68 | 2.17E−03 | 1.25 | 4.03E−03 | 1.25 | 4.03E−03 |
| SMARCAD1 | 0.19 | −5.01 | 2.79E−04 | −3.19 | 4.04E−03 | −4.28 | 3.30E−03 | −3.19 | 4.04E−03 |
| LINC00173 | 0.22 | −3.83 | 4.66E−04 | −4.70 | 5.47E−05 | −3.91 | 4.44E−03 | −3.83 | 4.44E−03 |
| HELQ | 0.20 | −4.27 | 6.70E−06 | −4.48 | 2.33E−06 | −2.81 | 4.50E−03 | −2.81 | 4.50E−03 |
| CERS6 | 0.27 | −3.18 | 1.21E−06 | −3.15 | 1.26E−06 | −4.21 | 4.75E−03 | −3.15 | 4.75E−03 |
| STK40 | 0.62 | −2.96 | 5.17E−03 | −3.39 | 2.05E−03 | −3.68 | 2.80E−03 | −2.96 | 5.17E−03 |
| WSB1 | 43.86 | −1.71 | 4.27E−05 | −0.97 | 5.21E−03 | −1.32 | 2.23E−03 | −0.97 | 5.21E−03 |
| PARP4 | 2.12 | −2.67 | 7.52E−05 | −2.66 | 1.63E−04 | −2.09 | 5.39E−03 | −2.09 | 5.39E−03 |
| PPP1R18 | 7.83 | −2.27 | 1.27E−03 | −2.15 | 1.58E−03 | −2.24 | 5.58E−03 | −2.15 | 5.58E−03 |
| FEM1C | 0.73 | −2.75 | 5.08E−06 | −1.35 | 5.32E−03 | −1.76 | 5.66E−03 | −1.35 | 5.66E−03 |
| ZHX1 | 2.01 | −1.94 | 4.89E−05 | −1.82 | 5.33E−05 | −2.69 | 5.69E−03 | −1.82 | 5.69E−03 |
| SNX2 | 17.24 | −2.30 | 1.01E−03 | −2.28 | 2.40E−03 | −1.97 | 5.95E−03 | −1.97 | 5.95E−03 |
| SRSF8 | 31.89 | 1.37 | 2.78E−03 | 1.95 | 4.87E−05 | 3.08 | 6.05E−03 | 1.37 | 6.05E−03 |
| YARS | 6.64 | −2.17 | 3.23E−03 | −2.04 | 6.09E−03 | −2.14 | 4.26E−03 | −2.04 | 6.09E−03 |
| NEXN | 0.23 | −1.78 | 6.15E−03 | −3.25 | 1.11E−05 | −4.59 | 3.12E−03 | −1.78 | 6.15E−03 |
| SESTD1 | 0.27 | −5.29 | 2.83E−03 | −4.59 | 6.60E−03 | −6.01 | 2.70E−03 | −4.59 | 6.60E−03 |
| OAS3 | 1.51 | −3.86 | 4.10E−05 | −2.38 | 2.36E−03 | −2.60 | 6.92E−03 | −2.38 | 6.92E−03 |
| HEMK1 | 0.50 | −3.26 | 1.16E−03 | −4.09 | 1.25E−04 | −4.50 | 7.15E−03 | −3.26 | 7.15E−03 |
| LGALS9C | 0.22 | 4.39 | 2.71E−04 | 5.17 | 1.86E−04 | 6.37 | 7.15E−03 | 4.39 | 7.15E−03 |
| IGHG4 | 0.18 | 6.89 | 4.37E−09 | 4.89 | 5.59E−04 | 5.90 | 7.47E−03 | 4.89 | 7.47E−03 |
| KLHL12 | 0.21 | −4.24 | 5.45E−04 | −3.69 | 2.36E−03 | −4.00 | 7.71E−03 | −3.69 | 7.71E−03 |
| SNX10 | 18.71 | −0.86 | 7.76E−03 | −0.97 | 4.61E−03 | −1.64 | 5.29E−03 | −0.86 | 7.76E−03 |
| SSH2 | 10.44 | −1.38 | 2.86E−04 | −1.43 | 3.26E−04 | −1.78 | 7.79E−03 | −1.38 | 7.79E−03 |
| MAPK14 | 4.79 | −2.11 | 7.99E−03 | −2.26 | 6.38E−03 | −2.59 | 3.13E−03 | −2.11 | 7.99E−03 |
| PAF1 | 0.44 | −3.60 | 8.10E−03 | −4.34 | 1.77E−03 | −5.33 | 2.14E−03 | −3.60 | 8.10E−03 |
| ABCC8 | 2.52 | 8.52 | 3.68E−03 | 6.77 | 8.39E−03 | 6.54 | 7.42E−03 | 6.54 | 8.39E−03 |
| PAK1IP1 | 2.87 | −2.58 | 8.84E−04 | −1.81 | 5.35E−03 | −2.46 | 8.44E−03 | −1.81 | 8.44E−03 |
| AP4B1 | 1.09 | −4.28 | 2.09E−03 | −2.75 | 7.35E−03 | −3.32 | 8.45E−03 | −2.75 | 8.45E−03 |
| NOL6 | 0.24 | −2.94 | 2.99E−03 | −2.36 | 9.35E−03 | −3.75 | 6.30E−03 | −2.36 | 9.35E−03 |
| RPS2L1 | 0.34 | 5.20 | 2.13E−04 | 2.49 | 9.57E−03 | 7.01 | 2.84E−03 | 2.49 | 9.57E−03 |
| GFM2 | 1.65 | −1.74 | 3.59E−03 | −2.06 | 1.05E−03 | −3.20 | 1.01E−02 | −1.74 | 1.01E−02 |
| FAM53C | 1.10 | −2.92 | 3.90E−03 | −2.69 | 8.22E−03 | −2.69 | 1.03E−02 | −2.69 | 1.03E−02 |
| DEC1 | 11.69 | 2.30 | 6.71E−04 | 1.56 | 5.31E−03 | 2.26 | 1.03E−02 | 1.56 | 1.03E−02 |
| RPS2P46 | 1.88 | 1.46 | 8.02E−03 | 1.48 | 1.04E−02 | 1.58 | 3.42E−03 | 1.46 | 1.04E−02 |
| RAET1K | 0.50 | 6.90 | 1.05E−02 | 7.30 | 8.96E−03 | 7.76 | 5.56E−03 | 6.90 | 1.05E−02 |
| TMEM8A | 0.13 | −4.40 | 3.07E−04 | −4.83 | 1.03E−04 | −5.90 | 1.15E−02 | −4.40 | 1.15E−02 |
| NOTCH3 | 4.13 | 5.54 | 1.41E−03 | 3.68 | 7.36E−03 | 3.03 | 1.17E−02 | 3.03 | 1.17E−02 |
| SLC35E2 | 0.75 | −1.50 | 1.19E−02 | −1.69 | 6.96E−03 | −2.36 | 7.53E−03 | −1.50 | 1.19E−02 |
| KIF13B | 0.90 | −1.72 | 1.44E−03 | −2.02 | 6.76E−05 | −3.38 | 1.22E−02 | −1.72 | 1.22E−02 |
| DIO2 | 3.52 | 9.59 | 1.05E−02 | 8.54 | 1.26E−02 | 11.01 | 7.82E−03 | 8.54 | 1.26E−02 |
| SEMA3B | 0.10 | 5.21 | 4.36E−03 | 4.18 | 1.26E−02 | 5.51 | 6.62E−03 | 4.18 | 1.26E−02 |
| ZNF33B | 1.47 | −1.84 | 1.49E−03 | −1.83 | 1.81E−03 | −2.54 | 1.26E−02 | −1.83 | 1.26E−02 |
| ZCCHC9 | 0.61 | −3.08 | 8.62E−05 | −2.84 | 1.50E−04 | −2.67 | 1.30E−02 | −2.67 | 1.30E−02 |
| LRRC59 | 0.54 | −3.39 | 2.14E−03 | −3.88 | 4.25E−06 | −3.45 | 1.34E−02 | −3.39 | 1.34E−02 |
| COX7B | 47.41 | 0.55 | 7.03E−03 | 0.50 | 1.11E−02 | 0.72 | 1.37E−02 | 0.50 | 1.37E−02 |
| ZNF148 | 1.23 | −2.79 | 1.11E−02 | −2.54 | 1.39E−02 | −3.28 | 6.84E−03 | −2.54 | 1.39E−02 |
| TREML3P | 1.82 | 9.94 | 1.14E−02 | 8.29 | 1.39E−02 | 10.83 | 1.18E−02 | 8.29 | 1.39E−02 |
| C1GALT1C1 | 0.28 | −3.82 | 3.89E−05 | −2.47 | 2.11E−03 | −5.09 | 1.41E−02 | −2.47 | 1.41E−02 |
| TMEM131 | 1.36 | −3.85 | 8.56E−05 | −3.05 | 2.25E−04 | −2.04 | 1.42E−02 | −2.04 | 1.42E−02 |
| MORC4 | 14.58 | 1.70 | 3.65E−03 | 1.37 | 1.47E−02 | 1.43 | 9.49E−03 | 1.37 | 1.47E−02 |
| TMEM164 | 0.95 | −1.96 | 1.48E−02 | −2.58 | 5.28E−03 | −2.89 | 9.98E−03 | −1.96 | 1.48E−02 |
| WHAMMP2 | 6.88 | 1.42 | 1.48E−02 | 1.66 | 8.02E−03 | 2.84 | 3.17E−03 | 1.42 | 1.48E−02 |
| GAPDHP72 | 1.06 | 5.91 | 1.41E−03 | 3.47 | 1.44E−02 | 5.52 | 1.50E−02 | 3.47 | 1.50E−02 |
| ALKBH4 | 10.83 | 3.60 | 3.12E−03 | 1.95 | 1.50E−02 | 3.25 | 1.64E−03 | 1.95 | 1.50E−02 |
| SAFB2 | 64.41 | 2.24 | 7.88E−06 | 1.57 | 1.50E−04 | 0.71 | 1.50E−02 | 0.71 | 1.50E−02 |
| CGN | 3.17 | 7.52 | 1.51E−02 | 7.68 | 1.35E−02 | 8.25 | 1.16E−02 | 7.52 | 1.51E−02 |
| TAF6 | 0.29 | −3.42 | 1.52E−02 | −3.41 | 1.37E−02 | −3.79 | 1.22E−02 | −3.41 | 1.52E−02 |
| DDX59 | 0.46 | −3.68 | 5.08E−03 | −4.45 | 1.43E−03 | −3.77 | 1.54E−02 | −3.68 | 1.54E−02 |
| C5orf17 | 10.61 | 3.45 | 1.01E−02 | 3.00 | 1.57E−02 | 3.53 | 1.02E−02 | 3.00 | 1.57E−02 |
| MMP2 | 2.72 | 10.70 | 1.60E−02 | 10.44 | 1.49E−02 | 11.41 | 1.52E−02 | 10.44 | 1.60E−02 |
| C11orf71 | 0.06 | −4.77 | 6.89E−04 | −4.30 | 1.65E−02 | −6.53 | 9.36E−03 | −4.30 | 1.65E−02 |
| ANKRD17 | 56.56 | 1.30 | 1.75E−03 | 1.69 | 1.77E−04 | 1.72 | 1.66E−02 | 1.30 | 1.66E−02 |
| OTUD7A | 0.31 | 4.44 | 1.67E−02 | 3.87 | 1.63E−02 | 5.62 | 5.06E−03 | 3.87 | 1.67E−02 |
| PAIP2B | 0.05 | −2.32 | 3.85E−03 | −2.81 | 1.88E−04 | −2.98 | 1.76E−02 | −2.32 | 1.76E−02 |
| FAM131A | 15.25 | 5.83 | 3.66E−04 | 3.48 | 1.54E−03 | 3.48 | 1.80E−02 | 3.48 | 1.80E−02 |
| AASDHPPT | 0.72 | −4.25 | 2.05E−06 | −3.77 | 1.16E−05 | −3.15 | 1.81E−02 | −3.15 | 1.81E−02 |

TABLE S3-continued

| Differentially expressed genes (DEGs) FIGS. 12F-G | | | | | | | | | |
|---|---|---|---|---|---|---|---|---|---|
| HTATSF1 | 29.19 | 0.85 | 5.57E−05 | 2.18 | 1.19E−04 | 2.92 | 1.87E−02 | 0.85 | 1.87E−02 |
| LFNG | 2.35 | −1.66 | 4.93E−03 | −1.76 | 3.18E−03 | −1.89 | 1.89E−02 | −1.66 | 1.89E−02 |
| ZDHHC12 | 80.48 | 2.03 | 2.00E−02 | 2.70 | 6.61E−03 | 3.75 | 2.80E−03 | 2.03 | 2.00E−02 |
| FAH | 69.43 | 3.66 | 2.59E−03 | 2.02 | 2.01E−02 | 4.63 | 1.57E−02 | 2.02 | 2.01E−02 |
| CYFIP1 | 1.27 | −3.61 | 4.76E−03 | −3.25 | 9.51E−03 | −2.97 | 2.01E−02 | −2.97 | 2.01E−02 |
| SRSF4 | 52.92 | 0.81 | 1.09E−02 | 0.74 | 2.03E−02 | 1.10 | 1.00E−02 | 0.74 | 2.03E−02 |
| SCOC | 0.34 | −5.45 | 2.86E−07 | −2.52 | 2.35E−03 | −3.24 | 2.05E−02 | −2.52 | 2.05E−02 |
| MAN1C1 | 21.33 | 5.38 | 1.13E−02 | 3.92 | 2.09E−02 | 4.46 | 1.21E−02 | 3.92 | 2.09E−02 |
| RPSA | 1297.55 | 0.44 | 1.45E−02 | 0.66 | 2.11E−02 | 0.66 | 4.50E−03 | 0.44 | 2.11E−02 |
| PDGFC | 0.02 | −5.19 | 2.12E−02 | −6.36 | 1.10E−02 | −9.31 | 6.23E−03 | −5.19 | 2.12E−02 |
| PREP | 31.38 | 3.39 | 1.74E−02 | 3.86 | 1.26E−02 | 3.29 | 2.14E−02 | 3.29 | 2.14E−02 |
| RPL23AP2 | 3.27 | 1.21 | 4.95E−03 | 1.74 | 2.19E−03 | 1.44 | 2.16E−02 | 1.21 | 2.16E−02 |
| WDR66 | 6.56 | 1.43 | 1.10E−03 | 1.11 | 6.54E−03 | 1.14 | 2.17E−02 | 1.11 | 2.17E−02 |
| IFIH1 | 0.93 | −2.98 | 4.37E−04 | −2.06 | 5.22E−03 | −3.50 | 2.20E−02 | −2.06 | 2.20E−02 |
| EIF3S5P1 | 1.16 | 7.94 | 2.21E−02 | 8.07 | 2.17E−02 | 10.18 | 1.62E−02 | 7.94 | 2.21E−02 |
| SNX1 | 4.02 | −3.07 | 3.67E−03 | −2.41 | 1.54E−02 | −2.69 | 2.25E−02 | −2.41 | 2.25E−02 |
| CDH26 | 3.20 | 9.17 | 1.35E−02 | 7.42 | 2.17E−02 | 6.60 | 2.30E−02 | 6.60 | 2.30E−02 |
| IFITM3 | 117.80 | −1.47 | 1.13E−02 | −1.51 | 8.69E−03 | −2.10 | 2.31E−02 | −1.47 | 2.31E−02 |
| MAN1A2 | 2.77 | −2.13 | 5.34E−07 | −2.09 | 4.84E−06 | −1.91 | 2.31E−02 | −1.91 | 2.31E−02 |
| MUL1 | 0.03 | −6.57 | 3.30E−04 | −6.68 | 4.00E−04 | −4.81 | 2.32E−02 | −4.81 | 2.32E−02 |
| NECAB1 | 0.55 | 4.33 | 2.33E−02 | 4.35 | 1.95E−02 | 5.40 | 1.28E−02 | 4.33 | 2.33E−02 |
| NEK6 | 0.09 | −2.78 | 7.24E−03 | −2.88 | 4.34E−03 | −5.77 | 2.39E−02 | −2.78 | 2.39E−02 |
| SCLT1 | 7.48 | −1.74 | 1.76E−04 | −1.38 | 9.82E−04 | −1.16 | 2.42E−02 | −1.16 | 2.42E−02 |
| ZNF439 | 0.55 | −2.74 | 7.74E−04 | −2.12 | 8.19E−03 | −2.55 | 2.42E−02 | −2.12 | 2.42E−02 |
| IMMP1L | 34.04 | 3.90 | 2.78E−03 | 2.42 | 1.23E−02 | 5.44 | 2.44E−02 | 2.42 | 2.44E−02 |
| ARHGDIG | 4.93 | 8.41 | 6.77E−07 | 6.09 | 3.09E−04 | 7.86 | 2.49E−02 | 6.09 | 2.49E−02 |
| CCZ1B | 99.76 | 1.56 | 2.46E−02 | 1.56 | 2.49E−02 | 2.10 | 1.91E−02 | 1.56 | 2.49E−02 |
| DEXI | 12.66 | 3.12 | 8.65E−03 | 2.12 | 2.49E−02 | 4.30 | 3.25E−03 | 2.12 | 2.49E−02 |
| PNPLA8 | 2.55 | −3.22 | 2.92E−03 | −3.24 | 2.41E−03 | −3.04 | 2.52E−02 | −3.04 | 2.52E−02 |
| SHMT2 | 3.05 | −2.57 | 2.86E−06 | −2.42 | 6.12E−07 | −2.06 | 2.52E−02 | −2.06 | 2.52E−02 |
| ZNF493 | 19.79 | 1.82 | 1.30E−02 | 1.52 | 2.22E−02 | 1.55 | 2.53E−02 | 1.52 | 2.53E−02 |
| ANKAR | 0.04 | −4.54 | 2.30E−02 | −3.83 | 2.54E−02 | −5.60 | 2.20E−02 | −3.83 | 2.54E−02 |
| PTPN4 | 18.06 | 1.85 | 2.57E−02 | 2.58 | 2.69E−03 | 1.50 | 2.06E−02 | 1.50 | 2.57E−02 |
| MYH11 | 13.72 | 4.11 | 1.67E−03 | 3.84 | 1.68E−03 | 2.85 | 2.60E−02 | 2.85 | 2.60E−02 |
| OR52E4 | 2.14 | 3.20 | 1.04E−02 | 3.49 | 1.03E−02 | 3.40 | 2.64E−02 | 3.20 | 2.64E−02 |
| MROH7 | 0.31 | −0.88 | 2.73E−02 | −1.49 | 2.43E−02 | −1.82 | 1.49E−02 | −0.88 | 2.73E−02 |
| GOLGA6L5 | 0.76 | 6.18 | 6.33E−03 | 4.51 | 2.73E−02 | 7.76 | 1.51E−03 | 4.51 | 2.73E−02 |
| TMEM144 | 0.50 | −2.66 | 3.44E−04 | −1.83 | 5.75E−03 | −4.70 | 2.74E−02 | −1.83 | 2.74E−02 |
| IVNS1ABP | 12.89 | −2.06 | 2.65E−02 | −2.42 | 1.48E−02 | −2.15 | 2.82E−02 | −2.06 | 2.82E−02 |
| ACADM | 6.82 | −1.91 | 5.86E−04 | −1.45 | 4.50E−02 | −2.03 | 2.82E−02 | −1.45 | 2.82E−02 |
| TRIO | 12.12 | −1.84 | 2.11E−02 | −1.67 | 2.83E−02 | −1.78 | 2.66E−02 | −1.67 | 2.83E−02 |
| PDCD2 | 4.71 | −2.43 | 3.78E−03 | −2.02 | 7.94E−03 | −1.86 | 2.86E−02 | −1.86 | 2.86E−02 |
| RELA | 48.61 | 2.00 | 5.18E−03 | 1.57 | 1.65E−02 | 1.60 | 2.87E−02 | 1.57 | 2.87E−02 |
| ATG4A | 0.02 | −5.51 | 2.88E−02 | −7.28 | 1.21E−02 | −6.74 | 2.78E−02 | −5.51 | 2.88E−02 |
| MPP7 | 1.16 | −4.15 | 8.41E−04 | −3.04 | 4.39E−03 | −3.06 | 2.89E−02 | −3.04 | 2.89E−02 |
| TRIM66 | 0.19 | −3.69 | 7.01E−05 | −2.38 | 1.31E−03 | −2.23 | 2.89E−02 | −2.23 | 2.89E−02 |
| CCDC92 | 0.45 | −1.96 | 2.36E−02 | −1.90 | 2.91E−02 | −3.90 | 3.24E−03 | −1.90 | 2.91E−02 |
| IGKC | 141.63 | 3.60 | 4.79E−03 | 3.24 | 6.62E−03 | 2.61 | 2.92E−02 | 2.61 | 2.92E−02 |
| FRG1CP | 0.58 | −3.85 | 3.32E−04 | −2.43 | 5.90E−03 | −3.46 | 2.93E−02 | −2.43 | 2.93E−02 |
| NUP153 | 0.39 | −2.69 | 2.93E−02 | −2.96 | 2.49E−02 | −3.35 | 1.59E−02 | −2.69 | 2.93E−02 |
| ZNF280C | 0.02 | −4.33 | 1.32E−02 | −3.58 | 2.99E−02 | −5.31 | 2.16E−02 | −3.58 | 2.99E−02 |
| SRP54 | 4.04 | −3.14 | 1.25E−02 | −2.47 | 2.99E−02 | −2.58 | 2.72E−02 | −2.47 | 2.99E−02 |
| IKBKG | 29.38 | 4.23 | 1.16E−03 | 2.85 | 6.46E−03 | 1.70 | 2.99E−02 | 1.70 | 2.99E−02 |
| RASSF8 | 4.93 | 3.73 | 2.11E−02 | 3.37 | 2.70E−02 | 3.04 | 3.06E−02 | 3.04 | 3.06E−02 |
| GSN | 176.65 | 0.72 | 6.62E−03 | 0.56 | 3.06E−02 | 1.16 | 3.04E−03 | 0.56 | 3.06E−02 |
| PCNX3 | 8.62 | 2.36 | 2.19E−02 | 2.03 | 3.09E−02 | 2.44 | 2.77E−02 | 2.03 | 3.09E−02 |
| MED13L | 2.74 | −2.41 | 1.53E−03 | −2.40 | 1.89E−03 | −2.07 | 3.10E−02 | −2.07 | 3.10E−02 |
| ARIH2OS | 0.13 | −3.58 | 2.38E−02 | −3.48 | 3.11E−02 | −6.33 | 2.73E−03 | −3.48 | 3.11E−02 |
| PPP2R2B | 28.08 | 7.02 | 4.86E−03 | 6.32 | 4.64E−03 | 3.19 | 3.12E−02 | 3.19 | 3.12E−02 |
| MKNK1 | 7.45 | −1.72 | 3.13E−02 | −2.15 | 1.31E−02 | −2.68 | 3.99E−03 | −1.72 | 3.13E−02 |
| ABCB5 | 9.53 | 8.20 | 2.75E−02 | 7.36 | 3.15E−02 | 7.24 | 2.71E−02 | 7.24 | 3.15E−02 |
| GPATCH2 | 0.60 | −2.74 | 1.37E−02 | −2.93 | 1.22E−02 | −2.67 | 3.18E−02 | −2.67 | 3.18E−02 |
| LBHD1 | 0.06 | −3.77 | 2.50E−02 | −5.23 | 9.97E−03 | −5.40 | 3.24E−02 | −3.77 | 3.24E−02 |
| DYNLT1 | 43.31 | −1.47 | 1.69E−02 | −1.27 | 2.71E−02 | −1.46 | 3.25E−02 | −1.27 | 3.25E−02 |
| PCCB | 2.13 | −2.42 | 2.14E−02 | −2.67 | 1.87E−02 | −2.67 | 3.27E−02 | −2.42 | 3.27E−02 |
| GABRP | 17.93 | 3.05 | 9.81E−03 | 4.91 | 3.29E−03 | 1.88 | 3.30E−02 | 1.88 | 3.30E−02 |
| LY6E | 33.98 | −1.31 | 1.16E−02 | −1.28 | 1.24E−02 | −1.86 | 3.34E−02 | −1.28 | 3.34E−02 |
| PIGT | 214.72 | 1.34 | 1.10E−03 | 1.37 | 1.19E−03 | 0.93 | 3.34E−02 | 0.93 | 3.34E−02 |
| PNMAL1 | 0.49 | 3.00 | 7.62E−04 | 1.39 | 2.73E−02 | 3.47 | 3.37E−02 | 1.39 | 3.37E−02 |
| NSMCE2 | 3.16 | −3.00 | 3.65E−06 | −2.53 | 2.03E−05 | −2.39 | 3.37E−02 | −2.39 | 3.37E−02 |
| ARL17A | 24.34 | 1.53 | 2.06E−02 | 1.30 | 3.32E−02 | 1.27 | 3.38E−02 | 1.27 | 3.38E−02 |
| OVCH2 | 0.98 | 7.86 | 3.39E−02 | 8.32 | 3.06E−02 | 7.70 | 2.99E−02 | 7.70 | 3.39E−02 |
| FRK | 6.68 | 1.71 | 2.67E−02 | 1.59 | 3.39E−02 | 1.51 | 3.42E−02 | 1.51 | 3.42E−02 |
| ZFP42 | 2.37 | 2.52 | 7.30E−03 | 1.79 | 2.26E−02 | 1.55 | 3.45E−02 | 1.55 | 3.45E−02 |
| SLC35C1 | 22.23 | 5.27 | 3.03E−02 | 4.61 | 3.47E−02 | 6.96 | 1.24E−02 | 4.61 | 3.47E−02 |
| SULT1E1 | 0.72 | 5.38 | 3.51E−02 | 5.98 | 2.65E−02 | 7.91 | 1.06E−02 | 5.38 | 3.51E−02 |
| DTX3L | 2.32 | −2.41 | 5.96E−03 | −2.13 | 1.27E−02 | −2.09 | 3.52E−02 | −2.09 | 3.52E−02 |
| YPEL2 | 0.78 | −2.00 | 1.85E−02 | −2.82 | 2.84E−03 | −3.19 | 3.53E−02 | −2.00 | 3.53E−02 |

TABLE S3-continued

| Differentially expressed genes (DEGs) FIGS. 12F-G | | | | | | | | | |
|---|---|---|---|---|---|---|---|---|---|
| OTUD4 | 1.01 | −2.89 | 2.16E−02 | −2.56 | 3.55E−02 | −3.23 | 1.78E−02 | −2.56 | 3.55E−02 |
| SLC35E2B | 0.72 | −2.20 | 2.09E−02 | −2.41 | 1.48E−02 | −2.34 | 3.56E−02 | −2.20 | 3.56E−02 |
| CALCOCO1 | 1.13 | −2.32 | 3.57E−02 | −3.20 | 1.52E−02 | −3.05 | 3.17E−02 | −2.32 | 3.57E−02 |
| DUX4L26 | 2.00 | 7.89 | 3.59E−02 | 8.54 | 3.17E−02 | 7.74 | 3.20E−02 | 7.74 | 3.59E−02 |
| MINOS1 | 116.93 | 0.57 | 1.11E−02 | 0.52 | 3.61E−02 | 0.58 | 1.41E−02 | 0.52 | 3.61E−02 |
| FRRS1L | 5.28 | 2.47 | 1.61E−02 | 1.91 | 2.98E−02 | 1.80 | 3.62E−02 | 1.80 | 3.62E−02 |
| RN7SL477P | 11.00 | 8.50 | 1.69E−02 | 6.60 | 3.62E−02 | 8.73 | 2.28E−02 | 6.60 | 3.62E−02 |
| NANOS3 | 5.78 | 11.48 | 3.39E−02 | 11.41 | 3.42E−02 | 10.21 | 3.63E−02 | 10.21 | 3.63E−02 |
| SSR3 | 44.52 | −1.48 | 2.50E−02 | −1.17 | 3.63E−02 | −1.77 | 1.04E−02 | −1.17 | 3.63E−02 |
| TTC7A | 2.63 | −1.63 | 3.64E−02 | −2.70 | 5.06E−03 | −2.93 | 4.37E−03 | −1.63 | 3.64E−02 |
| XRN1 | 7.70 | −2.45 | 2.25E−03 | −2.18 | 7.29E−03 | −1.51 | 3.66E−02 | −1.51 | 3.66E−02 |
| ELAVL3 | 1.65 | 8.46 | 1.78E−02 | 6.68 | 2.70E−02 | 6.80 | 3.69E−02 | 6.68 | 3.69E−02 |
| ZMYND10 | 5.62 | 8.83 | 2.57E−02 | 7.41 | 3.69E−02 | 8.13 | 2.44E−02 | 7.41 | 3.69E−02 |
| DESI2 | 0.85 | −2.31 | 2.47E−02 | −2.32 | 3.70E−02 | −3.49 | 8.84E−03 | −2.31 | 3.70E−02 |
| UBTF | 23.13 | 2.52 | 2.29E−03 | 1.40 | 1.09E−02 | 1.40 | 3.73E−02 | 1.40 | 3.73E−02 |
| ARMT1 | 0.11 | −5.39 | 2.12E−02 | −4.76 | 2.83E−02 | −5.32 | 3.74E−02 | −4.76 | 3.74E−02 |
| ZNF324 | 5.80 | 4.29 | 3.27E−02 | 4.33 | 2.82E−02 | 3.39 | 3.76E−02 | 3.39 | 3.76E−02 |
| GTF2H2C | 28.69 | 1.22 | 3.78E−02 | 1.76 | 3.53E−03 | 2.66 | 8.32E−03 | 1.22 | 3.78E−02 |
| KIF19 | 0.96 | 4.26 | 1.17E−02 | 5.80 | 2.81E−03 | 3.90 | 3.80E−02 | 3.90 | 3.80E−02 |
| VMP1 | 37.13 | −1.10 | 1.64E−03 | −0.95 | 4.60E−03 | −0.97 | 3.80E−02 | −0.95 | 3.80E−02 |
| TMOD3 | 4.19 | −1.70 | 9.74E−05 | −1.58 | 1.49E−04 | −2.42 | 3.83E−02 | −1.58 | 3.83E−02 |
| RYR2 | 4.21 | 10.61 | 1.07E−04 | 9.95 | 1.21E−04 | 6.93 | 3.83E−02 | 6.93 | 3.83E−02 |
| MZT2B | 67.55 | 2.66 | 1.40E−02 | 1.90 | 5.27E−03 | 0.90 | 3.84E−02 | 0.90 | 3.84E−02 |
| RELB | 37.53 | 3.23 | 1.52E−03 | 1.70 | 1.87E−02 | 1.42 | 3.85E−02 | 1.42 | 3.85E−02 |
| DUXAP9 | 5.17 | 6.26 | 2.46E−02 | 5.99 | 3.39E−02 | 8.16 | 3.86E−02 | 5.99 | 3.86E−02 |
| RF00156 | 41.32 | 11.35 | 2.02E−02 | 9.06 | 3.88E−02 | 13.02 | 1.21E−02 | 9.06 | 3.88E−02 |
| MREG | 1.22 | 6.86 | 3.94E−02 | 7.63 | 3.16E−02 | 7.76 | 2.48E−02 | 6.86 | 3.94E−02 |
| GRIN2C | 0.55 | 7.04 | 3.19E−02 | 6.39 | 3.94E−02 | 7.34 | 2.75E−02 | 6.39 | 3.94E−02 |
| SCGB3A2 | 32.62 | 5.68 | 1.05E−02 | 4.10 | 2.47E−02 | 3.20 | 3.95E−02 | 3.20 | 3.95E−02 |
| RNF175 | 0.06 | −3.92 | 3.97E−02 | −5.86 | 1.67E−02 | −6.40 | 1.97E−02 | −3.92 | 3.97E−02 |
| PEF1 | 5.00 | −3.12 | 2.08E−03 | −1.44 | 3.14E−02 | −1.81 | 3.98E−02 | −1.44 | 3.98E−02 |
| GALM | 0.65 | −2.53 | 5.75E−03 | −2.67 | 9.01E−03 | −2.42 | 4.00E−02 | −2.42 | 4.00E−02 |
| USP18 | 0.01 | −4.90 | 1.10E−02 | −3.72 | 4.04E−02 | −6.02 | 3.80E−02 | −3.72 | 4.04E−02 |
| C17orf101 | 0.98 | −2.68 | 4.04E−02 | −3.76 | 1.22E−02 | −3.48 | 2.62E−02 | −2.68 | 4.04E−02 |
| DDX19B | 1.85 | −3.31 | 4.37E−03 | −2.78 | 8.47E−03 | −2.67 | 4.05E−02 | −2.67 | 4.05E−02 |
| BUB3 | 5.20 | −3.14 | 2.40E−02 | −2.71 | 4.09E−02 | −2.96 | 3.51E−02 | −2.71 | 4.09E−02 |
| GTF3C3 | 4.64 | −3.27 | 5.62E−03 | −2.06 | 4.10E−02 | −2.39 | 2.72E−02 | −2.06 | 4.10E−02 |
| IGLL5 | 4.37 | 6.26 | 3.41E−02 | 5.54 | 4.02E−02 | 6.24 | 4.13E−02 | 5.54 | 4.13E−02 |
| SGPL1 | 1.20 | −2.03 | 2.88E−04 | −2.31 | 1.23E−04 | −2.04 | 4.16E−02 | −2.03 | 4.16E−02 |
| EXOC3L4 | 1.55 | 4.65 | 1.98E−02 | 5.47 | 1.09E−02 | 5.35 | 4.16E−02 | 4.65 | 4.16E−02 |
| APOL1 | 0.28 | −2.77 | 1.92E−02 | −2.26 | 4.17E−02 | −3.27 | 2.76E−02 | −2.26 | 4.17E−02 |
| MED27 | 0.38 | −3.05 | 3.07E−02 | −4.18 | 8.53E−03 | −4.02 | 4.18E−02 | −3.05 | 4.18E−02 |
| REC8 | 2.51 | −2.62 | 5.35E−03 | −1.63 | 1.91E−02 | −2.32 | 4.21E−02 | −1.63 | 4.21E−02 |
| PDE6D | 65.28 | 2.05 | 4.48E−02 | 2.59 | 9.38E−04 | 3.12 | 4.21E−02 | 2.05 | 4.21E−02 |
| MTHFS | 0.15 | −6.86 | 1.38E−02 | −5.31 | 4.21E−02 | −7.45 | 1.44E−02 | −5.31 | 4.21E−02 |
| OR2I1P | 0.37 | 4.41 | 4.22E−02 | 5.49 | 2.25E−02 | 7.64 | 7.49E−03 | 4.41 | 4.22E−02 |
| KMT2C | 73.41 | 1.08 | 3.64E−03 | 1.32 | 1.79E−04 | 1.72 | 4.23E−02 | 1.08 | 4.23E−02 |
| MAGI2 | 68.47 | 5.82 | 3.01E−02 | 4.63 | 4.27E−02 | 5.43 | 3.06E−02 | 4.63 | 4.27E−02 |
| USE1 | 6.09 | −1.94 | 3.90E−02 | −2.00 | 4.31E−02 | −2.69 | 1.83E−02 | −1.94 | 4.31E−02 |
| HSPA14 | 1.79 | −2.14 | 6.21E−03 | −1.63 | 2.08E−02 | −2.46 | 4.34E−02 | −1.63 | 4.34E−02 |
| C6orf132 | 3.30 | 2.29 | 3.41E−02 | 2.00 | 4.35E−02 | 2.74 | 1.69E−02 | 2.00 | 4.35E−02 |
| SLC25A38 | 0.57 | −4.29 | 1.82E−04 | −3.59 | 3.43E−03 | −3.95 | 4.36E−02 | −3.59 | 4.36E−02 |
| NHLRC3 | 5.70 | −1.34 | 2.76E−03 | −0.77 | 4.36E−02 | −1.64 | 3.28E−02 | −0.77 | 4.36E−02 |
| POLR2M | 25.08 | 2.15 | 1.59E−02 | 2.26 | 5.43E−03 | 2.97 | 4.37E−02 | 2.15 | 4.37E−02 |
| TOR1B | 0.05 | −4.59 | 1.01E−02 | −6.37 | 2.42E−03 | −5.30 | 4.39E−02 | −4.59 | 4.39E−02 |
| MOV10 | 4.37 | −2.38 | 3.71E−02 | −2.49 | 3.01E−02 | −2.50 | 4.42E−02 | −2.38 | 4.42E−02 |
| BTN3A1 | 4.95 | −1.35 | 1.92E−02 | −1.11 | 4.43E−02 | −2.06 | 3.03E−02 | −1.11 | 4.43E−02 |
| AGAP5 | 0.16 | −2.21 | 9.02E−03 | −2.15 | 7.85E−03 | −3.71 | 4.44E−02 | −2.15 | 4.44E−02 |
| ADA | 1.80 | −3.47 | 4.68E−05 | −1.45 | 2.90E−02 | −2.47 | 4.45E−02 | −1.45 | 4.45E−02 |
| PPRC1 | 0.76 | −3.46 | 1.06E−02 | −3.53 | 1.40E−02 | −3.58 | 4.51E−02 | −3.46 | 4.51E−02 |
| CHMP1B2P | 1.52 | 3.69 | 4.04E−02 | 3.68 | 4.51E−02 | 4.65 | 2.70E−02 | 3.68 | 4.51E−02 |
| TRMT13 | 0.30 | −4.47 | 1.32E−03 | −3.58 | 9.47E−03 | −4.21 | 4.58E−02 | −3.58 | 4.58E−02 |
| ARL8A | 0.24 | −2.40 | 4.59E−02 | −3.36 | 1.65E−02 | −3.40 | 3.30E−02 | −2.40 | 4.59E−02 |
| TNFRSF17 | 0.83 | 5.68 | 7.23E−03 | 5.19 | 1.05E−02 | 4.89 | 4.59E−02 | 4.89 | 4.59E−02 |
| FANCA | 36.95 | 5.13 | 1.58E−02 | 5.29 | 1.54E−02 | 2.72 | 4.65E−02 | 2.72 | 4.65E−02 |
| RPS2 | 2417.68 | 0.60 | 6.63E−03 | 0.76 | 4.66E−02 | 0.53 | 4.59E−02 | 0.53 | 4.66E−02 |
| PRSS23 | 4.55 | 1.69 | 1.84E−02 | 1.28 | 4.66E−02 | 1.79 | 1.86E−02 | 1.28 | 4.66E−02 |
| FAM26E | 0.12 | 4.69 | 3.04E−02 | 4.66 | 3.17E−02 | 4.54 | 4.71E−02 | 4.54 | 4.71E−02 |
| D2HGDH | 5.92 | 4.74 | 1.80E−02 | 3.80 | 3.53E−02 | 2.77 | 4.72E−02 | 2.77 | 4.72E−02 |
| MFN2 | 0.86 | −1.77 | 2.42E−02 | −2.22 | 2.03E−02 | −2.26 | 4.72E−02 | −1.77 | 4.72E−02 |
| ARHGAP10 | 1.16 | −1.13 | 4.75E−02 | −2.50 | 4.17E−04 | −2.53 | 3.28E−03 | −1.13 | 4.75E−02 |
| PECAM1 | 13.94 | −1.16 | 4.78E−02 | −1.26 | 4.57E−02 | −1.51 | 4.23E−02 | −1.16 | 4.78E−02 |
| DHX40 | 1.13 | −2.55 | 1.33E−03 | −1.74 | 7.07E−03 | −2.67 | 4.78E−02 | −1.74 | 4.78E−02 |
| SLC41A3 | 32.46 | 2.75 | 4.86E−02 | 2.75 | 4.06E−02 | 2.73 | 3.60E−02 | 2.73 | 4.86E−02 |
| MCF2L | 1.94 | 4.24 | 2.81E−02 | 3.46 | 4.88E−02 | 3.12 | 4.67E−02 | 3.12 | 4.88E−02 |
| CASP2 | 1.54 | −2.61 | 1.24E−06 | −2.94 | 8.31E−12 | −1.94 | 4.92E−02 | −1.94 | 4.92E−02 |

TABLE S3-continued

Differentially expressed genes (DEGs) FIGS. 12F-G

| ANKRD44 | 30.09 | −1.96 | 3.39E−04 | −1.16 | 1.05E−02 | −1.03 | 4.96E−02 | −1.03 | 4.96E−02 |
|---|---|---|---|---|---|---|---|---|---|
| MTHFR | 17.71 | 1.88 | 7.21E−03 | 1.04 | 4.98E−02 | 1.39 | 3.67E−02 | 1.04 | 4.98E−02 |

CD163+CD14− DC3 DEGs

| geneSymbol | tpm.CD14− | lfc.CD5+ | p.CD5+ | lfc.CD163− | p.CD163− | lfc.CD14+ | p.CD14+ | lfc.MostConservative | p.MostConservative |
|---|---|---|---|---|---|---|---|---|---|
| ZNF583 | 1.14 | 2.06 | 1.64E−02 | 2.11 | 4.13E−03 | 2.28 | 8.88E−03 | 2.06 | 1.64E−02 |
| RN7SL846P | 0.28 | 5.07 | 1.67E−02 | 8.24 | 5.60E−05 | 8.24 | 5.60E−05 | 5.07 | 1.67E−02 |
| FZD8 | 0.01 | 2.01 | 1.86E−02 | 2.59 | 1.45E−02 | 2.59 | 1.45E−02 | 2.01 | 1.86E−02 |
| DNMT3L | 0.01 | 3.26 | 1.94E−02 | 3.26 | 1.94E−02 | 3.26 | 1.94E−02 | 3.26 | 1.94E−02 |
| FBXO10 | 0.01 | 2.99 | 2.33E−02 | 3.57 | 1.01E−02 | 3.57 | 1.01E−02 | 2.99 | 2.33E−02 |
| GTF2H4 | 0.76 | 2.89 | 2.49E−02 | 7.43 | 5.96E−03 | 2.86 | 2.35E−02 | 2.86 | 2.49E−02 |
| PRG2 | 0.01 | 2.93 | 3.00E−02 | 3.62 | 1.19E−02 | 3.62 | 1.19E−02 | 2.93 | 3.00E−02 |
| RN7SL478P | 0.02 | 3.51 | 3.30E−02 | 4.90 | 3.28E−03 | 4.90 | 3.28E−03 | 3.51 | 3.30E−02 |
| CTTNBP2 | 0.38 | 3.68 | 4.06E−02 | 6.05 | 3.41E−02 | 6.80 | 1.88E−03 | 3.68 | 4.06E−02 |
| SMIM6 | 0.01 | 2.66 | 4.15E−02 | 3.13 | 1.70E−02 | 3.13 | 1.70E−02 | 2.66 | 4.15E−02 |
| KDM1B | 6.67 | 1.03 | 4.52E−02 | 1.29 | 2.75E−03 | 1.40 | 3.44E−02 | 1.03 | 4.52E−02 |
| CD109 | 2.49 | 1.61 | 4.62E−02 | 3.23 | 1.03E−02 | 3.38 | 5.00E−04 | 1.61 | 4.62E−02 |
| RN7SL385P | 0.01 | 2.31 | 4.92E−02 | 2.31 | 4.92E−02 | 2.31 | 4.92E−02 | 2.31 | 4.92E−02 |

CD163+CD14+ DC3 DEGs

| geneSymbol | tpm.CD14+ | lfc.CD5+ | p.CD5+ | lfc.CD163− | p.CD163− | lfc.CD14− | p.CD14− | lfc.MostConservative | p.MostConservative |
|---|---|---|---|---|---|---|---|---|---|
| RNY1P11 | 3.07 | 8.35 | 1.24E−04 | 11.59 | 6.23E−05 | 8.19 | 7.67E−06 | 8.19 | 1.24E−04 |
| RPS26P31 | 1.04 | 5.09 | 3.34E−04 | 10.02 | 2.51E−05 | 6.34 | 8.72E−06 | 5.09 | 3.34E−04 |
| AFF3 | 4.69 | −3.05 | 7.11E−08 | −2.13 | 3.61E−04 | −2.17 | 1.25E−05 | −2.13 | 3.61E−04 |
| RGS1 | 43.41 | −3.01 | 1.30E−06 | −2.47 | 2.46E−04 | −1.83 | 5.30E−04 | −1.83 | 5.30E−04 |
| RN7SL414P | 1.09 | 9.63 | 2.06E−04 | 10.09 | 5.93E−04 | 8.48 | 6.96E−05 | 8.48 | 5.93E−04 |
| ITM2C | 0.64 | −4.05 | 9.71E−08 | −2.45 | 9.37E−04 | −2.90 | 2.24E−05 | −2.45 | 9.37E−04 |
| S100A9 | 7898.61 | 4.54 | 7.82E−06 | 1.55 | 1.36E−03 | 2.02 | 8.68E−05 | 1.55 | 1.36E−03 |
| S100A8 | 2351.99 | 5.92 | 1.01E−05 | 1.65 | 1.41E−03 | 2.71 | 4.70E−05 | 1.65 | 1.41E−03 |
| ACAP3 | 5.09 | 3.73 | 3.18E−06 | 2.48 | 1.57E−03 | 1.60 | 1.62E−03 | 1.60 | 1.62E−03 |
| CLEC4E | 45.28 | 4.90 | 1.13E−05 | 3.51 | 2.32E−03 | 2.50 | 5.52E−04 | 2.50 | 2.32E−03 |
| CREM | 6.43 | −3.69 | 7.35E−05 | −2.91 | 2.64E−03 | −2.83 | 7.70E−04 | −2.83 | 2.64E−03 |
| TAX1BP1 | 27.20 | −1.44 | 4.49E−04 | −1.18 | 2.69E−03 | −1.15 | 1.52E−03 | −1.15 | 2.69E−03 |
| CKAP4 | 4.41 | 5.71 | 2.21E−07 | 3.34 | 3.93E−03 | 2.41 | 1.54E−03 | 2.41 | 3.93E−03 |
| LINC01272 | 18.16 | 3.44 | 1.60E−03 | 4.21 | 1.38E−03 | 2.90 | 3.99E−03 | 2.90 | 3.99E−03 |
| UBE2N | 8.82 | −2.80 | 3.58E−04 | −2.84 | 2.03E−03 | −1.99 | 4.13E−03 | −1.99 | 4.13E−03 |
| PSTPIP1 | 135.80 | 1.42 | 1.06E−03 | 1.11 | 4.50E−03 | 1.19 | 4.00E−03 | 1.11 | 4.50E−03 |
| CD300E | 41.66 | 2.47 | 1.80E−05 | 3.12 | 4.58E−03 | 1.15 | 2.36E−03 | 1.15 | 4.58E−03 |
| SPINT2 | 16.69 | −3.13 | 1.49E−03 | −3.43 | 3.77E−03 | −2.46 | 4.76E−03 | −2.46 | 4.76E−03 |
| CYBB | 71.72 | 1.69 | 1.06E−03 | 1.39 | 3.69E−03 | 1.33 | 5.24E−03 | 1.33 | 5.24E−03 |
| HIGD1A | 8.61 | −2.86 | 3.64E−04 | −2.99 | 5.15E−03 | −2.12 | 5.48E−03 | −2.12 | 5.48E−03 |
| XIAP | 1.80 | −1.87 | 3.03E−03 | −1.98 | 5.66E−03 | −2.18 | 9.13E−04 | −1.87 | 5.66E−03 |
| CTSD | 200.11 | 3.33 | 9.72E−07 | 1.86 | 5.69E−03 | 1.77 | 1.37E−04 | 1.77 | 5.69E−03 |
| NAPRT | 120.63 | 1.90 | 3.49E−05 | 1.16 | 1.42E−03 | 1.48 | 6.38E−03 | 1.16 | 6.38E−03 |
| SLC4A3 | 0.06 | −7.39 | 2.16E−13 | −6.90 | 6.54E−03 | −5.70 | 5.33E−09 | −5.70 | 6.54E−03 |
| IKBKE | 23.68 | 8.15 | 1.95E−04 | 7.80 | 7.71E−04 | 3.69 | 6.63E−03 | 3.69 | 6.63E−03 |
| YWHAZ | 135.82 | −1.21 | 1.01E−06 | −0.57 | 6.71E−03 | −0.61 | 2.39E−03 | −0.57 | 6.71E−03 |
| YPEL5 | 67.72 | −1.44 | 6.25E−06 | −0.96 | 4.55E−03 | −0.72 | 6.86E−03 | −0.72 | 6.86E−03 |
| RETN | 79.05 | 4.67 | 1.67E−05 | 1.58 | 7.04E−03 | 1.89 | 3.48E−03 | 1.58 | 7.04E−03 |
| RAD1 | 0.78 | −3.40 | 3.97E−04 | −5.32 | 4.62E−03 | −2.39 | 7.13E−03 | −2.39 | 7.13E−03 |
| SNRNP40 | 4.99 | −3.27 | 1.47E−04 | −3.43 | 7.15E−03 | −2.12 | 6.01E−03 | −2.12 | 7.15E−03 |
| VCAN | 254.33 | 3.32 | 1.41E−08 | 0.70 | 7.17E−03 | 1.19 | 2.65E−03 | 0.70 | 7.17E−03 |
| CLIC2 | 3.89 | −4.01 | 1.47E−11 | −3.61 | 7.91E−03 | −2.71 | 5.96E−08 | −2.71 | 7.91E−03 |
| DOK3 | 7.35 | 9.32 | 3.91E−04 | 6.81 | 8.15E−03 | 4.25 | 8.00E−03 | 4.25 | 8.15E−03 |
| BAIAP2 | 4.81 | −1.54 | 4.90E−03 | −3.31 | 8.95E−03 | −2.18 | 1.73E−04 | −1.54 | 8.95E−03 |
| ZNF629 | 0.57 | 4.44 | 4.60E−03 | 4.33 | 4.02E−03 | 3.89 | 1.02E−02 | 3.89 | 1.02E−02 |
| ACTG1 | 591.32 | −1.54 | 2.37E−06 | −0.78 | 7.84E−03 | −0.64 | 1.09E−02 | −0.64 | 1.09E−02 |
| LRRFIP1 | 93.99 | −0.89 | 4.15E−03 | −0.80 | 1.13E−02 | −0.90 | 3.40E−03 | −0.80 | 1.13E−02 |
| SENP7 | 25.44 | 1.03 | 5.80E−03 | 0.89 | 1.13E−02 | 0.88 | 7.02E−03 | 0.88 | 1.13E−02 |
| ZDHHC17 | 4.17 | −2.75 | 6.77E−08 | −1.71 | 1.20E−02 | −1.65 | 3.27E−04 | −1.65 | 1.20E−02 |
| CYP27A1 | 1.32 | 7.99 | 1.21E−02 | 8.39 | 1.05E−02 | 7.80 | 1.18E−02 | 7.80 | 1.21E−02 |
| CDC42EP2 | 0.17 | 4.91 | 5.29E−04 | 5.99 | 1.23E−02 | 4.25 | 2.87E−03 | 4.25 | 1.23E−02 |
| TBCA | 35.00 | −1.20 | 2.35E−03 | −1.52 | 1.22E−02 | −0.84 | 1.28E−02 | −0.84 | 1.28E−02 |
| FCGR1A | 54.54 | 6.16 | 9.73E−05 | 3.76 | 1.30E−02 | 2.76 | 1.02E−02 | 2.76 | 1.30E−02 |
| CLEC4A | 61.19 | −2.47 | 1.69E−03 | −2.04 | 4.81E−03 | −1.56 | 1.32E−02 | −1.56 | 1.32E−02 |
| ITGAM | 37.41 | 2.87 | 1.36E−04 | 3.83 | 1.33E−02 | 2.02 | 3.30E−03 | 2.02 | 1.33E−02 |
| C1orf228 | 31.86 | 6.42 | 1.53E−04 | 2.43 | 9.64E−03 | 2.30 | 1.36E−02 | 2.30 | 1.36E−02 |
| CHST15 | 4.45 | 8.20 | 1.69E−06 | 8.30 | 1.39E−02 | 6.35 | 2.72E−05 | 6.35 | 1.39E−02 |
| PHAX | 3.25 | −2.08 | 6.54E−03 | −3.61 | 1.42E−02 | −2.35 | 3.99E−03 | −2.08 | 1.42E−02 |
| GNAS | 130.66 | −0.87 | 7.00E−04 | −0.58 | 1.44E−02 | −0.62 | 8.99E−03 | −0.58 | 1.44E−02 |
| UTP18 | 7.01 | −1.78 | 6.18E−03 | −2.44 | 8.62E−03 | −1.51 | 1.44E−02 | −1.51 | 1.44E−02 |
| NDUFB7 | 269.24 | 0.85 | 1.37E−03 | 0.80 | 1.47E−02 | 0.93 | 6.29E−03 | 0.80 | 1.47E−02 |

TABLE S3-continued

| Differentially expressed genes (DEGs) FIGS. 12F-G | | | | | | | | | |
|---|---|---|---|---|---|---|---|---|---|
| RBM39 | 249.39 | −1.07 | 3.43E−08 | −0.76 | 1.32E−02 | −0.47 | 1.47E−02 | −0.47 | 1.47E−02 |
| CTNS | 17.59 | 3.31 | 1.81E−03 | 6.57 | 1.50E−02 | 3.27 | 2.24E−04 | 3.27 | 1.50E−02 |
| PTEN | 22.99 | −1.86 | 6.82E−04 | −1.40 | 1.52E−02 | −1.21 | 1.15E−02 | −1.21 | 1.52E−02 |
| SLAMF7 | 1.54 | −4.80 | 1.56E−09 | −1.63 | 1.54E−02 | −1.44 | 1.10E−02 | −1.44 | 1.54E−02 |
| C16orf86 | 1.68 | 5.67 | 4.84E−03 | 7.50 | 4.14E−03 | 4.54 | 1.54E−02 | 4.54 | 1.54E−02 |
| MAP3K6 | 26.02 | 4.31 | 6.98E−04 | 3.06 | 1.58E−02 | 3.47 | 4.14E−04 | 3.06 | 1.58E−02 |
| MTR | 1.30 | −1.64 | 1.58E−02 | −2.30 | 5.78E−03 | −1.86 | 8.96E−03 | −1.64 | 1.58E−02 |
| CD74 | 4100.48 | −2.26 | 2.30E−06 | −0.93 | 1.61E−02 | −1.09 | 1.48E−03 | −0.93 | 1.61E−02 |
| CFL1 | 593.00 | −1.61 | 4.72E−04 | −1.21 | 6.14E−03 | −0.86 | 1.62E−02 | −0.86 | 1.62E−02 |
| LAMP1 | 9.82 | 4.51 | 1.05E−05 | 1.60 | 1.63E−02 | 1.91 | 2.65E−03 | 1.60 | 1.63E−02 |
| SGK1 | 72.41 | −0.90 | 1.64E−02 | −1.37 | 5.18E−03 | −0.98 | 6.55E−03 | −0.90 | 1.64E−02 |
| CD1C | 101.31 | −3.43 | 1.96E−03 | −2.46 | 1.65E−02 | −2.32 | 1.17E−02 | −2.32 | 1.65E−02 |
| LILRB4 | 4.82 | −3.04 | 3.30E−03 | −2.51 | 1.57E−02 | −2.31 | 1.69E−02 | −2.31 | 1.69E−02 |
| ARL4C | 29.99 | −2.18 | 8.93E−06 | −1.82 | 1.75E−02 | −1.52 | 2.54E−04 | −1.52 | 1.75E−02 |
| GDI2 | 95.80 | −1.58 | 1.03E−04 | −0.84 | 1.77E−02 | −0.75 | 1.46E−02 | −0.75 | 1.77E−02 |
| IFI27L2 | 100.85 | 2.23 | 6.60E−05 | 1.00 | 1.81E−02 | 1.59 | 6.99E−04 | 1.00 | 1.81E−02 |
| CDK2AP2 | 33.44 | −1.31 | 2.86E−04 | −1.65 | 6.03E−04 | −0.73 | 1.85E−02 | −0.73 | 1.85E−02 |
| KMT2D | 17.53 | 3.03 | 2.26E−04 | 2.76 | 5.78E−03 | 1.31 | 1.86E−02 | 1.31 | 1.86E−02 |
| NCF1 | 119.49 | 2.00 | 3.40E−03 | 2.25 | 1.86E−02 | 1.72 | 6.49E−03 | 1.72 | 1.86E−02 |
| SPAST | 4.74 | −0.90 | 5.49E−03 | −1.70 | 4.06E−03 | −0.71 | 1.86E−02 | −0.71 | 1.86E−02 |
| ELOB | 211.09 | 1.20 | 1.26E−03 | 0.68 | 1.87E−02 | 0.94 | 5.01E−03 | 0.68 | 1.87E−02 |
| FCER1A | 348.19 | −2.64 | 4.02E−03 | −2.00 | 1.92E−02 | −1.79 | 1.60E−02 | −1.79 | 1.92E−02 |
| TGIF1 | 38.46 | −1.44 | 7.39E−06 | −1.44 | 1.93E−02 | −0.70 | 3.61E−03 | −0.70 | 1.93E−02 |
| S100A6 | 1726.87 | 1.44 | 3.04E−04 | 0.65 | 1.93E−02 | 0.93 | 1.12E−02 | 0.65 | 1.93E−02 |
| ATHL1 | 14.83 | 5.82 | 3.86E−04 | 2.82 | 2.03E−02 | 2.49 | 1.12E−02 | 2.49 | 2.03E−02 |
| C12orf75 | 1.04 | −4.70 | 1.52E−05 | −3.57 | 2.05E−02 | −2.83 | 3.20E−03 | −2.83 | 2.05E−02 |
| EIF2S3 | 65.60 | −1.22 | 2.42E−04 | −0.71 | 2.08E−02 | −0.68 | 1.40E−02 | −0.68 | 2.08E−02 |
| PARVB | 2.16 | −1.35 | 1.74E−03 | −1.97 | 2.11E−02 | −2.18 | 2.23E−05 | −1.35 | 2.11E−02 |
| PARP10 | 9.57 | 3.04 | 4.72E−03 | 2.85 | 2.11E−02 | 2.13 | 1.15E−02 | 2.13 | 2.11E−02 |
| POLR3G | 1.83 | 4.36 | 1.45E−02 | 5.44 | 2.13E−02 | 5.36 | 1.39E−02 | 4.36 | 2.13E−02 |
| RN7SL1 | 143.27 | 2.25 | 1.78E−03 | 1.29 | 2.16E−02 | 1.54 | 1.05E−02 | 1.29 | 2.16E−02 |
| MAFB | 18.64 | 6.69 | 1.66E−04 | 4.33 | 1.61E−02 | 2.11 | 2.16E−02 | 2.11 | 2.16E−02 |
| PHTF2 | 2.64 | −2.11 | 5.15E−03 | −1.94 | 1.77E−02 | −1.63 | 2.26E−02 | −1.63 | 2.26E−02 |
| CCT5 | 30.15 | −1.90 | 8.64E−04 | −1.18 | 2.34E−02 | −1.15 | 9.50E−03 | −1.15 | 2.34E−02 |
| PLCG1 | 0.80 | 6.25 | 7.34E−03 | 9.64 | 3.02E−03 | 4.91 | 2.39E−02 | 4.91 | 2.39E−02 |
| CHMP4A | 28.34 | −2.41 | 1.10E−03 | −1.85 | 2.41E−02 | −2.02 | 4.60E−03 | −1.85 | 2.41E−02 |
| MAN1A1 | 0.88 | −2.23 | 1.47E−02 | −2.33 | 2.46E−02 | −2.06 | 2.05E−02 | −2.06 | 2.46E−02 |
| C1orf162 | 276.57 | −2.05 | 2.05E−06 | −1.28 | 1.58E−03 | −0.65 | 2.57E−02 | −0.65 | 2.57E−02 |
| CCDC50 | 7.85 | −2.03 | 4.10E−03 | −2.21 | 4.90E−03 | −1.48 | 2.58E−02 | −1.48 | 2.58E−02 |
| TUSC2 | 22.60 | 1.35 | 2.63E−02 | 7.17 | 2.69E−02 | 1.16 | 2.24E−02 | 1.16 | 2.69E−02 |
| CCDC114 | 0.21 | 3.81 | 1.34E−03 | 1.78 | 2.70E−02 | 2.86 | 8.63E−03 | 1.78 | 2.70E−02 |
| LY96 | 80.69 | 0.97 | 2.39E−02 | 1.71 | 2.73E−02 | 1.00 | 2.31E−02 | 0.97 | 2.73E−02 |
| MYBBP1A | 9.84 | 1.86 | 7.13E−03 | 1.44 | 2.76E−02 | 1.95 | 1.38E−02 | 1.44 | 2.76E−02 |
| LITAF | 25.86 | −2.92 | 3.32E−04 | −2.45 | 6.11E−03 | −1.45 | 2.79E−02 | −1.45 | 2.79E−02 |
| TMEM109 | 66.16 | −1.30 | 2.21E−03 | −1.82 | 4.51E−03 | −0.73 | 2.79E−02 | −0.73 | 2.79E−02 |
| CYB561A3 | 4.42 | −2.34 | 5.93E−06 | −2.48 | 2.80E−02 | −1.86 | 6.41E−05 | −1.86 | 2.80E−02 |
| NBR2 | 0.02 | −5.73 | 3.06E−03 | −5.33 | 2.82E−02 | −4.62 | 8.55E−03 | −4.62 | 2.82E−02 |
| CYC1 | 106.49 | −1.06 | 3.43E−04 | −0.92 | 2.86E−02 | −0.85 | 2.53E−03 | −0.85 | 2.86E−02 |
| IL18 | 13.08 | −2.81 | 2.40E−03 | −2.43 | 1.19E−02 | −1.87 | 2.89E−02 | −1.87 | 2.89E−02 |
| KDM6B | 33.12 | 2.41 | 5.36E−03 | 3.16 | 1.04E−02 | 1.69 | 2.91E−02 | 1.69 | 2.91E−02 |
| SRSF3 | 125.15 | −1.22 | 1.24E−03 | −0.78 | 2.55E−02 | −0.68 | 2.93E−02 | −0.68 | 2.93E−02 |
| COMMD9 | 27.30 | −1.95 | 6.57E−04 | −1.19 | 3.00E−02 | −1.18 | 1.93E−02 | −1.18 | 3.00E−02 |
| CCDC92 | 6.65 | 1.94 | 3.02E−02 | 3.90 | 3.24E−03 | 2.00 | 2.88E−02 | 1.94 | 3.02E−02 |
| NFE2L1 | 8.28 | 2.62 | 4.11E−04 | 2.31 | 3.04E−02 | 1.74 | 1.82E−03 | 1.74 | 3.04E−02 |
| CD63 | 390.16 | 1.27 | 2.87E−08 | 0.56 | 3.08E−02 | 0.79 | 1.22E−02 | 0.56 | 3.08E−02 |
| CGREF1 | 0.13 | 5.83 | 6.00E−04 | 5.38 | 3.11E−02 | 4.35 | 6.22E−03 | 4.35 | 3.11E−02 |
| SLC25A5 | 143.80 | −1.81 | 2.00E−03 | −1.65 | 3.22E−02 | −1.20 | 2.72E−02 | −1.20 | 3.22E−02 |
| CCT2 | 42.26 | −0.94 | 8.34E−04 | −1.25 | 3.23E−02 | −1.00 | 3.38E−04 | −0.94 | 3.23E−02 |
| PTBP3 | 9.19 | −1.40 | 8.05E−03 | −1.21 | 3.19E−02 | −0.98 | 3.25E−02 | −0.98 | 3.25E−02 |
| CHPT1 | 4.72 | −2.17 | 2.21E−03 | −2.19 | 3.27E−02 | −1.72 | 1.10E−02 | −1.72 | 3.27E−02 |
| HNRNPLL | 1.61 | −2.80 | 7.11E−03 | −3.85 | 2.23E−02 | −1.79 | 3.32E−02 | −1.79 | 3.32E−02 |
| UBL7 | 23.18 | −1.89 | 3.56E−04 | −1.88 | 1.94E−03 | −0.96 | 3.33E−02 | −0.96 | 3.33E−02 |
| MIR7845 | 8.19 | 11.03 | 1.28E−05 | 13.00 | 3.46E−04 | 6.72 | 3.34E−02 | 6.72 | 3.34E−02 |
| SPRED2 | 0.01 | −4.24 | 2.99E−02 | −5.50 | 2.87E−02 | −3.98 | 3.36E−02 | −3.98 | 3.36E−02 |
| RPL3 | 1062.54 | −0.86 | 5.29E−03 | −0.89 | 6.49E−03 | −0.56 | 3.41E−02 | −0.56 | 3.41E−02 |
| PTPN9 | 1.51 | −2.52 | 6.50E−04 | −2.69 | 3.44E−02 | −1.52 | 1.99E−02 | −1.52 | 3.44E−02 |
| TK2 | 30.66 | 1.77 | 3.44E−02 | 1.52 | 2.04E−02 | 2.12 | 6.78E−03 | 1.52 | 3.44E−02 |
| SH2B3 | 9.97 | −2.56 | 1.02E−05 | −1.63 | 3.44E−02 | −1.53 | 1.37E−03 | −1.53 | 3.44E−02 |
| SUB1 | 191.45 | −1.04 | 3.74E−04 | −0.56 | 3.45E−02 | −0.64 | 1.12E−02 | −0.56 | 3.45E−02 |
| CSNK2B | 63.02 | −1.78 | 1.54E−03 | −1.18 | 3.45E−02 | −1.10 | 1.73E−02 | −1.10 | 3.45E−02 |
| VPS33A | 1.71 | −2.27 | 1.69E−03 | −2.02 | 3.47E−02 | −2.32 | 1.46E−03 | −2.02 | 3.47E−02 |
| KIAA0513 | 5.36 | 2.22 | 1.80E−02 | 2.16 | 2.49E−02 | 1.79 | 3.48E−02 | 1.79 | 3.48E−02 |
| GLG1 | 14.06 | −1.44 | 2.15E−02 | −1.46 | 2.48E−02 | −1.25 | 3.53E−02 | −1.25 | 3.53E−02 |
| FOLR2 | 34.27 | 10.79 | 3.31E−04 | 6.93 | 3.53E−02 | 8.55 | 5.97E−04 | 6.93 | 3.53E−02 |
| EMP3 | 350.50 | 1.50 | 9.47E−08 | 0.72 | 3.56E−02 | 0.75 | 5.50E−03 | 0.72 | 3.56E−02 |
| N4BP2L1 | 10.73 | −2.01 | 1.91E−02 | −2.49 | 2.66E−02 | −1.85 | 3.59E−02 | −1.85 | 3.59E−02 |
| NONO | 35.40 | −1.95 | 2.73E−03 | −1.44 | 3.59E−02 | −1.24 | 2.41E−02 | −1.24 | 3.59E−02 |
| GRID1 | 0.42 | 5.51 | 1.85E−02 | 4.78 | 3.24E−02 | 4.31 | 3.63E−02 | 4.31 | 3.63E−02 |

TABLE S3-continued

| | Differentially expressed genes (DEGs) FIGS. 12F-G | | | | | | | |
|---|---|---|---|---|---|---|---|---|
| PUM1 | 12.84 | −1.59 | 1.58E−02 | −1.87 | 9.33E−03 | −1.31 | 3.64E−02 | −1.31 | 3.64E−02 |
| EDEM1 | 3.16 | −3.24 | 8.42E−03 | −2.87 | 2.56E−02 | −2.54 | 3.66E−02 | −2.54 | 3.66E−02 |
| BRI3 | 131.94 | 1.85 | 5.31E−04 | 1.29 | 9.44E−03 | 0.75 | 3.67E−02 | 0.75 | 3.67E−02 |
| IL1B | 101.41 | −1.70 | 1.65E−03 | −1.41 | 3.69E−02 | −1.44 | 4.16E−03 | −1.41 | 3.69E−02 |
| AGTRAP | 307.73 | 2.33 | 1.03E−03 | 0.95 | 3.71E−02 | 1.48 | 1.35E−02 | 0.95 | 3.71E−02 |
| C14orf145 | 0.56 | −3.89 | 3.04E−08 | −3.54 | 3.74E−02 | −2.90 | 1.91E−05 | −2.90 | 3.74E−02 |
| ST5 | 0.04 | −5.44 | 2.37E−02 | −6.08 | 3.75E−02 | −5.00 | 2.54E−02 | −5.00 | 3.75E−02 |
| THEM4 | 1.30 | −3.55 | 8.18E−07 | −2.50 | 3.77E−02 | −1.92 | 1.41E−03 | −1.92 | 3.77E−02 |
| MFHAS1 | 4.98 | 3.41 | 2.43E−02 | 4.89 | 1.28E−02 | 3.49 | 3.77E−02 | 3.41 | 3.77E−02 |
| ARIH2OS | 10.68 | 2.75 | 3.78E−02 | 6.33 | 2.73E−03 | 2.85 | 3.01E−02 | 2.75 | 3.78E−02 |
| ALS2CR12 | 4.68 | 4.67 | 2.01E−02 | 6.04 | 3.80E−02 | 3.62 | 3.21E−02 | 3.62 | 3.80E−02 |
| DUT | 21.29 | −1.89 | 1.57E−04 | −1.72 | 3.88E−02 | −1.29 | 2.14E−03 | −1.29 | 3.88E−02 |
| NKRF | 0.26 | −3.65 | 2.87E−03 | −4.30 | 3.88E−02 | −2.44 | 2.70E−02 | −2.44 | 3.88E−02 |
| LGALS9B | 0.86 | 7.73 | 1.69E−02 | 7.47 | 3.13E−02 | 5.98 | 3.89E−02 | 5.98 | 3.89E−02 |
| RNMTL1 | 1.50 | −1.92 | 1.04E−02 | −2.67 | 3.90E−02 | −1.66 | 3.35E−02 | −1.66 | 3.90E−02 |
| PPIF | 17.87 | −2.40 | 2.14E−04 | −1.60 | 3.92E−02 | −1.93 | 1.07E−03 | −1.60 | 3.92E−02 |
| SYNPO2 | 1.32 | 5.06 | 2.00E−02 | 3.59 | 3.97E−02 | 4.71 | 2.77E−02 | 3.59 | 3.97E−02 |
| EIF4E3 | 7.44 | 4.21 | 6.30E−03 | 2.75 | 3.98E−02 | 3.08 | 1.49E−02 | 2.75 | 3.98E−02 |
| UBE2L6 | 92.42 | −1.53 | 1.25E−04 | −1.13 | 2.83E−02 | −0.65 | 4.00E−02 | −0.65 | 4.00E−02 |
| ACY1 | 0.40 | −4.45 | 2.15E−02 | −6.27 | 1.41E−02 | −4.06 | 4.02E−02 | −4.06 | 4.02E−02 |
| OR6R2P | 0.28 | 6.63 | 2.93E−02 | 8.15 | 1.74E−02 | 6.13 | 4.02E−02 | 6.13 | 4.02E−02 |
| ARGLU1 | 89.61 | 0.34 | 4.04E−02 | 0.58 | 1.02E−02 | 0.94 | 1.10E−02 | 0.34 | 4.04E−02 |
| FCGR3A | 3.60 | 7.50 | 3.45E−02 | 6.03 | 4.04E−02 | 6.77 | 3.83E−02 | 6.03 | 4.04E−02 |
| CACNB1 | 0.44 | 5.96 | 5.93E−03 | 7.32 | 4.82E−03 | 4.18 | 4.07E−02 | 4.18 | 4.07E−02 |
| NNAT | 0.05 | 4.39 | 3.60E−02 | 5.62 | 1.79E−02 | 4.20 | 4.07E−02 | 4.20 | 4.07E−02 |
| GIMAP8 | 3.93 | 4.66 | 1.90E−02 | 6.23 | 1.48E−02 | 3.77 | 4.12E−02 | 3.77 | 4.12E−02 |
| MALT1 | 6.80 | −1.54 | 2.10E−02 | −1.66 | 4.16E−02 | −1.40 | 3.28E−02 | −1.40 | 4.16E−02 |
| ANKRD13A | 10.60 | −1.12 | 2.22E−03 | −1.36 | 4.17E−02 | −0.92 | 5.96E−03 | −0.92 | 4.17E−02 |
| DHRS7B | 19.01 | 3.07 | 3.19E−02 | 3.32 | 2.15E−02 | 2.57 | 4.18E−02 | 2.57 | 4.18E−02 |
| MANBA | 20.44 | −1.23 | 3.81E−04 | −1.49 | 4.18E−02 | −1.16 | 3.03E−04 | −1.16 | 4.18E−02 |
| VPS54 | 1.41 | −2.27 | 4.22E−02 | −3.28 | 2.59E−02 | −2.42 | 4.14E−02 | −2.27 | 4.22E−02 |
| NUDT1 | 35.17 | −1.03 | 4.30E−03 | −1.25 | 4.23E−02 | −0.96 | 6.78E−03 | −0.96 | 4.23E−02 |
| CIITA | 51.31 | −1.45 | 1.03E−02 | −1.22 | 4.24E−02 | −1.19 | 2.18E−02 | −1.19 | 4.24E−02 |
| FAM198B | 8.60 | 5.31 | 3.05E−06 | 3.06 | 4.24E−02 | 2.27 | 3.62E−03 | 2.27 | 4.24E−02 |
| SMIM4 | 26.75 | 2.79 | 1.10E−03 | 2.81 | 2.85E−02 | 1.21 | 4.27E−02 | 1.21 | 4.27E−02 |
| HIC2 | 1.40 | 3.45 | 6.45E−03 | 4.18 | 2.52E−02 | 1.26 | 4.33E−02 | 1.26 | 4.33E−02 |
| EVA1B | 6.17 | 5.70 | 3.19E−03 | 5.85 | 2.81E−02 | 3.10 | 4.35E−02 | 3.10 | 4.35E−02 |
| ATP5C1 | 116.68 | −1.46 | 3.72E−03 | −1.20 | 4.03E−02 | −0.77 | 4.36E−02 | −0.77 | 4.36E−02 |
| AREG | 16.68 | −3.31 | 9.33E−03 | −2.95 | 4.38E−02 | −2.51 | 2.89E−02 | −2.51 | 4.38E−02 |
| STARD7 | 28.11 | −0.92 | 7.87E−03 | −1.04 | 4.39E−02 | −0.76 | 2.01E−02 | −0.76 | 4.39E−02 |
| NEXMIF | 0.13 | 4.85 | 1.27E−02 | 4.67 | 3.05E−02 | 3.37 | 4.46E−02 | 3.37 | 4.46E−02 |
| ZNF865 | 0.05 | 2.83 | 7.48E−03 | 4.46 | 2.24E−02 | 2.30 | 4.50E−02 | 2.30 | 4.50E−02 |
| RN7SL138P | 12.88 | 7.25 | 2.77E−03 | 10.25 | 4.50E−02 | 5.11 | 1.85E−02 | 5.11 | 4.50E−02 |
| NOG | 1.57 | 1.57 | 1.11E−04 | 0.57 | 4.53E−02 | 0.85 | 1.15E−02 | 0.57 | 4.53E−02 |
| SLC35F2 | 0.05 | −6.56 | 1.41E−05 | −3.42 | 4.54E−02 | −4.28 | 2.16E−03 | −3.42 | 4.54E−02 |
| ALDH2 | 23.08 | −2.09 | 5.40E−03 | −1.47 | 4.54E−02 | −1.45 | 3.73E−02 | −1.45 | 4.54E−02 |
| RN7SL113P | 5.69 | 6.04 | 4.68E−02 | 9.82 | 1.03E−02 | 6.15 | 3.05E−02 | 6.04 | 4.68E−02 |
| PDE4B | 4.89 | −2.41 | 1.60E−03 | −1.42 | 4.71E−02 | −1.84 | 6.88E−03 | −1.42 | 4.71E−02 |
| NDST2 | 19.98 | 2.43 | 3.51E−03 | 4.08 | 4.72E−02 | 1.18 | 2.75E−02 | 1.18 | 4.72E−02 |
| SIGLEC16 | 2.42 | 6.36 | 1.64E−02 | 8.35 | 4.76E−02 | 5.92 | 2.11E−02 | 5.92 | 4.76E−02 |
| MED22 | 8.42 | 2.43 | 2.22E−02 | 3.73 | 4.73E−02 | 1.97 | 4.79E−02 | 1.97 | 4.79E−02 |
| APBB3 | 13.96 | 2.94 | 3.77E−02 | 6.78 | 1.05E−02 | 2.22 | 4.80E−02 | 2.22 | 4.80E−02 |
| PNPT1 | 1.79 | −2.78 | 5.05E−08 | −2.75 | 4.88E−02 | −2.11 | 1.30E−05 | −2.11 | 4.88E−02 |
| PCIF1 | 11.04 | −1.49 | 2.75E−02 | −2.27 | 5.33E−03 | −1.25 | 4.90E−02 | −1.25 | 4.90E−02 |
| STAB1 | 115.39 | 7.37 | 2.12E−08 | 1.76 | 4.91E−02 | 2.50 | 5.32E−05 | 1.76 | 4.91E−02 |
| TCTN2 | 1.46 | 1.60 | 4.93E−02 | 1.78 | 1.24E−02 | 1.42 | 3.62E−02 | 1.42 | 4.93E−02 |
| OPHN1 | 2.47 | −2.20 | 4.11E−03 | −1.62 | 4.93E−02 | −1.46 | 2.30E−02 | −1.46 | 4.93E−02 |
| PCBP2 | 96.84 | −1.34 | 7.64E−04 | −0.84 | 4.94E−02 | −0.61 | 4.71E−02 | −0.61 | 4.94E−02 |
| C1QA | 9.97 | 8.52 | 8.22E−04 | 13.28 | 8.53E−04 | 4.07 | 4.95E−02 | 4.07 | 4.95E−02 |
| SLC11A1 | 28.46 | 4.24 | 3.45E−03 | 2.24 | 4.96E−02 | 1.93 | 3.79E−02 | 1.93 | 4.96E−02 |
| EXTL2 | 0.05 | −5.41 | 5.00E−02 | −7.69 | 3.14E−02 | −5.19 | 4.12E−02 | −5.19 | 5.00E−02 |

TABLE S4

| | Clinical data FIGS. 12A-D | | | | | | | |
|---|---|---|---|---|---|---|---|---|
| ID | disease | Sex | Year of Birth | anti-dsDNA (IU/mL) | low complement | SLEDAI | Activity | Immunosuppressants |
| SLE1 | SLE | F | 1959 | 18 | no | 8 | Arthritis, alopecia, dsDNA | Hydroxychloroquine |

TABLE S4-continued

Clinical data FIGS. 12A-D

| ID | disease | Sex | Year of Birth | anti-dsDNA (IU/mL) | low complement | SLEDAI | Activity | Immunosuppressants |
|---|---|---|---|---|---|---|---|---|
| SLE2 | SLE | F | 1991 | 9.7 | yes | 6 | Proteinuria (=class V), complement | Hydroxychloroquine |
| SLE3 | SLE | F | 1954 | 186 | yes | 4 | complement, dsDNA | Hydroxychloroquine |
| SLE4 | SLE | M | 1977 | 8.5 | no | 0 | none | Hydroxychloroquine |
| SLE5 | SLE | F | 1971 | 1.3 | no | 0 | none | Prednisone 5, Azathioprine, Hydroxycloroquine |
| SLE6 | SLE | F | 1964 | 4.1 | no | 0 | none | none |
| SLE7 | SLE | F | 1983 | 19 | yes | 4 | dsDNA, complement | Prednisone 5, Azathioprine, Hydroxycloroquine |
| SLE8 | SLE | F | 1961 | 21 | yes | 5 | complement, dsDNA, fever | colchicine, prednisone 5, |
| SLE9 | SLE | F | 1982 | 30 | yes | 6 | complement, dsDNA, rash | Belimumab, Prednisone 7.5, Azathioprine, Colchicine, Hydroxychloroquine |
| SLE10 | SLE | F | 1981 | 52 | yes | 12 | rash, arthritis, ulcers, dsDNA, complement | Prednisone 10, Hydroxychloroquine, MMF |
| dsSSC01 | dSSc | F | 1965 | NA | NA | NA | NA | NA |
| dsSSC02 | dSSc | M | 1959 | NA | NA | NA | NA | NA |
| dsSSC03 | dSSc | NA | NA | NA | NA | NA | NA | NA |
| dsSSC04 | dSSc | F | 1979 | NA | NA | NA | NA | NA |
| dsSSC05 | dSSc | M | 1978 | NA | NA | NA | NA | NA |
| lsSSC01 | LcSSc | F | 1939 | NA | NA | NA | NA | NA |
| lsSSC02 | LcSSc | F | 1977 | NA | NA | NA | NA | NA |
| lsSSC03 | LcSSc | F | 1951 | NA | NA | NA | NA | NA |
| lsSSC04 | LcSSc | F | 1967 | NA | NA | NA | NA | NA |
| lsSSC05 | LcSSc | F | 1951 | NA | NA | NA | NA | NA |
| eaSSC01 | eaSSc | F | 1969 | NA | NA | NA | NA | NA |
| eaSSC02 | eaSSc | F | 1968 | NA | NA | NA | NA | NA |
| eaSSC03 | eaSSc | F | 1977 | NA | NA | NA | NA | NA |
| eaSSC04 | eaSSc | F | 1982 | NA | NA | NA | NA | NA |
| eaSSC05 | eaSSc | NA | 1982 | NA | NA | NA | NA | NA |
| Healthy 1 | Healthy | F | 1983 | NA | NA | NA | NA | NA |
| Healthy 2 | Healthy | F | 1968 | NA | NA | NA | NA | NA |
| Healthy 3 | Healthy | F | 1970 | NA | NA | NA | NA | NA |
| Healthy 4 | Healthy | F | 1960 | NA | NA | NA | NA | NA |
| Healthy 5 | Healthy | F | 1963 | NA | NA | NA | NA | NA |
| Healthy 6 | Healthy | F | 1953 | NA | NA | NA | NA | NA |
| Healthy 7 | Healthy | F | 1988 | NA | NA | NA | NA | NA |
| Healthy 8 | Healthy | F | 1968 | NA | NA | NA | NA | NA |
| Healthy 9 | Healthy | NA | NA | NA | NA | NA | NA | NA |
| Healthy 10 | Healthy | NA | NA | NA | NA | NA | NA | NA |

TABLE S5

Clinical data FLT3L-inj

| ID | disease | Sex | Year of Birth | treatment (FLT3L) |
|---|---|---|---|---|
| Flt-7003 | FL* | M | 1954 | 25 ucg/kg daily days 1-5, 8-11 |
| Flt-7004 | FL | M | 1954 | 25 ucg/kg daily days 1-5, 8-11 |
| Flt-7005 | SLL** | M | 1955 | 25 ucg/kg daily days 1-5, 8-11 |
| Flt-7008 | FL | F | 1963 | 25 ucg/kg daily days 1-5, 8-11 |
| Flt-7013 | FL | M | 1969 | 25 ucg/kg daily days 1-5, 8-11 |
| Flt-7014 | FL | M | 1960 | 25 ucg/kg daily days 1-5, 8-11 |
| Flt-7015 | FL | F | 1963 | 25 ucg/kg daily days 1-5, 8-11 |
| Flt-7006 | FL | M | 1973 | 25 ucg/kg daily days 1-5, 8-11 |
| Flt-7007 | FL | F | 1967 | 25 ucg/kg daily days 1-5, 8-11 |

*follicular lymphoma (FL),
**small lymphocytic lymphoma (SLL)

TABLE S6

| | | | | | | | | |
|---|---|---|---|---|---|---|---|---|
| | | | | | | | Clinical data FIGS. 14A-E | |

| ID | disease | Sex | Year of Birth | anti-dsDNA (IU/mL) | low complement | SLEDAI | Activity | Immunosuppressants |
|---|---|---|---|---|---|---|---|---|
| Serum-SLE001 | SLE | F | 1973 | 497 | 1 | 16 | Active | HCQ*, Pred** 15, AZA*** |
| Serum-SLE022 | SLE | F | 1974 | 109 | 1 | 4 | Active | HCQ, Pred 5, AZA |
| Serum-SLE026 | SLE | M | 1958 | 131 | 1 | 8 | Active | Pred 2.5, AZA |
| Serum-SLE037 | SLE | F | 1972 | 171 | 1 | 6 | Active | HCQ, Pred 10, AZA |
| Serum-SLE078 | SLE | F | 1983 | 179 | 1 | 14 | Active | HCQ, Pred 7.5, AZA |
| Serum-SLE109 | SLE | F | 1974 | 129 | 1 | 4 | Active | Pred 5, AZA |
| Serum-SLE122 | SLE | F | 1958 | 281 | 1 | 8 | Active | HCQ, Pred 2.5, AZA |
| Serum-SLE125 | SLE | F | 1983 | 269 | 1 | 20 | Active | HCQ, Pred 7.5, AZA |
| Serum-SLE132 | SLE | F | 1991 | 116 | 1 | 20 | Active | HCQ, Pred 2.5, AZA |
| Serum-SLE136 | SLE | F | 1979 | 111 | 1 | 6 | Active | HCQ, Pred 5, AZA |
| Serum-SLE139 | SLE | F | 1988 | 173 | 1 | 6 | Active | HCQ, Pred 10, MTX |
| Serum-SLE161 | SLE | F | 1993 | 1618 | 1 | 12 | Active | HCQ, Pred 10, |
| Serum-SLE011 | SLE | F | 1978 | 1.8 | 0 | 0 | Inactive | — |
| Serum-SLE016 | SLE | F | 1971 | 1.9 | 0 | 0 | Inactive | HCQ, Pred 7.5, AZA |
| Serum-SLE027 | SLE | F | 1966 | 9.2 | 0 | 0 | Inactive | HCQ |
| Serum-SLE040 | SLE | F | 1965 | 1.7 | 0 | 0 | Inactive | — |
| Serum-SLE051 | SLE | F | 1961 | 10 | 0 | 0 | Inactive | — |
| Serum-SLE059 | SLE | F | 1988 | 8.7 | 0 | 0 | Inactive | HCQ, Pred 5, MMF |
| Serum-SLE060 | SLE | F | 1974 | 13 | 0 | 0 | Inactive | HCQ, AZA |
| Serum-SLE084 | SLE | F | 1958 | 1 | 0 | 0 | Inactive | — |
| Serum-SLE093 | SLE | F | 1993 | 1.3 | 0 | 0 | Inactive | — |
| Serum-SLE099 | SLE | F | 1962 | 2.2 | 0 | 0 | Inactive | — |
| Serum-SLE123 | SLE | F | 1984 | 5.4 | 0 | 0 | Inactive | — |
| Serum-SLE155 | SLE | F | 1972 | 2 | 0 | 0 | Inactive | — |
| Serum-SLE004 | Healthy | F | 1970 | NA | NA | NA | NA | — |
| Serum-SLE012 | Healthy | F | 1966 | NA | NA | NA | NA | — |
| Serum-SLE017 | Healthy | F | 1966 | NA | NA | NA | NA | — |
| Serum-SLE019 | Healthy | F | 1065 | NA | NA | NA | NA | — |
| Serum-SLE020 | Healthy | F | 1965 | NA | NA | NA | NA | — |
| Serum-SLE034 | Healthy | F | 1969 | NA | NA | NA | NA | — |
| Serum-SLE043 | Healthy | F | 1954 | NA | NA | NA | NA | — |
| Serum-SLE058 | Healthy | F | 1976 | NA | NA | NA | NA | — |
| Serum-SLE079 | Healthy | F | 1984 | NA | NA | NA | NA | — |
| Serum-SLE120 | Healthy | F | 1964 | NA | NA | NA | NA | — |
| Serum-SLE130 | Healthy | F | 1959 | NA | NA | NA | NA | — |
| Serum-SLE147 | Healthy | F | 1985 | NA | NA | NA | NA | — |

*HCQ (Hydroxychloroquine),
**Pred (Prednisone)
***AZA (Azathioprine)

40

TABLE S7

| | | | | |
|---|---|---|---|---|
| | | | FACS antibodies | |

| Target | Conjugate | Isotype | Clone | Provider |
|---|---|---|---|---|
| CADM1 | Purified | chicken IgY | 3E1 | MBL |
| CD11b | Biotin | rat IgG2b | M1/70 | BD Biosciences |
| CD303 | Biotin | mouse IgG1 | AC144 | Miltenyi |
| CD14 | BUV737 | mouse IgG2a | M5E2 | BD Biosciences |
| CD123 | BUV395 | mouse IgG2a | 7G3 | BD Biosciences |
| HLA-DR | BV785 | mouse IgG2a | L243 | Biolegend |
| CD5 | BV711 | mouse IgG1 | UCHT2 | BD Biosciences |
| CD135 | BV711 | mouse IgG1 | 4G8 | BD Biosciences |
| CD3 | BV650 | mouse IgG1 | SP34-2 | BD Biosciences |
| CD14 | BV650 | mouse IgG2a | M5E2 | BD Biosciences |
| CD16 | BV650 | mouse IgG1 | 3G8 | BD Biosciences |
| CD19 | BV650 | mouse IgG1 | SJ25C1 | BD Biosciences |
| CD20 | BV650 | mouse IgG2b | 2H7 | BD Biosciences |
| CD11c | BV650 | mouse IgG1 | B-Ly6 | BD Biosciences |
| CD163 | BV605 | mouse IgG1 | GHI/61 | Biolegend |
| CD45 | V500 | mouse IgG1 | HI30 | BD Biosciences |
| CD89 | BV510 | mouse IgG1 | A59 | BD Biosciences |
| CD1c | PercP/Cy5.5 | mouse IgG1 | L161 | Biolegend |
| CD1c | BV421 | mouse IgG1 | L161 | Biolegend |
| CD2 | BV421 | mouse IgG1 | RPA-2.10 | BD Biosciences |
| FceRIa | PerCP | mouse IgG2b | AER-37 (CRA-1) | Biolegend |
| IRF8 | PercP/eFluor710 | mouse IgG1 | V3GYWCH | eBioscience |
| CD45RA | FITC | mouse IgG1 | 5H9 | BD Biosciences |
| IKAROS | BV421 | mouse IgG1 | R32-1149 | BD Biosciences |

TABLE S7-continued

| | | FACS antibodies | | |
|---|---|---|---|---|
| Target | Conjugate | Isotype | Clone | Provider |
| RelB | Alexa Fluor 488 | rabbit IgG | EP613Y | Abcam |
| CD1c | PE/Cy7 | mouse IgG1 | L161 | Biolegend |
| CD45RA | PE/Cy7 | mouse IgG1 | L48 | BD Biosciences |
| CD88 | PE/Cy7 | mouse IgG2a | S5/1 | Biolegend |
| CD33 | PE/CF594 | mouse IgG1 | WM53 | BD Biosciences |
| CD206 | PE/CF594 | mouse IgG1 | 19.2 | BD Biosciences |
| CD268 | PE/Dazzle594 | mouse IgG1 | 11C1 | Biolegend |
| CD169 | PE | mouse IgG1 | 7-239 | BD Biosciences |
| CD301 | PE | mouse IgG2a | H037G3 | Biolegend |
| IRF4 | PE | rat IgG1 | 3E4 | eBioscience |
| LAMP5 | PE | mouse IgG1 | 124-40B | Biolegend |
| NOTCH2 | PE | rat IgG1 | 16F11 | eBioscience |
| CD16 | APC/Cy7 | mouse IgG1 | 3G8 | Biolegend |
| FceRIa | APC/Cy7 | mouse IgG2b | AER-37 (CRA-1) | Biolegend |
| CD14 | AF700 | Mouse IgG2a, κ | BM-16 | Biolegend |
| CD34 | AF700 | mouse IgG1 | 581 | BD Biosciences |
| PU.1 | Alexa Fluor 647 | mouse IgG1 | 7C6B05 | Biolegend |
| CD89 | APC | mouse IgG1 | A59 | Biolegend |
| CD141 | APC | mouse IgG1 | AD5-14H12 | Miltenyi |
| KLF4 | APC | goat IgG (polycII) | NA | R&D Systems |

Figures 9F, 9G:
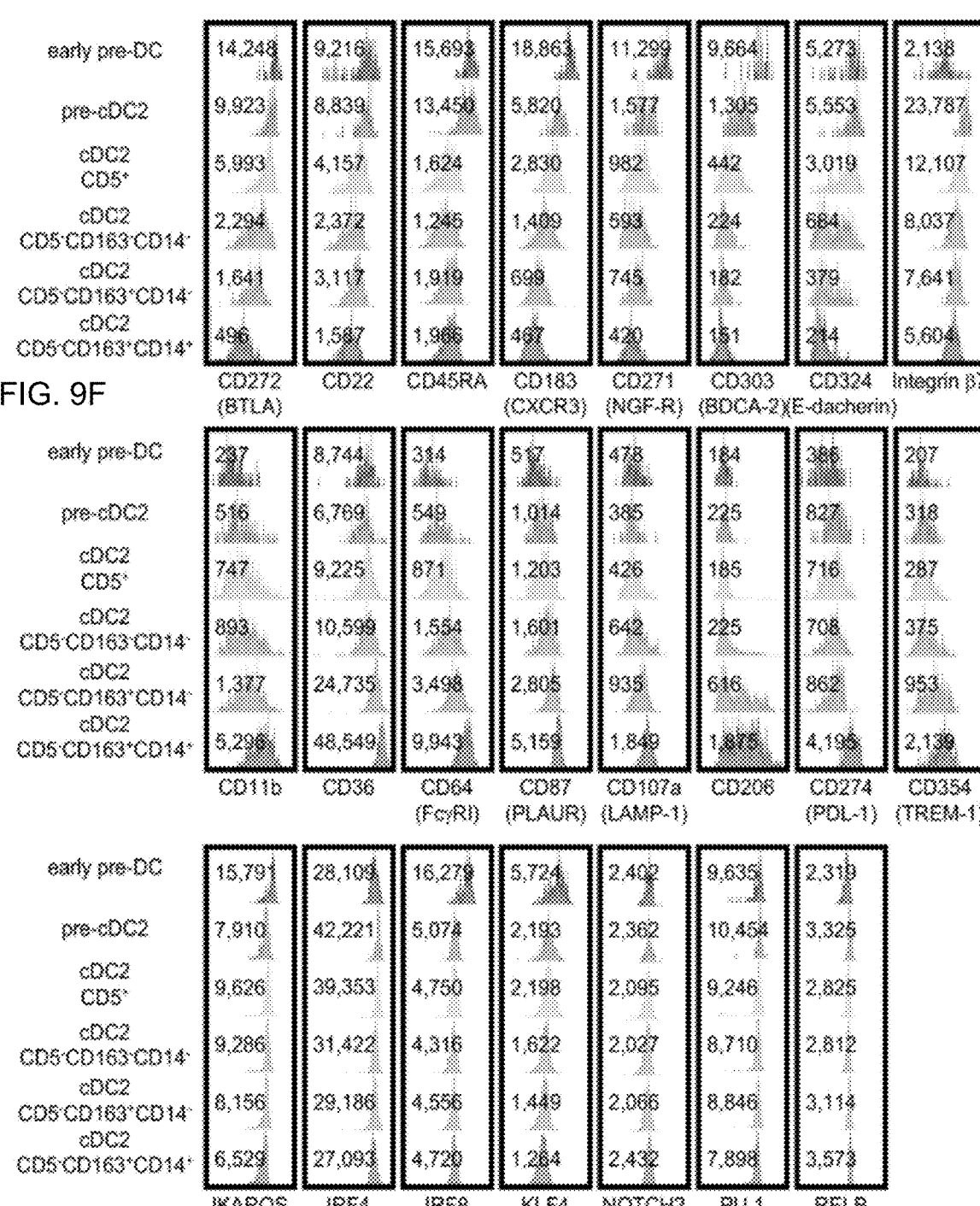
Figures 9H, 9I, 9J, 9K, 9L:
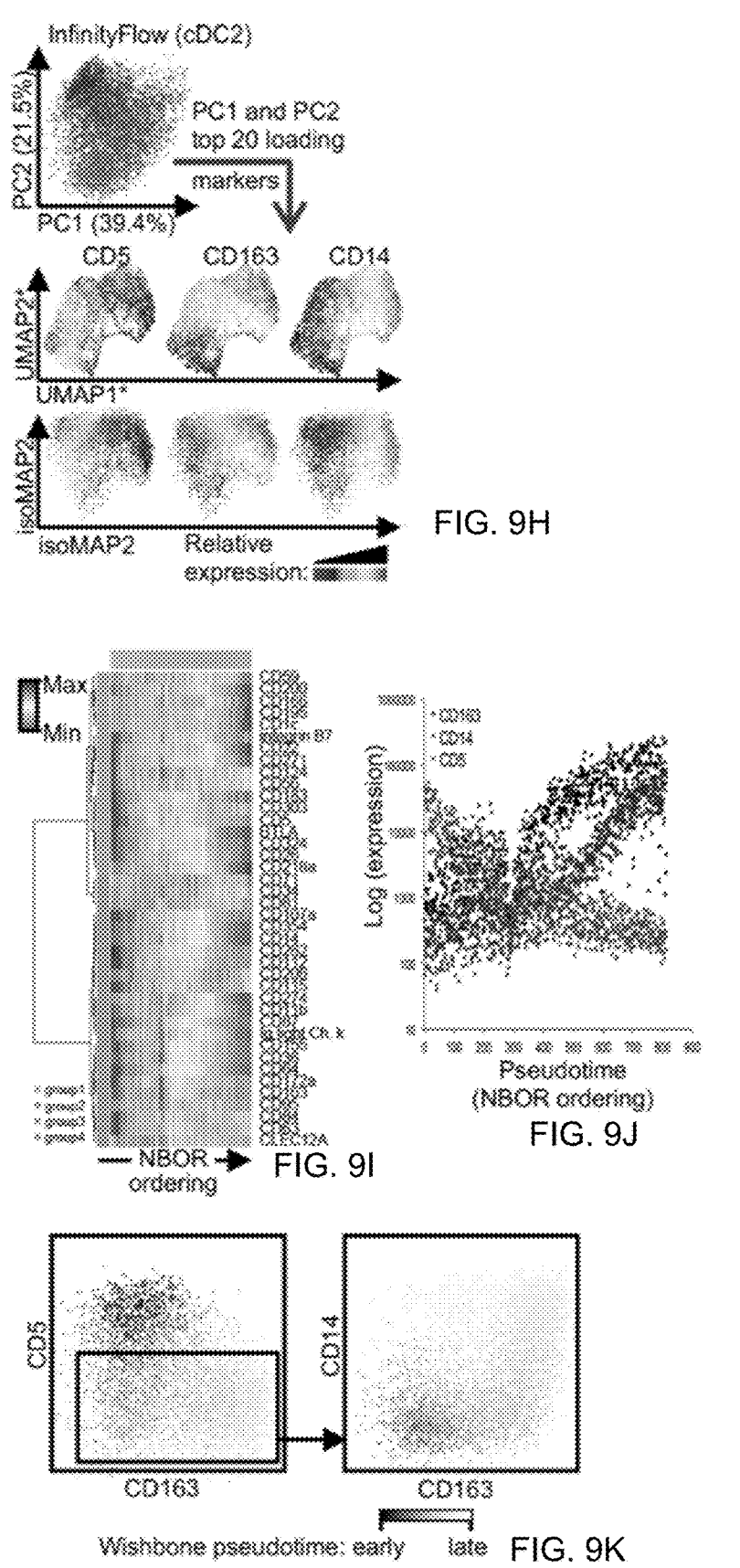
Figure 9M:
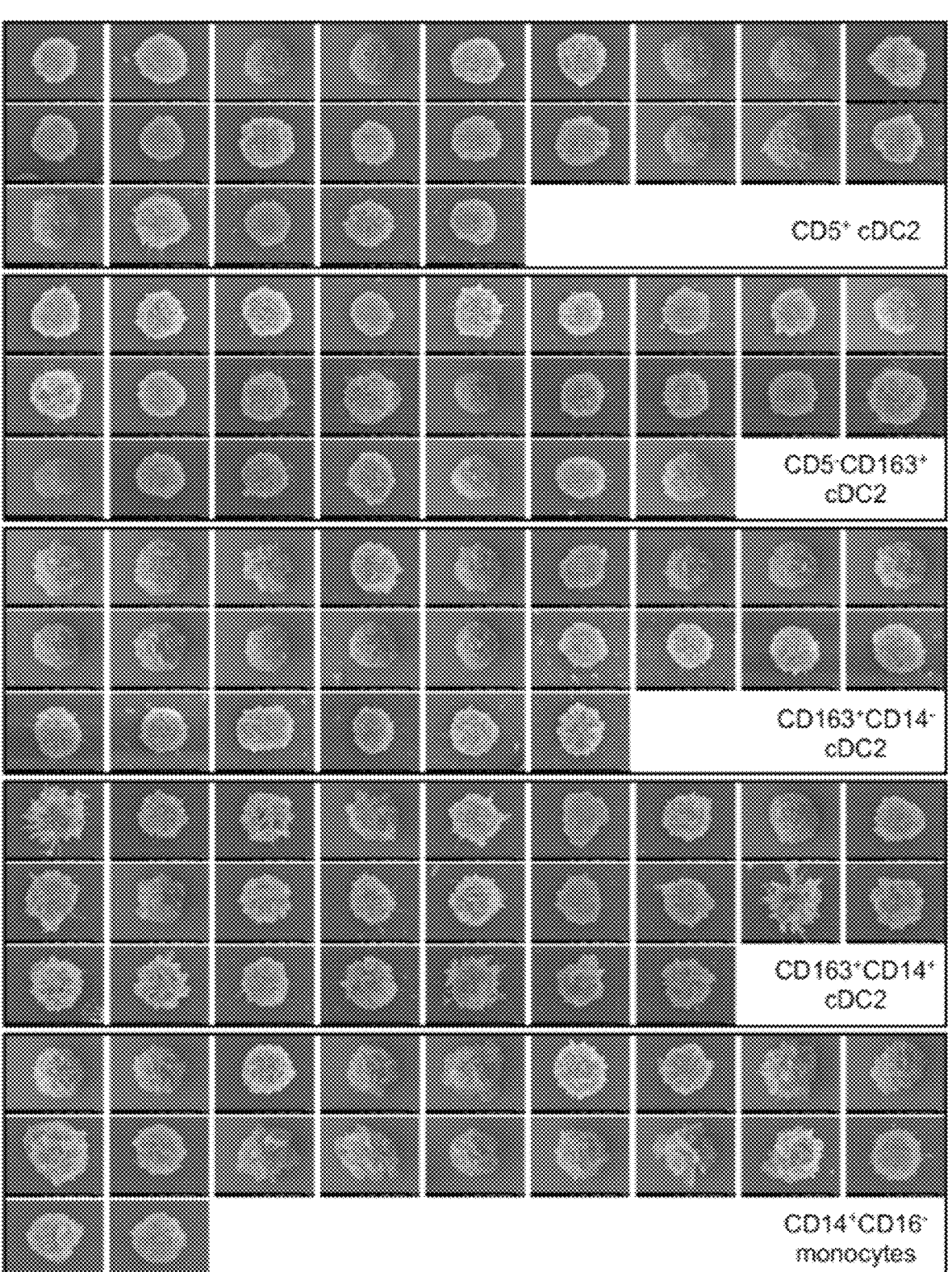

| Panel | Data in. | Cyto-meter (BD) | UV (355 nm) A 740/35 | UV (355 nm) B 450/59 | UV (355 nm) C 379/28 | Violet (405 nm) A 780/60 | Violet (405 nm) B 710/50 | Violet (405 nm) C 670/30 | Violet (405 nm) D 610/20 | Violet (405 nm) E 525/50 | Violet (405 nm) F 450/50 | Blue (488 nm) A 685/35 | Blue (488 nm) B 525/50 | Yellow-green (561 nm) A 780/80 | Yellow-green (561 nm) C 610/20 | Yellow-green (561 nm) D 586/15 | Red (640 nm) A 783/60 | Red (640 nm) B 730/45 | Red (640 nm) C 670/14 |
|---|---|---|---|---|---|---|---|---|---|---|---|---|---|---|---|---|---|---|---|
| FLT3L-treated patients stainings | FIG. 4J | FOR-TESSA | BDC42-biot+ Str-BUV737 | L/D Blue | CD123 BUV395 | HLA-DR BV786 | CD135 BV711 | CD3/14/19/20 BV650 | CD11c BV605 | CD45 V500 | CD2 BV421 | IRF8 PP/eF710* | CD45RA FITC | CD1c PE/Cy7 | CD33 PE/CF594 | CD169 PE | CD16 APC/Cy7 | CD34 AF700 | CADM1+ a-CHK-AF647 |
| FIG 4D new markers validation panel | FIG. 4D | FOR-TESSA | CADM1+ a-chk-biot+ Str-BUV737 | L/D Blue | CD123 BUV395 | HLA-DR BV786 | CD5 BV711 | CD3/19/20 BV650 | CD163 BV605 | CD45 V500 | CD1c BV421 | FceRI PercP | CD45RA FITC | CD88 PE/Cy7 | CD206 PE/CF594 | CD301 PE | CD16 APC/Cy7 | Ca14 AF700 | CD89 APS |
| PU.1 staining | FIG. 9G | FOR-TESSA | CADM1+ a-chk-biot+ Str-BUV737 | L/D Blue | CD123 BUV395 | HLA-DR BV786 | CD5 BV711 | CD3/19/20 BV650 | CD163 BV605 | CD45 V500 | CD1c BV421 | FceRI PercP | CD45RA FITC | CD88 PE/Cy7 | CD206 PE/CF594 | LAMP5 PE | CD16 APC/Cy7 | CD14 AF700 | PU.1 AF647 |
| NOTCH2 KLF4 staining | FIG. 4L & FIG. 9G | FOR-TESSA | CADM1+ a-chk-biot+ Str-BUV737 | L/D Blue | CD123 BUV395 | HLA-DR BV786 | CD5 BV711 | CD3/19/20 BV650 | CD163 BV605 | CD45 V500 | CD1c BV421 | FceRI PercP | CD45RA FITC | CD88 PE/Cy7 | CD206 PE/CF594 | NOTCH2 PE | CD16 APC/Cy7 | CD14 AF700 | KLF4 APC |
| IRF4 IRF8 staining | FIG. 4L & FIG. 9G | FOR-TESSA | CD11biot+ str-BUV737 | L/D Blue | CD123 BUV395 | HLA-DR BV786 | CD5 BV711 | CD3/19/20 BV650 | CD163 BV605 | CD45 V500 | CD1c BV421 | IRF8 PP/eF710* | CD45RA FITC | CD88 PE/Cy7 | CD206 PE/CF594 | IRF4 PE | CD16 APC/Cy7 | CD14 AF700 | KLF4 APC |
| IKAROS RelB IRF4 KLF4 staining | FIG. 9G | FOR-TESSA | CADN- a-chk-biot+ Str-BUV737 | L/D Blue | CD123 BUV395 | HLA-DR BV786 | CD5 BV711 | CD3/19/20 BV650 | CD163 BV605 | CD45 V500 | IKAROS BV421 | FceRI Parep | RelB AF488 | CD45RA PE/Cy7 | CD206 PE/CF594 | IRF4 PE | CD16 APC/Cy7 | CD14 AF700 | KLF4 APC |
| Indexed-sorting panel | FIG. 7A & FIG. 6A-D | ARIAIII | CD11biot+ Str-BUV737 | L/D Blue | CD123 BUV395 | HLA-DR BV786 | CD5 BV711 | CD3/14/19/20 BV650 | CD163 BV605 | CD45 V500 | CD1c BV421 | FceRI PercP | CD45RA FITC | CD88 PE/Cy7 | CD206 PE/CF594 | CD169 PE | CD16 APC/Cy7 | CD1a AF700 | CD141 APC |
| Sort panel for cDC2 subsets bulk RNAseq | FIG. 10B-D, G & FIG. 12F-H | ARIAIII | CADM1+ a-chk-biot+ Str-BUV737 | L/D Blue | CD123 BUV395 | HLA-DR BV786 | CD5 BV711 | CD3/19/20 BV650 | CD163 BV605 | CD45 V500 | CD1c BV421 | FceRI PercP | CD45RA FITC | CD88 PE/Cy7 | BAFF-R PE/Dazz94 | CD169 PE | CD16 APC/Cy7 | CD14 AF700 | CD89 APC |
| Sort panel by cultures in serum & luminex | FIG. 14A | FOR-TESSA | | L/D Blue | CD123 BUV395 | HLA-DR BV786 | CD5 BV711 | CD3/19/20 BV650 | CD163 BV605 | CD45 V500 | CD1c BV421 | FceRI PercP | CD45RA FITC | CD88 PE/Cy7 | | CD169 PE | | CD14 AF700 | CD141 APC |

-continued

| Lazer detector Band pass filter Cytometer (BD) Data in. | UV (355 nm) A 740/35 | UV (355 nm) B 450/59 | UV (355 nm) C 379/28 | Violet (405 nm) A 780/60 | Violet (405 nm) B 710/50 | Violet (405 nm) C 670/30 | Violet (405 nm) D 610/20 | Violet (405 nm) E 525/50 | Violet (405 nm) F 450/50 | Blue (488 nm) A 685/35 | Blue (488 nm) B 525/50 | Yellow-green (561 nm) A 780/80 | Yellow-green (561 nm) C 610/20 | Yellow-green (561 nm) D 586/15 | Red (640 nm) A 783/60 | Red (640 nm) B 730/45 | Red (640 nm) C 670/14 |
|---|---|---|---|---|---|---|---|---|---|---|---|---|---|---|---|---|---|
| T cell proliferation and lcs panel FIG 10E FORTESSA | | L/D Blue | | | | CD3 BV650 | CD4 eVolve605 | | CellTrate Hotel | CD8 PercP/Cy5.5 | IL-4 PE/Cf7 | | | | IFNg APC/ eF780 | | IL-17A. eF660 |

*Intracellular staining are italized

TABLE S9

CyTOF antibodies
Metal__Marker

102Pd__BC*102
103Rh__BC103
104Pd__BC104
106Pd__BC106
108Pd__BC108
110Pd__BC110
112Cd__CD14
141Pr__Clec12$^A$
142Nd__CD5
143Nd__CD2
144Nd__CD64
145Nd__CD68
146Nd__CD19
146Nd__CD20
146Nd__CD3
147Sm__CD86
148Nd__CD45RA
149Sm__HLA-DR
150Nd__CD80
151Eu__CD141
152Sm__CD1c
153Eu__FcER1A
154Sm__CD87
155Gd__CD33
156Gd__CD22
157Gd__CXCR3
158Gd__CD82
159Tb__CD301
160Gd__CD206
161Dy__CD123
162Dy__CD88
163Dy__BTLA
164Dy__CD89
165Ho__CD71
166Er__CD85d
167Er__Integrin-B7
168Er__CD26
169Tm__CD163
170Er__CD35
171Yb__CD166
172Yb__HLA-DQ
173Yb__CD294
174Yb__CD354
175Lu__CD172b
176Yb__CD11b
209Bi__CD16
89Y__CD45

*Bar code

REFERENCES

Aliberti, J., Schulz, O., Pennington, D. J., Tsujimura, H., Reis e Sousa, C., Ozato, K., and Sher, A. (2003). Essential role for ICSBP in the in vivo development of murine CD8alpha+ dendritic cells. Blood 101, 305-310.

Becher, B., Schlitzer, A., Chen, J., Mair, F., Sumatoh, H. R., Teng, K. W., Low, D., Ruedl, C., Riccardi-Castagnoli, P., Poidinger, M., et al. (2014). High-dimensional analysis of the murine myeloid cell system. Nat Immunol 15, 1181-1189.

Becht, E., McInnes, L., Healy, J., Dutertre, C.-A., Kwok, I. W. H., Ng, L. G., Ginhoux, F., and Newell, E. W. (2018). Dimensionality reduction for visualizing single-cell data using UMAP. Nat. Biotechnol.

Becht, E., Simoni, Y., Coustan-Smith, E., Evrard, M., Cheng, Y., Ng, L. G., Campana, D., and Newell, E. W. (2019). Reverse-engineering flow-cytometry gating strategies for phenotypic labelling and high-performance cell sorting. Bioinforma. Oxf. Engl. 35, 301-308.

Brynjolfsson, S. F., Magnusson, M. K., Kong, P. L., Jensen, T., Kuijper, J. L., Håkansson, K., Read, C. B., Stennicke, V. W., Sjövall, H., and Jo Wick, M. (2016). An Antibody Against Triggering Receptor Expressed on Myeloid Cells 1 (TREM-1) Dampens Proinflammatory Cytokine Secretion by Lamina Propria Cells from Patients with IBD. Inflamm. Bowel Dis. 22, 1803-1811.

Calzetti, F., Tamassia, N., Micheletti, A., Finotti, G., Bianchetto-Aguilera, F., and Cassatella, M. A. (2018). Human dendritic cell subset 4 (DC4) correlates to a subset of CD14dim/−CD16++ monocytes. J. Allergy Clin. Immunol. 141, 2276-2279.e3.

Chen, H., Lau, M. C., Wong, M. T., Newell, E. W., Poidinger, M., and Chen, J. (2016). Cytofkit: A Bioconductor Package for an Integrated Mass Cytometry Data Analysis Pipeline. PLoS Comput. Biol. 12, e1005112.

Davis, S., and Meltzer, P. S. (2007). GEOquery: a bridge between the Gene Expression Omnibus (GEO) and Bio-Conductor. Bioinforma. Oxf. Engl. 23, 1846-1847.

DiGiuseppe, J. A., Cardinali, J. L., Rezuke, W. N., and Pe'er, D. (2018). PhenoGraph and viSNE facilitate the identification of abnormal T-cell populations in routine clinical flow cytometric data. Cytometry B Clin. Cytom. 94, 588-601.

Dress, R., and Ginhoux, F. (2019). Plasmacytoid dendritic cell differentiation is distinct from the myeloid lineage and occurs from Ly6D+ early lymphoid progenitors. Nat. Immunol.

Dutertre, C.-A., Amraoui, S., DeRosa, A., Jourdain, J.-P., Vimeux, L., Goguet, M., Degrelle, S., Feuillet, V., Liovat, A.-S., Müller-Trutwin, M., et al. (2012). Pivotal role of M-DC8+ monocytes from viremic HIV-infected patients in TNFα overproduction in response to microbial products. Blood 120, 2259-2268.

Dutertre, C.-A., Wang, L.-F., and Ginhoux, F. (2014). Aligning bona fide dendritic cell populations across species. Cell. Immunol. 291, 3-10.

Finck, R., Simonds, E. F., Jager, A., Krishnaswamy, S., Sachs, K., Fantl, W., Pe'er, D., Nolan, G. P., and Bendall, S. C. (2013). Normalization of mass cytometry data with bead standards. Cytom. Part J. Int. Soc. Anal. Cytol. 83, 483-494.

Ginhoux, F., and Guilliams, M. (2016). Tissue-Resident Macrophage Ontogeny and Homeostasis. Immunity 44, 439-449.

Guilliams, M., Ginhoux, F., Jakubzick, C., Naik, S. H., Onai, N., Schraml, B. U., Segura, E., Tussiwand, R., and Yona, S. (2014). Dendritic cells, monocytes and macrophages: a unified nomenclature based on ontogeny. Nat Rev Immunol 14, 571-578.

Guilliams, M., Dutertre, C. A., Scott, C. L., McGovern, N., Sichien, D., Chakarov, S., Van Gassen, S., Chen, J., Poidinger, M., De Prijck, S., et al. (2016a). Unsupervised High-Dimensional Analysis Aligns Dendritic Cells across Tissues and Species. Immunity 45, 669-684.

Guilliams, M., Dutertre, C.-A., Scott, C. L., McGovern, N., Sichien, D., Chakarov, S., Van Gassen, S., Chen, J., Poidinger, M., De Prijck, S., et al. (2016b). Unsupervised High-Dimensional Analysis Aligns Dendritic Cells across Tissues and Species. Immunity 45, 669-684.

Günther, P. (2019). Rule-based data-informed generation of cellular consensus maps. BioRxiv.

Hamers Anouk A. J., Dinh Huy Q., Thomas Graham D., Marcovecchio Paola, Blatchley Amy, Nakao Catherine S., Kim Cheryl, McSkimming Chantel, Taylor Angela M., Nguyen Anh T., et al. (2019). Human Monocyte Heterogeneity as Revealed by High-Dimensional Mass Cytometry. Arterioscler. Thromb. Vasc. Biol. 39, 25-36.

Haniffa, M., Shin, A., Bigley, V., McGovern, N., Teo, P., See, P., Wasan, P. S., Wang, X. N., Malinarich, F., Malleret, B., et al. (2012). Human tissues contain CD141hi cross-presenting dendritic cells with functional homology to mouse CD103+ nonlymphoid dendritic cells. Immunity 37, 60-73.

Harrow, J., Frankish, A., Gonzalez, J. M., Tapanari, E., Diekhans, M., Kokocinski, F., Aken, B. L., Barrell, D., Zadissa, A., Searle, S., et al. (2012). GENCODE: the reference human genome annotation for The ENCODE Project. Genome Res. 22, 1760-1774.

Hildner, K., Edelson, B. T., Purtha, W. E., Diamond, M., Matsushita, H., Kohyama, M., Calderon, B., Schraml, B. U., Unanue, E. R., Diamond, M. S., et al. (2008). Batf3 deficiency reveals a critical role for CD8alpha+ dendritic cells in cytotoxic T cell immunity. Science 322, 1097-1100.

Klarquist, J., Zhou, Z., Shen, N., and Janssen, E. M. (2016). Dendritic Cells in Systemic Lupus Erythematosus: From Pathogenic Players to Therapeutic Tools. Mediators Inflamm. 2016, 5045248.

Kuryliszyn-Moskal, A., Klimiuk, P. A., Sierakowski, S., and Ciolkiewicz, M. (2007). Vascular endothelial growth factor in systemic lupus erythematosus: relationship to disease activity, systemic organ manifestation, and nailfold capillaroscopic abnormalities. Arch. Immunol. Ther. Exp. (Warsz.) 55, 179-185.

Lamb, J., Crawford, E. D., Peck, D., Modell, J. W., Blat, I. C., Wrobel, M. J., Lerner, J., Brunet, J.-P., Subramanian, A., Ross, K. N., et al. (2006). The Connectivity Map: using gene-expression signatures to connect small molecules, genes, and disease. Science 313, 1929-1935.

Levine, J. H., Simonds, E. F., Bendall, S. C., Davis, K. L., Amir el, A. D., Tadmor, M. D., Litvin, O., Fienberg, H. G., Jager, A., Zunder, E. R., et al. (2015). Data-Driven Phenotypic Dissection of AML Reveals Progenitor-like Cells that Correlate with Prognosis. Cell 162, 184-197.

Li, H.-H., Cheng, H.-H., Sun, K.-H., Wei, C.-C., Li, C.-F., Chen, W.-C., Wu, W.-M., and Chang, M.-S. (2008). Interleukin-20 targets renal mesangial cells and is associated with lupus nephritis. Clin. Immunol. Orlando Fla. 129, 277-285.

Liao, X., Pirapakaran, T., and Luo, X. M. (2016). Chemokines and Chemokine Receptors in the Development of Lupus Nephritis. Mediators Inflamm. 2016, 6012715.

McInnes, L., Healy, J., and Melville, J. (2018). UMAP: Uniform Manifold Approximation and Projection for Dimension Reduction. ArXiv180203426 Cs Stat.

Menon, M., Blair, P. A., Isenberg, D. A., and Mauri, C. (2016). A Regulatory Feedback between Plasmacytoid Dendritic Cells and Regulatory B Cells Is Aberrant in Systemic Lupus Erythematosus. Immunity 44, 683-697.

Merad, M., Sathe, P., Helft, J., Miller, J., and Martha, A. (2013). The dendritic cell lineage: ontogeny and function of dendritic cells and their subsets in the steady state and the inflamed setting. Annu. Rev. Immunol. 31, 563-604.

Newell, E. W., Sigal, N., Bendall, S. C., Nolan, G. P., and Davis, M. M. (2012). Cytometry by time-of-flight shows combinatorial cytokine expression and virus-specific cell niches within a continuum of CD8+ T cell phenotypes. Immunity 36, 142-152.

Newman, A. M., Liu, C. L., Green, M. R., Gentles, A. J., Feng, W., Xu, Y., Hoang, C. D., Diehn, M., and Alizadeh, A. A. (2015). Robust enumeration of cell subsets from tissue expression profiles. Nat. Methods 12, 453-457.

Nguyen-Lefebvre, A. T., Ajith, A., Portik-Dobos, V., Horuzsko, D. D., Arbab, A. S., Dzutsev, A., Sadek, R., Trinch-

86 ieri, G., and Horuzsko, A. (2018). The innate immune receptor TREM-1 promotes liver injury and fibrosis. J. Clin. Invest. 128, 4870-4883.

Nielepkowicz-Goździńska, A., Fendler, W., Robak, E., Kulczycka-Siennicka, L., Górski, P., Pietras, T., Brzezianska, E., and Antczak, A. (2014). Exhaled IL-8 in systemic lupus erythematosus with and without pulmonary fibrosis. Arch. Immunol. Ther. Exp. (Warsz.) 62, 231-238.

Parks, C. G., Cooper, G. S., Dooley, M. A., Treadwell, E. L., St Clair, E. W., Gilkeson, G. S., and Pandey, J. P. (2004). Systemic lupus erythematosus and genetic variation in the interleukin 1 gene cluster: a population based study in the southeastern United States. Ann. Rheum. Dis. 63, 91-94.

Parks, D. R., Roederer, M., and Moore, W. A. (2006). A new "Logicle" display method avoids deceptive effects of logarithmic scaling for low signals and compensated data. Cytom. Part J. Int. Soc. Anal. Cytol. 69, 541-551.

Patro, R., Duggal, G., Love, M. I., Irizarry, R. A., and Kingsford, C. (2017). Salmon provides fast and bias-aware quantification of transcript expression. Nat. Methods 14, 417-419.

Picelli, S., Faridani, O. R., Björklund, A. K., Winberg, G., Sagasser, S., and Sandberg, R. (2014). Full-length RNA-seq from single cells using Smart-seq2. Nat. Protoc. 9, 171-181.

Rodrigues, P. F., Alberti-Servera, L., Eremin, A., Grajales-Reyes, G. E., Ivanek, R., and Tussiwand, R. (2018). Distinct progenitor lineages contribute to the heterogeneity of plasmacytoid dendritic cells. Nat. Immunol. 19, 711-722.

Samy, E., Wax, S., Huard, B., Hess, H., and Schneider, P. (2017). Targeting BAFF and APRIL in systemic lupus erythematosus and other antibody-associated diseases. Int. Rev. Immunol. 36, 3-19.

Schlitzer, A., McGovern, N., Teo, P., Zelante, T., Atarashi, K., Low, D., Ho, A. W. S., See, P., Shin, A., Wasan, P. S., et al. (2013). IRF4 transcription factor-dependent CD11b+ dendritic cells in human and mouse control mucosal IL-17 cytokine responses. Immunity 38, 970-983.

Schlitzer, A., McGovern, N., and Ginhoux, F. (2015a). Dendritic cells and monocyte-derived cells: Two complementary and integrated functional systems. Semin. Cell Dev. Biol. 41, 9-22.

Schlitzer, A., Sivakamasundari, V., Chen, J., Sumatoh, H. R. B., Schreuder, J., Lum, J., Malleret, B., Zhang, S., Larbi, A., Zolezzi, F., et al. (2015b). Identification of cDC1- and cDC2-committed DC progenitors reveals early lineage priming at the common DC progenitor stage in the bone marrow. Nat. Immunol. 16, 718-728.

Schölkopf, B., Smola, A. J., Williamson, R. C., and Bartlett, P. L. (2000). New support vector algorithms. Neural Comput. 12, 1207-1245.

See, P., Dutertre, C.-A., Chen, J., Gunther, P., McGovern, N., Irac, S. E., Gunawan, M., Beyer, M., Handler, K., Duan, K., et al. (2017). Mapping the human DC lineage through the integration of high-dimensional techniques. Science 356.

Segura, E., Touzot, M., Bohineust, A., Cappuccio, A., Chiocchia, G., Hosmalin, A., Dalod, M., Soumelis, V., and Amigorena, S. (2013). Human inflammatory dendritic cells induce Th17 cell differentiation. Immunity 38, 336-348.

Setty, M., Tadmor, M. D., Reich-Zeliger, S., Angel, O., Salame, T. M., Kathail, P., Choi, K., Bendall, S., Friedman, N., and Pe'er, D. (2016). Wishbone identifies bifurcating developmental trajectories from single-cell data. Nat. Biotechnol. 34, 637-645.

Smyth, G. K. (2004). Linear models and empirical bayes methods for assessing differential expression in microarray experiments. Stat. Appl. Genet. Mol. Biol. 3, Article3.

Smyth, G. K. (2005). limma: Linear Models for Microarray Data. In Bioinformatics and Computational Biology Solutions Using R and Bioconductor, R. Gentleman, V. J. Carey, W. Huber, R. A. Irizarry, and S. Dudoit, eds. (New York, NY: Springer New York), pp. 397-420.

Sun, F., Teng, J., Yu, P., Li, W., Chang, J., and Xu, H. (2018). Involvement of TWEAK and the NF-κB signaling pathway in lupus nephritis. Exp. Ther. Med. 15, 2611-2619.

Tan-Garcia, A., Wai, L.-E., Zheng, D., Ceccarello, E., Jo, J., Banu, N., Khakpoor, A., Chia, A., Tham, C. Y. L., Tan, A. T., et al. (2017). Intrahepatic CD206+ macrophages contribute to inflammation in advanced viral-related liver disease. J. Hepatol. 67, 490-500.

Tang-Huau, T.-L., and Segura, E. (2018). Human in vivo-differentiated monocyte-derived dendritic cells. Semin. Cell Dev. Biol.

Tenenbaum, J. B., de Silva, V., and Langford, J. C. (2000). A global geometric framework for nonlinear dimensionality reduction. Science 290, 2319-2323.

Tussiwand, R., Everts, B., Grajales-Reyes, G. E., Kretzer, N. M., Iwata, A., Bagaitkar, J., Wu, X., Wong, R., Anderson, D. A., Murphy, T. L., et al. (2015). Klf4 expression in conventional dendritic cells is required for T helper 2 cell responses. Immunity 42, 916-928.

Van der Maaten, L., and Hinton, G. (2008). Visualizing data using t-SNE. J. Mach. Learn. Res. 9, 2579-2605.

Villani, A.-C., Satija, R., Reynolds, G., Sarkizova, S., Shekhar, K., Fletcher, J., Griesbeck, M., Butler, A., Zheng, S., Lazo, S., et al. (2017). Single-cell RNA-seq reveals new types of human blood dendritic cells, monocytes, and progenitors. Science 356.

APPLICATIONS

Human mononuclear phagocytes comprise phenotypically and functionally overlapping subsets of dendritic cells (DC) and monocytes, but their identification remains elusive. Embodiments of the method disclosed herein combined high dimensional protein and RNA expression data of human circulating DC and monocytes with machine-learning-based approaches to precisely delineate these cells and unravel their heterogeneity. Embodiments of the method clearly delineated monocytes from conventional DC2 (cDC2), and identified new markers including CD88/CD89 for monocytes and HLA-DQ/FcεRIα for cDC2, allowing their unambiguous characterization in blood and tissues.

The disclosure also found that blood CD1c⁺CD163⁺ CD14⁺ pro-inflammatory cells were not monocytes but one of the four phenotypically and functionally distinct subsets contained in the broader cDC2 gate, and also related to the DC3 subpopulation defined by Villani et al. (Villani et al., 2017). Indeed, as shown in the disclosure, cDC2 can be subdivided into phenotypically and functionally distinct subsets based on CD5, CD163 and CD14 expression, including a unique subset of circulating inflammatory CD5⁻ CD163⁺CD14⁺ cells related to the previous defined DC3 subpopulation.

The relevance and importance of these cDC subsets was confirmed with the specific accumulation of CD163⁺ DC3, which comprise CD14⁺ DC3, in the blood of patients with systemic lupus erythematosus (SLE). These inflammatory DC3 were expanded in systemic lupus erythematosus patients, correlating with disease activity. At the transcriptional level, these cells exhibited a strong pro-inflammatory profile and functional activation features, including a strong capacity to prime naïve CD4⁺ T cells towards Th2 and Th17 cells and secrete pro-inflammatory mediators that might contribute to disease physiopathology.

This disclosure offers new insights into MNP heterogeneity, clarifying the identification of monocyte vs cDC populations, as well as the heterogeneity of DC sub-populations in health and disease, thereby paving the way for the design of therapeutic strategies based on manipulating specific DC2 and DC3 subsets or specific DC subset-targeting therapies.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A method of characterising CD1c⁺ dendritic cells, the method comprising:
   determining an expression of one or more of CD5, CD14 and CD163 in the dendritic cells,
   wherein where the dendritic cells are determined to be CD5−, CD14+ and CD163+, identifying the dendritic cells as pro-inflammatory dendritic cells.

2. The method according to claim 1, wherein where the dendritic cells are determined to be CD163+CD14+, identifying the dendritic cells as highly pro-inflammatory dendritic cells that are more pro-inflammatory than CD163− or CD14− dendritic cells.

3. The method according to claim 1, the method further comprising determining a ratio of CD163+CD14+ dendritic cells to a total number of dendritic cells in a sample.

4. The method according to claim 1, the method further comprising determining an expression of one or more of CD11b, CD36, CD64, CD87, CD107a, CD206, CD274, CD354, FcεRIα, HLA-DQ, CD2, CD59, CD81, CD166, CD229, CD271 and Integrin β7 in the dendritic cells.

5. The method according to claim 1, wherein the dendritic cells have one or more of the following properties:
   (i) is a conventional CD1c⁺ dendritic cell 2 (cDC2);
   (ii) is dependent on IRF4 for differentiation;
   (iii) is dependent on KLF4 for differentiation;
   (iv) is dependent on FLT3 ligand (FLT3L) for differentiation; and
   (v) is capable of activating and/or polarizing T cells.

6. The method according to claim 1, the method further comprising determining a ratio of CD163+CD14+ dendritic cells to a total number of dendritic cells having one or more of the properties selected from the group consisting of:
   (i) a conventional dendritic cell;
   (ii) dependent on IRF4 for differentiation;
   (iii) dependent on KLF4 for differentiation;
   (iv) dependent on FLT3 ligand (FLT3L) for differentiation; and
   (v) capable of activating and/or polarizing T cells.

7. A kit for characterising CD1c⁺ dendritic cells, inflammation and/or inflammatory disease, the kit comprising reagents for detecting CD5, CD14 and CD163, wherein the kit further comprises methods for identifying dendritic cells to be pro-inflammatory dendritic cells where the dendritic cells are determined to be CD5−, CD14+ and CD163+.

\* \* \* \* \*